US012042536B2

(12) United States Patent
Houghton et al.

(10) Patent No.: US 12,042,536 B2
(45) Date of Patent: Jul. 23, 2024

(54) HEPATITIS C VIRUS IMMUNOGENIC COMPOSITIONS AND METHODS OF USE THEREOF

(71) Applicants: The Governors of the University of Alberta, Edmonton (CA); Helmholtz Center for Infection Research, Braunschweig (DE)

(72) Inventors: Michael Houghton, Danville, CA (US); Abdolamir Landi, Edmonton (CA); Carlos A. Guzman, Braunschweig (DE); Thomas Ebensen, Braunschweig (DE); Darren Hockman, Edmonton (CA); John L. Law, Edmonton (CA); Michael Logan, Edmonton (CA)

(73) Assignees: The Governors of the University of Alberta, Edmonton (CA); Helmholtz Center for Infection Research, Braunschweig (DE)

( * ) Notice: Subject to any disclaimer, the term of this patent is extended or adjusted under 35 U.S.C. 154(b) by 0 days.

(21) Appl. No.: 18/099,035

(22) Filed: Jan. 19, 2023

(65) Prior Publication Data

US 2024/0058438 A1 Feb. 22, 2024

Related U.S. Application Data

(63) Continuation of application No. 17/122,627, filed on Dec. 15, 2020, now Pat. No. 11,576,968, which is a continuation of application No. 16/336,732, filed as application No. PCT/CA2017/051192 on Oct. 5, 2017, now Pat. No. 10,881,726.

(60) Provisional application No. 62/406,770, filed on Oct. 11, 2016.

(51) Int. Cl.

| | |
|---|---|
| ***A61K 39/29*** | (2006.01) |
| ***A61K 39/00*** | (2006.01) |
| ***A61K 39/12*** | (2006.01) |
| ***A61K 39/39*** | (2006.01) |
| ***A61P 31/14*** | (2006.01) |
| ***A61P 37/04*** | (2006.01) |
| ***C01F 11/02*** | (2006.01) |
| ***C07D 323/00*** | (2006.01) |
| ***C07K 14/005*** | (2006.01) |
| ***C07K 14/18*** | (2006.01) |
| ***C07K 14/28*** | (2006.01) |
| ***C07K 14/33*** | (2006.01) |
| ***C07K 14/34*** | (2006.01) |
| ***C12N 15/86*** | (2006.01) |

(52) U.S. Cl.
CPC .............. *A61K 39/29* (2013.01); *A61K 39/12* (2013.01); *A61K 39/39* (2013.01); *A61P 31/14* (2018.01); *A61P 37/04* (2018.01); *C01F 11/02* (2013.01); *C07D 323/00* (2013.01); *C07K 14/005* (2013.01); *C07K 14/18* (2013.01); *C07K 14/28* (2013.01); *C07K 14/33* (2013.01); *C07K 14/34* (2013.01); *C12N 15/86* (2013.01); *A61K 2039/543* (2013.01); *A61K 2039/545* (2013.01); *A61K 2039/55511* (2013.01); *A61K 2039/55588* (2013.01); *C12N 2770/24234* (2013.01)

(58) Field of Classification Search
CPC .. A61K 39/12; A61K 39/29; A61K 2039/545; A61K 2039/575; A61P 31/14
See application file for complete search history.

(56) References Cited

U.S. PATENT DOCUMENTS

| | | | |
|---|---|---|---|
| 6,121,020 | A | 9/2000 | Selby et al. |
| 2008/0286296 | A1 | 11/2008 | Ebensen et al. |
| 2016/0074507 | A1 | 3/2016 | Manel et al. |

FOREIGN PATENT DOCUMENTS

| | | |
|---|---|---|
| CN | 101426514 A | 5/2009 |
| CN | 105228450 A | 1/2016 |
| CN | 105263517 A | 1/2016 |
| CN | 109963587 A | 7/2019 |
| WO | WO 2001/026683 | 4/2001 |
| WO | WO 2003/002065 | 1/2003 |
| WO | WO 2005/087238 | 9/2005 |
| WO | WO 2007/054279 | 5/2007 |
| WO | WO 2007/112567 | 10/2007 |
| WO | WO 2007/121491 | 11/2007 |
| WO | WO 2014/189805 | 11/2014 |
| WO | WO 2015/132619 | 9/2015 |

OTHER PUBLICATIONS

Aghasadeghi, et al.; "Induction of Strong and Specific Humoral and T-helper 1 Cellular Responses by HBsAg Entrapped in the *Methanobrevibacter smithii* Archaeosomes"; Avicenna Journal of Medical Biotechnology; vol. 6, No. 4, pp. 238-245 (2014).

(Continued)

*Primary Examiner* — Barry A Chestnut
(74) *Attorney, Agent, or Firm* — Bozicevic, Field & Francis LLP; Shweta Chandra

(57) ABSTRACT

The present disclosure provides immunogenic compositions comprising: a) hepatitis C virus (HCV) E1E2 heterodimers, HCV E2, or HCV E1; and b) an adjuvant, where the adjuvant is a cyclic dinucleotide or an archaeosome. The present disclosure provides methods of inducing an immune response in an individual to HCV, the methods comprising administering to an individual an effective amount of an immunogenic composition of the present disclosure.

16 Claims, 52 Drawing Sheets

Specification includes a Sequence Listing.

(56) References Cited

OTHER PUBLICATIONS

Conlan, et al.; "Immunization of mice with lipopeptide antigens encapsulated in novel liposomes prepared from the polar lipids of various Archaeobacteria elicits rapid and prolonged specific protective immunity against infection with the facultative intracellular pathogen, Listeria monocytogenes"; Vaccine; vol. 19, No. 25-26, pp. 3509-3517 (May 14, 2001).
Dubensky, et al.; "Rationale, progress and development of vaccines utilizing STING-activating cyclic dinucleotide adjuvants"; Therapeutic Advances in Vaccines; vol. 1, No. 4, pp. 131-143 (2013).
Frey, et al.; "Safety and immunogenicity of HCV E1E2 vaccine adjuvanted with MF59 administered to healthy adults"; Vaccine; vol. 28, pp. 6367-6373 (2010).
Haq, et al.; "Archaeal lipid vaccine adjuvants for induction of cell-mediated immunity"; Expert Review of Vaccines; vol. 15, No. 12, pp. 1557-1566 (2016).
Krishnan, et al.; "Archaeosomes as Self-adjuvanting Delivery Systems for Cancer Vaccines"; Journal of Drug Targeting; vol. 11, No. 8-10, pp. 515-524 (2003).
Krishnan, et al.; "Archaeosomes Induce Long-Term CD8+ Cytotoxic T Cell Response to Entrapped Soluble Protein by the Exogenous Cytosolic Pathway, in the Absence of CD4+ T Cell Help"; J. Immunol.; vol. 165, No. 9, pp. 5177-5185 (2000).
Landi, et al.; "Superior immunogenicity of HCV envelope glycoproteins when adjuvanted with cyclic-di-AMP, a STING activator or archaeosomes"; Vaccine; vol. 35, pp. 6949-6956 (2017).
Ma, et al.; "DNA-based vaccination against hepatitis C virus (HCV): effect of expressing different forms of HCV E2 protein and use of CpG-optimized vectors in mice"; Vaccine; vol. 20, pp. 3263-3271 (2002).
Patel, et al.; "Mucosal and systemic immune responses by intranasal immunization using archaeal lipid-adjuvanted vaccines"; Vaccine; vol. 25, pp. 8622-8636 (2007).
Patel, et al.; "Safety of archaeosome adjuvants evaluated in a mouse model"; J. Liposome. Res.; vol. 12, No. 4, pp. 353-372 (Nov. 2002).
Patel, et al.; "Safety of intranasally administered archaeal lipid mucosal vaccine adjuvant and delivery (AMVAD) vaccine in mice"; International Journal of Toxicology; vol. 27, pp. 329-339 (2008).
Skrnjug; et al.; "The Mucosal Adjuvant Cyclic di-AMP Exerts Immune Stimulatory Effects on Dendritic Cells and Macrophages"; PLoS One; vol. 9, No. 4, 9 pages (Apr. 2014).

| Group | Name | Sequence (positions 640–750) |
|---|---|---|
| | Consensus | YVGGVEHRLXAACNWTRGERCDLDDRDRSELSPLLLSTTQWQVLPCSFTTLPALSTGLIHLHQNIVDVQYLYGVGSSXVSWAIKWEYVILLFLLLADARICXCLWMMLLISQAEA |
| | | E2 protein peptide |
| 1A | AVI1a129 | YLGGVEHRLEAACNWTRGERCDLEDRDRSELSPLLLSTTQWQVLPCSFTTLPALSTGLIHLHQNIVDVQYLYGVGSSVASWAIKWDYVVLLFLLLADARICSCLWMMLLISQAEA |
| 1A | NP_671491(H77) | YVGGVEHRLEAACNWTRGERCDLEDRDRSELSPLLLSTTQWQVLPCSFTTLPALSTGLIHLHQNIVDVQYLYGVGSSIASWAIKWEYVVLLFLLLADARVCSCLWMMLLISQAEA |
| 1A | EU155269 | YVGGVEHRLEVACNWTRGERCDLDDRDRSELSPLLLSTTQWQVLPCSFTTLPALTTGLIHLHQNIVDVQYLYGVGSSIVSWAIKWEYVILLFLLLADARICSCLWMMLLISQAEA |
| 1A | EU781810 | YVGGVEHRLEVACNWTRGERCDLDDRDRSELSPLLLSTTQWQVLPCSFTTLPALTTGLIHLHQNIVDVQYLYGVGSSLVSWAIKWEYVILLFLLLADARICSCLWMMLLISQAEA |
| 1A | EU781771 | YVGGVEHRLQAACNWTRGERCDLDDRDRSELSPLLLSTTQWQVLPCSFTTLPALTTGLIHLHQNIVDVQYLYGVGSSIVSWAIKWEYVILLFLLLADARICSCLWMMLLISQAEA |
| 1A | AB520610 | YVGGVEHRLEVACNWTRGERCDLDDRDRSELSPLLLSTTQWQVLPCSFTTLPALTTGLIHLHQNIVDVQYLYGVGSSIVSWAIKWEYVILLFLLLADARICSCLWMMLLISQAEA |
| 1A | EU781752 | YVGGVEHRLVAACNWTYGERCNLDDRDRSELSPLLLSTTQWQVLPCSFTTLPALTTGLIHLHQNIVDVQYLYGVGSSIVSWAIKWEYVILLFLLLADARICSCLWMMLLISQAEA |
| 1A | EU781759 | YVGGVEHRLEAACNWTRGERCDLDDRDRSELSPLLLSTTQWQVLPCSFTTLPALTTGLIHLHQNIVDVQYLYGVGSSIVSWAIKWEYVILLFLLLADARICSCLWMMLLISQAEA |
| 1A | EF407439 | YVGGVEHRLEAACNWTRGERCNLDDRDRSELSPLLLSTTQWQVLPCSFTTLPALTTGLIHLHQNIVDVQYLYGVGSSIVSWAIKWEYVILLFLLLADARVCSCLWMMLLISQVEA |
| 1A | EF407427 | YVGGVEHRLDVACNWTRGERCNLDDRDRSELSPLLLSTTQWQVLPCSFTTLPALSTGLIHLHQNIVDVQYLYGVGSSIVSWAIKWEYVILLFLLLADARICSCLWMMLLISQAEA |
| 1A | EU362905 | YVGGVEHRLDVACNWTRGERCNLDDRDRSELSPLLLSTTQWQVLPCSFTTLPALSTGLIHLHQNIVDVQYLYGVGSSIVSWAIKWEYVILLFLLLADARICSCLWMMLLISQAEA |
| 1A | EF407413 | YVGGVEHRLDVACNWTRGERCNLDDRDRSELSPLLLSTTQWQVLPCSFTTLPALSTGLIHLHQNIVDVQYLYGVGSSIVSWAIKWEYVILLFLLLADARICSCLWMMLLISQAEA |
| 1A | EU781808 | YVGGIEHRLEVACNWTRGERCNLDDRDRSELSPLLLTTTQWQVLPCSFTTLPALTTGLIHLHQNVVDVQYLYGVGSSIVSWAIKWEYVILLFLLLADARICSCLWMMLLISQAEA |
| 1A | EU781790 | YVGGVEHRLEVACNWTRGERCNLDDRDRSELSPLLLSTTQWQVLPCSFTTLPALTTGLIHLHQNIVDVQYLYGVGSSIVSWAVKWEYVILLFLLLADARICSCLWMMLLISQAEA |
| 1B | AJ238799(Con1) | YVGGVEHRLEAACNWTRGERCNLEDRDRSELSPLLLSTTEWQVLPCSFTTLPALSTGLIHLHQNVVDVQYLYGIGSAVVSFAIKWEYVLLLFLLLADARVCACLWMMLLIAQAEA |
| 1B | AAK97744 | YVGGVEHRLDAACNWTRGERCNLEDRDRLELSPLLLSTTEWQVLPCSFTTLPALSTGLIHLHQNIVDVQYLYGIGSAVVSFAIKWDYIVILFLLLADARVCACLWMMLLIAQAEA |
| 1B | AF139594 | YVGGVEHRLNAACNWTRGERCNLDDRDRSELSPLLLSTTEWQVLPCSFTTLPALSTGLIHLHQNIVDVQYLYGIGSAVVSFAIKWEYVVLLFLLLADARVCACLWMMLLIAQAEA |
| 1B | AF176573 | YVGGVEHRLNAACNWTRGERCDLEDRDRSELSPLLLSTTEWQVLPCSFTTLPALSTGLIHLHQNIVDVQYLYGIGSAVIPFAIKWEYVLLLFLLLADARVCACLWMMLLIAQAEA |
| 1B | BAA19625 | YVGGIEHRLDAACNWTRGERCDLEDRDRSELSPLLLSTTEWQILPCSFTTLPALSTGLIHLHRNIVDVQYLYGIGSAVVSFAIKWEYVLLLFLLLADARVCACLWMMLLIAQAEA |
| 1B | BAA25076 | YVGGVEHRLDAACNWTRGERCDLEDRDRAELSPLLLSTTEWQILPCSYTTLPALSTGLIHLHQNIVDIQYLYGIGSAVVSIAIKWEYVVLLFLLLADARVCACLWMMLLIAQAEA |
| 1B | BAC54896 | YVGGIEHRLDAACNWTRGERCDLEDRDRSELSPLLLSTTEWQILPCSFTTLPALSTGLIHLHRNIVDVQYLYGIGSAVVSFAIKWEYILLLFLLLADARVCACLWMMLLIAQAEA |
| 1B | BAD91386 | YVGGVEHRLDAACNWTRGERCNVEDRDRSELSPLLLSTTEWQILPCSFTTLPALSTGLIHLHQNIVDVQYLYGVGSVVVSVVIRWEYVVLLFLLLADARVCACLWMMLLIAQAEA |
| 1B | BAF46764 | YVGGVEHRLTAACNWTRGERCDLEDRDRSELSPLLLSTTEWQIMPCSFTTLPALSTGLIHLHQNIVDIQYLYGIGSAAVSFAIRWEYVLLLFLLLADARVCACLWMMLLIAQAEA |
| 1B | BAG30950 | YVGGVEHRLTAACNWTRGERCDLEDRDRSELSPLLLSTTEWQIMPCSFTTLPALSTGLIHLHQNIVDIQYLYGIGSAAVSFAIRWEYVLLLFLLLADARVCACLWMMLLIAQAEA |
| 1B | CAB41951 | YVGGIEHRLSAACNWTRGERCDLEDRDRSELSPLLLSTTEWQILPCSFTTLPALSTGLIHLHQNTVDVQYLYGVGSVLVSFAIKWEYILLFFLLLADARVCACLWMMLLIAQAEA |
| 1C | AAK95832 | FVGGIEHRLTAACNWTRGERCDLDDRDRAELSPLLLSTTQWQVLPCSFTTLPALSTGLIHLHQNIVDVQYLYGLSSVVTSWAIRWEYVVLLFLLLADARICACLWMMLLISQVEA |
| 1C | AAT69968 | FVGGVEHRLDAACNWTRGERCDLDDRDRAELSPLLLSTTQWQVLPCSFTTLPALSTGLIHLHQNIVDVQYLYGLSSAVTSWVIKWEYVVLLFLLLADARICACLWMMLLISQVEA |
| 1C | BAA03581 | FVGGVEHRLDAACNWTRGERCDLDDRDRAELSPLLLSTTQWQVLPCSFTTLPALSTGLIHLHQNIVDVQYLYGLSSAVTSWVIKWEYVVLLFLLLADARICACLWMMLLISQVEA |

FIG. 1C

```
                       270         280         290         300         310         320         330         340
Consensus              HIDMVVMSATLCSALYVGDLCGGVMLAAQXFIVSPQRHWFVQECNCSIYPGTITGHRMAWDMMMNWSPTATMILAYAMRVPEVIIDI
                                                                 E1
2A AB047639 (JFH1)     HIDMVVMSATFCSALYVGDLCGGVMLAAQVFIVSPQYHWFVQECNCSIYPGTITGHRMAWDMMMNWSPTATMILAYVMRVPEVIIDI
   AB047645            HIDMVVMSATLCSALYVGDLCGGVMLAAQMFIISPQHHWFVQECNCSIYPGTITGHRMAWDMMMNWSPTTTMILAYVMRVPEVIIDI
   AF238482            HIDMVVMSATLCSALYVGDLCGGVVLAAQLFIVSPRRHWFVQECNCSIYPGAITGHRMAWDMMMNWSPTTTMVLAYAMRVPEVIIDI
   AF169005            HIDMVVMSATLCSALYVGDLCGGVMLAAQMFIVSPQHHHFVQECNCSIYPGAITGHRMAWDMMMNWSPTATMILAYAMRVPEVIIDI
   AY746460            HIDIVVMSATLCSALYVGDLCGGVMLAAQMFVVSPEHHWFVQECNCSIYPGTITGHRMAWDMMMNWSPTATMILAYAMRVPEVIIDI
   HPCPOLP             HIDMVVMSATLCSALYVGDLCGGVMLAAQMFIVSPQHHWFVQDCNCSIYPGTITGHRMAWDMMMNWSPTATMILAYAMRVPEVIIDI
   NC_009823           HIDMVVMSATLCSALYVGDLCGGVMLAAQMFIVSPQHHWFVQDCNCSIYPGTITGHRMAWDMMMNWSPTATMILAYAMRVPEVIIDI

2B HPCJ8G HC-J8        HVDMIVMAATACSALYVGDVCGAVMILSQAFMVSPQRHNFTQECNCSIYQGHITGHRMAWDMMLSWSPTLTMILAYAARVPELVLEI
   AY232730            HVDVIVVAATVCSALYVGDVCGAVMIASQALIVSPARHNFTQECNCSIYQGRITGHHMAWDMMLNWSPTITMILAYAARIPELVLEV
   AY232747            HVDVIVMAATVCSALYVGDICGAVMIVSQAFIISPERHNFTQECNCSMYQGHITGHRMAWDMMLNWSPTLTMILAYAARVPELVLEV
   AB030907            HVDVIVMAATVCSALYVGDVCGAVMIVSQALIVSPERHNFTQECNCSIYQGHITGQRMAWDMMLNWSPTLTMILAYAARVPELVLEI
   DQ430817            HVDMIVMAATVCSALYVGDVCGAVMIVSQAFIMS?ERHNFTQECNCSIYQGHITGHRMAWDMMLGWSPTLTMILAYAARVPE?VLEV
                    350         360         370         380         390         400         410         420         430
Consensus              IFGAHWGVMFGLAYFSMQGAWAKVIVILLLXAGVDARTHTVGGSXGRTTSGXAGLFSSGPKQNIQLINTNGSWHINRTALNCNDSLQ
                                         E1                                       E2
2A AB047639 (JFH1)     VSGAHWGVMFGLAYFSMQGAWAKVIVILLLAAGVDAGTTTVGGAVARSTNVIAGVFSHGPQQNIQLINTNGSWHINRTALNCNDSLN
   AB047645            IGGAHWGVMFGLAYFSMQGAWAKVVVILLLAAGVDAHTRT-GSSVGYATSGIVGLFTSGPKQNIQLINTNGSWHINRTALNCNDSLN
   AF238482            ISGAHWGVMFGLAYFSMQGAWAKVAVILLLTAGVEARTHTTGSVAGRTTSGFAGIFTSGPKQNIQLINTNGSWHINRTALNCNDSLN
   AF169005            ISGAHWGVMFGLAYFSMQGAWAKVVVILLLTAGVDAHTRSIAGSVAHATSGLAGLFTSGAKQNIQLINTNGSWHINRTALNCNDSLN
   AY746460            IGGAHWGVMFGLAYFSMQGAWAKVVVILLLAAGVDAYTHTVGGAAASTANSIAGLLSRGPRQNLQLINSNGSWHINRTALNCHDSLQ
   HPCPOLP             IGGAHWGVMFGLAYFSMQGAWAKVVVILLLAAGVDAQTHTVGGSTAHNARTLTGMFSLGARQKIQLINTNGSWHINRTALNCNDSLH
   NC_009823           ISGAHWGVMFGLAYFSMQGAWAKVVVILLLAAGVDARTHTVGGSAAQTTGRLTSLFDMGPRQKIQLVNTNGSWHINRTALNCNDSLH

2B HPCJ8G HC-J8        IFGGHWGVVFGLAYFSMQGAWAKVIAILLLVAGVDATTYSSGQEAGRTVAGFAGLFTTGAKQNLYLINTNGSWHINRTALNCNDSLQ
   AY232730            IFGGHWGVMFGLAYFSMQGAWAKVIVILLLVAGVDARHHTTGLQAGKTLARVTSLFSIGAKQNIQLINTNGSWHINRTALNCNDSLQ
   AY232747            IFGGHWGVVFGLAYFSMQGAWAKVIAILLLVAGVDANTYSSGVTVGHTTSTFANIFSVGPSQKINLINTNGSWHINRTALNCNDSLQ
   AB030907            VFGGHWGVVFGLAYFSMQGAWAKVIAILLLVAGVDATTYSTGATVGRTVGSFAGLFKLGAQQNVQLINTNGSWHINRTALNCNDSLH
   DQ430817            VFGGHWGVVFGLAYFSMQGAWAKVIAILLLVAGVDAGTYSSGATIGQGTRGLV?LFSAGPSQKISLINTNGSWHINRT?LNCNDSLQ
                    440         450         460         470         480         490         500         510         520
Consensus              TGFIASLFYTXNFNSSGCPERLSACRGIEAFRIGWGTLQYEDNVTNPEDMRPYCWHYPPKXCGIVPARSVCGPVYCFTPSPVVVGTT
                                                                 E2
2A AB047639 (JFH1)     TGFLAALFYTNRFNSSGCPGRLSACRNIEAFRIGWGTLQYEDNVTNPEDMRPYCWHYPPKPCGVVPARSVCGPVYCFTPSPVVVGTT
   AB047645            TGFIVSLFYARNFNSTGCPERLSACRGIEGFRIGWGTLQYEDNVTNPEDMRPYCWHYPPKQCGIVPAGSVCGPVYCFTPSPVVVGTT
   AF238482            TGFMAALFYTKNFNSSGCPERLS?CRNIEAFRIGWGTLQYEDDVTNPEDMRPYCWHYPPKQCGIFPAGSVCGPVYCFTPSPVVVGTT
   AF169005            TGFIASLFYTYRFNSSGCPERLSACRGIQAFRIGWGTLRYEDNVTNPEDMRPYCWHYPPKQCGIVSARSVCGPVYCFTPSPVVVGTT
   AY746460            TGFITALFYARHFNSSGCPERLAACRNIEAFRVGWGALQYEDNVTNPEDMRPYCWHYPPKQCGIVPARSVCGPVYCFTPSPVVVGTT
   HPCPOLP             TGFLASLFYTHSFNSSGCPERMSACRSIEAFRVGWGALQYEDNVTNPEDMRPYCWHYPPRQCGVVSASSVCGPVYCFTPSPVVVGTT
   NC_009823           TGFIASLFYTHSFNSSGCPERMSACRSIEAFRVGWGALQYEDNVTNPEDMRPYCWHYPPRQCGVVSAKTVCGPVYCFTPSPVVVGTT

2B HPCJ8G HC-J8        TGFLASLFYTHKFNSSGCPERLSSCRGLDDFRIGWGTLEYETNVTNDGDMRPYCWHYPPRPCGIVPARTVCGPVYCFTPSPVVVGTT
   AY232730            TGFIASLFYVNNINSSGCPERMSSCRELDDFRIGWGTLEYETNVTNDEDMRPYCWHYPPKPCGIVPARTVCGPVYCFTPSPIVVGTT
   AY232747            TGFLASLFYVRNFNSSGCRERLSSCRRLDDFRIGWGTLEYETNVTNDEDMRPYCWHYPPKPCGIVSARTVCGPVYCFTPSPVVVGTT
   AB030907            TGFMAALFYANKFNSSGCPERLSSCRGLDDFRIGWGTLEYETNVTNVEDMRPYCWHYPPKPCGIVPAQSVCGPVYCFTPSPVVVGTT
   DQ430817            TGFIASLFYAKSFNSSGCPERLSSCRGLDDFRIGWGTLEYENNVTNDEDMRPYCWHYPPKPCGIVPARTVCGPVYCFTPSPVVVGTT
```

FIG. 2B

Positions 530–600 (region E2)

| Group | Sequence | Alignment |
|---|---|---|
| | Consensus | DRLGVPTYTWGENETDVFLLNSTRPPRGSWFGCTWMNSTGFTKTCGAPPCRIRADFNASTDLLCPTDCFRKHPDATYJKCGSGPWLT |
| 2A | AB047639 (JFH1) | DRRGVPTYTWGENETDVFLLNSTRPPQGSWFGCTWMNSTGFTKTCGAPPCRTRADFNASTDLLCPTDCFRKHPDATYIKCGSGPWLT |
| 2A | AB047645 | DRLGVPTYTWGENETDVFLLNSTRPPVGSWFGCTWMNSTGFTKTCGAPPCRIRADFNASTDLLCPTDCFRKHPEATYIKCGSGPWLT |
| 2A | AF238482 | NKLGVPTYTWGENETDVFILNSTRPPRGSWFGCTWMNSTGFTKTCGAPPCRIRADFNASTDLLCPTDCFRKHPEATYIKCGSGPWLT |
| 2A | AF169005 | DRLGVPTYTWGENETDVFILNSTRPPGGSWFGCTWMNSTGFTKTCGAPPCRIRADFNASMDLLCPTDCFRKHPDATYIKCGSGPWLT |
| 2A | AY746460 | DKLGVPTYTWGENETDVFLLNSTRPPQGPWFGCTWMNSTGFTKTCGAPPCRTRADFNASTDLLCPTDCFRKHPDATYNKCGSGPWLT |
| 2A | HPCPOLP | DRLGAPTYTWGENETDVFLLNSTRPPQGSWFGCTWMNSTGYTKTCGAPPCRIRADFNASMDLLCPTDCFRKHPDTTYIKCGSGPWLT |
| 2A | NC_009823 | DRLGAPTYTWGENETDVFLLNSTRPPLGSWFGCTWMNSSGYTKTCGAPPCRTRADFNASTDLLCPTDCFRKHPDTTYLKCGSGPWLT |
| 2B | HPCJ8G HC-J8 | DKQGVPTYTWGENETDVFLLNSTRPPRGAWFGCTWMNGTGFTKTCGAPPCRIRKDYNSTIDLLCPTDCFRKHPDATYLKCGAGPWLT |
| 2B | AY232730 | DKQGVPTYSWGENETDVFLLNSTRPPRGSWFGCTWMNGTGFTKTCGAPPCRIRRDYNSTLDLLCPTDCFRKHPDTTYLKCGSGPWLT |
| 2B | AY232747 | DRQGVPTYSWGENETDVFLLNSTRPPRGAWFGCTWMNGTGFTKTCGAPPCRIRRDYNSTLDLLCPTDCFRKHPDTTYLKCGAGPWLT |
| 2B | AB030907 | DRQGVPTYNWGDNETDVFLLNSTRPPRGAWFGCTWMNGTGFTKTCGAPPCRIRKDFNSTLDLLCPTDCFRKHPDATYVKCGAGPWLT |
| 2B | DQ430817 | DKQGVPTYSWGENETDVFLLNSTRPPQGAWFGCTWMNGTGFTKTCGAPPCRIRRDHTSTLDLLCPTDCFRKHPDTTYLKCGAGPWLT |

Positions 610–690 (region E2)

| Group | Sequence | Alignment |
|---|---|---|
| | Consensus | PRCLVDYPYRLWHYPCTVNXTIFKIRMYVGGVEHRLTAACNFTRGDRCNLEDRDRXQLSPLLHSTTEWAILPCSXSDLPALSTGLLH |
| 2A | AB047639 (JFH1) | PKCLVHYPYRLWHYPCTVNFTIFKIRMYVGGVEHRLTAACNFTRGDRCDLEDRDRSQLSPLLHSTTEWAILPCTYSDLPALSTGLLH |
| 2A | AB047645 | PRCLVDYPYRLWHYPCTVNYSIFKIRMYVGGVEHRLTAACNFTRGDRCNLEDRDRSQLTPLLHSTTEWAILPCTYSDLPALSTGLLH |
| 2A | AF238482 | PRCLVDYPYRLWHYPCTVNYSIFKIRMYVGGVEHRLTAACNFSRGDRCNLEDRDRSQLTPLLHSTTEWAILPCSYSDLPALSTGLLH |
| 2A | AF169005 | PRCLVDYPYRLWHYPCTINYTIFKIRMYVGGVEHRLTAACNFTRGDPCNLEDRDRSQLSPLLHSTTEWAILPCSYSDLPALSTGLLH |
| 2A | AY746460 | PRCLIDYPYRLWHYPCTVNYTTFKIRMYVGGVEHRLMAACNFTRGDSCDLSQRDRGQLSPLLHSTTEWAILPCSFSDLPALSTGLLH |
| 2A | HPCPOLP | PRCLIDYPYRLWHYPCTVNYTIFKIRMYVGGVEHRLTAACNFTRGDRCNLEDRDRSQLSPLLHSTTEWAILPCTYSDLPALSTGLLH |
| 2A | NC_009823 | PRCLIDYPYRLWHYPCTVNYTIFKIRMYVGGVEHRLTAACNFTRGDRCNLEDRDRSQLSPLLHSTTEWAILPCSYSDLPALSTGLLH |
| 2B | HPCJ8G HC-J8 | PRCLVDYPYRLWHYPCTVNFTIFKARMYVGGVEHRFSAACNFTRGDRCRLEDRDRGQQSPLLHSTTEWAVLPCSFSDLPALSTGLLH |
| 2B | AY232730 | PKCLVEYPYRLWHYPCTVNFTIFKVRMYVGAVEHRFSAACNFTRGDRCRLEDRDRGQQSPLLHSTTEWAVLPCSFSDLPALSTGLLH |
| 2B | AY232747 | PKCLVDYPYRLWHYPCTVNFTIFKVRMYVGGVEHRLSAACNFTRGDRCGLEDRDRGQQSPLLHSTTEWAVLPCSFSDLPALSTGLLH |
| 2B | AB030907 | PRCLIDYPYRLWHYPCTVNFTIFKVRMYVGGVEHRFSAACNFTRGDRCRLEDRDRGQQSPLLHSTTEWAVLPCSFSDLPALSTGLLH |
| 2B | DQ430817 | PKCLVDYPYRLWHYPCT?NFTIFKVRMYVGGVEHRFSAACNFTRGDRCRLEDRDRGQQSPLLHSTTEWAVLPCSFSDLPALSTGLLH |

Positions 700–751 (region E2)

| Group | Sequence | Alignment |
|---|---|---|
| | Consensus | LHQNIVDVQYMYGLSPALTKYIVRWEWVVLLFLLLADARVCACLWMLILLGQAEA |
| 2A | AB047639 (JFH1) | LHQNIVDVQYMYGLSPAITKYVVRWEWVVLLFLLLADARVCACLWMLILLGQAEA |
| 2A | AB047645 | LHQNIVDVQYMYGLSPALTKYVVRWEWVVLLFLLLADARVCACVWMLILLGQAEA |
| 2A | AF238482 | LHQNIVDVQYMYGLTPALTKYVVRWEWVVLLFLLLADARVCACLWMLILLGQAEA |
| 2A | AF169005 | LHQNIVDVQYMYGLSPALTKYIVRWEWVVLLFLLLADARVCACLWMLILLGQAEA |
| 2A | AY746460 | LHQNIVDVQYMYGLSPALTKYIVRWEWVVLLFLLLADARVCACIWMLILLGQAEA |
| 2A | HPCPOLP | LHQNIVDVQFMYGLSPALTKYIVRWEWVVLLFLLLADARVCACLWMLILLGQAEA |
| 2A | NC_009823 | LHQNIVDVQFMYGLSPALTKYIVRWEWVILLFLLLADARVCACLWMLILLGQAEA |
| 2B | HPCJ8G HC-J8 | LHQNIVDVQYLYGLSPALTRYIVKWEWVILLFLLLADARICACLWMLIILGQAEA |
| 2B | AY232730 | LHQNIVDVQYLYGLSPAITRYIVKWEWVVLLFLLLADARVCACLWMLIILGQAEA |
| 2B | AY232747 | LHQNIVDVQYLYGLSPAITRYIVKWEWVVLLFLLLADARVCACLWMLIILGQAEA |
| 2B | AB030907 | LHQNIVDVQYLYGLSPAVTKYIVKWEWVVLLFLLLADARICACLWMLIILGQAEA |
| 2B | DQ430817 | LHQNIVDVQYLYGLSPAITKYIVKWEWVILLFLLLADARVCACLWMLIILGQAEA |

FIG. 2C

```
                     270       280       290       300       310       320       330       340       350
   Consensus         LLVGAATMCSALYVGDMCGAVFLVGQAFTFRPRRHQTVQTCNCSLYPGHLSGHRMAWDMMMNWSPAVGMVVAHVLRLPQTLFDIIAGA
                                                              E1
   AVI3a177          LLVGAATLCSALYVGDMCGAVFLVGQAFTFRPRRHQTVQTCNCSLYPGHLTGHRMAWDMMMNWSPAVGMVVAHVLRMPQTVFDIIAGA
   ADF97232(S52)     LLVGAATLCSALYVGDMCGAVFLVGQAFTFRPRRHQTVQTCNCSLYPGHVSGHRMAWDMMMNWSPAVGMVVAHILRLPQTLFDILAGA
   YP_001469631      LLVGAATMCSALYVGDMCGAVFLVGQAFTFRPRRHQTVQTCNCSLYPGHLSGHRMAWDMMMNWSPAVGMVVAHVLRLPQTLFDIMAGA
   CAA54244          LLVGAATMCSALYVGDMCGAVFLVGQAFTFRPRRHQTVQTCNCSLYPGHLSGHRMAWDMMMNWSPAVGMVVSHVLRLPQTLFDIIAGA
3A AAC03058          LLVGAATMCSALYVGDMCGAVFLVGQAFTFRPRRHQTVQTCNCSLYPGHLSGHRMAWDMMMNWFPALGMAVAHVLRVPQTLFDIIAGA
   AAY29642          LLVGAATMCSALYVGDMCGAVFLVGQAFTFRPRRHQTVQTCNCSLYPGHLTGHRMAWDMMMNWSPAVGMVVAHVLRLPQTLFDIIAGA
   ABD85062          LLVGAATMCSALYVGDMCGAVFLVGQAFTFRPRRHQTVQTCNCSLYPGHLSGHRMAWDMMMNWSPAAGMVVAHILRLPQTLFDIIAGA
   ABD85063          LLVGAATMCSALYVGDMCGAVFLVGQAFTFRPRRHQTVQTCNCSLYPGHLSGHRMAWDMMMNWSPAAGMVVAHILRLPQTLFDIIAGA
   ABD97104          LLVGAATMCSALYVGDMCGAVFLVGQAFTFRPRRHQTVQTCNCSLYPGHLSGHRMAWDMMMNWSPAVGMVVAHVLRLPQTLFDIIAGA
   BAA06044          LLVGAGTMCSALYVGDMCGPVFLVGQAFTFRPRRHRTVQTCNCSLYPGHLSGQRMAWDMMMNWSPAVGMVVAHILRLPQTLFDVVAGA

3B BAA08372          MLVAPPTLCSALYVEDAFGAVSLVGQAFTFRPRQHKTVQTCNCSIYPGHVSGHRMAWDMMMNWSPAIGLVISHLMRLPQTFFDLVVGA

3K BAA09890          MMVGAATLCSALYVGDLCGALFLVGQGFSWRHRQHWTVQDCNCSIYPGHLTGHRMAWDMMMNWSPAMTLIVSQVLRLPQTMFDLVIGA

                          360       370       380       390       400       410       420       430       440
   Consensus         HWGILAGLAYYSMQGNWAKVAIIMVMFSGVDATTYTTGGSAARGARGLTSLFSVGAKQKLQLVNTNGSWHINSTALNCNXSINTGFIA
                                    E1                                  E2
   AVI3a177          HWGILAGLAYYSMQGNWAKVAIIMVMFSGVDAETHTTGGTAARNAFTLTGLFTQGARQKLELINTNGSWHINRTALNCNESLNTGFIA
   ADF97232(S52)     HWGILAGLAYYSMQGNWAKVAIVMIMFSGVDAETYVTGGSVAHSARGLTSLFSMGAKQKLQLVNTNGSWHINSTALNCNESINTGFIA
   YP_001469631      HWGILAGLAYYSMQGNWAKVAIIMVMFSGVDAHTYTTGGTASRHTQAFAGLFDIGPQQKLQLVNTNGSWHINSTALNCNESINTGFIA
   CAA54244          HWGILAGLAYYSMQGNWAKVAVIMVMFSGVDAETYITGGSAAHGVSTLTSLFSSGPQQKLQLVKTNGSWHINSTALNCNESINTGFIA
3A AAC03058          HWGILAGLAYYSMQGNWAKVAIIMVMFSGVDAVTYTTGGSAAHATRGLTSLFSVGAQQKLQLVNTNGSWHINSTALNCNESINTGFIA
   AAY29642          HWGILAGLAYYSMQGNWAKVIIIMVMFSGVDATTHVTGGTAGLTAFRLTGLFTVGPQQKLQLVNTNGSWHINRTALNCNDSLNTGFIA
   ABD85062          HWGILAGLAYYSMQGNWAKVAIIMVMFSGVDATTYTSGGSVAQQARGLADLFSVGAKQNLQLVNTNGSWHINSTALNCDDSINTGFIA
   ABD85063          HWGILAGLAYYSMQGNWAKVAIIMVMFSGVDATTYTSGGSVAQQARGLADLFSVGAKQNLQLVNTNGSWHINSTALNCDDSINTGFIA
   ABD97104          HWGILAGLAYYSMQGNWAKVAIIMVMFSGVDATTYTTGGNAARGASGIVSLFTPGAKQNLQLVNTNGSWHINRTALNCNDSINTGFIA
   BAA06044          HWGIIAGLAYYSMQGNWAKVAIIMVMFSGVDASTHVTAGQAARNAYGITSLFSVGAKQNLQLINTNGSWHINRTALNCNESINTGFIA

3B BAA08372          HWGVMAGLAYFSMQGNWAKVVIVLIMFSGVDATTHTTGGSAAQATAGFTSFFTRGPSQNLQLVNSNGSWHINSTALNCNDSLNTGFIA

3K BAA09890          HWGVMAGVAYYSMQGNWAKVFLVLCLFSGVDASTTITGGVAASGAFTITSLFSTGAKQPLHLVNTNGSWHINRTALNCNDSLNTGFIA

                               450       460       470       480       490       500       510       520
   Consensus         GLFYYHKFNSTGCPQRLSSCKPITFFXQGWGPLTDANITGPSDDKPYCWHYAPRPCDVVPASSVCGPVYCFTPSPVVVGTTDAKGVPT
                                                              E2
   AVI3a177          GLFYLHKFNSTGCPERLSSCKPITFFRQGWGSLTDANITGPSDDKPYCWHYAPRPCEVVPALNVCGPVYCFTPSPVVVGTTDRQGVPT
   ADF97232(S52)     GLFYYHKFNSTGCPQRLSSCKPIISFRQGWGPLTDANITGPSDDRPYCWHYAPRPCSVVPASSVCGPVYCFTPSPVVVGTTDIKGKPT
   YP_001469631      GLFYYHKFNSTGCPQRLSSCKPITFFRQGWGPLTDANITGPSDDRPYCWHYAPRPCDIVPASSVCGPVYCFTPSPVVVGTTDARGVPT
   CAA54244          GLFYYHKFNSTGCPQRLSSCKPITFFRQGWGSLTDANVTGASADKPYCWHYAPRPCDVVPALNVCGPVYCFTPSPVVVGTTDRKGVPT
3A AAC03058          GLFYYHRFNSTGCPQRLSSCKPITFFKQGWGPLTDANISGPSDDKPYCWHYAPRPCKVVPASGVCGPVYCFTPSPVVVGTTDAKGVPT
   AAY29642          GLFRFHKFNSTGCPEMLSSCKPITSFKQGWGPLTDANITIPSDDRPYCWHYPPRSCEVVPALSVCGPVYCFTPSPVVVGTTDAKGVPT
   ABD85062          GLFYYHKFNSTGCPQRLSDCKPITFFKQGWGPLTDANITGPSDDKPYCWHYAPRRCGVVPASSVCGPVYCFTPSPVVVGTTDAKGVPT
   ABD85063          GLFYYHKFNSTGCPQRLSDCKPITFFKQGWGPLTDANITGPSDDKPYCWHYAPRRCGVVPASSVCGPVYCFTPSPVVVGTTDAKGVPT
   ABD97104          GLIYYHKFNSTGCPQRLSSCKPITFFRQGWGSLTDANITGPSDDKPYCWHYPPRPCDTIRASSVCGPVYCFTPSPVVVGTTDAKGAPT
   BAA06044          GLFYYHKFNSTGCPQRLSSCKPITFFKQGWGPLTDANITGPSDDKPYCWHYAPRPCGIVPALNVCGPVYCFTPSPVVVGTTDAKGAPT

3B BAA08372          GLFYYHKFNSSGCPERMSSCKPITYFNQGWGPLTDANINGPSEDRPYCWHYPPRPCNITKPLNVCGPVYCFTPSPVVVGTTDIKGLPT

3K BAA09890          GLLYYHKFNSSGCVERMSACSPLDRFAQGWGPLGPANISGPSSEKPYCWHYAPRPCDTVPAQSVCGPVYCFTPSPVVVGATDKRGAPT
```

FIG. 3B

```
                   530       540       550       560       570       580       590       600       610
      Consensus    YTWGENETDVFLLESLRPPSGRWFGCTWMNSTGFVKTCGAPPCNIYGGGGNPH-NESDLFCPTDCFRKHPEATYSRCGAGPWLTPRCM
                                                             E2
      AVI3a177     YTWGENETDVFLLRSLRPPSGQWFGCTWMNSTGFVKTCGAPPCDIYGGGGNRC-NESDLFCPTDCFRKHPEATYSRCGAGPWLTPRCL
      ADF97232(S52) YNWGENETDVFLLESLRPPSGRWFGCAWMNSTGFLKTCGAPPCNIYGGEGDPE-NETDLFCPTDCFRKHPEATYSRCGAGPWLTPRCM
      YP_001469631 YTWGENEKDVFLLKSQRPPSGRWFGCSWMNSTGFLKTCGAPPCNIYGGEGNPH-NESDLFCPTDCFRKHPETTYSRCGAGPWLTPRCM
      CAA54244     YNWGENESDVFLLESLRPPSGRWFGCAWMNSTGFLKTCGAPPCNIYGGGGNPN-NESHLFCPTDCFRKHPDATYSRCGAGPWLTPRCM
3A    AAC03058     YTWGANDTDVFLLESLRPPGGRWFGCTWMNSTGFVKTCGASPCDIYGGGGNSG-NESDLFCPTDCFRKHPEATYSRCGAGPWLTPRCM
      AAY29642     YTWGENETDVFLLKSLRPPGGRWFGCTWMNSTGFVQTCGAPPCNIYGGGGDLK-NESDLFCPTDCFRKHPEATYSRCGAGPWLTPRCM
      ABD85062     YTWGANETDVFLLESLRPPSGRWFGCAWMNSTGFLKTCGAPPCNIYGGGGNPH-NESDLFCPTDCFRKHPEATYSRCGAGPWLTPRCM
      ABD85063     YTWGANETDVFLLESLRPPSGRWFGCAWMNSTGFLKTCGAPPCNIYGGGGNPH-NESDLFCPTDCFRKHPEATYSRCGAGPWLTPRCM
      ABD97104     YNWGANETDMFLLQSLRPPSGRWFGCTWMNSTGFTKTCGAPPCNIYGGGGNLN-NESDLFCPTDCFRKHPEATYSRCGAGPWLTPRCL
      BAA06044     YTWGANKTDVFLLESLRPPSGRWFGCTWMNSTGFVKTCGAPPCNIYGDGRDAQ-NESDLFCPTDCFRKHPEATYSRCGAGPWLTPRCL

3B    BAA08372     YRFGVNESDVFLLTSLRPPQGRWFGCVWMNSTGFVKTCGAPPCNIYGGMKDIEANQTHLKCPTDCFRKHHDATFTRCGSGPWLTPRCL

3K    BAA09890     YTWGENESDVFLLESARPPTEPWFGCTWMNGSGYVKTCGAPPCHIYGGREGK--SNNSLVCPTDCFRKHPDATYNRCGAGPWLTPRCL
                     620       630       640       650       660       670       680       690       700
      Consensus    VDYPYRLWHYPCTVNFTLFKVRMFVGGFEHRFTAACNWTRGERCDIEDRDRSEQHPLLHSTTELAILPCSFTPMPALSTGLIHLHQNI
                                                             E2
      AVI3a177     VDYPYRLWHYPCTVNFTLFKVRMFVGGFEHRFTAACNWTRGERCNIEDRDRSEQHPLLHSTTELAILPCSFTPMPALSTGLIHLHQNI
      ADF97232(S52) VDYPYRLWHYPCTVNFTLFKVRMFVGGFEHRFTAACNWTRGERCNIEDRDRSEQHPLLHSTTELAILPCSFTPMPALSTGLIHLHQNI
      YP_001469631 VDYPYRLWHYPCTVDFRLFKVRMFVGGFEHRFTAACNWTRGERCDIEDRDRSEQHPLLHSTTELAILPCSFTPMPALSTGLIHLHQNI
      CAA54244     VDYPYRLWHYPCTVNFTLFKVRMFVGGFEHRFTAACNWTRGERCNIEDRDRSEQHPLLHSTTELAILPCSFTPMPALSTGLIHLHQNI
3A    AAC03058     VDYPYRLWHYPCTVNFTLFKVRMFVGGFEHRFTAACNWTRGERCDIEDRDRSEQHPLLHSTTELAILPCSFTPMPALSTGLIHLHQNI
      AAY29642     VDYPYRLWHYPCTVNFTLFKVRMFVGGFEHRFTAACNWTRGERCDIEDRDRSELHPLLHSTTELAILPCSFTPMPALSTGLIHLHQNI
      ABD85062     VDYPYRLWHYPCTVNFTLFKMRTFVGGFEHRFTAACNWTRGERCDIEDRDRSEQHPLLHSTTELAILPCSFTPMPALSTGLIHLHQNI
      ABD85063     VDYPYRLWHYPCTVNFTLFKMRTFVGGFEHRFTAACNWTRGERCDIEDRDRSEQHPLLHSTTELAILPCSFTPMPALSTGLIHLHQNI
      ABD97104     VDYPYRLWHYPCTVNFTLFRMRTFVGGFEHRFTAACNWTRGERCNIEDRDRSEQHPLLHSTTELAILPCSFTPMPALSTGLIHLHQNI
      BAA06044     VDYPYRLWHYPCTVNFTLFKVRMFVGGFEHRFTAACNWTRGERCDIEDRDRSEQHPLLHSTTELAILPCSFTPMPALSTGLIHLHQNI

3B    BAA08372     VDYPYRLWHYPCTVNFSIFKVRMFVGGHEHRFSAACNWTRGERCDLEDRDRSEQQPLLHSTTDSLILPCSFTPMRRLSTGLIHLHQNI

3K    BAA09890     VDYPYRLWHYPCTVNYTIFKVRMFVGGLEHRFNAACNWTRGERCNLEDRDRSEMYPLLHSTTEQAILPCSFVPIPALSTGLIHLHQNI
                     710       720       730       740       750  754
      Consensus    VDVQYLYGVGSGMVGWALKWEFVILVFLLLADARVCVALWLMLMISQAEA
                                      E2
      AVI3a177     VDVQYLYGVGSGVVGWALRWEFVVLVFLLLADARVCVALWLMLMISQAEA
      ADF97232(S52) VDVQYLYGVGSDMVGWALKWEFVILVFLLLADARVCVALWLMLMVSQAEA
      YP_001469631 VDVQYLYGVGSGMVGWALKWEFVILVFLLLADARVCVALWLMLMISQTEA
      CAA54244     VDVQYLYGVGSGMVGWALKWEFVILIFLLLADARVCVALWLMLMISQAEA
3A    AAC03058     VDVQYLYGVGSGMVGWALKWEFVILIFLLLADRRVCVALWLMLMITQAEA
      AAY29642     VDVQYLYGVGSGMVGWAVKWEFVILVFLLLADARVCVALWLMLMISQAEA
      ABD85062     VDVQYLYGVGSGMVGWALKWEFVILVFLLLADARVCVALWLMLMISQAEA
      ABD85063     VDVQYLYGVGSGMVGWALKWEFVILVFLLLADARVCVALWLMLMISQAEA
      ABD97104     VDVQYLYGIGSGVVGWALKWEFVILVFLLLADARVCVALWLMLMISQAEA
      BAA06044     VDVQYLYGIGSGMVGWALKWEFVILIFLLLADARVCVALWLILTISQAEA

3B    BAA08372     VDVQYLYGVGSAVVGWALKWEFVVLVFLLLADARVCVALWMMLLISQAEA

3K    BAA09890     VDVQYLYGISSGLVGWAIKWEFVILIFLLLADARVCVVLWMMMLISQAEA
```

FIG. 3C

FIG. 5A
GenBank 3S7G_A
*Homo sapiens* IgG1 Fc
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044
*Homo sapiens* IgG2 Fc (amino acids 99-325)
227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtknq
241 vsltclvkgf ypsdiavewe sngqpennyk ttppmldsdg sfflyskltv dksrwqqgnv
301 fscsvmheal hnhytqksls lspgk
```

GenBank AAW65947
*Homo sapiens* IgG3 Fc (amino acids 19-246)
238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

FIG. 5B

GenBank AAA52770
*Homo sapiens* IgD Fc (amino acids 162-383)
222 aa

```
  1 ptkapdvfpi isgcrhpkdn spvvlaclit gyhptsvtvt wymgtqsqpq rtfpeiqrrd
 61 syymtssqls tplqqwrqge ykcvvqhtas kskkeifrwp espkaqassv ptaqpqaegs
121 lakattapat trntgrggee kkkekekeeq eeretktpec pshtqplgvy lltpavqdlw
181 lrdkatftcf vvgsdlkdah ltwevagkvp tggveeglle rhsngsqsqh srltlprslw
241 nagtsvtctl nhpslppqrl malrepaaqa pvklslnlla ssdppeaasw llcevsgfsp
301 pnillmwled qrevntsgfa parpppqprs ttfwawsvlr vpappspqpa tytcvvshed
361 srtllnasrs levsyvtdhg pmk
```

GenBank 0308221A
*Homo sapiens* IgM Fc
276 aa

```
  1 vtstltikzs dwlgesmftc rvdhrgltfq qnassmcvpd qdtairvfai ppsfasiflt
 61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

FIG. 5C

GenBank P01876
*Homo sapiens* IgA Fc (amino acids 120-353)
234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprlslh rpaledlllg seanltctlt glrdasgvtf twtpssgksa vqgpperdlc
181 gcysvssvlp gcaepwnhgk tftctaaype sktpltatls ksgntfrpev hllpppseel
241 alnelvtltc largfspkdv lvrwlqgsqe lprekyltwa srqepsqgtt tfavtsilrv
301 aaedwkkgdt fscmvgheal plaftqktid rlagkpthvn vsvvmaevdg tcy
```

GenBank 1F6A_B
*Homo sapiens* IgE Fc (amino acids 6-222)
212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsgffv
181 fsrlevtrae weqkdeficr avheaaspsq tvqravsvnp gk
```

GenBank P01861
*Homo sapiens* IgG4 Fc (amino acids 100-327)
228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk ckvsnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

FIG. 6

Table 1. Conserved Regions based on the conserved CD4 epitopes

| No. | Residues* | Length | Sequence | Genotype Conservancy | # of included Epitopes |
|---|---|---|---|---|---|
| **CD4-R1** | 1251-1265 | 15 | VLVLNPSVAATLGFG | HCV1a, 1b, 2a, 2b, 3, 4, 5, 6, 7 | 2 |
| **CD4-R2** | 1295-1309 | 15 | TYGKFLADGGCSGGA | HCV1a, 1b, 3, 4, 5, 6, 7 | 2 |
| **CD4-R3** | 1387-1401 | 15 | GGRHLIFCHSKKKCD | HCV1a, 1b, 2a, 2b, 3, 4, 5, 6, 7 | 4 |
| **CD4-R4** | 1415-1425 | 11 | VAYYRGLDVSV | HCV1a, 1b, 2b, 3, 4, 7 | 4 |
| **CD4-R5** | 1436-1453 | 18 | ATDALMTGFTGDFDSVID | HCV1a, 1b, 3, 4, 7 | 2 |
| **CD4-R6** | 1563-1577 | 15 | TGLTHIDAHFLSQTK | HCV1a, 1b, 2a, 2b, 3, 7 | 1 |
| **CD4-R7** | 1773-1785 | 13 | QYLAGLSTLPGNP | HCV1a, 1b, 2a, 2b, 3, 4, 5, 6, 7 | 4 |
| **CD4-R8** | 1881-1888 | 8 | NLLPAILS | HCV1a, 1b, 2b, 3, 4, 7 | 1 |
| **CD4-R9** | 1904-1930 | 27 | RHVGPGEGAVQWMNRLIAFASRGNHVS | HCV1a, 1b, 3, 4 | 3 |
| **CD4-R10** | 2201-2215 | 15 | SSASQLSAPSLKATC | HCV1a, 1b, 2b, 3, 4, 5, 6 | 1 |
| **CD4-R11** | 2788-2792 | 5 | SNVSV | HCV1a, 1b, 2a, 2b, 3, 4, 5, 6, 7 | 1 |

* Numbers are based on HCV1a genotype sequence. R = region

FIG. 7

Table 2. Number of located HCV CD8 T cell epitopes and anchor positions for common each HLA-I Alleles in USA

| MHC-I Allele | Total Epitopes (#) | Located Epitopes (#) | Allele-specific Anchor Positions | | | |
|---|---|---|---|---|---|---|
| | | | 2 | | 9 | Others |
| **A*02:01** | 48 | 29 | **M#**, **L**, Q, V, I | | **V**, **L**, **I**, A, M | F (1, 3, 7) |
| **A*24:02** | 33 | 20 | **Y**, **W**, F | | **F**, **I**, **W**, L, M | F, W (7) |
| **A*03:01** | 10 | 6 | **M**,**L**, **I**, **V**, **T**, S, Q, A | | **K**, Y, R | F & Y (3), K & R (1) |
| **A*01:01** | 4 | 3 | **T**, **S**, A, V, M, I, L | | **Y**, F | **D** (3) |
| **B*35:01** | 1 | 1 | **P**, G, A | | **Y**, **M**, **F**, H | M (1), A (8), W (1), F (1), Y (1), P (8) |
| | | | **5** | | **9** | **Others** |
| **B*08:01** | 2 | 1 | **R**, **K**, **H**, F | | **L**, **M**, **I**, **F**, **V**, A, W | K (3), R (3), L (2), F (6), M (1, 2, 3), P (2), S (8) |
| | | | **1** | **2** | **9** | **Others** |
| **B*40:02** | 2 | 2 | **Y**, **K**, **R**, **A**, **H**, **W**, **G**, **F**, Q, L, S, C, I, T, M, V | **E**, D | **I**, **L**, **A**, **V**, **F**, **M**, **T**, W, S, C | F (3), P (8), A (8) |
| **C*03:03** | 2 | 2 | NA## | | NA | NA |
| **A*33:03** | 1 | 0 | - | | - | - |
| **A*02:06** | 1 | 0 | - | | - | - |
| **A*26:01** | 1 | 0 | - | | - | - |
| **A*31:01** | 1 | 0 | - | | - | - |
| **Total** | 106 | 64 | | | | |

Bold Anchor positions describe the optimal amino acid for that location. ## Not Available

FIG. 8

Table 3. Conserved Regions based on the conserved CD8 Epitopes

| No. | Residues* | Length | Sequence | Conserved HCV1a, 1b, & 3 | Conserved 9** Genotypes | # of epitopes |
|---|---|---|---|---|---|---|
| CD8-R1 | 1292-1300 | 9 | TYSTYGKFL | Yes | Yes | 2 |
| CD8-R2 | 1391-1399 | 9 | LIFCHSKKK | Yes | Yes | 2 |
| CD8-R3 | 1436-1451 | 16 | ATDALMTGFTGDFDSV | Yes | No | 2 |
| CD8-R4 | 1666-1675 | 10 | VLAALAAYCL | Yes | No | 1 |
| CD8-R5 | 1851-1859 | 9 | ILAGYGAGV | Yes | No | 1 |
| CD8-R6 | 1373-1380 | 8 | IPFYGKAI | Yes | No | 1 |
| CD8-R7 | 1596-1604 | 9 | RAQAPPPSW | Yes | No | 1 |
| CD8-R8 | 1910-1945 | 36 | EGAVQWMNRLIAFASRGN HVSPTHYVPESDAAARVT | Yes | No | 3 |
| CD8-R9 | 2290-2298 | 9 | RPDYNPPLL | Yes | No | 1 |
| CD8-R10 | 2557-2565 | 9 | TIMAKNEVF | Yes | Yes | 1 |

* Numbers are based on HCV1a genotype sequence.

** Nine genotypes include HCV1a, 1b, 2a, 2b, 3, 4, 5, 6, and 7

FIG. 9A. CD4 and CD8 epitopes for Core, P7, and NS2 regions

| Name | Type of epitope | Start* | End* |
|---|---|---|---|
| **Core-1** | CD4 | 1 | 20 |
| **Core-2** | CD4 | 11 | 30 |
| **Core-3** | CD4 | 21 | 40 |
| **Core-4** | CD4 | 39 | 63 |
| **Core-5** | CD4 | 47 | 70 |
| **Core-6** | CD4 | 61 | 80 |
| **Core-7** | CD4 | 71 | 90 |
| **Core-8** | CD4 | 81 | 100 |
| **Core-9** | CD4 | 91 | 110 |
| **Core-10** | CD4 | 101 | 115 |
| **Core-11** | CD4 | 111 | 130 |
| **Core-12** | CD4 | 125 | 139 |
| **Core-13** | CD4 | 131 | 150 |
| **Core-14** | CD4 | 151 | 170 |
| **Core-15** | CD4 | 161 | 180 |
| **Core-16** | CD8 | 35 | 44 |
| **Core-17** | CD8 | 43 | 51 |
| **Core-18** | CD8 | 51 | 59 |
| **Core-19** | CD8 | 129 | 137 |
| **Core-20** | CD8 | 131 | 140 |
| **Core-21** | CD8 | 150 | 158 |
| **Core-22** | CD8 | 154 | 162 |
| **Core-23** | CD8 | 168 | 176 |
| **Core-24** | CD8 | 177 | 187 |
| **Core-25** | CD8 | 178 | 187 |
| **P7-1** | CD8 | 803 | 811 |
| **NS2-1** | CD4 | 955 | 974 |
| **NS2-2** | CD4 | 975 | 994 |
| **NS2-3** | CD4 | 985 | 1,004 |
| **NS2-4** | CD4 | 1,015 | 1,034 |
| **NS2-5** | CD4 | 1,035 | 1,054 |
| **NS2-6** | CD8 | 924 | 933 |
| **NS2-7** | CD8 | 961 | 970 |
| **NS2-8** | CD8 | 989 | 997 |

* Start and End numbers are based on sequence designated "Consensus" in Fig. 12A-12L.

FIG. 9B. CD4 and CD8 epitopes that are conserved among genotypes 1a, 1b, 2a, 2b, and 3

| Name | Type of epitope | Start* | End* |
|---|---|---|---|
| **NS3-1** | CD4 | 1,265 | 1,279 |
| **NS3-2** | CD4 | 1,309 | 1,323 |
| **NS3-3** | CD4 | 1,401 | 1,415 |
| **NS3-4** | CD4 | 1,402 | 1,412 |
| **NS3-5** | CD4 | 1,429 | 1,439 |
| **NS3-6** | CD4 | 1,450 | 1,464 |
| **NS3-7** | CD4 | 1,453 | 1,467 |
| **NS3-8** | CD4 | 1,577 | 1,591 |
| **NS3-9** | CD8 | 1,306 | 1,314 |
| **NS3-10** | CD8 | 1,387 | 1,394 |
| **NS3-11** | CD8 | 1,405 | 1,413 |
| **NS3-12** | CD8 | 1,450 | 1,458 |
| **NS3-13** | CD8 | 1,457 | 1,465 |
| **NS3-14** | CD8 | 1,610 | 1,618 |
| **NS4a-1** | CD8 | 1,683 | 1,692 |
| **NS4b-1** | CD4 | 1,790 | 1,801 |
| **NS4b-2** | CD4 | 1,792 | 1,802 |
| **NS4b-3** | CD4 | 1,898 | 1,905 |
| **NS4b-4** | CD4 | 1,921 | 1,935 |
| **NS4b-5** | CD4 | 1,922 | 1,941 |
| **NS4b-6** | CD4 | 1,928 | 1,947 |
| **NS4b-7** | CD8 | 1,868 | 1,876 |
| **NS4b-8** | CD8 | 1,927 | 1,942 |
| **NS4b-9** | CD8 | 1,932 | 1,940 |
| **NS4b-10** | CD8 | 1,948 | 1,962 |
| **NS5a-1** | CD4 | 2,218 | 2,232 |
| **NS5a-2** | CD8 | 2,309 | 2,317 |
| **NS5b-1** | CD4 | 2,847 | 2,851 |
| **NS5b-2** | CD8 | 2,602 | 2,610 |

* Start and End numbers are based on sequence designated "Consensus" in Fig. 12A-12L.

FIG. 10A

| Name | Sequence* | Start** | End** | Contained Epitopes |
|---|---|---|---|---|
| **TP29** | AIPLEVIKGGRHLIFCHSKKKCDELAAKL | 1,393 | 1,421 | NS3-3, NS3-4, NS3-11 |
| **TP50** | LGALTGTYVYNHLTPLRDWAHNGLRDLAVAVEPVVFSQMETKLITWGADT | 955 | 1,004 | NS2-1, NS2-2, NS2-3, NS2-7, NS2-8 |
| **TP52** | AIPLEVIKGGRHLIFCHSKKKCDELAAKLVALGINAVAYYRGLDVSVIPTSG | 1,393 | 1,444 | NS3-3, NS3-4, NS3-5, NS3-11 |
| **TP70** | KGGRHLIFCHSKKKCDELAAKLVALGINAVAYYRGLDVSVIPTSGDVVVVATDALMTGFTGDFDSVIDCN | 1,400 | 1,469 | NS3-3, NS3-4, NS3-5, NS3-6, NS3-7, NS3-11, NS3-12, NS3-13 |
| **TP100** | VALSTTGEIPFYGKAIPLEVIKGGRHLIFCHSKKKCDELAAKLVALGINAVAYYRGLDVSVIPTSGDVVVVATDALMTGFTGDFDSVIDCNTCVTQTVDF | 1,379 | 1,478 | NS3-3, NS3-4, NS3-5, NS3-6, NS3-7, NS3-10, NS3-11, NS3-12, NS3-13 |
| **TP171** | MSTNPKPQRKTKRNTNRRPQDVKFPGGGQIVGGVYLLPRRGPRLGVRATRKTSERSQPRGRRQPIPKARRPEGRTWAQPGYPWPLYGNEGCGWAGWLLSPRGSRPSWGPTDPRRRSRNLGKVIDTLTCGFADLMGYIPLVGAPLGGAARALAHGVRVLEDGVNYATGNLPG | 1 | 171 | Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, Core-22 |
| **TP228** | LHAPTGSGKSTKVPAAYAAQGYKVLVLNPSVAATLGFGAYMSKAHGIDPNIRTGVRTITTGSPITYSTYGKFLADGGCSGGAYDIIICDECHSTDATSILGIGTVLDQAETAGARLVVLATATPPGSVTVPHPNIEEVALSTTGEIPFYGKAIPLEVIKGGRHLIFCHSKKKCDELAAKLVALGINAVAYYRGLDVSVIPTSGDVVVVATDALMTGFTGDFDSVIDCN | 1,242 | 1,469 | NS3-1, NS3-2, NS3-3, NS3-4, NS3-5, NS3-6, NS3-7, NS3-9, NS3-10, NS3-11, NS3-12, NS3-13 |
| **TP553** | QASLLKVPYFVRVQGLLRICALARKMAGGHYVQMAIIKLGALTGTYVYNALTPLRDWAHNGLRDLAVAVEPVVFSQMETKLITWGADTAACGDIINGLPVSARRGREILLGPADGMVSKGWRLLAPITAYAQQTRGLLGCIITSLTGRDKNQVEGEVQIVSTAAQTFLATCINGVCWTVYHGAGTRTIASPKGPVIQMYTNVDQDLVGWPAPQGARSLTPCTCGSSDLYLVTRHADVIPVRRRGDSRGSLLSPRPISYLKGSAGGPLLCPAGHAVGIFRAAVCTRGVAKAVDFIPVENLETTMRSPVFTDNSSPPAVPQSFQVAHLHAPTGSGKSTKVPAAYAAQGYKVLVLNPSVAATLGFGAYMSKAHGIDPNIRTGVRTITTGSPITYSTYGKFLADGGCSGGAYDIIICDECHSTDATSILGIGTVLDQAETAGARLVVLATATPPGSVTVPHPNIEEVALSTTGEIPFYGK | 917 | 1,469 | NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, NS3-13 |

FIG. 10B

| | | | | |
|---|---|---|---|---|
| | AIPLEVIKGGRHLIFCHSKKKCDELAAKLV ALGINAVAYYRGLDVSVIPTSGDVVVVAT DALMTGFTGDFDSVIDCN | | | |
| **TP778** | LHAPTGSGKSTKVPAAYAAQGYKVLVLNP SVAATLGFGAYMSKAHGIDPNIRTGVRTIT TGSPITYSTYGKFLADGGCSGGAYDIIICDE CHSTDATSILGIGTVLDQAETAGARLVVLA TATPPGSVTVPHPNIEEVALSTTGEIPFYGK AIPLEVIKGGRHLIFCHSKKKCDELAAKLV ALGINAVAYYRGLDVSVIPTSGDVVVVAT DALMTGFTGDFDSVIDCNTCVTQTVDFSL DPTFTIETTTLPQDAVSRTQRRGRTGRGKP GIYRFVAPGERPSGMFDSSVLCECYDAGCA WYELTPAETTVRLRAYMNTPGLPVCQDHL EFWEGVFTGLTHIDAHFLSQTKQSGENLPY LVAYQATVCARAQAPPPSWDQMWKCLIR LKPTLHGPTPLLYRLGAVQNEVTLTHPITK YIMTCMSADLEVVTSTWVLVGGVLAALA AYCLSTGCVVIVGRIVLSGKPAIIPDREVLY REFDEMEECSQHLPYIEQGMMLAEQFKQK ALGLLQTASRQAEVIAPAVQTNWQKLEAF WAKHMWNFISGIQYLAGLSTLPGNPAIASL MAFTAAVTSPLTTSQTLLFNILGGWVAAQ LAAPGAATAFVGAGLAGAAIGSVGLGKVL VDILAGYGAGVAGALVAFKIMSGEVPSTE DLVNLLPAILSPGALVVGVVCAAILRRHVG PGEGAVQWMNRLIAFASRGNHVSPTHYVP ESDAAARVTAILSSLTVTQLLRRLHQWISS ECTTPCSGSWLRDIWDWICEVLSDFKTWL KAKLMPQLPG | 1,242 | 2,022 | NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10 |

FIG. 10C

| | | | | |
|---|---|---|---|---|
| **TP1985** | APITAYAQQTRGLLGCIITSLTGRDKNQVEGEVQIVSTAAQTFLATCINGVCWTVYHGAGTRTIASPKGPVIQMYTNVDQDLVGWPAPQGARSLTPCTCGSSDLYLVTRHADVIPVRRRGDSRGSLLSPRPISYLKGSAGGPLLCPAGHAVGIFRAAVCTRGVAKAVDFIPVENLETTMRSPVFTDNSSPPAVPQSFQVAHLHAPTGSGKSTKVPAAYAAQGYKVLVLNPSVAATLGFGAYMSKAHGIDPNIRTGVRTITTGSPITYSTYGKFLADGGCSGGAYDIIICDECHSTDATSILGIGTVLDQAETAGARLVVLATATPPGSVTVPHPNIEEVALSTTGEIPFYGKAIPLEVIKGGRHLIFCHSKKKCDELAAKLVALGINAVAYYRGLDVSVIPTSGDVVVVATDALMTGFTGDFDSVIDCNTCVTQTVDFSLDPTFTIETTTLPQDAVSRTQRRGRTGRGKPGIYRFVAPGERPSGMFDSSVLCECYDAGCAWYELTPAETTVRLRAYMNTPGLPVCQDHLEFWEGVFTGLTHIDAHFLSQTKQSGENLPYLVAYQATVCARAQAPPPSWDQMWKCLIRLKPTLHGPTPLLYRLGAVQNEVTLTHPITKYIMTCMSADLEVVTSTWVLVGGVLAALAAYCLSTGCVVIVGRIVLSGKPAIIPDREVLYREFDEMEECSQHLPYIEQGMMLAEQFKQKALGLLQTASRQAEVIAPAVQTNWQKLEAFWAKHMWNFISGIQYLAGLSTLPGNPAIASLMAFTAAVTSPLTTSQTLLFNILGGWVAAQLAAPGAATAFVGAGLAGAAIGSVGLGKVLVDILAGYGAGVAGALVAFKIMSGEVPSTEDLVNLLPAILSPGALVVGVVCAAILRRHVGPGEGAVQWMNRLIAFASRGNHVSPTHYVPESDAAARVTAILSSLTVTQLLRRLHQWISSECTTPCSGSWLRDIWDWICEVLSDFKTWLKAKLMPQLPGIPFVSCQRGYRGVWRGDGIMHTRCHCGAEITGHVKNGTMRIVGPRTCRNMWSGTFPINAYTTGPCTPLPAPNYTFALWRVSAEEYVEIRQVGDFHYVTGMTTDNLKCPCQVPSPEFFTELDGVRLHRFAPPCKPLLREEVSFRVGLHEYPVGSQLPCEPEPDVAVLTSMLTDPSHITAEAAGRRLARGSPPSVASSSASQLSAPSLKATCTANHDSPDAELIEANLLWRQEMGGNITRVESENKVVILDSFDPLVAEEDEREISVPAEILRKSRRFAPALPIWARPDYNPPLLETWKKPDYEPPVVHGCPLPPPQSPPVPPPRKKRTVVLTESTVSTALAELATKSFGSSSTSGITGDNTTTSSEPAPSGCPPDSDAESYSSMPPLEGE | 1041 | 3073 | NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, NS5b-2 |

FIG. 10D

| | | | | |
|---|---|---|---|---|
| | PGDPDLSDGSWSTVSSEADTEDVVCCSMS<br>YSWTGALVTPCAAEEQKLPINALSNSLLRH<br>HNLVYSTTSRSACQRQKKVTFDRLQVLDS<br>HYQDVLKEVKAAASKVKANLLSVEEACSL<br>TPPHSAKSKFGYGAKDVRCHARKAVNHIN<br>SVWKDLLEDSVTPIDTTIMAKNEVFCVQPE<br>KGGRKPARLIVFPDLGVRVCEKMALYDVV<br>SKLPLAVMGSSYGFQYSPGQRVEFLVQAW<br>KSKKTPMGFSYDTRCFDSTVTESDIRTEEAI<br>YQCCDLDPQARVAIKSLTERLYVGGPLTNS<br>RGENCGYRRCRASGVLTTSCGNTLTCYIK<br>ARAACRAAGLQDCTMLVCGNNLVVICESA<br>GVQEDAASLRAFTEAMTRYSAPPGDPPQP<br>EYDLELITSCSSNVSVAHDGAGKRVYYLTR<br>DPTTPLARAAWETARHTPVNSWLGNIIMF<br>APTLWARMILMTHFFSVLIARDQLEQALD<br>CEIYGACYSIEPLDLPPIIQRLHGLSAFSLHS<br>YSPGEINRVAACLRKLGVPPLRAWRHRAR<br>SVRARLLSRGGRAAICGKYLFNWAVRTKL<br>KLTPIAAAGQLDLSGWFTAGYSGGDIYHS<br>VSHARPRWFWFCLLLLAAGVGIYLLPNR | | | |

* TP sequences are based on HCV1a consensus sequence and gaps were removed

** Start and End numbers are based on sequence designated "Consensus" in Fig. 16A-16L.

230 240 250 260 270 280 290
E1
HCV1a consensus TPGCVPCVR-EGNASRCWVAVTPTVATRDGKLPTTQLRRHIDLLVGSATLCSALYVGDLCGSVFLVGQLFTFSP 300 310 320 330 340 350 360 370
E1
HCV1a consensus RRHWTTQDCNCSIYPGHITGHRMAWDMMMNWSPTTALVVAQLLRIPQAILDMIAGAHWGVLAGIAYFSMVGNWA 380 390 400 410 420 430 440
E1 E2
HCV1a consensus KVLVVLLLFAGVDAETHVTGGSAARTTSGLASLFTPGAKQNIQLINTNGSWHINRTALNCNDSLNTGWLAGLFY

HCV1a consensus YHKFNSSGCPERLASCRPLTDFDQGWGPISYANG-SGP-DQRPYCWHYPPKPCGIVPAKSVCGPVYCFTP--SP 520 530 540 550 560 570 580 590

E2

HCV1a consensus VVVGTTDRSGAPTYNWGENDTDVFVLNNTRPPLGNWFGCTWMNST-GFTKVCGAPPCVI-GGVGN-----NTLH 600 610 620 630 640 650 660

E2

HCV1a consensus CPTDCFRKHPEATYSRCGSGPWITPRCLVDYPYRLWHYPCTINYTIFKVRMYVGGVEHRLEAACNWTRGERCDL

FIG. 11C

HCV1a consensus  VNSWLGNIIMFAPTLWARMILMTHFFSVLIARDQLEQALDCEIYGACYSIEPLDLPPIIQRLHGLSAFSLHSYS
                 2,890   2,900   2,910   2,920   2,930   2,940   2,950   2,960
                                          NS5b HCV1a consensus  PGEINRVAACLRKLGVPPLRAWRHRARSVRARLLSRGGRAAICGKYLFNWAVRTKLKLTPIAAAGQLDLSGWFT
                 2,970   2,980   2,990   3,000   3,010   3,020   3,030
                                          NS5b HCV1a consensus  AGYSGGDIYHSVSHARPRWFWFCLLLLAAGVGIYLLPNRX
                 3,040   3,050   3,060   3,070 3,074
                                 NS5b

```
                    1        10        20        30        40        50        60        70        80
Consensus           MSTNPKPQRKTKRNTNRRPQDVKFPGGGQIVGGVYLLPRRGPRLGVRATRKTSERSQPRGRRQPIPKARRSEGRSWAQPGYPWPLY
                    Core

1. HCV1a consensus  MSTNPKPQRKTKRNTNRRPQDVKFPGGGQIVGGVYLLPRRGPRLGVRATRKTSERSQPRGRRQPIPKARRPEGRTWAQPGYPWPLY
2. HCV1b consensus  MSTNPKPQRKTKRNTNRRPQDVKFPGGGQIVGGVYLLPRRGPRLGVRATRKTSERSQPRGRRQPIPKARRPEGRAWAQPGYPWPLY
3. HCV2a Consensus  MSTNPKPQRKTKRNTNRRPQDVKFPGGGQIVGGVYLLPRRGPRLGVRATRKTSERSQPRGRRQPIPKDRRSTGKSWGKPGYPWPLY
4. HCV2b Consensus  MSTNPKPQRKTKRNTNRRPQDVKFPGGGQIVGGVYLLPRRGPRLGVRATRKTSERSQPRGRRQPIPKDRRSTGKSWGKPGYPWPLY
5. HCV 3 Consensus  MSTLPKPQRKTKRNTIRRPQDVKFPGGGQIVGGVYVLPRRGPRLGVRATRKTSERSQPRGRRQPIPKARRSEGRSWAQPGYPWPLY
6. HCV 4 Consensus  MSTNPKPQRKTKRNTNRRPMDVKFPGGGQIVGGVYLLPRRGPRLGVRATRKTSERSQPRGRRQPIPKARRSEGRSWAQPGYPWPLY
7. HCV5 consensus   MSTNPKPQRKTKRNTNRRPQDVKFPGGGQIVGGVYLLPRRGPRLGVRATRKTSERSQPRGRRQPIPKARRPTGRSWGQPGYPWPLY
8. HCV6 consensus   MSTLPKPQRKTKRNTNRRPMDVKFPGGGQIVGGVYLLPRRGPRLGVRATRKTSERSQPRGRRQPIPKARQPTGRHWAQPGYPWPLY
9. HCV7: ABN05226  MSTNPKPQRLTKRNTVRRPQNVKFPGGGQIVGGVYLLPRRGPRLGVRGTRKSSERSQPRGRRQRIPKAASSQGKAWGKPGYPWPLY
14. AVI1a-129       MSTNPKPQRKTKRNTNRRPQDVKFPGGGQIVGGVYLLPRRGPRLGVRATRKTSERSQPRGRRQPIPKARRPEGRTWAQPGYPWPLY
15. AVI3a-177       MSTLPKPQRKTKRNTIRRPQDVKFPGGGQIVGGVYVLPRRGPRLGVRATRKTSERSQPRERRQPIPKARRSDGRSWAQPGYPWPLY

                      90       100       110       120       130       140       150       160       170
Consensus           GNEGCGWAGWLLSPRGSRPSWGPTDPRRRSRNLGKVIDTLTCGFADLMGYIPLVGAPLGGVARALAHGVRVLEDGINYATGNLPGC
                    Core

1. HCV1a consensus  GNEGCGWAGWLLSPRGSRPSWGPTDPRRRSRNLGKVIDTLTCGFADLMGYIPLVGAPLGGAARALAHGVRVLEDGVNYATGNLPGC
2. HCV1b consensus  GNEGMGWAGWLLSPRGSRPSWGPTDPRRRSRNLGKVIDTLTCGFADLMGYIPLVGAPLGGAARALAHGVRVLEDGVNYATGNLPGC
3. HCV2a Consensus  GNEGLGWAGWLLSPRGSRPSWGPTDPRHRSRNVGKVIDTLTCGFADLMGYIPVVGAPLGGVARALAHGVRVLEDGVNYATGNLPGC
4. HCV2b Consensus  GNEGCGWAGWLLSPRGSRPTWGPTDPRHRSRNLGKVIDTITCGFADLMGYIPVVGAPVGGVARALAHGVRVLEDGINYATGNLPGC
5. HCV 3 Consensus  GNEGCGWAGWLLSPRGSRPSWGPNDPRRRSRNLGKVIDTLTCGFADLMGYIPLVGAPVGGVARALAHGVRALEDGINFATGNLPGC
6. HCV 4 Consensus  GNEGCGWAGWLLSPRGSRPSWGPNDPRRRSRNLGKVIDTLTCGFADLMGYIPLVGAPVGGVARALAHGVRAVEDGINYATGNLPGC
7. HCV5 consensus   ANEGLGWAGWLLSPRGSRPNWGPNDPRRKSRNLGKVIDTLTCGFADLMGYIPLVGGPVGGVARALAHGVRVLEDGINYATGNLPGC
8. HCV6 consensus   GNEGCGWAGWLLSPRGSRPHWGPNDPRRRSRNLGKVIDTLTCGFADLMGYIPVVGAPLGGVAAALAHGVRAIEDGINYATGNLPGC
9. HCV7: ABN05226  GNEGCGWAGWLLSPRGSRPTWGPTDPRHRSRNLGKVIDTMTCGFADLMGYIPVLGAPLGGVARALAHGVRVLEDGVNYATGNLPGC
14. AVI1a-129       GNEGCGWAGWLLSPRGSRPSWGPTDPRRRSRNLGKVIDTLTCGFADLMGYIPLVGAPLGGAARALAHGVRVLEDGVNYATGNLPGC
15. AVI3a-177       GNEGCGWAGWLLSPRGSRPSWGPNDPRRRSRNLGKVIDTLTCGFADLMGYIPIVGAPVGGVARALAHGVRALEDGINFATGNLPGC

                        180       190       200       210       220       230       240       250
Consensus           SFSIFLLALLSCLTVPASAYEVRNXSGLYHVTNDCPNSSIVYEADDAILHTPGCVPCVR-EGNTSRCWVXVTPTVAVRYXGAPTTS
                    Core                E1

1. HCV1a consensus  SFSIFLLALLSCLTVPASAYQVRNSTGLYHVTNDCPNSSIVYEAADAILHTPGCVPCVR-EGNASRCWVAVTPTVATRDGKLPTTQ
2. HCV1b consensus  SFSIFLLALLSCLTIPASAYEVRNVSGVYHVTNDCSNSSIVYEAADMIMHTPGCVPCVR-ENNSSRCWVALTPTLAARNASVPTTT
3. HCV2a Consensus  SFSIFLLALLSCITVPVSAAQVKNTSSSYMVTNDCSNDSITWQLQAAVLHVPGCVPCEKVGNNTSRCWIPVSPNVAVXQPGALTQG
4. HCV2b Consensus  SFSIFLLALLSCVTVPVSAVEVRNISSSYYATNDCSNNSITWQLTNAVLHLPGCVPCEN-DNGTLRCWIQVTPNVAVKHRGALTHN
5. HCV 3 Consensus  SFSIFLLALFSCLIHPAASLEWRNTSGLYVLTNDCSNSSIVYEADDVILHTPGCIPCVQTDGNTSTCWTPVTPTVAVKYVGATTAS
6. HCV 4 Consensus  SFSIFLLALLSCLTVPASAINYRNTSGIYHVTNDCPNSSIVYEADHHILHLPGCVPCVR-XGNQSRCWVALTPTVAAPYIGAPLES
7. HCV5 consensus   SFSIFXLALLSCLTVPXSAVPYRNASGVYHVTNDCPNSSIVYEAENLILHAPGCVPCVR-XGNVSRCWVQITPTLSAPSXGAVTAX
8. HCV6 consensus   SFSIFLLALLSCLTTPASAVHYXNSSGIYHLTNDCPNSSIVYEADAMILHLPGCVPCVR-VGNQSXCWVPVSPTLAVPNASTPATG
9. HCV7: ABN05226  SFSIFLLALLSCLTVPASAYEVRNSSGVYHLTNDCPNASIVYETDNAILHEPGCVPCVR-EGNTSRCWEPVAPTLAVRYRGALTDD
14. AVI1a-129       SFSIFLLALLSCLTVPASAYQVRNSTGLYHVTNDCPNSSIVYEAADAILHTPGCVPCVR-EGNTSRCWVAMTPTVATRDGKLPTTQ
15. AVI3a-177       SFSIFLLALLSCLIHPAASLEWRNTSGLYILTNDCPNSSIVYEADDVILHTPGCIPCVQ-DGNTSTCWTSVSPTVAVRYVGATTAS
```

FIG. 12A

```
                     260       270       280       290       300       310       320       330       340
Consensus            LRRHVDLLVGAATLCSALYVGDLCGAVFLVGQXFTFSPRRHWTVQDCNCSIYPGHITGHRMAWDMMMNWSPTTXLVXAQLLRIPQX
                                                           E1

1. HCV1a consensus   LRRHIDLLVGSATLCSALYVGDLCGSVFLVGQLFTFSPRRHWTTQDCNCSIYPGHITGHRMAWDMMMNWSPTTALVVAQLLRIPQA
2. HCV1b consensus   IRRHVDLLVGAAAFCSAMYVGDLCGSVFLVSQLFTFSPRRHETVQDCNCSIYPGHVSGHRMAWDMMMNWSPTTALVVSQLLRIPQA
3. HCV2a Consensus   LRTHIDMVVMSATLCSALYVGDLCGGVMLAAQMFIVSPQHHWFVQECNCSIYPGTITGHRMAWDMMMNWSPTATMILAYAMRVPEV
4. HCV2b Consensus   LRTHVDMIVMAATVCSALYVGDVCGAVMIVSQALIVSPERHNFTQECNCSIYQGHITGHRMAWDMMLNWSPTLTMILAYAARVPEL
5. HCV 3 Consensus   IRSHVDLLVGAATMCSALYVGDMCGAVFLVGQAFTFRPRRHQTVQTCNCSLYPGHLSGHRMAWDMMMNWSPAVGMVVAHVLRLPQT
6. HCV 4 Consensus   LRSHVDLMVGAATVCSALYIGDLCGGLFLVGQMFSFRPRRHWTTQDCNCSIYTGHITGHRMAWDMMMNWSPTTTLVLAQVMRIPST
7. HCV5 consensus    LRRAVDYLAGGAALCSALYVGDACGAVXLVGQMFTYSPRXHTXVQDCNCSIYSGHITGHRMAWDMMMNWSPTTALXMAQLLRIPQV
8. HCV6 consensus    FRRHVDLLVGAAAFCSALYIGDLCGGVFLVGQLFTFRPRRHQTVQDCNCSIYTGHVTGHRMAWDMMMNWSPTATLVLSSILRVPQL
9. HCV7: ABN05226   LRTHIDLVVASATLCSALYVGDICGAIFIASQAVLWKPGGGRIVQDCNCSIYPGHVTGHRMAWDMMQNWAPALSMVAAYAVRVPGV
14. AVI1a-129        LRRHIDLLVGSATLCSALYVGDLCGSVFLVGQMFTFSPRRHWTTQDCNCSLYPGHITGHRMAWDMMMNWSPTAALITAQLLRIPQA
15. AVI3a-177        IRSHVDLLVGAATLCSALYVGDMCGAVFLVGQAFTFRPRRHQTVQTCNCSLYPGHLTGHRMAWDMMMNWSPAVGMVVAHVLRMPQT

                         350       360       370       380       390       400       410       420       430
Consensus            XLDIIAGAHWGVLAGLAYFSMQGNWAKVJXVLLLFAGVDAETHTTGGXAARTTSGLTSLFSPGPXQNLQLINTNGSWHINRTALNC
                                E1                                        E2

1. HCV1a consensus   ILDMIAGAHWGVLAGIAYFSMVGNWAKVLVVLLLFAGVDAETHVTGGSAARTTSGLASLFTPGAKQNIQLINTNGSWHINRTALNC
2. HCV1b consensus   VVDMVAGAHWGVLAGLAYYSMVGNWAKVLIVMLLFAGVDG-THVTGGAAARTTSGFTSLFSPGPSQKIQLINTNGSWHINRTALNC
3. HCV2a Consensus   IIDIISGAHWGVMFGLAYFSMQGAWAKVVVILLLAAGVDAGTHTVGGSAAHTTSGLAGLFSXGXXQNIQLINTNGSWHINRTALNC
4. HCV2b Consensus   VLEVVFGGHWGVVFGLAYFSMQGAWAKVIAILLLVAGVDATTYSSGAQAGRTTSGFAGLFSPGPKQNIQLINTNGSWHINRTALNC
5. HCV 3 Consensus   LFDIIAGAHWGILAGLAYYSMQGNWAKVAIIMVMFSGVDAXTHTTGGSAARGARGLTSLFSVGPXQNLQLVNTNGSWHINRTALNC
6. HCV 4 Consensus   LVDLLAGGHWGVLVGVAYFSMQANWAKVILVLFLFAGVDAETHVSGGAAGRTTXGLTSLFSPGXQQNLQLINSNGSWHINRTALNC
7. HCV5 consensus    VIDIIAGAHWGVLFAAAYFASXANWAKVILVLFLFAGVDAXTXTVGGXAGQGXXXLTSFFXPGPQQNLQLINTNGSWHINRTALNC
8. HCV6 consensus    LLDIFLGGHWGVLGAVLYYSMVANWAKVLAVLLLFAGVDATT-TTGXAAGRTTSGLTXLFXPGAKQNLQLINTNGSWHINRTALNC
9. HCV7: ABN05226   IITTVAGGHWGVLFGLAYFGMAGNWAKVILIMLLMSGVDAETMAVGARAAHTTGALVSLLNPGPSQRLQLINTNGSWHINRTALNC
14. AVI1a-129        ILDMIAGAHWGVLAGIAYFSMVGNWAKVLVVLLLFAGVDAQTHVTGGRAAHITAGLTSLFSPGPSQKLQLVNTNGSWHINSTALNC
15. AVI3a-177        VFDIIAGAHWGILAGLAYYSMQGNWAKVAIIMVMFSGVDAETHTTGGTAARNAFTLTGLFTQGARQKLQLINTNGSWHINRTALNC

                             440       450       460       470       480       490       500       510
Consensus            NDSLXTGFIAGLFYTHKFNSSGCPERLASCRPLTDFDQGWGPLTYANXISGPSDDRPYCWHYPPRPCGIVPARSVCGPVYCFTP--
                                                           E2

1. HCV1a consensus   NDSLNTGWLAGLFYYHKFNSSGCPERLASCRPLTDFDQGWGPISYANG-SGP-DQRPYCWHYPPKPCGIVPAKSVCGPVYCFTP--
2. HCV1b consensus   NDSLQTGFLAALFYTHKFNSSGCPERMASCRPIDKFAQGWGPITYA---EPSSDQRPYCWHYAPRPCGIVPASQVCGPVYCFTP--
3. HCV2a Consensus   NDSLNTGFLASLFYTHRFNSSGCPERLSACRNIEAFRIGWGTLQYEDNVTNPEDMRPYCWHYPPKQCGIVPARSVCGPVYCFTP--
4. HCV2b Consensus   NDSLQTGFIASLFYTNNFNSSGCPERLSSCRGLDDFRIGWGTLEYETNVTNDEDMRPYCWHYPPKPCGIVSARTVCGPVYCFTP--
5. HCV 3 Consensus   NDSINTGFIAGLFYYHKFNSTGCPQRLSSCKPITFFRQGWGPLTDANNITGPSDDKPYCWHYAPRPCDVVPASSVCGPVYCFTPHH
6. HCV 4 Consensus   NDSLNTGFLASLFYTHKFNSSGCPERLASCKSLDSFDQGWGPLGVANNISGPSDDRPYCWHYPPRPCGIVPASSVCGPVYCFTP--
7. HCV5 consensus    NDSLQTGFIAGLXYXHKFNSSGCPQRMASCRPLAAFDQGWGTISYAX-VSGPSDDKPYCWHYPPRPCGVVPARXVCGPVYCFTP--
8. HCV6 consensus    NDSLQTGFIAGLFYTHKFNSSGCPERMSSCKPLTDFDQGWGPITYAN-ISGPSEDRPYCWHYAPRPCDVVPARTVCGPVYCFTP--
9. HCV7: ABN05226   NDSLQTGFIAALFYTHRFNSSGCPERMASCKPLSDFDQGWGPLWY-NSTERPSDQRPYCWHYAPSPCGIVPAKDVCGPVYCFTP--
14. AVI1a-129        NDSLKTGWIAGLLYSYKFNSSGCPERLASCRRLTDFAQGWGPISHANG-SGP-DERPYCWHYPPRPCGIVPAKSVCGPVYCFTP--
15. AVI3a-177        NESLNTGFIAGLFYLHKFNSTGCPERLSSCKPITFFRQGWGSLTDAN-ITGPSDDKPYCWHYAPRPCEVVPALNVCGPVYCFTP--
```

FIG. 12B

```
                     520       530       540       550       560       570       580       590       600
Consensus            SPVVVGTTDRXGVPTYTWGENETDVFLLNSTRPPQGNWFGCTWMNST-GFTKTCGAPPCNI-GGGGN-----NDLLCPTDCFRKHP
                     E2

1. HCV1a consensus   SPVVVGTTDRSGAPTYNWGENDTDVFVLNNTRPPLGNWFGCTWMNST-GFTKVCGAPPCVI-GGVGN-----NTLHCPTDCFRKHP
2. HCV1b consensus   SPVVVGTTDRFGVPTYSWGENETDVLLLNNTRPPQGNWFGCTWMNST-GFTKTCGGPPCNI-GGVGN-----NTLTCPTDCFRKHP
3. HCV2a Consensus   SPVVVGTTDRLGVPTYTWGENETDVFLLNSTRPPQGSWFGCTWMNST-GFTKTCGAPPCRI-RADFNAS---TDLLCPTDCFRKHP
4. HCV2b Consensus   SPVVVGTTDRQGVPTYSWGENETDVFLLNSTRPPQGAWFGCTWMNGT-GFTKTCGAPPCRI-RRDYNST---LDLLCPTDCFRKHP
5. HCV 3 Consensus   SPVVVGTTDAKGVPTYTWGENETDVFLLESLRPPSGRWFGCTWMNSTRGFVKTCGAPPCNIYGGGGNPXNNESDLFCPTDCFRKHP
6. HCV 4 Consensus   SPVVVGTTDRLGVPTYTWGENESDVFLLNSTRPPQGAWFGCVWMNST-GFTKACGAPPCEVRTNNGTS----TDWPCPTDCFRKHP
7. HCV5 consensus    SPVVVGTTDRXGXPTYXWGXNETDIFLLNNTRPPXGNWFGCTWMNST-GFVKTCGAPPCNL-GPTGN-----NSLKCPTDCFRKHP
8. HCV6 consensus    SPVVVGTTDRRGLPTYTWGENETDVFLLESLRPPTGGWFGCTWMNST-GFVKTCGAPPCNIXPNSSN-----NSLLCPTDCFRKHP
9. HCV7: ABN05226   SPVVVGTTDRRGVPTYTWGENESDVFLLNSTRPPQGSWFGCSWMNTT-GFTKTCGGPPCKIRPQGAQSN---TSLTCPTDCFRKHP
14. AVI1a-129        SPVVVGTTDKSGAPTYNWGENDWDVFVLNNTRPPLGNWFGCTWMNST-GFTKVCGAPPCVI-GGAGN-----NTLRCPTDCFRKHP
15. AVI3a-177        SPVVVGTTDRQGVPTYTWGENETDVFLLRSLRPPSGQWFGCTWMNST-GFVKTCGAPPCDIYGGGGNRCN-ESDLFCPTDCFRKHP

                           610       620       630       640       650       660       670       680
Consensus            EATYSXCGSGPWLTPRCLVDYPYRLWHYPCTVNFTIFKVRMYVGGVEHRLEAACNWTRGERCDLEDRDRSELSPLLHSTTEWAILP
                     E2

1. HCV1a consensus   EATYSRCGSGPWITPRCLVDYPYRLWHYPCTINYTIFKVRMYVGGVEHRLEAACNWTRGERCDLEDRDRSELSPLLLSTTQWQVLP
2. HCV1b consensus   EATYTKCGSGPWLTPRCLVDYPYRLWHYPCTVNFTIFKVRMYVGGVEHRLNAACNWTRGERCDLEDRDRSELSPLLLSTTEWQILP
3. HCV2a Consensus   EATYIKCGSGPWLTPRCLVDYPYRLWHYPCTVNYTIFKIRMYVGGVEHRLTAACNFTRGDRCNLEDRDRSQLSPLLHSTTEWAILP
4. HCV2b Consensus   DATYLKCGAGPWLTPRCLVDYPYRLWHYPCTVNFTIFKVRMYVGGVEHRLSAACNFTRGDRCRLEDRDRGQQSPLLHSTTEWAVLP
5. HCV 3 Consensus   EATYSRCGAGPWLTPRCMVDYPYRLWHYPCTVNFTLFKVRMFVGGFEHRFTAACNWTRGERCDIEDRDRSEQHPLLHSTTELAILP
6. HCV 4 Consensus   ETTYAKCGSGPWITPRCLIHYPYRLWHYPCTVNFTVFKIRTFIGGIEHRMEAACNWTRGEVCGLEHRDRAELSPLLLSTTTWQXLP
7. HCV5 consensus    DATYTKCGSGPWLTPRCLVHYPYRLWHYPCTVNYTIFKVRMFIGGLEHRLEAACNWTRGERCDLEDRDRAELSPLLHTTTQWAILP
8. HCV6 consensus    EATYARCGSGPWLTPRCLVDYPYRLWHYPCTVNFTIHKVRMFVGGVEHRFDAACNWTRGERCELDDRDRIEMSPLLFSTTELAILP
9. HCV7: ABN05226   RATYSACGSGPWLTPRCMVHYPYRLWHYPCTVNFTIHKVRLYIGGVEHRLDAACNWTRGERCDLEDRDRVDMSPLLHSTTELAILP
14. AVI1a-129        DATYSRCGSGPWITPRCLVDYPYRLWHYPCTVNYSIFKIRMYLGGVEHRLEAACNWTRGERCDLEDRDRSELSPLLLSTTQWQVLP
15. AVI3a-177        EATYSRCGAGPWLTPRCLVDYPYRLWHYPCTVNFTLFKVRMFVGGFEHRFTAACNWTRGERCNIEDRDRSEQHPLLHSTTELAILP

                     690       700       710       720       730       740       750       760       770
Consensus            CSFTTLPALSTGLIHLHQNIVDVQYLYGVGSAVVSWAXKWEYVVLLFLLLADARVCACLWMMLLISQAEAALENLVVLNAASAAGT
                     E2                                                                      P7

1. HCV1a consensus   CSFTTLPALSTGLIHLHQNIVDVQYLYGVGSSIASWAIKWEYVVLLFLLLADARVCSCLWMMLLISQAEAALENLVVLNAASLAGT
2. HCV1b consensus   CSFTTLPALSTGLIHLHQNIVDVQYLYGIGSAVVSFAIKWEYVLLLFLLLADARVCACLWMMLLIAQAEAALENLVVLNAASVAGA
3. HCV2a Consensus   CSYSDLPALSTGLLHLHQNIVDVQYMYGLSPALTKYVVRWEWVVLLFLLLADARVCACLWMLILLGQAEAALEKLVVLHAASAASC
4. HCV2b Consensus   CSFSDLPALSTGLLHLHQNIVDVQYLYGLSPAITRYIVKWEWVVLLFLLLADARVCACLWMLIILGQAEAALEKLIILHSASAASA
5. HCV 3 Consensus   CSFTPMPALSTGLIHLHQNIVDVQYLYGVGSGMVGWALKWEFVILVFLLLADARVCVALWLMLMISQAEAALENLVTLNAVAAAGT
6. HCV 4 Consensus   CSFTTLPALSTGLIHLHQNIVDVQYLYGVGSAVVSWALKWEYVVLAFLLLADARVSACLWMMFMVSQVEAALSNLININAASAAGT
7. HCV5 consensus    CSFTPTPALSTGLIHLHQNIVDTQYLYGLSSSIVSWAVKWEYIVLXFLLLADARICTCLWILLLXCQAEAALENVIVLNAAAAAGX
8. HCV6 consensus    CSFTTMPALSTGLIHLHQNIVDVQYLYGVSSSVVSWAVKWEYVVLAFLVLADARICACLWLMLLIGQAEAALENLIVLNAASAAST
9. HCV7: ABN05226   CSFVPLPALSTGLIHLHQNIVDAQYLYGLSPAIISWAIRWEWVVLVFLLLADARICACLWMMMLMAQAEAALENLIHLNAASLAGT
14. AVI1a-129        CSFTTLPALSTGLIHLHQNIVDVQYLYGVGSSVASWAIKWDYVVLLFLLLADARICSCLWMMLLISQAEAALENLVVLNAASLAGT
15. AVI3a-177        CSFTPMPALSTGLIHLHQNIVDVQYLYGVGSGVVGWALRWEFVVLVFLLLADARVCVALWLMLMISQAEAALENLVTLNAVAAAGT
```

FIG. 12C

```
                       780       790       800       810       820       830       840       850       860
Consensus              HGIXWFLVFFCAAWYLK--GRLVPXATYALXGLWPLLLLLLALPQRAYALDREVAASLGXAVLVXLTIFTLSPHYKHLLSRXLWWL
                       P7                                                                  NS2

1. HCV1a consensus     HGLVSFLVFFCFAWYLK--GRWVPGAAYALYGMWPLLLLLLALPQRAYALDTEVAASCGGVVLVGLMALTLSPYYKRYISWCLWWL
2. HCV1b consensus     HGILSFLVFFCAAWYIK--GRLVPGAAYAFYGVWPLLLLLLALPPRAYAMDREMAASCGGAVFVGLALLTLSPHYKVFLARLIWWL
3. HCV2a Consensus     NGFLYFVIFFVAAWYIK--GRAVPLAAYSLTGLWPFCLLLLALPQQAYAYDASVHGQIGAALLILITLFTLTPGYKTLLSRCLWWL
4. HCV2b Consensus     NGPLWFFIFFTAAWYLK--GRVVPVATYSVLGLWSFLLLVLALPQQAYALDAAEQGELGLVILVIISIFTLTPAYKILLSRSVWWL
5. HCV 3 Consensus     HGIGWYLVAFCAAWHVRRAGKLVPLVTYSLTGLWSLALLVLLLPQRAYAWSGEDSATLGAGILVLFGFFTLSPWYKHWIGRLMWWN
6. HCV 4 Consensus     HGFWYAIFFICIAWHVK--GRLPAAATYAACGMWPLLLLLLMLPERAYAYDREVAGSLGGAVVVALTILTLSPHYKSWLARGLWWI
7. HCV5 consensus      HGFFWGLLVXCXAWHXK--GRLVPGATYLCLGXWPLLLLLLLLPQRALALDSSDGGTVGCLVLXILTIFTLTPGYKKXVVLVXWWL
8. HCV6 consensus      QGWWWGLLFLCCAWYVK--GRLVPACTYALLQLWPLLLLVLALPRRAYAYDNEQAASLGALVLLVITIFTLTPAYKQLLVSFLWWN
9. HCV7: ABN05226      HGIWWLLLVFCASWHLR--GRVVPLVTYGICGMWPFFLMLLSLPPRAYALDREVSAALGTGMLAIILLVTLGPHYKRLLALILWWV
14. AVI1a-129          HGLAPFLVFFCLAWYLK--GKWAPGAVYAVYGMWPLLLLLLALPQRAYALDTEVAASCGGAVLVGLMVLTLSPHYKHYISWCLWWL
15. AVI3a-177          HGIGWYLVAFCAAWHLR--GKLVPLVTYSLTGLWSLAVLVLLLPQRAYAWSGEDSATLGAGILVLFGFFTLSPWYKHWIGRLMWWN

                              870       880       890       900       910       920       930       940
Consensus              QYFITRAEAXLQVWVPPLNVRGGRDXXILLTCLLHPXLVFDITKLLLAVLGPLYLLQASLLRVPYFVRAHALLRXCMLVRXLAGGK
                                                          NS2

1. HCV1a consensus     QYFLTRVEAQLHVWVPPLNVRGGRDAVILLMCVVHPTLVFDITKLLLAVFGPLWILQASLLKVPYFVRVQGLLRICALARKMAGGH
2. HCV1b consensus     QYFITRAEAHLQVWIPPLNVRGGRDAIILLTCAVHPELIFDITKLLLAILGPLMVLQAGITRVPYFVRAQGLIRACMLVRKVAGGH
3. HCV2a Consensus     CYLLTLGEAMVQEWAPPMQARGGRDGIIWAATIFCPGVVFDITKWLLAVLGPAYLLRDALTRVPYFVRAHALLRMCTMVRHLAGGR
4. HCV2b Consensus     SYMLVLAEAQIQQWVPPLEARGGRDGIIWVAVILHPRLVFEVTKWLLAILGPAYLLKASLLRVPYFVRAHALLRVCTLVRHLAGAR
5. HCV 3 Consensus     QYTICRCEAALQVWVPPLLARGSRDGVILLTSLLYPSLIFDITKLLIAVLGPLYLIQAAITTTPYFVRAHVLVRLCMLVRSVMGGK
6. HCV 4 Consensus     QYFIARAEALLHVYVPSFDVRGPRDSLIILAVLACPHLVFDITKYLLAILGPLYILQASLLRVPYFVRAHALVKICSLLRGVVYGK
7. HCV5 consensus      QYFIARVEAXIHVWVPPLQVRGGRDAIIMLTCLFHPALGFEVTKILLGILGPLYLLQXSLXKVPYFXRARALLRACLLAKHLVXGK
8. HCV6 consensus      QYFIARAEAMLHVWVPSLRVRGGRDAVILLTCLLHPQLGFEVTKILLALLGPLYLLQYSLLKVPYFVRAHILLRACLLVRRLAGGK
9. HCV7: ABN05226      TYFLTRCEAALQTWVPPLNPRGGRDGFILCVLLCYPGLVFDITKWLLVMMCPLYLLQLCLVRTPYFVRAQALIRVCSLFKTLAGGR
14. AVI1a-129          QYFLTRAEAQLHVWVPPLNVRGGRDAVILLMCVVHPTLVFDITKLLLAV?GPLWILQTSLLKVPYFVRVQGLLRICALARKIAGGH
15. AVI3a-177          QYTICRCEAALQVWVPPLLARGSRDGAILLTSLLYPSLIFDITKLLIAVLGPLYLIQAAITTTPYFVRAHVLVRLCMLVRSVMGGK

                       950       960       970       980       990       1,000     1,010     1,020     1,030
Consensus              YVQMALLKLGRWTGTYIYDHLXPLSDWAAAGLRDLAVAVEPVIFSPMEKKVITWGADTAACGDILCGLPVSARLGREILLGPADDY
                                                          NS2

1. HCV1a consensus     YVQMAIIKLGALTGTYVYNHLTPLRDWAHNGLRDLAVAVEPVVFSQMETKLITWGADTAACGDIINGLPVSARRGREILLGPADGM
2. HCV1b consensus     YVQMAFMKLAALTGTYVYDHLTPLRDWAHAGLRDLAVAVEPVVFSDMETKIITWGADTAACGDIILGLPVSARRGREILLGPADSL
3. HCV2a Consensus     YVQMALLALGRWTGTYIYDHLTPMSDWAASGLRDLAVAVEPIIFSPMEKKVIVWGAETAACGDILHGLPVSARLGREILLGPADGY
4. HCV2b Consensus     YIQMLLITIGRWTGTYIYDHLSPLSTWAAQGLRDLAVAVEPVVFSPMEKKVIVWGAETVACGDILHGLPVSARLGREVLLGPADSY
5. HCV 3 Consensus     YFQMIILSIGRWFNTYLYDHLAPMQHWAAAGLKDLAVATEPVIFSPMEIKVITWGADTAACGDILCGLPVSARLGREVLLGPADDY
6. HCV 4 Consensus     YCQMAVLKVGALTGTYIYDHLTPLSDWAAEGLRDLAVALEPVVFTPMEKKVIVWGADTAACGDIIXGLPVSARLGNEILLGPADSE
7. HCV5 consensus      YVQAALLHLGRLTGTYIYDHLAPMKDWAASGLRDLAVATEPIIFSPMETKVITWGADTAACGDILAGLPVSARRGREIFLGPADDI
8. HCV6 consensus      YVQACLLRLGAWTGTYIYDHLAPLSDWASDGLRDLAVAVEPVIFSPMEKKVITWGADTAACGDILAGLPVSARRGNLVLLGPADDM
9. HCV7: ABN05226      YVQAALLTIGRWTGTYIYNHLAPLETWAAGGLRDLAVAVEPVIFSPMEKKIIVWGAETTACGDILCGLPVSARLGREVLLGPADDY
14. AVI1a-129          YVQMAIIKLGALTGTYIYDHLTPLRDWAHNGLRDLAVAVEPVVFSRMETKLITWGADTAACGDIINGLPVSARRGQEILLGPADGM
15. AVI3a-177          YFQMIILSIGRWFNTYLYDHLAPMQHWAAAGLKDLAVATEPVIFSPMEIKVITWGADTAACGDILCGLPVSARLGHEVLLGPADDY
```

FIG. 12D

| | 1,040 1,050 1,060 1,070 1,080 1,090 1,100 1,110 |
|---|---|
| Consensus | XSKGWRLLAPITAYAQQTRGLLGTIVTSLTGRDKNEVEGEVQVLSTATQTFLGTCINGVMWTVYHGAGSKTLAGPKGPVXQMYTNV |
| | NS2 NS3 |
| 1. HCV1a consensus | VSKGWRLLAPITAYAQQTRGLLGCIITSLTGRDKNQVEGEVQIVSTAAQTFLATCINGVCWTVYHGAGTRTIASPKGPVIQMYTNV |
| 2. HCV1b consensus | EGQGWRLLAPITAYSQQTRGLLGCIITSLTGRDKNQVEGEVQVVSTATQSFLATCVNGVCWTVYHGAGSKTLAGPKGPITQMYTNV |
| 3. HCV2a Consensus | TSKGWRLLAPITAYAQQTRGLLGAIVVSMTGRDKTEQAGEIQVLSTVTQSFLGTSISGVLWTVYHGAGNKTLAGSRGPVTQMYSSA |
| 4. HCV2b Consensus | TSKGWKLLAPITAYTQQTRGLLGAIVVSLTGRDKNEQAGQVQVLSSVTQSFLGTSISGVLWTVYHGAGNKTLAGPKGPVTQMYTSA |
| 5. HCV 3 Consensus | REMGWRLLAPITAYAQQTRGLLGTIVTSLTGRDKNVVTGEVQVLSTATQTFLGTTVGGVMWTVYHGAGSRTLAGAKHPALQMYTNV |
| 6. HCV 4 Consensus | TSKGWRLLAPITAYAQQTRGLFSTIITSLTGRDTNENCGEVQVLSTATQSFLGTAVNGVMWTVYHGAGSKTISGPKGPVNQMYTNV |
| 7. HCV5 consensus | XXAGWRLLAPITAYAQQTRGVLGAIVVSLTGRDKNEAEGEVQVLSTATQTFLGTCINGVMWTVFHGAGXKTLAGPKGPVVQMYTNV |
| 8. HCV6 consensus | KRGGWRLLAPITAYAQQTRGLLGTIVTSLTGRDKNEVEGEVQVVSTATQSFLATSINGVLWTVYHGAGSKTLAGPKGPVCQMYTNV |
| 9. HCV7: ABN05226 | RSMGWQLLAPISAYAQQTRGLISTLVVSLTGRDKNETAGEVQVLSTSTQTFLGTNVGGVMWGPYHGAGTRTVAGRGGPVLQMYTSV |
| 14. AVI1a-129 | VSKGWRLLAPITAYAQQTRGLLGCIITSLTGRDKNQVEGEVQIVSTAAQTFLATCINGVCWTVYHGAGTRTIASPKGPVIQMYTNV |
| 15. AVI3a-177 | REMGWRLLAPITAYAQQTRGLLGTIVTSLTGRDKNVVTGEVQVLSTATQTFLGTTIGGVMWTVYHGAGSRTLAGVKHPALQMYTNV |

| | 1,120 1,130 1,140 1,150 1,160 1,170 1,180 1,190 1,200 |
|---|---|
| Consensus | DQDLVGWPAPPGAKSLTPCTCGSSDLYLVTRHADVIPXRRRGDSRGSLLSPRPISXLKGSSGGPVLCPSGHAVGIFRAAVCTRGVA |
| | NS3 |
| 1. HCV1a consensus | DQDLVGWPAPQGARSLTPCTCGSSDLYLVTRHADVIPVRRRGDSRGSLLSPRPISYLKGSSGGPLLCPAGHAVGIFRAAVCTRGVA |
| 2. HCV1b consensus | DQDLVGWQAPPGARSLTPCTCGSSDLYLVTRHADVIPVRRRGDSRGSLLSPRPVSYLKGSSGGPLLCPSGHAVGIFRAAVCTRGVA |
| 3. HCV2a Consensus | EGDLVGWPSPPGTKSLEPCTCGAVDLYLVTRNADVIPARRRGDKRGALLSPRPLSTLKGSSGGPVLCPRGHAVGIFRAAVCSRGVA |
| 4. HCV2b Consensus | EGDLVGWPSPPGTKSLDPCTCGAVDLYLVTRNADVIPVRRKDDRRGALLSPRPLSTLKGSSGGPVLCPRGHAVGLFRAAVCARGVA |
| 5. HCV 3 Consensus | DQDLVGWPAPPGAKSLEPCACGSADLYLVTRDADVIPARRRGDSTASLLSPRPLACLKGSSGGPVMCPSGHVAGIFRAAVCTRGVA |
| 6. HCV 4 Consensus | DQDLVGWPAPPGVKSLAPCTCGASDLYLVTRHADVVPVRRRGDTRGALLSPRPISTLKGSSGGPLLCPMGHAAGIFRAAVCTRGVA |
| 7. HCV5 consensus | DKDLVGWPXPPGXRSLTPCTCGSADLYLVTRHADVIPARRRGDTRASLLSPRPISYLKGSSGGPIMCPSGHVVGVFRAAVCTRGVA |
| 8. HCV6 consensus | DQDLVGWPAPPGARSLTPCTCGSSDLYLVTRNADVIPARRRGDTRAALLSPRPISTLKGSSGGPILCPSGHVVGLFRAAVCTRGVA |
| 9. HCV7: ABN05226 | SDDLVGWPAPPGSKSLEPCSCGSADLYLVTRNADVLPLRRKGDGTASLLSPRPVSSLKGSSGGPVLCPQSHCVGIFRAAVCTRGVA |
| 14. AVI1a-129 | DKDLVGWPAPPGSRSLTPCTCGSSDLYLVTRHADVIPVRRRGDSRGSLLSPRPISYLKGSSGGPLLCPAGHAVGIFRAAVCTRGVA |
| 15. AVI3a-177 | DQDLVGWPAPPGAKSLEPCSCGSTDLYLVTREADVIPARRRGDSTASLLSPRPLACLKGSSGGPVMCPSGHVAGIFRAAVCTRGVA |

| | 1,210 1,220 1,230 1,240 1,250 1,260 1,270 1,280 1,290 |
|---|---|
| Consensus | KAVDFIPVESLETTMRSPXFTDNSTPPAVPQXYQVGYLHAPTGSGKSTKVPAAYAAQGYKVLVLNPSVAATLGFGAYMSKAHGIDP |
| | NS3 |
| 1. HCV1a consensus | KAVDFIPVENLETTMRSPVFTDNSSPPAVPQSFQVAHLHAPTGSGKSTKVPAAYAAQGYKVLVLNPSVAATLGFGAYMSKAHGIDP |
| 2. HCV1b consensus | KAVDFVPVESMETTMRSPVFTDNSSPPAVPQTFQVAHLHAPTGSGKSTKVPAAYAAQGYKVLVLNPSVAATLGFGAYMSKAHGVDP |
| 3. HCV2a Consensus | KSIDFIPVETLDIVTRSPTFSDNSTPPAVPQTYQVGYLHAPTGSGKSTKVPVAYAAQGYKVLVLNPSVAATLGFGAYLSKAHGINP |
| 4. HCV2b Consensus | KSIDFIPVESLDIATRTPSFSDNSTPPAVPQSYQVGYLHAPTGSGKSTKVPAAYASQGYKVLVLNPSVAATLGFGAYMSKAHGINP |
| 5. HCV 3 Consensus | KALQFIPVETLSTQARSPSFSDNSTPPAVPQSYQVGYLHAPTGSGKSTKVPAAYVAQGYNVLVLNPSVAATLGFGSFMSRAYGIDP |
| 6. HCV 4 Consensus | KAVDFVPVESLETTMRSPVFTDNSTPPAVPQTYQVAHLHAPTGSGKSTKVPAAYAAQGYKVLVLNPSVAATLGFGAYMSKAYGIDP |
| 7. HCV5 consensus | KALDFIPVENLETTMRSPVFTDNSTPPAVPHEFQVGHLHAPTGSGKSTKVPAAYAAQGYKVLVLNPSVAATLGFGAYMSRAYGVDP |
| 8. HCV6 consensus | KSLDFVPVENMETTMRSPSFTDNSTPPAVPQTYQVGYLHAPTGSGKSTKVPAAYASQGYKVLVLNPSVAATLGFGSYMSKAHGIDP |
| 9. HCV7: ABN05226 | KAVQFVPIEKMQVAQRSPSFSDNSTPPAVPSTYQVGYLHAPTGSGKSTKVPAAYASQGYKVLVLNPSVAATLGFGAYMSKAYGIDP |
| 14. AVI1a-129 | KAVDFIPVESLETTMRSPVFTDNSSPPVVPQSFQVAHLHAPTGSGKSTKVPAAYAAQGYKVLVLNPSVAATL?FGAYMSKAHGVDP |
| 15. AVI3a-177 | KALQFIPVETLSAQARSPSFSDNSTPPIVPQSYQVGYLHAPTGSGKSTKVPAAYVAQGYNVLVLNPSVAATLGFGSFMSRAYGIDP |

FIG. 12E

```
                    1,300     1,310     1,320     1,330     1,340     1,350     1,360     1,370
Consensus           NIRTGVRTVTTGAPITYSTYGKFLADGGCSGGAYDIIICDECHSTDATTILGIGTVLDQAETAGVRLVVLATATPPGSVTVPHPNI
                    NS3

1. HCV1a consensus  NIRTGVRTITTGSPITYSTYGKFLADGGCSGGAYDIIICDECHSTDATSILGIGTVLDQAETAGARLVVLATATPPGSVTVPHPNI
2. HCV1b consensus  NIRTGVRTITTGAPITYSTYGKFLADGGCSGGAYDIIICDECHSTDSTTILGIGTVLDQAETAGARLVVLATATPPGSVTVPHPNI
3. HCV2a Consensus  NIRTGVRTVTTGEAITYSTYGKFLADGGCAGGAYDIIICDECHAVDATTILGIGTVLDQAETAGVRLTVLATATPPGSVTTPHPNI
4. HCV2b Consensus  NIRTGVRTVTTGDPITYSTYGKFLADGGCSAGAYDVIICDECHSVDATTILGIGTVLDQAETAGARLVVLATATPPGTVTTPHSNI
5. HCV 3 Consensus  NIRTGNRTVTTGAKLTYSTYGKFLADGGCSGGAYDVIICDECHAQDATSILGIGTVLDQAETAGVRLTVLATATPPGSITVPHSNI
6. HCV 4 Consensus  NIRSGVRTITTGAPITYSTYGKFLADGGCSGGAYDIIICDECHSTDSTTILGIGTVLDQAETAGVRLVVLATATPPGSVTTPHSNI
7. HCV5 consensus   NIRTGVRTVTTGAAITYSTYGKFLADGGCSGGAYDIIICDECHSQDATTILGIGTVLDQAETAGARLVVLATATPPGSVTTPHPNI
8. HCV6 consensus   NIRTGVRTITTGGAITYSTYGKFLADGGCSGGAYDIIICDECHSTDPTTVLGIGTVLDQAETAGVRLTVLATATPPGSVTVPHPNI
9. HCV7: ABN05226  SVRTGARTVTTGAPITYSTYGKFLADGGCSGGAYDIIICDECHAIDATTVVGIGTVLDQAETSGVRLVVLATATPPGSVTVPHPNI
14. AVI1a-129      NIRTGVRTITTGSPITYSTYGKFLADGGCSGGAYDIIICDECHSTDATSILGIGTVLDQAETAGARLVVLATATPPGSVTVPHPNI
15. AVI3a-177      NIRTGNRTVTTGAKLTYSTYGKFLADGGCSGGAYDVIICDECHAQDATSILGIGTVLDQAETAGVRLTVLATATPPGSITVPHSNI

                    1,380     1,390     1,400     1,410     1,420     1,430     1,440     1,450     1,460
Consensus           EEVALGTXGEIPFYGKAIPLEXIKGGRHLIFCHSKKKCDELAAKLXGLGLNAVAYYRGLDVSVIPTSGDVVVVATDALMTGFTGDF
                    NS3

1. HCV1a consensus  EEVALSTTGEIPFYGKAIPLEVIKGGRHLIFCHSKKKCDELAAKLVALGINAVAYYRGLDVSVIPTSGDVVVVATDALMTGFTGDF
2. HCV1b consensus  EEVALSNTGEIPFYGKAIPIETIKGGRHLIFCHSKKKCDELAAKLSGLGLNAVAYYRGLDVSVIPTSGDVVVVATDALMTGFTGDF
3. HCV2a Consensus  EEVALGQEGEIPFYGRAIPLSYIKGGRHLIFCHSKKKCDELAAALRGMGLNAVAYYRGLDVSIIPTQGDVVVVATDALMTGYTGDF
4. HCV2b Consensus  EEVALGHEGEIPFYGKAIPLAFIKGGRHLIFCHSKKKCDELAAALRGMGVNAVAYYRGLDVSVIPTQGDVVVVATDALMTGYTGDF
5. HCV 3 Consensus  EEVALGSEGEIPFYGKAIPIAQLKGGRHLIFCHSKKKCDEIASKLRGMGLNAVAYYRGLDVSVIPTTGDVVVCATDALMTGFTGDF
6. HCV 4 Consensus  EEVALPTTGEIPFYGKAIPLELIKGGRHLIFCHSKKKCDELAKQLTSLGLNAVAYYRGLDVSVIPTSGDVVVCATDALMTGFTGDF
7. HCV5 consensus   EEVALPSEGEIPFYGRAIPLXLIKGGRHLIFCHSKKKCDELAKQLTSLGVNAVAYYRGLDVAVIPATGDVVVCSTDALMTGFTGDF
8. HCV6 consensus   TETALPTTGEIPFYGKAIPLEYIKGGRHLIFCHSKKKCDELAKQLTSLGLNAVAFYRGVDVSVIPTSGDVVVCATDALMTGYTGDF
9. HCV7: ABN05226  EEVALGNDGEIPFYGKAIPLQHIKGGRHLIFCHSKKKCDELAGKLTSLGLTAVAYYRGLDVSVIPTSGDVVVVATDALMTGFTGDF
14. AVI1a-129      EEVALSTTGEIPFYGKAIPLEVIKGGRHLIFCHSKKKCDELAAKLVALGINAVAYYRGLDVSVIPTSGDVVVVATDALMTGYTGDF
15. AVI3a-177      EEVALGSEGEIPFYGKAIPLAQLKGGRHLIFCHSKKKCDEMASKLRGMGLNAVAYYRGLDVSVIPTAGDVVVCATDALMTGFTGDF

                    1,470     1,480     1,490     1,500     1,510     1,520     1,530     1,540
Consensus           DSVIDCNVAVTQTVDFSLDPTFTIETTTVPQDAVSRSQRRGRTGRGRLGIYRYVSPGERPSGMFDSVVLCECYDAGCAWYELTPAE
                    NS3

1. HCV1a consensus  DSVIDCNTCVTQTVDFSLDPTFTIETTTLPQDAVSRTQRRGRTGRGKPGIYRFVAPGERPSGMFDSSVLCECYDAGCAWYELTPAE
2. HCV1b consensus  DSVIDCNTCVTQTVDFSLDPTFTIETTTVPQDAVSRSQRRGRTGRGRRGIYRFVTPGERPSGMFDSSVLCECYDAGCAWYELTPAE
3. HCV2a Consensus  DSVIDCNVAVTQVVDFSLDPTFTITTQTVPQDAVSRSQRRGRTGRGRLGIYRYVSTGERASGMFDSVVLCECYDAGAAWYELTPAE
4. HCV2b Consensus  DSVIDCNVAVTQIVDFSLDPTFTITTQTVPQDAVSRSQRRGRTGRGRLGIYRYVSSGERPSGMFDSVVLCECYDAGAAWYELTPAE
5. HCV 3 Consensus  DSVIDCNVAVEQYVDFSLDPTFSIETRTAPQDAVSRSQRRGRTGRGRLGTYRYVTPGERPSGMFDSVVLCECYDAGCSWYDLQPAE
6. HCV 4 Consensus  DSVIDCNTSVIQTVDFSLDPTFSIETTTVPQDAVSRSQRRGRTGRGRLGIYRYVTPGERPSGIFDTSVLCECYDAGCAWYELTPAE
7. HCV5 consensus   DSVIDCNTAVTQTVDFSLDPTFTIETTTVPQDAVSRSQRRGRTGRGRHGIYRYVSSGERPSGIFDSVVLCECYDAGCAWYDLTPAE
8. HCV6 consensus   DSVIDCNVAVTQVVDFSLDPTFSIETTTVPQDAVSRSQRRGRTGRGKPGVYRYVSQGERPSGMFDTVVLCEAYDTGCAWYELTPSE
9. HCV7: ABN05226  DSVIDCNVAVTQTVDFSLDPTFTIETTTVPQDSVSRSQRRGRTGRGRLGIYRYVSSGERPSGMFDTSVLCECYDLGCSWYELTPSE
14. AVI1a-129      DSVIDCNTCVTQTVDFSLDPTFTIETTTLPQDAVSRTQRRGRTGRGKPGIYRFVAPGERPSGMFDSSVLCECYDAGCAWYELTPAE
15. AVI3a-177      DSVIDCNVTVEQYVDFSLDPTFSIETRTAPQDAVSRSQRRGRTGRGRLGTYRYVAPGERPSGMFDSVVLCECYDAGCSWYDLQPAE
```

FIG. 12F

| | 1,550 1,560 1,570 1,580 1,590 1,600 1,610 1,620 1,630 |
|---|---|
| Consensus | TTVRLRAYLNTPGLPVCQDHLEFWEGVFTGLTHIDAHFLSQTKQSGENFPYLVAYQATVCARAXAPPPSWDXMWKCLIRLKPTLHG |
| | NS3 |
| 1. HCV1a consensus | TTVRLRAYMNTPGLPVCQDHLEFWEGVFTGLTHIDAHFLSQTKQSGENLPYLVAYQATVCARAQAPPPSWDQMWKCLIRLKPTLHG |
| 2. HCV1b consensus | TSVRLRAYLNTPGLPVCQDHLEFWESVFTGLTHIDAHFLSQTKQAGDNFPYLVAYQATVCARAQAPPPSWDQMWKCLIRLKPTLHG |
| 3. HCV2a Consensus | TTVRLRAYFNTPGLPVCQDHLEFWEAVFTGLTHIDAHFLSQTKQSGENFAYLVAYQATVCARAKAPPPSWDVMWKCLTRLKPTLVG |
| 4. HCV2b Consensus | TTVRLRAYFNTPGLPVCQDHLEFWEAVFTGLTHIDAHFLSQTKQGGDNFAYLTAYQATVCARAKAPPPSWDVMWKCLTRLKPTLTG |
| 5. HCV 3 Consensus | TTVRLRAYLSTPGLPVCQDHLDFWESVFTGLTHIDAHFLSQTKQQGLNFSYLTAYQATVCARAQAPPPSWDETWKCLVRLKPTLHG |
| 6. HCV 4 Consensus | TTTRLRAYFNTPGLPVCQDHLEFWESVFTGLTQIDGHFLSQTKQSGENFPYLVAYQATVCARALAPPPSWDTMWKCLIRLKPTLHG |
| 7. HCV5 consensus | TTVRLRAYLNTPGLPVCQDHLEFWEGVFTGLTNIDAHMLSQTKQGGENFPYLVAYQATVCVRAKAPPPSWDTMWKCMXRLKPTLTG |
| 8. HCV6 consensus | TTVRLRAYLNTPGLPVCQDHLEFWEGVFTGLTHIDAHFLSQTKQGGENFAYLVAYQATVCARAKAPPPSWDTMWKCLIRLKPMLTG |
| 9. HCV7: ABN05226 | TTTRLRAYLNCPGLPVCQDHLEFWEGVFTGLTHIDAHFLSQTKQEGQNYAYLTAYQATVCARAKAPPPSWDVQWKCLQRLKPLLVG |
| 14. AVI1a-129 | TTVRLRAYMNTPGLPVCQDHLEFWEGVFTGLTHIDAHFLSQTKQSGENFPYLVAYQATVCARAQAPPPSWDQMWKCLIRLKPTLHG |
| 15. AVI3a-177 | TTVRLRAYLSTPGLPVCQDHLDFWESVFTGLTHIDAHFLSQTKQQGLNFSYLTAYQATVCARAQAPPPSWDEMWKCLLRLKPTLHG |

| | 1,640 1,650 1,660 1,670 1,680 1,690 1,700 1,710 1,720 |
|---|---|
| Consensus | PTPLLYRLGAVQNEVTLTHPITKYIMTCMSADLEVVT---STWVLVGGVLAALAAYCLSTGCVVIVGRIVLSGKPAKIPDREVLYQ |
| | NS3 NS4a |
| 1. HCV1a consensus | PTPLLYRLGAVQNEVTLTHPITKYIMTCMSADLEVVT---STWVLVGGVLAALAAYCLSTGCVVIVGRIVLSGKPAIIPDREVLYR |
| 2. HCV1b consensus | PTPLLYRLGAVQNEVTLTHPITKYIMACMSADLEVVT---STWVLVGGVLAALAAYCLTTGSVVIVGRIILSGKPAIIPDREVLYQ |
| 3. HCV2a Consensus | PTPLLYRLGSVTNEVTLTHPVTKYIATCMQADLEVMT---STWVLAGGVLAAVAAYCLATGCVSIIGRLHINQRAVVAPDKEVLYE |
| 4. HCV2b Consensus | PTPLLYRLGAVTNEVTLTHPVTKYIATCMQADLEIMT---STWVLAGGVLAAVAAYCLATGCISIIGRLHLNDQVVVAPDKEILYE |
| 5. HCV 3 Consensus | PTPLLYRLGPVQNEICLTHPITKYIMACMSADLEVTTSTWSTWVLLGGVLAALAAYCLSVGCVVIVGHIELGGKPALVPDKEVLYQ |
| 6. HCV 4 Consensus | PTPLLYRLGSVQNEVTLTHPITKYIMACMSADLEVVT---STWVLVGGVLAALAAYCLSVGSVVIVGRVVLSGQPAVIPDREVLYQ |
| 7. HCV5 consensus | PTPLLYRLGAVQNEITLTHPITKYIMACMSADLEVIT---STWVLVGGVVAALAAYCLTVGSVAIVGRIILSGRPAIIPDREVLYQ |
| 8. HCV6 consensus | PTPLLYRLGAVQNEITTTHPITKYIMTCMSADLEVIT---STWVLVGGVLAALAAYCLSVGCVVICGRITTTGKPAVIPDREVLYQ |
| 9. HCV7: ABN05226 | PTPLLYRLGSVTNEVTFTHPITKYIATCMAADLEVTT---STWVIVGGVLAAVAAYCMSTGSVVVVGRVVLGSNVVIAPDREVLYQ |
| 14. AVI1a-129 | PTPLLYRLGAVQNEVVLTHPITKYIMTCMSADLEVVT---STWVLVGGVLAALAAYCLSTGCVVIVGRVVLSGKPAIIPDREVLYQ |
| 15. AVI3a-177 | PTPLLYRLGPVQNETCLTHPVTKYIMACMSADLEVTT---STWVLLGGVLAALAAYCLSVGCVVIVGHIELGGKPALIPDKEVLYQ |

| | 1,730 1,740 1,750 1,760 1,770 1,780 1,790 1,800 |
|---|---|
| Consensus | QFDEMEECSQHLPYIEQGQQIAEQFKQKALGLLQTATKQAEVIAPAVQXNWQKLEQFWAKHMWNFISGIQYLAGLSTLPGNPAVAS |
| | NS4a NS4b |
| 1. HCV1a consensus | EFDEMEECSQHLPYIEQGMMLAEQFKQKALGLLQTASRQAEVIAPAVQTNWQKLEAFWAKHMWNFISGIQYLAGLSTLPGNPAIAS |
| 2. HCV1b consensus | EFDEMEECASHLPYIEQGMQLAEQFKQKALGLLQTATKQAEAAAPVVESKWRALE-FWAKHMWNFISGIQYLAGLSTLPGNPAIAS |
| 3. HCV2a Consensus | AFDEMEECASRAALIEEGQRIAEMLKSKIQGLLQQASKQAQDIQPAVQASWPKVEQFWAKHMWNFISGIQYLAGLSTLPGNPAVAS |
| 4. HCV2b Consensus | AFDEMEECASKAALIEEGQRMAEMLKSKIQGLLQQATRQAQDIQPAIQSSWPKLEQFWAKHMWNFISGIQYLAGLSTLPGNPAVAS |
| 5. HCV 3 Consensus | QYDEMEECSQAAPYIEQAQVIAHQFKEKVLGLLQRATQQQAVIEPIVATNWQKLEAFWHKHMWNFVSGIQYLAGLSTLPGNPAVAS |
| 6. HCV 4 Consensus | QFDEMEECSKHLPLVEHGLQLAEQFKQKAVGLLNFAGKQAQEATPVIQSNFAKLEQFWAKHMWNFISGIQYLAGLSTLPGNPAIAS |
| 7. HCV5 consensus | QFDEMEECSASLPYMDEARAIAEQFKEKVLGLIGTAGQKAETLKPAATSMWXKAEQFWAKHMWNFVSGIQYLAGLSTLPGNPAVAT |
| 8. HCV6 consensus | QFDEMEECSRHIPYLAEGQQIAEQFKQKVLGLLQTTAKQAEELKPAVHSAWPKLEQFWQKHLWNFVSGIQYLAGLSTLPGNPAVAS |
| 9. HCV7: ABN05226 | HFDEMEECSKAPELLKHAQTIGGMFKDKALAVLDTLKPAAQAAVPIVETNFQKVEKLWNQHMWNFISGIQYLAGLSTLPGNPTVAS |
| 14. AVI1a-129 | EFDEMEECSQHLPYIEQGMMLAEQFKQKALGLLQTASRQAEVIAPAVQTNWQKLEAFWAKHMWNFISGIQYLAGLSTLPGTPAIAS |
| 15. AVI3a-177 | QYDEMEECSQAAPYVEQAQAIAHQFKEKLLGLLQRATQQQAVIEPIVATNWQKLEAFWHKHMWNFVSGIQYLAGLSTLPGNPAVAS |

FIG. 12G

| | 1,810 … 1,890 |
|---|---|
| Consensus | LMAFTAAVTSPLTTSQTLLFNILGGWVASQLAPPTAATAFVVSGLAGAAVGSIGLGKVLVDILAGYGAGVAGALVAFKIMSGEXPS |
| | NS4b |
| 1. HCV1a consensus | LMAFTAAVTSPLTTSQTLLFNILGGWVAAQLAAPGAATAFVGAGLAGAAIGSVGLGKVLVDILAGYGAGVAGALVAFKIMSGEVPS |
| 2. HCV1b consensus | LMAFTASITSPLTTQHTLLFNILGGWVAAQLAPPSAASAFVGAGIAGAAVGSIGLGKVLVDILAGYGAGVAGALVAFKVMSGEMPS |
| 3. HCV2a Consensus | MMAFSAALTSPLSTSTTILLNILGGWLASQIAPPAGATGFVVSGLVGAAVGSIGLGKVLVDILAGYGAGISGALVAFKIMSGEKPS |
| 4. HCV2b Consensus | MMAFSAALTSPLPTSTTILLNIMGGWLASQIAPPAGATGFVVSGLVGAAVGSIGLGKILVDVLAGYGAGISGALVAFKIMSGEKPS |
| 5. HCV 3 Consensus | LMAFTASVTSPLTTNQTMFFNILGGWVATHLAGPQSSSAFVVSGLAGAAIGGIGLGRVLLDILAGYGAGVSGALVAFKIMGGELPT |
| 6. HCV 4 Consensus | LMSFTAAVTSPLTTQQTLLFNILGGWVASQIATPTASTAFVVSGLAGAAVGSVGLGKILVDILAGYGAGVAGAVVTFKIMSGEMPS |
| 7. HCV5 consensus | LMSFTAAVTSPLTTQQTLLFNILGGWVASQIAPPTAATAFVVSGMAGAAVGSIGLGRVLIDILAGYGAGVAGALVAFKIMCGERPT |
| 8. HCV6 consensus | LMSFSASLTSPLSTSTTLLLNILGGWVASQLAPPTASTAFVVSGLAGAAVGSIGLGRVLVDILAGYGAGVSGALVAFKIMSGETPA |
| 9. HCV7: ABN05226 | LMAFTASVTSPLATSTTLLVNILGGWFASQLAPPSAATTFVVSGLAGAAVGSVGLGKVLVDVLAGYGAGIAGALVAFKIMSGEVPS |
| 14. AVI1a-129 | LMAFTAAVTSPLTTSQTLLFNILGGWVAAQLAAPGAATAFVGAGLAGAAIGSVGLGKVLVDILAGYGAGVAGALVAFKIMSGE?PS |
| 15. AVI3a-177 | LMAFTASVTSPLTTNQTMFFNILGGWVATHLAGPQSSSAFVVSGLAGAAIGGIGLGRVLLDILAGYGAGVSGALVAFKIMGGEIPT |

| | 1,900 … 1,970 |
|---|---|
| Consensus | TEDLVNLLPAILSPGALVVGVVCAAILRRHVGPGEGAVQWMNRLIAFASRGNHVSPTHYVPESDAAARVTQILSSLTVTSLLRRLH |
| | NS4b |
| 1. HCV1a consensus | TEDLVNLLPAILSPGALVVGVVCAAILRRHVGPGEGAVQWMNRLIAFASRGNHVSPTHYVPESDAAARVTAILSSLTVTQLLRRLH |
| 2. HCV1b consensus | TEDLVNLLPAILSPGALVVGVVCAAILRRHVGPGEGAVQWMNRLIAFASRGNHVSPTHYVPESDAAARVTQILSSLTITQLLKRLH |
| 3. HCV2a Consensus | MEDVVNLLPGILSPGALVVGVICAAILRRHVGPGEGAVQWMNRLIAFASRGNHVAPTHYVTESDASQRVTQLLGSLTITSLLRRLH |
| 4. HCV2b Consensus | VEDVVNLLPAILSPGALVVGVICAAILRRHVGQGEGAVQWMNRLIAFASRGNHVAPTHYVAESDASQRVTQVLSSLTITSLLRRLH |
| 5. HCV 3 Consensus | AEDMVNLLPAILSPGALVVGVICAAILRRHVGPGEGAVQWMNRLIAFASRGNHVSPTHYVPESDAAARVTALLSSLTVTSLLRRLH |
| 6. HCV 4 Consensus | TEDLVNLLPAILSPGALVVGVVCAAILRRHVGPGEGAVQWMNRLIAFASRGNHVSPTHYVPESDAAARVTQILSSLTVTSLLRRLH |
| 7. HCV5 consensus | AEDLVNLLPSILCPGALVVGVICAAVLRRHIGPGEGAVQWMNRLIAFASRGNHVSPTHYVPETDASAKVTQLLSSLTVTSLLKRLH |
| 8. HCV6 consensus | XEDMVNLLPALLSPGALVVGVVCAAILRRHVGPAEGATQWMNRLIAFASRGNHVSPTHYVPETDASRXVTTILSSLTITSLLRRLH |
| 9. HCV7: ABN05226 | TEDLANLLPAILSPGALVVGVVCAAIIKRHTGTSEGVTQWMNRLIAFASRGNHVSPTHYIQDDDASKRVMGILSSLTITSLIKRVL |
| 14. AVI1a-129 | TEDLVNLLPAILSPGALVVGVVCAAILRRHVGPGEGAVQWMNRLIAFASRGNHVSPTHYVPESDAAARVTAILSSLTVTQLLRRLH |
| 15. AVI3a-177 | AEDMVNLLPAILSPGALVVGVICAAILRRHVGPGEGAVQWMNRLIAFASRGNHVSPTHYVPESDAAARVTALLSSLTVTSLLRRLH |

| | 1,980 … 2,060 |
|---|---|
| Consensus | QWINEDCSTPCSGSWLRDIWDWVCTVLSDFKTWLKAKLLPQLPGIPFLSCQRGYKGVWRGDGVMHTRCPCGAEITGHVKNGSMRIV |
| | NS4b NS5a |
| 1. HCV1a consensus | QWISSECTTPCSGSWLRDIWDWICEVLSDFKTWLKAKLMPQLPGIPFVSCQRGYRGVWRGDGIMHTRCHCGAEITGHVKNGTMRIV |
| 2. HCV1b consensus | QWINEDCSTPCSGSWLRDVWDWICTVLTDFKTWLQSKLLPRLPGVPFLSCQRGYKGVWRGDGIMQTTCPCGAQITGHVKNGSMRIV |
| 3. HCV2a Consensus | NWITEDCPIPCAGSWLRDVWDWVCTILTDFKNWLTSKLFPKMPGLPFISCQKGYKGVWAGTGIMTTRCPCGANISGNVRLGSMRIT |
| 4. HCV2b Consensus | AWITEDCPVPCSGSWLRDIWDWVCSILTDFKNWLSSKLLPKMPGLPFISCQKGYRGVWAGTGVMTTRCPCGANISGHVRMGTMKIT |
| 5. HCV 3 Consensus | QWINEDYPSPCSGDWLRTIWDWVCTVLSDFKTWLSAKIMPALPGLPFISCQKGYKGVWRGDGVMSTRCPCGASITGHVKNGSMRLA |
| 6. HCV 4 Consensus | KWINEDCSTPCAESWLWEVWDWVCTVLSDFKTWLKAKLLPLMPGIPFLSCQRGYKGEWRGDGVMHTTCPCGAELAGHIKNGSMRIT |
| 7. HCV5 consensus | TWIGEDYSTPCDGTWLRAIWDWVCTALTDFKAWLQAKLLPQLPGVPFLSCQRGYKGVWRGDGVNSTKCPCGATISGHVKNGTMRIV |
| 8. HCV6 consensus | EWINXDWSTPCATSWLRDIWDWVCTVLSDFKTWLKAKLVPSLPGIPFLSCQRGFRGVWRGDGVCHTTCTCGAVIAGHVKNGTMKIS |
| 9. HCV7: ABN05226 | AWAQTDYSAPCAGSWLREVWDWVCMVLSDFASWLKAKVLPSLPGIPFLSCQKGYKGEWRNDGIMNTKCPCGALIAGHVKNGSMRIV |
| 14. AVI1a-129 | QWISSECTTPCSGSWLRDIWDWICEVLSDFKTWLKAKLMPQLPGIPFVSCQRGYRGVWRGDGIMHTRCHCGAEITGHVKNGTMRIV |
| 15. AVI3a-177 | HWINEDYPSPCSGDWLRTIWDWVCMVLSDFRTWLSAKIMPALPGLPFLSCQKGYKGVWRGDGVVSTRCPCGASITGHVKNGSMRLA |

FIG. 12H

| | 2,070 2,080 2,090 2,100 2,110 2,120 2,130 2,140 2,150 |
|---|---|
| Consensus | GPKTCSNTWHGTFPINAYTTGPXXPXPAPNYKRALWRVXAEEYVEVRRVGDFHYVTGXTTDNLKCPCQVPAPEFFTEVDGVRLHRX |
| | NS5a |
| 1. HCV1a consensus | GPRTCRNMWSGTFPINAYTTGPCTPLPAPNYTFALWRVSAEEYVEIRQVGDFHYVTGMTTDNLKCPCQVPSPEFFTELDGVRLHRF |
| 2. HCV1b consensus | GPKTCSNTWHGTFPINAYTTGPCTPSPAPNYSRALWRVAAEEYVEVTRVGDFHYVTGMTTDNVKCPCQVPAPEFFTEVDGVRLHRY |
| 3. HCV2a Consensus | GPKTCMNTWQGTFPINCYTEGQCVPKPAPNFKTAIWRVAASEYAEVTQHGSYSYITGLTTDNLKVPCQLPSPEFFSWVDGVQIHRF |
| 4. HCV2b Consensus | GPKTCLNLWQGTFPINCYTEGPCVPKPPPNYKTAIWRVAASEYVEVTQHGSFSYVTGLTSDNLKVPCQVPAPEFFSWVDGVQIHRF |
| 5. HCV 3 Consensus | GPRTCANMWHGTFPINEYTTGPSTPCPSPNYTRALWRVAANSYVEVRRVGDFHYITGATEDELKCPCQVPAAEFFTEVDGVRLHRY |
| 6. HCV 4 Consensus | GPKTCSNTWHGTFPINAYTTGPGVPIPAPNYKFALWRVSAEEYVEVRRVGDFHYVTGVTQDNIKCPCQVPAPEFFTEVDGIRLHRH |
| 7. HCV5 consensus | GPKLCSNTWHGTFPINATTTGPSVPAPAPNYKFALWRVGAADYAEVRRVGDYHYITGVTQDNLKCPCQVPSPEFFTELDGVRIHRY |
| 8. HCV6 consensus | GPRTCSNTWHGTFPINATTTGPSVPIPEPNYKRALWRVSAEDYVEVVRVGDCHYVVGATADNLKCPCQVPAPEFFTEVDGVRLHRY |
| 9. HCV7: ABN05226 | GPKTCRNTWWGTFPINSHTTGPSSPVPSHCYQRALWRVSATEYVEILRHNDQHYVVGVTAEDLKCPCQVPSPEFFSFVDGVRIHRF |
| 14. AVI1a-129 | GPRTCRNMWSGTFPINAYTTGPCTPLPAPNYKFALWRVSAEEYVEIRQVGDFHYVTGMTTDDLKCPCQVPSPEFFTELDGVRLHRF |
| 15. AVI3a-177 | GPRTCANMWHGTFPINEYTTGPSTPCPSPNYTRALWRVAANSYVEVRQVGDFHYITGATEDGLKCPCQVPAAEFFTEVDGVRLHRY |

| | 2,160 2,170 2,180 2,190 2,200 2,210 2,220 2,230 |
|---|---|
| Consensus | APPCKPLLRDEVTFSVGLNSYVVGSQLPCEPEPDVAVLTSMLTDPSHITAETAARRLARGSPPSLASSSASQLSAPSLKATCTTHH |
| | NS5a |
| 1. HCV1a consensus | APPCKPLLREEVSFRVGLHEYPVGSQLPCEPEPDVAVLTSMLTDPSHITAEAAGRRLARGSPPSVASSSASQLSAPSLKATCTANH |
| 2. HCV1b consensus | APACKPLLREEVTFQVGLNQYLVGSQLPCEPEPDVAVLTSMLTDPSHITAETAKRRLARGSPPSLASSSASQLSAPSLKATCTTRH |
| 3. HCV2a Consensus | APTPKPFFRDEVSFCVGLNSFVVGSQLPCDPEPDTDVLMSMLTDPSHITAEAAARRLARGSPPSEASSSASQLSAPSLRATCTTHG |
| 4. HCV2b Consensus | APTPGPFFRDEVTFTVGLNSFVVGSQLPCDPEPDTEVLASMLTDPSHITAEAAARRLARGSPPSQASSSASQLSAPSLKATCTTHK |
| 5. HCV 3 Consensus | APPCKPLLRDEITFMVGLNSYAIGSQLPCEPEPDVSVLTSMLRDPSHITAETAARRLARGSPPSEASSSASQLSAPSLKATCQTHR |
| 6. HCV 4 Consensus | APKCKPLLRDEVSFSVGLNSFVVGSQLPCEPEPDVAVLTSMLTDPSHITAETASRRLARGSPPSLASSSASQLSAPSLKATCTARH |
| 7. HCV5 consensus | APPCNPLLREEVCFSVGLHSYVVGSQLPCEPEPDVTVLTSMLSDPAHITAETAKRRLDRGSPPSLASSSASQLSAPSLKATCTTQG |
| 8. HCV6 consensus | APPCKPLLRDEVTFSVGLSSYAIGSQLPCEPEPDVTVVTSMLTDPSHITAETAARRLARGSPPSLASSSASQLSAPSLKATCTTHG |
| 9. HCV7: ABN05226 | APEPKPMIREEAAFVVGLHSYVVGSQLPCEPEPDVQTVSQLLTDPSHITAETAARRLRRGSPPSNASSSASQLSAPSLKATHTTLP |
| 14. AVI1a-129 | APPCKPLLREEVSFRVGLHAYPVGSQLPCEPEPDVAVLTSMLTDPSHITAETA?RRLARGSPPSVASSSASQLSAPSLKATCTANH |
| 15. AVI3a-177 | APPCKPLLRDEITFMVGLNSYAIGSQLPCEPEPDVSVLTSMLRDPSHITAETAARRLARGSPPSEASSSASQLSAPSLKATCQTHR |

| | 2,240 2,250 2,260 2,270 2,280 2,290 2,300 2,310 2,320 |
|---|---|
| Consensus | DHPDAELIEANLLWRQEMGGNITRVESENKVVILDSFDPLVAE-EDDREISVPAECLRKXR-KFPPALPIWARPDYNPPLLETWKR |
| | NS5a |
| 1. HCV1a consensus | DSPDAELIEANLLWRQEMGGNITRVESENKVVILDSFDPLVAE-EDEREISVPAEILRKSR-RFAPALPIWARPDYNPPLLETWKK |
| 2. HCV1b consensus | DSPDADLIEANLLWRQEMGGNITRVESENKVVILDSFDPLRAE-EDEREVSVPAEILRKSR-KFPPAMPIWARPDYNPPLLESWKD |
| 3. HCV2a Consensus | KTYDVDMVDANLF----MGGDVTRIESESKVVVLDSLDPM-AEERSDLEPSIPSEYMLPRN-RFPPALPAWARPDYNPPLVESWKR |
| 4. HCV2b Consensus | MAYDCDMVDANLF----MGGDVTRIESDSKVIVLDSLDSM-TEVEDDREPSVPSEYLIRRR-KFPPALPPWARPDYNPPVIETWKR |
| 5. HCV 3 Consensus | PHPDAELVDANLLWRQEMGSNITRVESETKVVILDSFEPLRAE-TDDAELSVAAECFKKPP-KYPPALPIWARPDYNPPLLDRWKA |
| 6. HCV 4 Consensus | DSPGTDLLEANLLW----GSTATRVETDEKVIILDSFEPCVAEPDDDREVSVAAEILRPTK-KFPPALPIWARPDYNPPLTETWKQ |
| 7. HCV5 consensus | HHPDADLIEANLLWRQCMGGNITRVEAENKVVILDSFEPLKXE-EDDREISVSADCFRRGP-AFPPALPIWARPGYDPPLLETWKR |
| 8. HCV6 consensus | DHPDAELIEANLLWRQEMGGNITRVESENKVIVLDSFDPLVAE-YDDREISVSAECHRPPRPKFPPALPIWARPDYNPPLLETWKA |
| 9. HCV7: ABN05226 | QHPDAELIEANLMWEHKVGA-IRRMETDTKVIILDSFDSA-SSVEDDMEPSTAAECLRTRK-VFPPAMPIWARPDYNPPVVENWKD |
| 14. AVI1a-129 | DSPDAELIEANLLWRQEMGGNITRVESENKVVILDSFDPLVAE-EDEREISVPAEILRKSR-RFTQALPVWARPDYNPPLVEAWKK |
| 15. AVI3a-177 | PHPDAELVDANLLWRQEMGSNITRVESETKVVILDSFEPLRAE-ADDAELSVAAECFKKPP-KYPPALPIWARPDYNPPLLDRWKT |

FIG. 12I

```
                    2,330     2,340     2,350     2,360     2,370     2,380     2,390     2,400
Consensus           PDYEPPTVHGCALPPPXAPPVPPPRRK-RTVXLTESTVSTALAELAEKSFGSSEXSGXX-SXSGXDTTSSXXSXPP-DCDAXSDAE
                    NS5a

1. HCV1a consensus  PDYEPPVVHGCPLPPPQSPPVPPPRKK-RTVVLTESTVSTALAELATKSFGSSSTSGI----TGDNTTTSSEPAPS-GCPPDSDAE
2. HCV1b consensus  PDYVPPVVHGCPLPPTKAPPIPPPRRK-RTVVLTESTVSSALAELATKTFGSSESSA-----VDSGTATAPPDQPSDDGDAGSDVE
3. HCV2a Consensus  PDYQPPTVAGCALPPPKKTPTPPPRRR-RTVGLSESTIGDALQQLAIKTFGQPPPSGDSGLSTGADAADSGGRTPP-DELALSETG
4. HCV2b Consensus  PGYEPPTVLGCALPPTPQAPVPPPRRR-RAKVLTQDNVEGVLREMADKVLSPLQDHNDSGHSTGADTGGDSVQQPS-DETAASEAG
5. HCV 3 Consensus  PDYVPPTVHGCALPPRGAPPVPPPRRK-RTIQLDGSNVSAALAALAEKSFPSSKPQEENSSSSGVDTQSSTTSKVPPSPGGESDSE
6. HCV 4 Consensus  QDYKPPTVHGCALPPSKQPPVPPPRRK-RTVQLTESVVSTALAELAAKTFGQSELGSDSGADLTTGPTETTDSGPILVDDA-SDDG
7. HCV5 consensus   PDYDPPQVSGCPLPPAGLPPVPPPRRKRKPVELSDSTVSQVLADLADARF-KXDTPSIEGQDSAVGTSSQXDSGPEEKRDDXSDAA
8. HCV6 consensus   PDYEPPVVSGCALPPPGPPPIPPPRRK-KVVHLDESTVSHALAQLAEKSFPESSSDSTS-SDSGLSITSSGSPEPTTDDDACSEAG
9. HCV7: ABN05226   PEYAPPQVSGCALPPAQTPPVPPPRRKRAVIQLTESAVSTALAELAERSFPKEEAPP---SDSAISLDSPAANDPPSDCDQGSEI-
14. AVI1a-129       PDYEPPVVHGCPLPPPKSPPVPPPRKK-RTVVLTESTLSTALAELATKSFGSSSTSGI----TGDNTTTSSEPAPP-GCSPDSDAE
15. AVI3a-177       PDYVPPTVHGCALPPRGAPPVPPPRRK-RTVQLDGSNVSAALAALAEKSFPSLEPQGENSSSSGIDIQSSTASEVPPSPEGESDSE

                  2,410     2,420     2,430     2,440     2,450     2,460     2,470     2,480     2,490
Consensus           SYSSMPPLEGEPGDPDLSD--------------------GSWSTVSDEE--DSVVCCSMSYSWTGALITPCAAEEEKLPINPLSNS
                    NS5a                                                    NS5b

1. HCV1a consensus  SYSSMPPLEGEPGDPDLSD--------------------GSWSTVSSEADTEDVVCCSMSYSWTGALVTPCAAEEQKLPINALSNS
2. HCV1b consensus  SYSSMPPLEGEPGDPDLSD--------------------GSWSTVSEEAS-EDVVCCSMSYTWTGALITPCAAEESKLPINALSNS
3. HCV2a Consensus  SISSMPPLEGEPGDPDLEPEQVELQPPPQGGEVAPGSDSGSWSTCSEED--DSVVCCSMSYSWTGALITPCSPEEEKLPINPLSNS
4. HCV2b Consensus  SLSSMPPLEGEPGDPDLEFEPAGSAPPSEGECEVIDSDSKSWSTVSDQE--DSVICCSMSYSWTGALITPCGPEEEKLPINPLSNS
5. HCV 3 Consensus  SCSSMPPLEGEPGDPDLSCDQVELQPPPQGGGVAPGSGSGSWSTVSDSEE-QSVVCCSMSYSWTGALITPCSAEEEKLPISPLSNS
6. HCV 4 Consensus  SYSSMPPLEGEPGDPDLTSDQVELQPPPQGGGVAPGSGSGSWSTVSGSE--DTVVCCSMSYSWTGALVTPCAAEESKLPISPLSNS
7. HCV5 consensus   SYSSMPPLEGEPGDPDLSS--------------------GSWSTVSDE---DSVVCCSMSYSWTGALITPCSAEEEKLPINPLSNT
8. HCV6 consensus   SYSSMPPLEGEPGDPDLSS--------------------GSWSTVSEE---DSVVCCSMSYSWTGALITPCAAEEEKLPINPLSNS
9. HCV7: ABN05226   SFSSMPPLEGEPGDPDLSD--------------------GSWSTVSTR---SDVICCSMSYSWTGALVTPSGPEEERLPINALSNT
14. AVI1a-129       SCSSMPPLEGEPGDPDLSD--------------------GSWSTVSSEADTEDVVCCSMSYTWTGALITPCAAEEQKLPINALSNS
15. AVI3a-177       SCTSMPPLEGEPGDPDLSC--------------------DSWSTVSDSEE-QSVVCCSMSYSWTGALITPCSAEEEKLPISPLSNS

                      2,500     2,510     2,520     2,530     2,540     2,550     2,560     2,570     2,580
Consensus           LLRHHNLVYSTTSRSASQRQKKVTFDRLQVLDDHYXDVLKEVKAXASKVKARLLSVEEACALTPPHSARSKFGYGAKDVRSLSRKA
                    NS5b

1. HCV1a consensus  LLRHHNLVYSTTSRSACQRQKKVTFDRLQVLDSHYQDVLKEVKAAASKVKANLLSVEEACSLTPPHSAKSKFGYGAKDVRCHARKA
2. HCV1b consensus  LLRHHNMVYATTSRSASQRQKKVTFDRLQVLDDHYRDVLKEMKAKASTVKAKLLSVEEACKLTPPHSARSKFGYGAKDVRNLSSKA
3. HCV2a Consensus  LLRYHNKVYCTTSKSASLRAKKVTFDRMQVLDAHYDSVLKDIKLAASKVSARLLTLEEACQLTPPHSARSKYGFGAKEVRSLSGRA
4. HCV2b Consensus  LMRFHNKVYSTTSRSASLRAKKVTFDRVQVLDAHYDSVLQDVKRAASKVSARLLSVEEACALTPPHSAKSRYGFGAKEVRSLSRRA
5. HCV 3 Consensus  LLRHHNLVYSTSSRSASQRQKKVTFDRLQVLDDHYKTALKEVKERASRVKARMLTIEEACALVPPHSARSKFGYSAKDVRSLSSKA
6. HCV 4 Consensus  LLRHHNMVYATTTRSAVTRQKKVTFDRLQVVDNHYNETLKEIKARASRVKARLLTTEEACDLTPPHSAKSKFGYGAKDVRSHSRKA
7. HCV5 consensus   LLRHHNLVYSTSSRSAGLRQKKVTFDRLQVLDDHYREVVDEMKRLASKVKARLLPLEEACGLTPPHSARSKYGYGAKEVRSLDKKA
8. HCV6 consensus   LIRHHNLVYSTTSRSASLRQKKVTFDRVQVLDQHYQDVLKEIKLRASQVQARLLSTEEACDLTPPHSARSKFGYGAKDVRSHASKA
9. HCV7: ABN05226   MLRHYNMVYSTTSRSASQRAKKVTFDRLQVLDDHYKRALADVKADASTVKAQLLSVEEAALTPAHSARSKFGYGAKEVRSLAPKA
14. AVI1a-129       LLRHHNLVYSTTSRSACQRQKKVTFDRLQVLDNHYQDVLKEVKAAASKVKANLLSVEEACSLTPPHSAKSKFGYGAKDVRCHARKA
15. AVI3a-177       LLRHHNLVYSTSSRSASQRQKKVTFDRLQVLDDHYKAVLKEVKERASRVKARMLTIEEACALVPPHSARSKFGYSAKDVRSLSGRA
```

FIG. 12J 2,590 2,600 2,610 2,620 2,630 2,640 2,650 2,660

Consensus VNHIXSVWXDLLEDSTTPIPTTIMAKNEVFCVDPXKGGRKPARLIVYPDL-GVRVCEKRALYDVXQKLPKAVMGSSYGFQYSPAQR NS5b 1. HCV1a consensus VNHINSVWKDLLEDSVTPIDTTIMAKNEVFCVQPEKGGRKPARLIVFPDL-GVRVCEKMALYDVVSKLPLAVMGSSYGFQYSPGQR
2. HCV1b consensus VNHIRSVWKDLLEDTETPIDTTIMAKNEVFCVQPEKGGRKPARLIVFPDL-GVRVCEKMALYDVVSTLPQAVMGSSYGFQYSPGQR
3. HCV2a Consensus VNHIKSVWKDLLEDSQTPIPTTIMAKNEVFCVDPTKGGKKAARLIVYPDL-GVRVCEKMALYDVTQKLPQAVMGASYGFQYSPAQR
4. HCV2b Consensus VNHIRSVWEDLLEDQHTPIDTTIMAKNEVFCVDPTKGGKKPARLIVYPDL-GVRVCEKMALYDIAQKLPKAIMGPSYGFQYSPAER
5. HCV 3 Consensus INQIRSVWEDLLEDTTTPIPTTIMAKNEVFCVDPAKGGRKPARLIVYPDL-GVRVCEKRALYDVIQKLSIETMGSAYGFQYSPQQR
6. HCV 4 Consensus INHINSVWEDLLEDNNTPIPTTIMAKNEVFAVNPAKGGRKPARLIVYPDLGGVRVCEKRALHDVINQLPKAVMGAAYGFQYSPAQR
7. HCV5 consensus LXHIEGVWQDLLDDSDTPLPTTIMAKNEVFAVEPSKGGKKPARLIVYPDL-GVRVCEKRALYDXAQKLPTALMGPSYGFQYSPAQR
8. HCV6 consensus INHINSVWEDLLEDNQTPIPTTIMAKNEVFCVDPSKGGRKPARLIVYPDL-GVRVCEKRALYDITRKLPVAVMGDAYGFQYSPKQR
9. HCV7: ABN05226 MSHIKEVWKDLLQDMTTPIPTTIMAKNEVFCVNPAKGGKKPARLIVYPDL-GVRVCEKRALYDIAQKLPKAIMGQAYGFQYSPSQR
14. AVI1a-129 VNHINSVWKDLLEDSVTPIDTTIMAKNEVFCVQPEKGGRKPARLIVFPDL-GVRVCEKMALYDVVSKLPLAVMGDSYGFQYSPGQR
15. AVI3a-177 VNQIRSVWEDLLEDTTTPIPTTIMAKNEVFCVDPSKGGRKPARLIVYPDL-GVRVCEKRALYDVIQKLSIATMGSAYGFQYSPQQR 2,670 2,680 2,690 2,700 2,710 2,720 2,730 2,740 2,750

Consensus VEFLLKAWKSKKTPMG--FSYDTRCFDSTVT-EXDIRTEEXIYQCCDLDPEARKAIXSLTERLYVGGPMXNSKGQXCGYRRCRASG NS5b 1. HCV1a consensus VEFLVQAWKSKKTPMG--FSYDTRCFDSTVT-ESDIRTEEAIYQCCDLDPQARVAIKSLTERLYVGGPLTNSRGENCGYRRCRASG
2. HCV1b consensus VEFLVNAWKSKKCPMG--FAYDTRCFDSTVT-ESDIRVEESIYQCCDLAPEARQAIRSLTERLYIGGPLTNSKGQNCGYRRCRASG
3. HCV2a Consensus VEFLLKAWAEKKDPMG--FSYDTRCFDSTVT-ERDIRTEESIYQACSLPEEARTAIHSLTERLYVGGPMFNSKGQTCGYRRCRASG
4. HCV2b Consensus VDFLLKAWGSKKDPMG--FSYDTRCFDSTVT-ERDIRTEESIYQACSLPQEARTVIHSLTERLYVGGPMTNSKGQSCGYRRCRASG
5. HCV 3 Consensus VERLLKMWTSKKTPLGVLFSYDTRCFDSTVTGEQDIRVEEEIYQCCNLEPEARKVISSLTERLYCGGPMFNSKGAQCGYRRCRASG
6. HCV 4 Consensus VEFLLTSWKSKKTPMG--FSYDTRCFDSTVT-EKDIRTEEEVYQCCDLEPEARKVITALTERLYVGGPMHNSKGDLCGYRRCRASG
7. HCV5 consensus VEFLLKTWKSKKXPMA--FSYDTRCFDSTVT-EHDIMTEESIYQSCDLQPEARXAIRSLTQRLYCGGPMYNSKGQQCGYRRCRASG
8. HCV6 consensus VDYLLKMWRSKKTPMG--FSYDTRCFDSTVT-ERDIRTEHDIYQSCQLDPEARKAITSLTERLYVGGPMYNSKGQSCGYRRCRASG
9. HCV7: ABN05226 VEYLVKTWKSKRTPMG--FSYDTRCFDSTVT-EQDIRTESEIYQCCNLDPEARTIINALTERLYVGGPMFNSKGQRVGYRRCRASG
14. AVI1a-129 VEFLVQAWKSKKTPMG--FSYDTRCFDSTVT-ESDIRTEEAIYQCCDLDPQARVAIKSLTERLYVGGPLTNSRGENCGYRRCRASG
15. AVI3a-177 VERLLEMWTSKKTPMG--FSYDTRCFDSTVT-EQDIRVEEEIYQCCNLEPEARKVISSLTERLYCGGPMFNSKGAQCGYRRCRASG 2,760 2,770 2,780 2,790 2,800 2,810 2,820 2,830

Consensus VLTTSMGNTLTCYIKAXAACRAAGLRDCTMLVCGDDLVVICESAGVZEDAAXLRAFTEAMTR-----YSAPPGDPP-----QPEYD NS5b 1. HCV1a consensus VLTTSCGNTLTCYIKARAACRAAGLQDCTMLVCGDDLVVICESAGVQEDAASLRAFTEAMTR-----YSAPPGDPP-----QPEYD
2. HCV1b consensus VLTTSCGNTLTCYLKASAACRAAKLQDCTMLVCGDDLVVICESAGTQEDAASLRVFTEAMTR-----YSAPPGDPP-----QPEYD
3. HCV2a Consensus VLTTSMGNTITCYVKALAACKAAGIVAPTMLVCGDDLVVISESQGTEEDERNLRAFTEAMTR-----YSAPPGDPP-----RPEYD
4. HCV2b Consensus VFTTSMGNTMTCYIKALAACKAAGIVDPIMLVCGDDLVVISESQGNEEDERNLRAFTEAMTR-----YSAPPGDLP-----RPEYD
5. HCV 3 Consensus VLPTSFGNTITCYIKATAAARAAGLRNPDFLVCGDDLVVVAESDGVDEDRAALRAFTEAMTRLWTRYYSAPPGDAPHRPTLQPTYD
6. HCV 4 Consensus VYTTSFGNTLTCYLKATAAIKAAGLRDCTMLVCGDDLVVIAESDGVEEDNRALRAFTEAMTR-----YSAPPGDAP-----QPAYD
7. HCV5 consensus VFTTSMGNTMTCYIKALASCRAAKLRDCTLLVCGDDLVAICESQGTHEDEASLRAFTEAMTR-----YSAPPGDPP-----VPAYD
8. HCV6 consensus VLPTSLGNTLTCYLKAQAACRAAGLKDFDMLVCGDDLVVISESAGVQEDAAALRAFTEAMTR-----YSAPPGDEP-----QPTYD
9. HCV7: ABN05226 VFPTSMGNTMTCYIKAKAAAAAAGLESTDFLVCGDDLVVICESKGVERDRADLQAFAAAMTR-----YSAPPGDMP-----QPAYD
14. AVI1a-129 VLTTSCGNTLTCYIKAKAACRAAGLQNCTMLVCGDDLVVICESAGVQEDAASLRAFTEAMTR-----YSAPPGDPP-----QPEYD
15. AVI3a-177 VLPTSFGNTITCYIKATAAARAAGLRNPDFLVCGDDLVLVAESDGVDEDRAALRAFTEAMTR-----YSAPPGDAP-----QPTYD

FIG. 12K

```
                   2,840     2,850     2,860     2,870     2,880     2,890     2,900     2,910     2,920
Consensus          LELITSCSSNVSVAHDXSGKRVYYLTRDPTTPLARAAWETARHTP---VNSWLGNIIMYAPTIWVRMVLMTHFFSILQXQEQLEXA
                   NS5b

1. HCV1a consensus LELITSCSSNVSVAHDGAGKRVYYLTRDPTTPLARAAWETARHTP---VNSWLGNIIMFAPTLWARMILMTHFFSVLIARDQLEQA
2. HCV1b consensus LELITSCSSNVSVAHDASGKRVYYLTRDPTTPLARAAWETARHTP---VNSWLGNIIMYAPTLWARMILMTHFFSILLAQEQLEKA
3. HCV2a Consensus LELITSCSSNVSVALGPQGRRRYYLTRDPTTPIARAAWETVRHSP---VNSWLGNIIQYAPTIWVRMVLMTHFFSILMAQDTLDQN
4. HCV2b Consensus LELITSCSSNVSVALDSRGRRRYFLTRDPTTPITRAAWETVRHSP---VNSWLGNIIQYAPTIWVRMVIMTHFFSILLAQDTLNQN
5. HCV 3 Consensus LELITSCSSNVSVARDNKGKRYYYLTRDATTPLARAAWETARHTPGWGVNSWLGNIIMYAPTIWVRMVMMTHFFSILQSQEILDRP
6. HCV 4 Consensus LELITSCSSNVSVAHDATGKKVYYLTRDPETPLARAAWETVRHTP---VNSWLGNIIVYAPTIWVRMVLMTHFFSILQSQEALEKA
7. HCV5 consensus  LELVTSCSSNVSVARDASGNRVYYLTRDPQVPLARAAWETAKHSP---VNSWLGNIIMYAPTLWARIVLMTHFFSVLQSQEQLEKA
8. HCV6 consensus  LELITSCSSNVSVAHDGTGQRYYYLTRDPTTPLARAAWETARHTP---VNSWLGNIIMYAPTIWVRMVLMTHFFQILQSQEQLHKA
9. HCV7: ABN05226 LEHIDSCSSNVSVARDNSGKRVYYLTRDPTNPLSRAAWETARHSP---VNSWVGNIIMFAPTIWVRMVLMTHFFALLLNEERLNDP
14. AVI1a-129      LELITSCSSNVSVAHDGAGKRVYYLTRDPTTPLARAAWETARHTP---VNSWLGNIIMFAPTLWARMVLMTHFFSVLIARDQLEQA
15. AVI3a-177      LELITSCSSNVSVARDNKGKRYYYLTRDATTPLARAAWETARHTP---VNSWLGNIIMYAPTIWVRMVMMTHFFSILQSQEILDRP
                     2,930     2,940     2,950     2,960     2,970     2,980     2,990     3,000     3,010
Consensus          LDFEMYGATYSVTPLDLPAIIQRLHGLSAFSLHSYSPGELNRVAACLRKLGVPPLRAWRHRARAVRAKLIAQGGRAAICGKYLFNW
                   NS5b

1. HCV1a consensus LDCEIYGACYSIEPLDLPPIIQRLHGLSAFSLHSYSPGEINRVAACLRKLGVPPLRAWRHRARSVRARLLSRGGRAAICGKYLFNW
2. HCV1b consensus LDCQIYGACYSIEPLDLPQIIQRLHGLSAFSLHSYSPGEINRVASCLRKLGVPPLRVWRHRARSVRAKLLSQGGRAATCGKYLFNW
3. HCV2a Consensus LNFEMYGSVYSVSPLDLPAIIERLHGLDAFSLHTYTPHELTRVASALRKLGAPPLRAWKSRARAVRASLISRGGRAAVCGRYLFNW
4. HCV2b Consensus LNFEMYGAVYSVNPLDLPAIIERLHGLDAFSLHTYSPHELSRVAATLRKLGAPPLRAWKSRARAVRASLIAQGGRAAICGRYLFNW
5. HCV 3 Consensus LDFEMYGATYSVTPLDLPAIIERLHGLSAFTLHSYSPVELNRVAGTLRKLGCPPLRAWRHRARAVRAKLIAQGGKAKICGLYLFNW
6. HCV 4 Consensus LDFDMYGVTYSITPLDLPAIIQRLHGLSAFTLHGYSPHELNRVAGSLRKLGVPPLRAWRHRARAVRAKLIAQGGKAKICGIYLFNW
7. HCV5 consensus  LAFEMYGSVYSVTPLDLPAIIQRLHGLSAFSLHSYSPSEINRVASCLRKLGVPPLRAWRHRARAVRAKLIAQGGKAAICGIYLFNW
8. HCV6 consensus  LDFDIYGVTYSITPLDLPAIIQRLHGMAAFSLHGYSPGELNRVAACLRKLGAPPLRAWRHRARAVRAKLIAQGGKAAICGKYLFNW
9. HCV7: ABN05226 VSFEMYGATYTVCPTDLPDIIQRLHGLRAFELHTYSPAELTRVAATLRKLGVPPLRTWRQRARKVRAGLIGQGGRARICGLYLFNW
14. AVI1a-129      LDCEIYGACYSIEPLDLPPIIQRLHGLSAFSLHSYSPGEINRVAACLRKLGVPPLRTWRHRARSVRAKLLSRGGRAAICGKYLFNW
15. AVI3a-177      LDFEMYGATYSVTPLDLPAIIERLHGLSAFTLHSYSPVELNRVAGTLRKLGCPPLRAWRHRARAVRAKLIAQGGKAKICGLYLFNW
                         3,020     3,030     3,040     3,050     3,060          3,074
Consensus          AVRTKLKLTPLPAAGXLDLSSWFTVGAGGGDIYHSVSRARPRWLLLCLLLLXVGVGIFLLPARX
                   NS5b

1. HCV1a consensus AVRTKLKLTPIAAAGQLDLSGWFTAGYSGGDIYHSVSHARPRWFWFCLLLLAAGVGIYLLPNRX
2. HCV1b consensus AVRTKLKLTPIPAASQLDLSGWFVAGYSGGDIYHSLSRARPRWFMWCLLLLSVGVGIYLLPNRX
3. HCV2a Consensus AVKTKLKLTPLPEARLLDLSSWFTVGAGGGDIYHSVSRARPRLLLLSLLLLXVGVGLFLLPAR
4. HCV2b Consensus AVKTKLKLTPLPEASRLDLSGWFTVGAGGGDIFHSVSHARPRLLLLCLLLLSVGVGIFLLPAR
5. HCV 3 Consensus AVRTKTKLTPLPAAGQLDLSSWFTVGVGGNDIYHSVSRARTRXLLLCLLLLTVCVGIFLLPAR
6. HCV 4 Consensus AVKTKLKLTPLPAAANLDLSSWFTVGAGGGDIYHSVSRARPRYLLLCLLLLSVGVGIFLLPAR
7. HCV5 consensus  AVKTKRKLTPLADADRLDLSSWFTVGAGGGDIYHSMSRARPRXJLLCLLLLXVGVGIFLLPAR
8. HCV6 consensus  AVKTKLKLTPLRGASKLDLSGWFVAGYSGGDIYHSVSRARPRMLLLCLLLLTVGVGIFLLPAR
9. HCV7: ABN05226 AVRTKIKLTPLAGAGRLDLSSWFSVCAGEADVDHSTPRAHPRPLLLCLLLLAVGVGIFLLPAR
14. AVI1a-129      AVRTKLKLTPIAAAGRLDLSGWFTAGYSGGDIYHSVSHARPRWFWFCLLLLAAGVGIYLLPNR
15. AVI3a-177      AVRTKTNLTPLPAAGQLDLSSWFTVGVGGNDIYHSVSRARTRHLLLCLLLLTVGVGIFLLPAR
```

FIG. 12L

HEPATITIS C VIRUS IMMUNOGENIC COMPOSITIONS AND METHODS OF USE THEREOF

CROSS-REFERENCE

This application is a continuation of U.S. patent application Ser. No. 17/122,627, now U.S. Pat. No. 11,576,968, filed Dec. 12, 2020, which is a continuation of U.S. patent application Ser. No. 16/336,732, now U.S. Pat. No. 10,881, 726, filed Mar. 26, 2019, which is a U.S. National Phase Application of PCT Application No. PCT/CA2017/051192, which claims the benefit of U.S. Provisional Patent Application No. 62/406,770, filed Oct. 11, 2016, which applications are incorporated herein by reference in their entirety.

INCORPORATION BY REFERENCE OF SEQUENCE LISTING PROVIDED AS A SEQUENCE LISTING XML FILE

A Sequence Listing is provided herewith as a Sequence Listing XML, "UALB-035CON2_SEQ_LIST" created on Jun. 1, 2023 and having a size of 319,002 bytes. The contents of the Sequence Listing XML are incorporated by reference herein in their entirety.

INTRODUCTION

Hepatitis C virus (HCV) is a blood-borne pathogen that is estimated to infect 150-200 million people worldwide. Infection by HCV may be non-symptomatic, and can be cleared by patients, sometimes without medical intervention. However, the majority of patients develop a chronic HCV infection, which may lead to liver inflammation, scarring, and even to liver failure or liver cancer. In the United States alone, over 3 million people have a chronic infection.

The HCV virion contains a positive-sense single stranded RNA genome of about 9.5 kb. The genome encodes a single polyprotein of 3,010 to 3,030 amino acids. The structural proteins comprise a core protein forming the viral nucleocapsid and two envelope glycoproteins, E1 and E2.

A vaccine based on the recombinant envelope glycoproteins (rE1E2) from a single genotype 1a strain (HCV-1) protected chimpanzees from chronic infection following homologous and heterologous genotype 1a (gt1a) viral challenge (reviewed in Houghton, M Immunol Rev 2011). Antisera from the immunized chimpanzees were shown to exhibit in vitro cross-neutralizing activity (Meunier et al. (2011) *J. Infect. Dis.* 204:1186). A phase I clinical trial was conducted in human volunteers with a similar antigen (Frey et al. (2010) *Vaccine* 28:6367). Antisera from selected vaccinated individuals were similarly capable of neutralizing chimeric cell culture-derived viruses (HCVcc) expressing the structural proteins of strains representing all 7 major HCV genotypes in vitro (Law et al. (2013) *PLoS One* 8:e59776) and to be able to compete with the binding of numerous discrete monoclonal antibodies with broad cross-neutralizing activities (Wong et al. (2014) *J. Virol.* 88:14278).

There is a need in the art for compositions and methods for inducing immune responses to HCV.

SUMMARY

The present disclosure provides immunogenic compositions comprising: a) hepatitis C virus (HCV) E1E2 heterodimers, HCV E2, or HCV E1; and b) an adjuvant, where the adjuvant is a cyclic dinucleotide or an archaeosome. The present disclosure provides methods of inducing an immune response in an individual to HCV, the methods comprising administering to an individual an effective amount of an immunogenic composition of the present disclosure.

BRIEF DESCRIPTION OF THE DRAWINGS

FIG. 1A-1C provide an amino acid sequence alignment of examples of the core-E1-E2 coding regions of a HCV genotype 1 virus, specifically representative HCV IA, 1B and 1C genotypes. Genbank database sequences for the coding region core-E1-E2 were aligned using Geneious software v5.6.4. Numbering of amino acids is according to strain NP_671941 (H77). Consensus: SEQ ID NO:1; AVI1a129: SEQ ID NO:2; NP_671491 (H77): SEQ ID NO:3; EU155269: SEQ ID NO:4; EU781810: SEQ ID NO:5; EU781771: SEQ ID NO:6; AB250610: SEQ ID NO:7; EU781752: SEQ ID NO:8; EU781759: SEQ ID NO:9; EF407439: SEQ ID NO:10; EF407427: SEQ ID NO:11; EU362905: SEQ ID NO:12; EF407413: SEQ ID NO:13; EU781808: SEQ ID NO:14; EU78170: SEQ ID NO:15; AJ238799 (Coni): SEQ ID NO:16; AAK97744: SEQ ID NO:17; AF139594: SEQ ID NO:18; AF176573: SEQ ID NO:19; BAA19625: SEQ ID NO:20; BAA25076: SEQ ID NO:21; BAC54896: SEQ ID NO:22; BAD91386: SEQ ID NO:23; BAF46764: SEQ ID NO:24; BAG30950: SEQ ID NO:25; CAB41951: SEQ ID NO:26; AAK95832: SEQ ID NO:27; AAT69968: SEQ ID NO:28; and BAA03581: SEQ ID NO:29.

FIG. 2A-2C provide an alignment of amino acid sequences of the core-E1-E2 coding region of representative HCV 2A and HCV2B subtypes. Genbank database sequences for the coding region core-E1-E2 were aligned using Geneious software v5.6.4. The amino acid numbering depicted is in accordance to the common HCV strains: ABO47639 (JFH1) and HPCJ8G-J8 (J8) for HCV2A and HCV2B, respectively. AB047639 (JFH1): SEQ ID NO:30; AB047645: SEQ ID NO:31; AF169003: SEQ ID NO:32; AF169005: SEQ ID NO:33; AF238482: SEQ ID NO:34; AY746460: SEQ ID NO:35; HPCPOLP: SEQ ID NO:36; NC_009823: SEQ ID NO:37; HPCJ8G HC-J8: SEQ ID NO:38; AB030907: SEQ ID NO:39; AY232730: SEQ ID NO:40; AY232747: SEQ ID NO:41; and DQ430817: SEQ ID NO:42.

FIG. 3A-3C provide an amino acid sequence alignment of the core-E1-E2 coding region for representative HCV 3A, 3B and 3K genotypes. Genbank database sequences for the coding region core-E1-E2 were aligned using Geneious software v5.6.4. Consensus: SEQ ID NO:43; AVI3a177: SEQ ID NO:44; YP_0014696: SEQ ID NO:45; CAA54244: SEQ ID NO:46; AAC03058: SEQ ID NO:47; AAY29642: SEQ ID NO:48; ABD85062: SEQ ID NO:49; ABD85063: SEQ ID NO:50; ABD97104: SEQ ID NO:51; BAA06044: SEQ ID NO:52; BAA08372: SEQ ID NO:53; and BAA09890: SEQ ID NO:54.

FIG. 5A-5C provide amino acid sequences of immunoglobulin Fc regions for GenBank 3S7G_A *Homo sapiens* IgG1 Fc: SEQ ID NO:56; GenBank AAN76044 *Homo sapiens* IgG2 Fc: SEQ ID NO: 57; GenBank AAW65947

*Homo sapiens* IgG3 Fc: SEQ ID NO:58; GenBank AAA52770 *Homo sapiens* IgD Fc: SEQ ID NO:59; GenBank 0308221A *Homo sapiens* IgM Fc: SEQ ID NO:60; GenBank P01876 *Homo sapiens* IgA Fc: SEQ ID NO:61; GenBank IF6A_B *Homo sapiens* IgE Fc: SEQ ID NO:62; and GenBank P01861 *Homo sapiens* IgG4 Fc: SEQ ID NO:63.

FIG. 6 presents Table 1, which provides conserved regions based on conserved CD4 epitopes ($CD4^+$ T cell epitopes) conserved among HCV genotypes. Top to Bottom: SEQ ID NOs.:64-74.

FIG. 7 presents Table 2, which provides the number of located HCV $CD8^+$ T cell epitopes and anchor positions for common human leukocyte antigen (HLA)-I Alleles in the United States.

FIG. 8 presents Table 3, which provides conserved regions based on CD8 epitopes ($CD8^+$ T cell epitopes) conserved among HCV genotypes. Top to Bottom: SEQ ID NOs.:75-84.

FIGS. 9A-9B provide a list of CD4 and CD8 epitopes that are conserved among HCV genotypes 1a, 1b, 2a, 2b, and 3.

FIG. 10A-10D provide amino acid sequences of examples of polypeptides comprising multiple T-cell epitopes (TP29: SEQ ID NO:85; TP50: SEQ ID NO:86; TP52: SEQ ID NO:87; TP70: SEQ ID NO:88; TP100: SEQ ID NO:89; TP171: SEQ ID NO:90; TP228: SEQ ID NO:91; TP553: SEQ ID NO:92; TP778: SEQ ID NO:93; and TP1985: SEQ ID NO:94). The start and end amino acids are based on the sequence designated "Consensus" in FIG. 12A-12L. The T-cell epitopes contained within each polypeptide are provided; the T-cell epitope designations correspond to those presented in FIGS. 11A-11N.

Figure 11A:
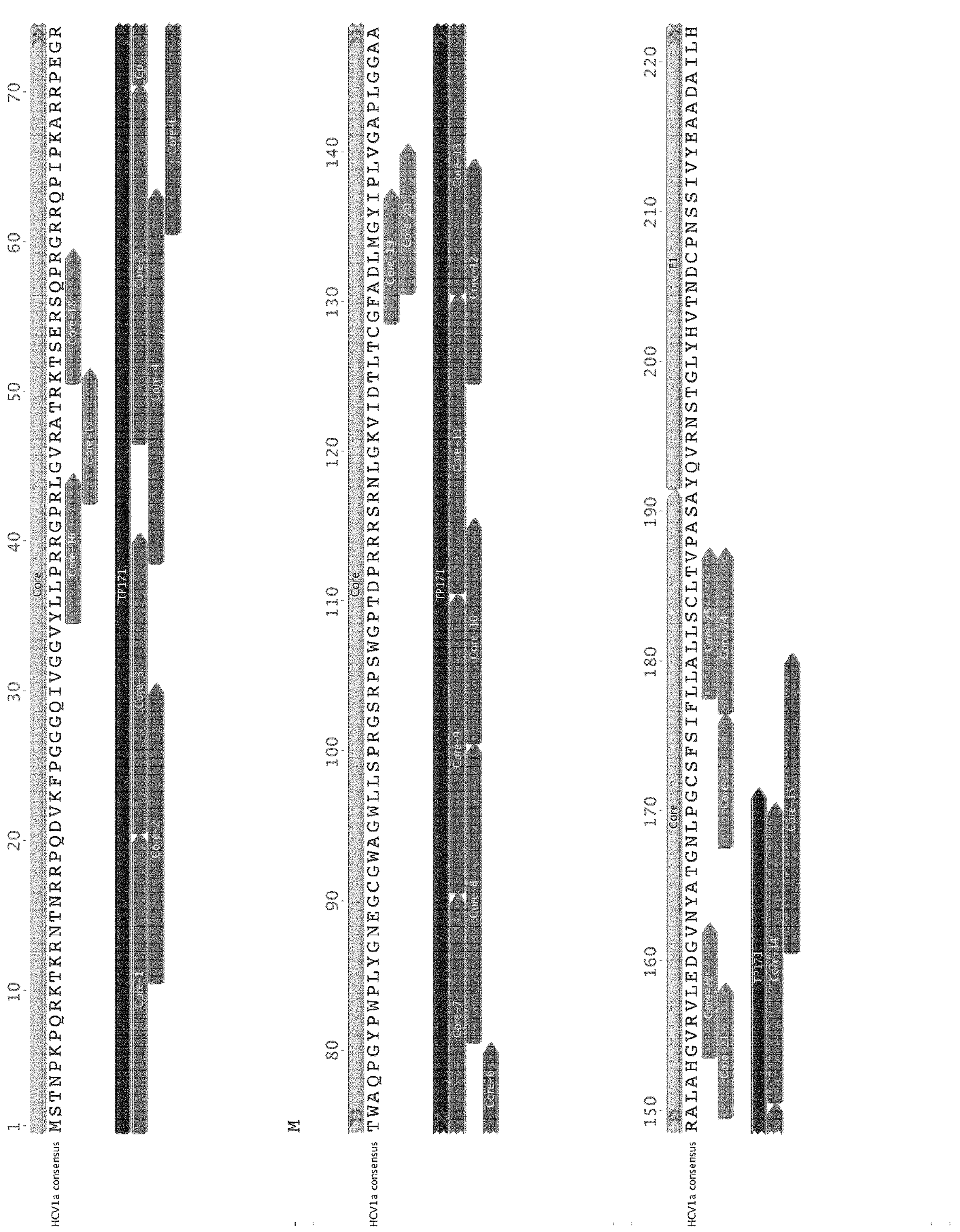
Figure 11D:
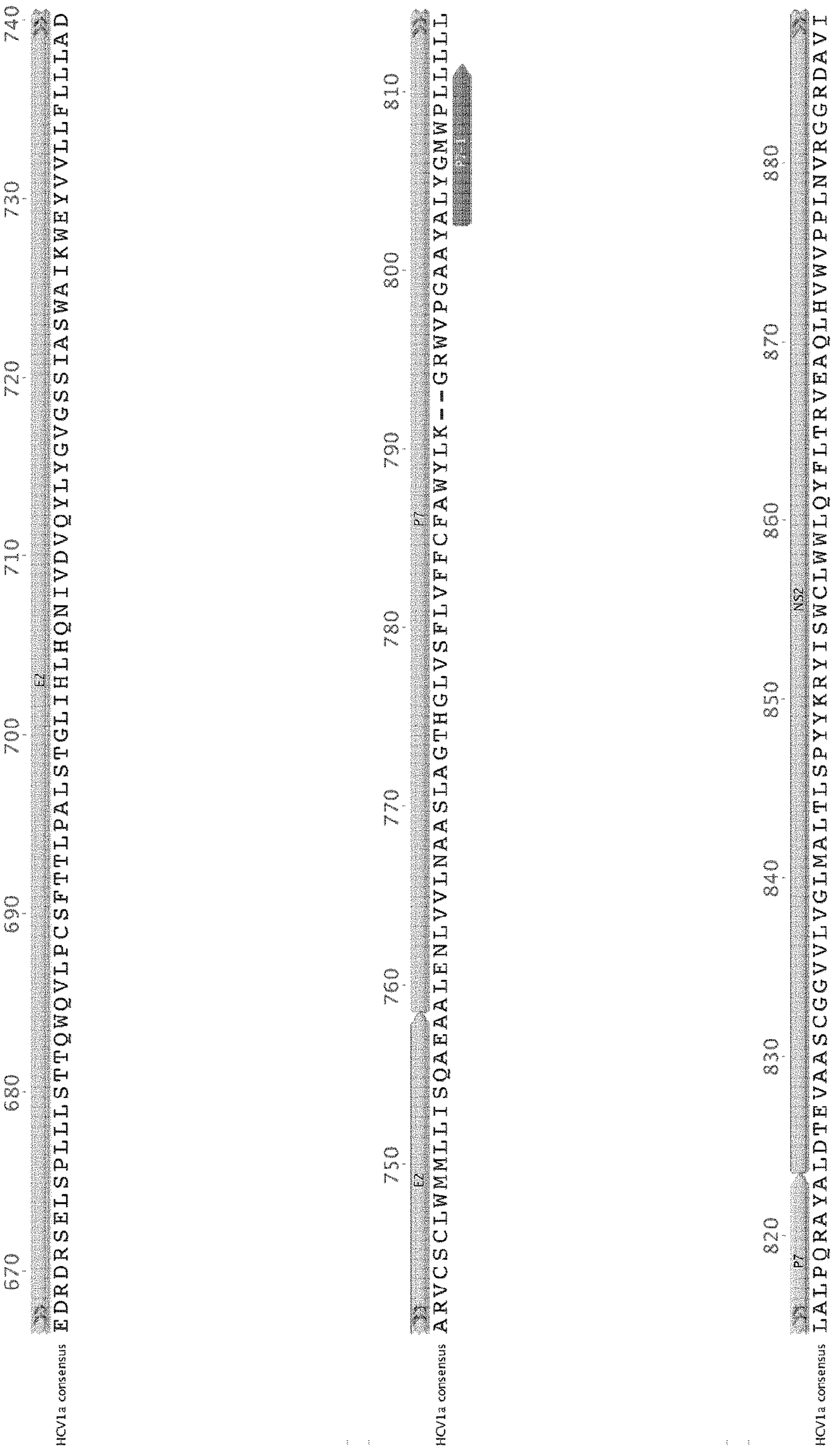
Figure 11E:
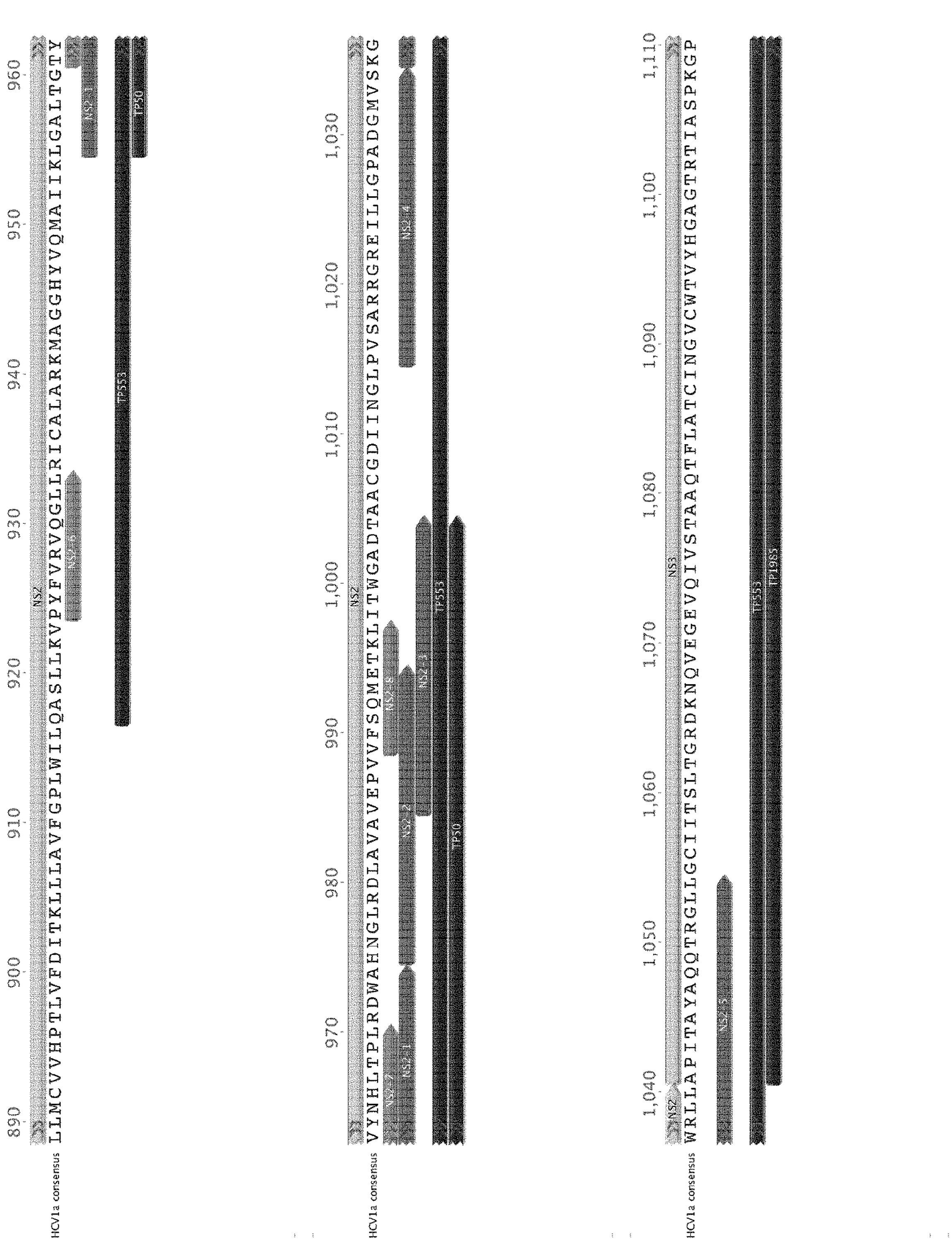
Figure 11F:
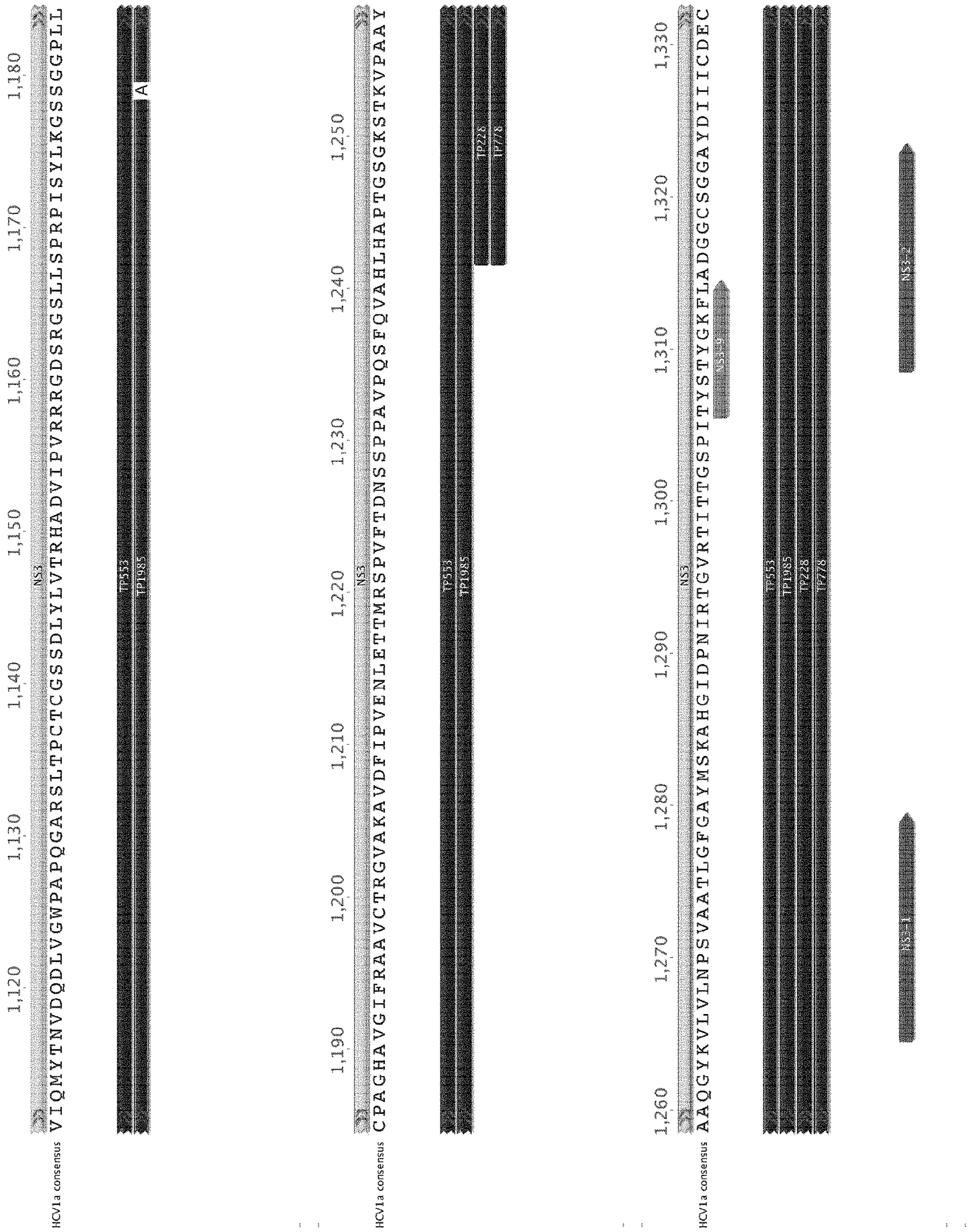
Figure 11G:
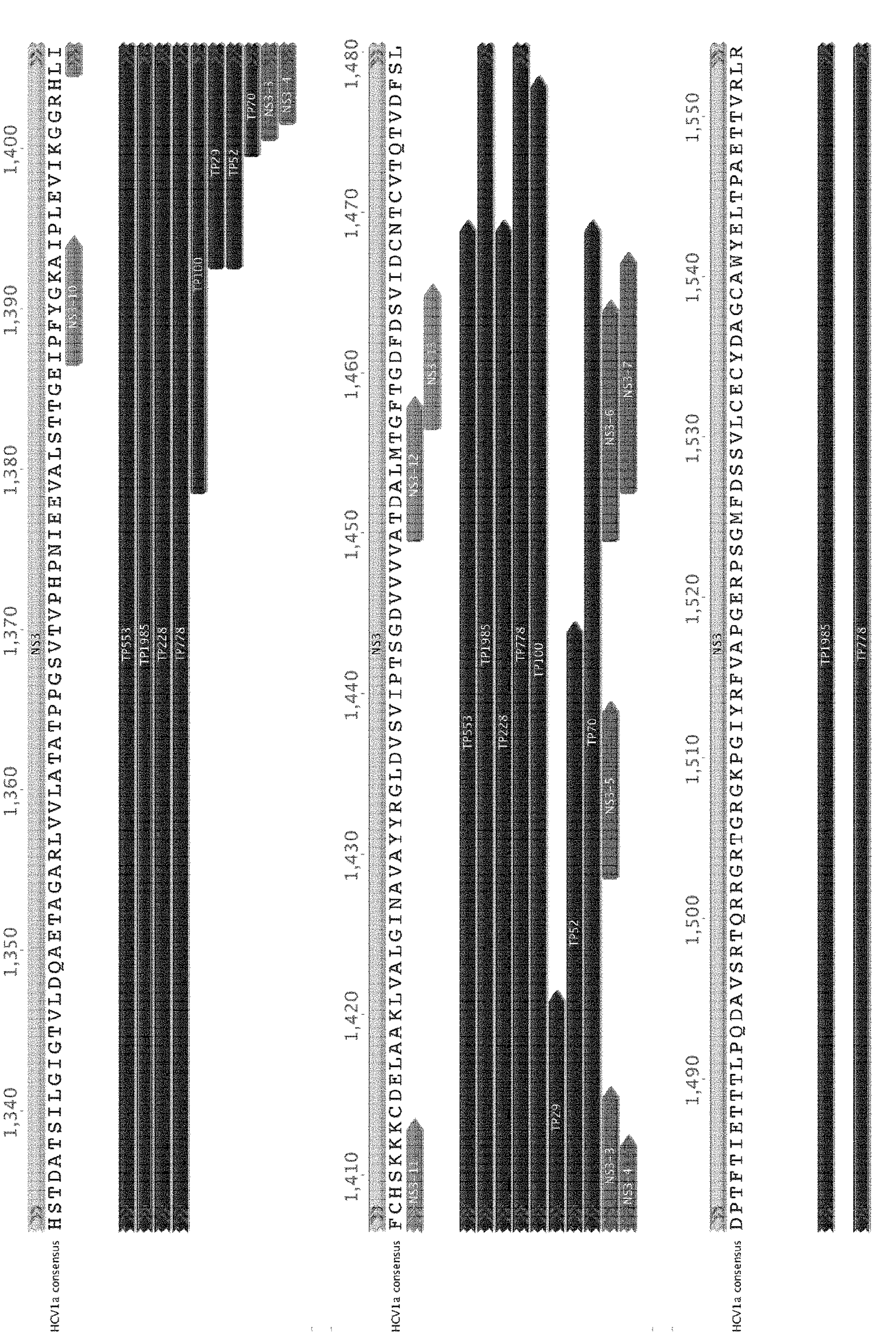
Figure 11H:
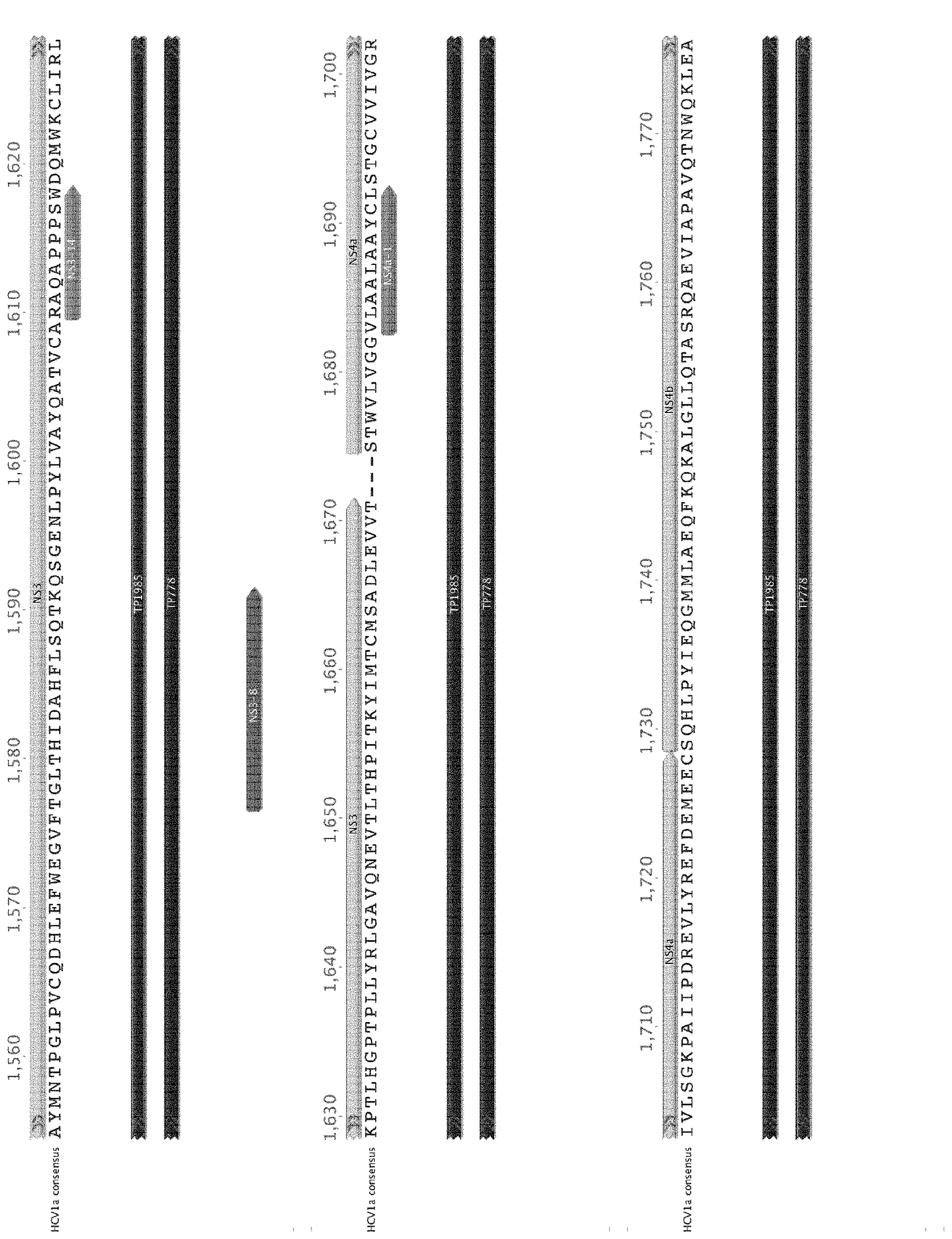
Figure 11I:
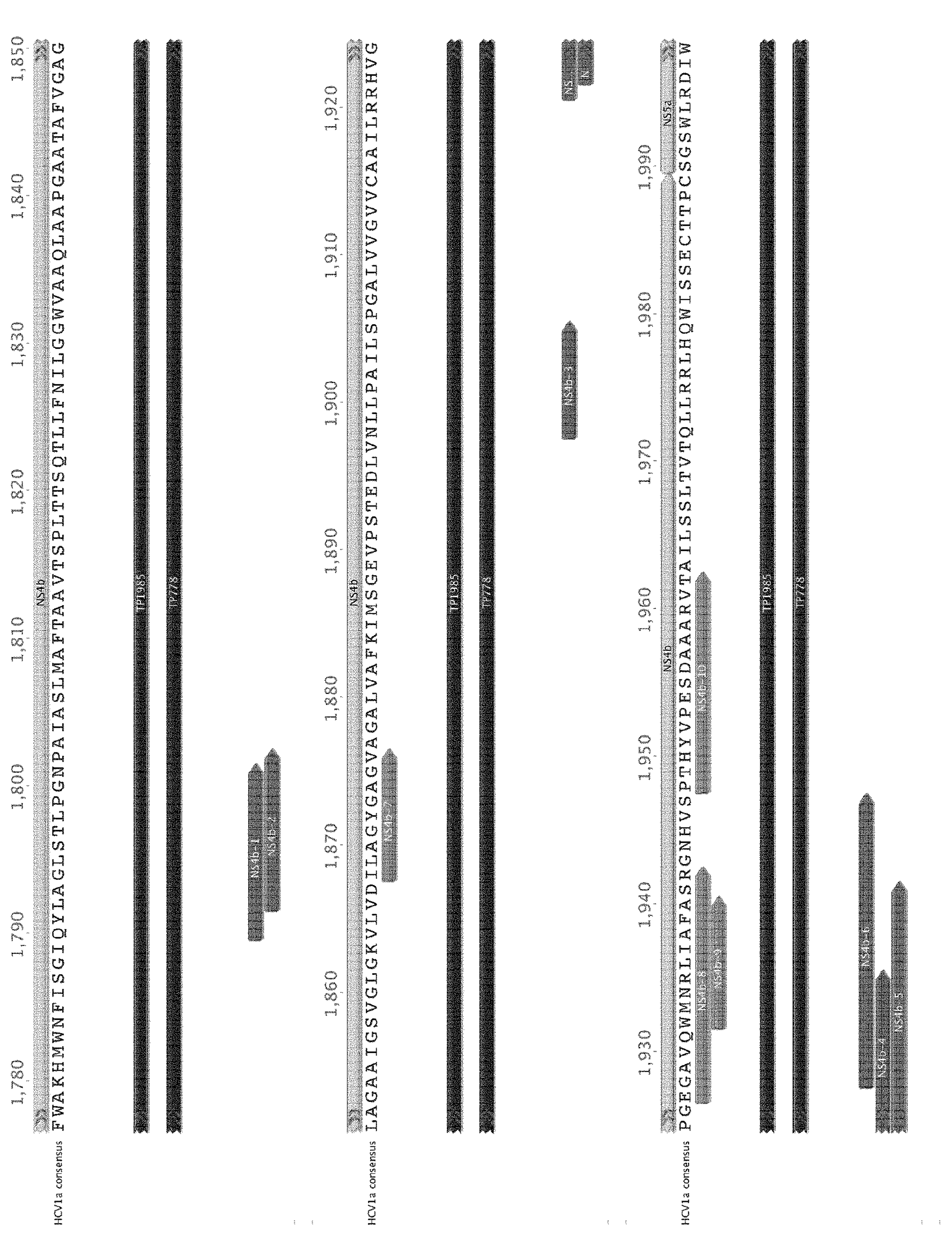
Figure 11J:
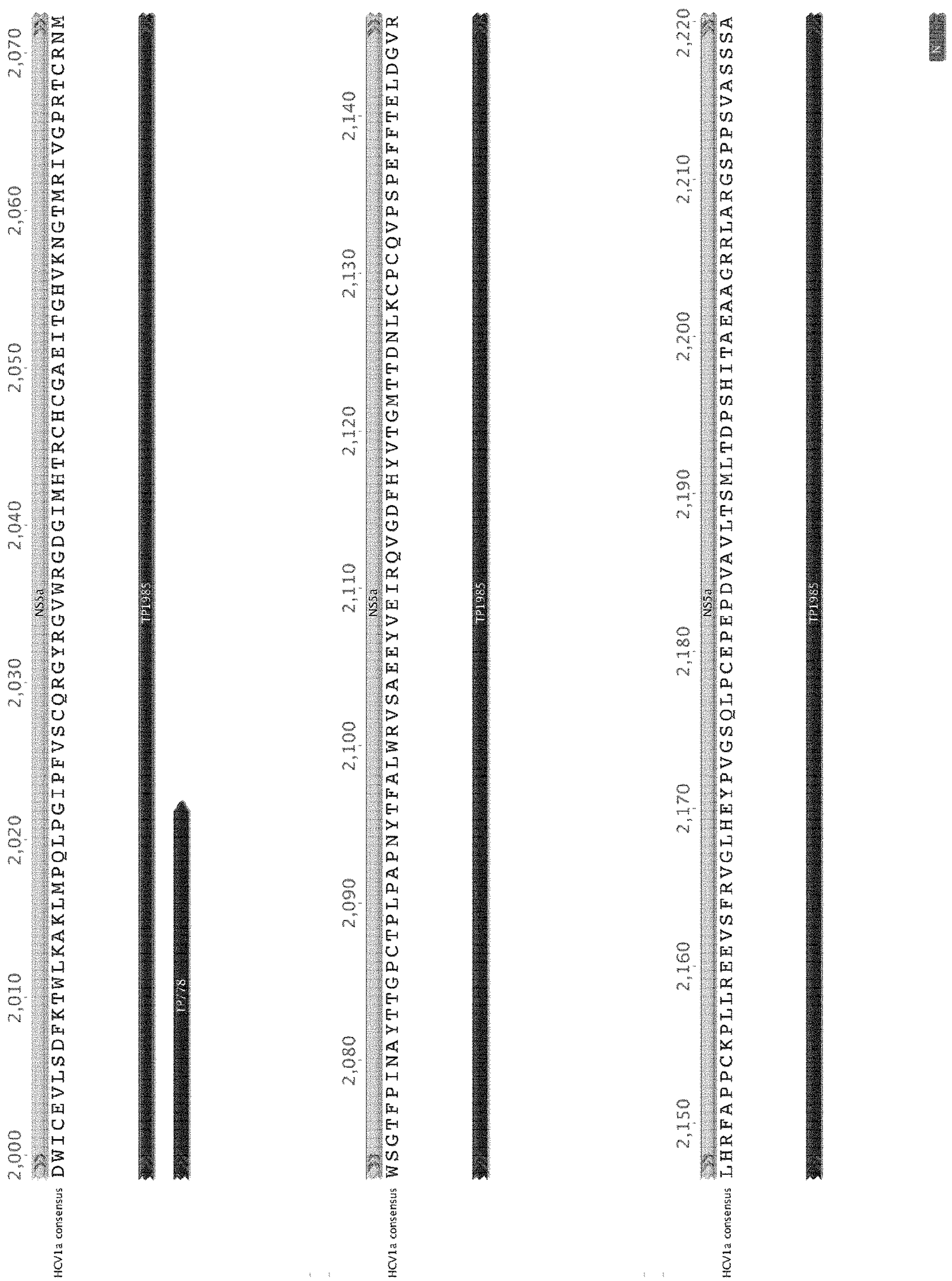
Figure 11K:
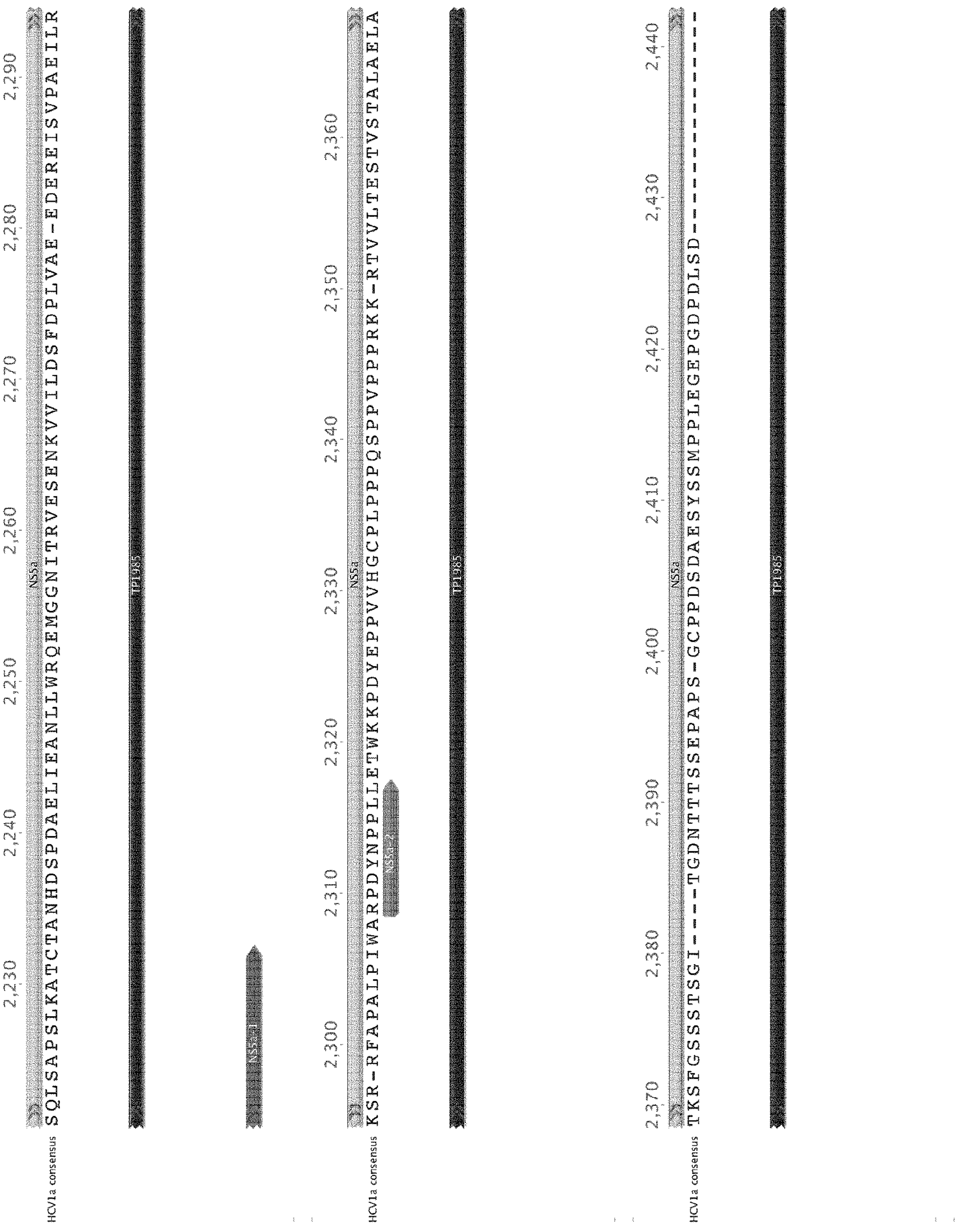
Figure 11L:
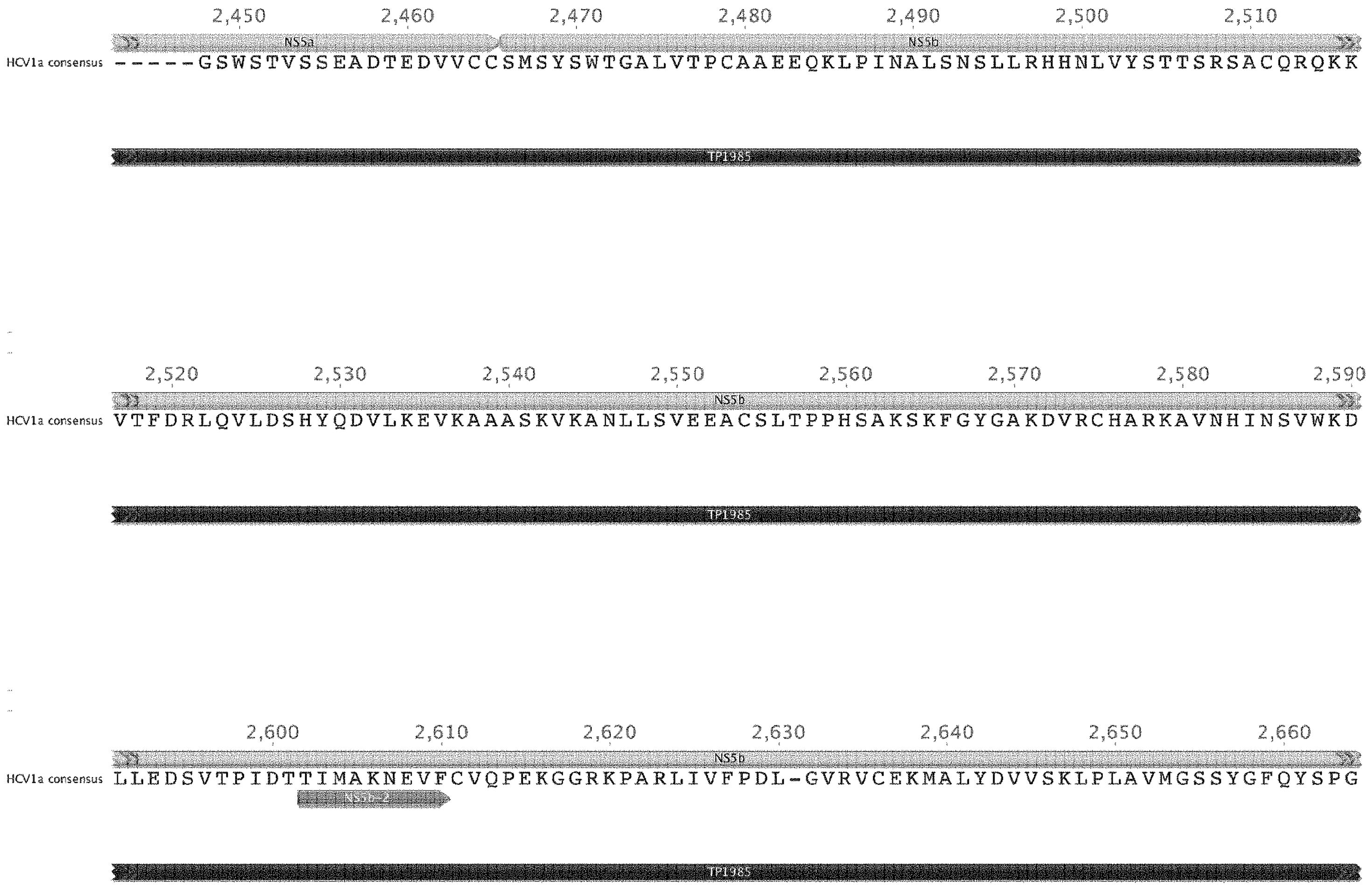
Figure 11M:
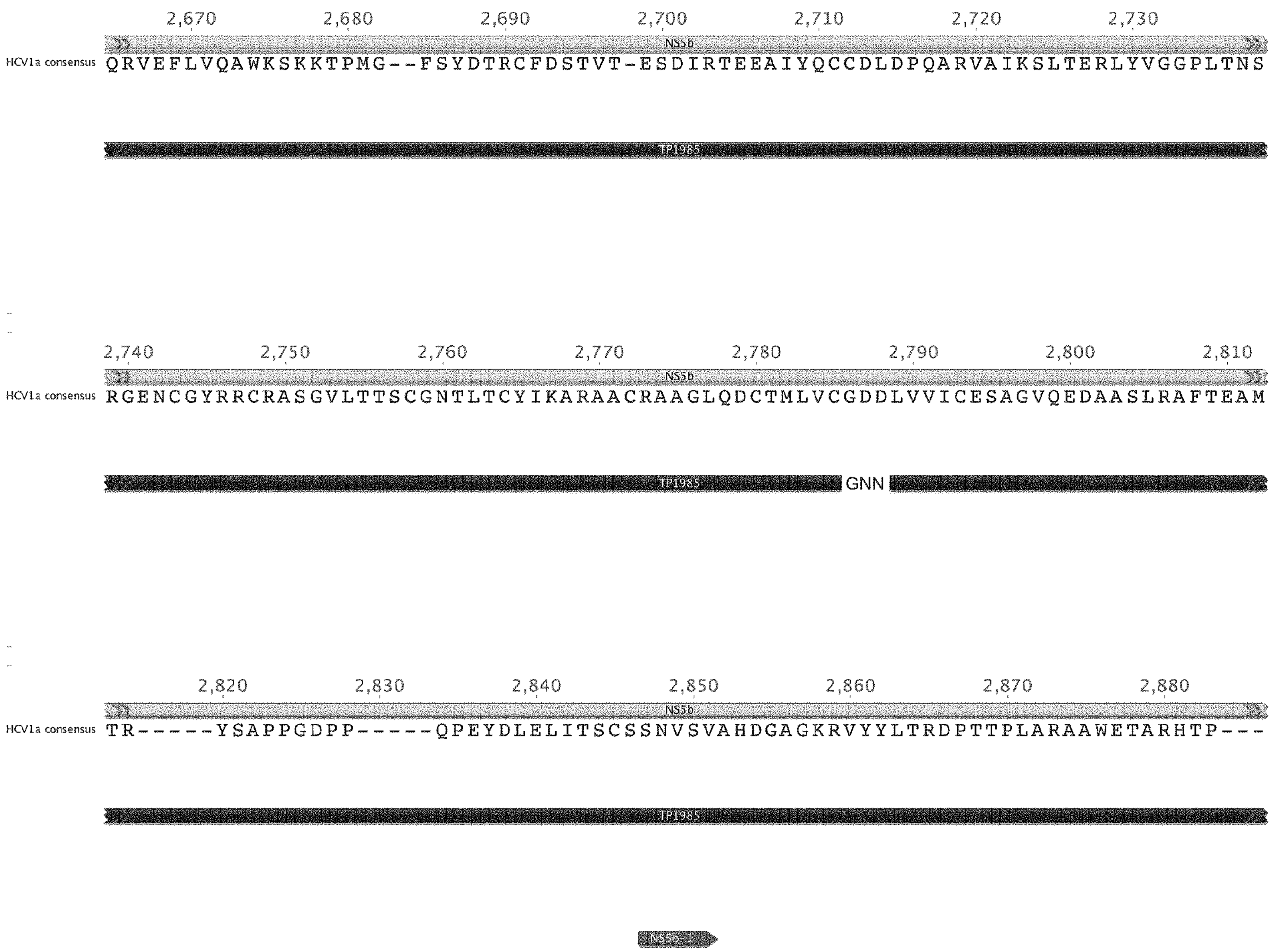
Figure 11N:
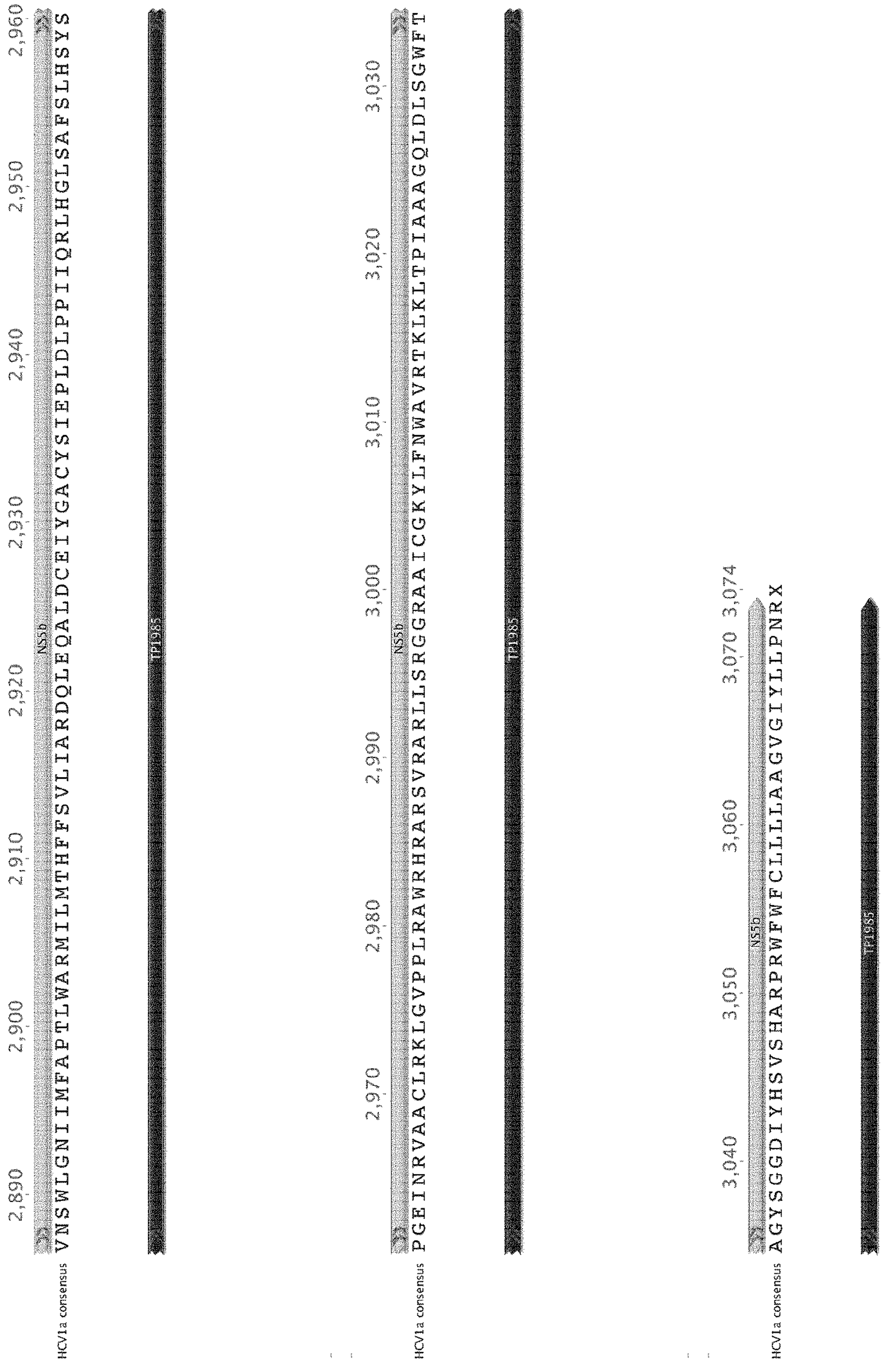

FIGS. 11A-11N provide consensus amino acid sequences of HCV polypeptides; and depict the locations of T-cell epitopes (SEQ ID NO:95).

FIG. 12A-12L provide consensus amino acid sequences of HCV polypeptides (SEQ ID NOs.96-107).

Figure 13:
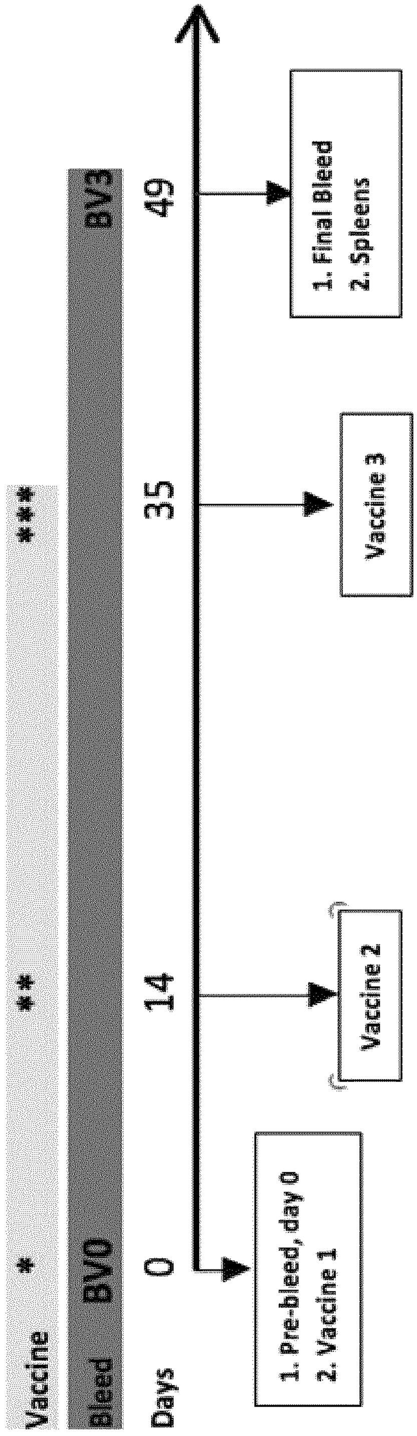

FIG. 13 depicts the experimental protocol.

Figure 14:
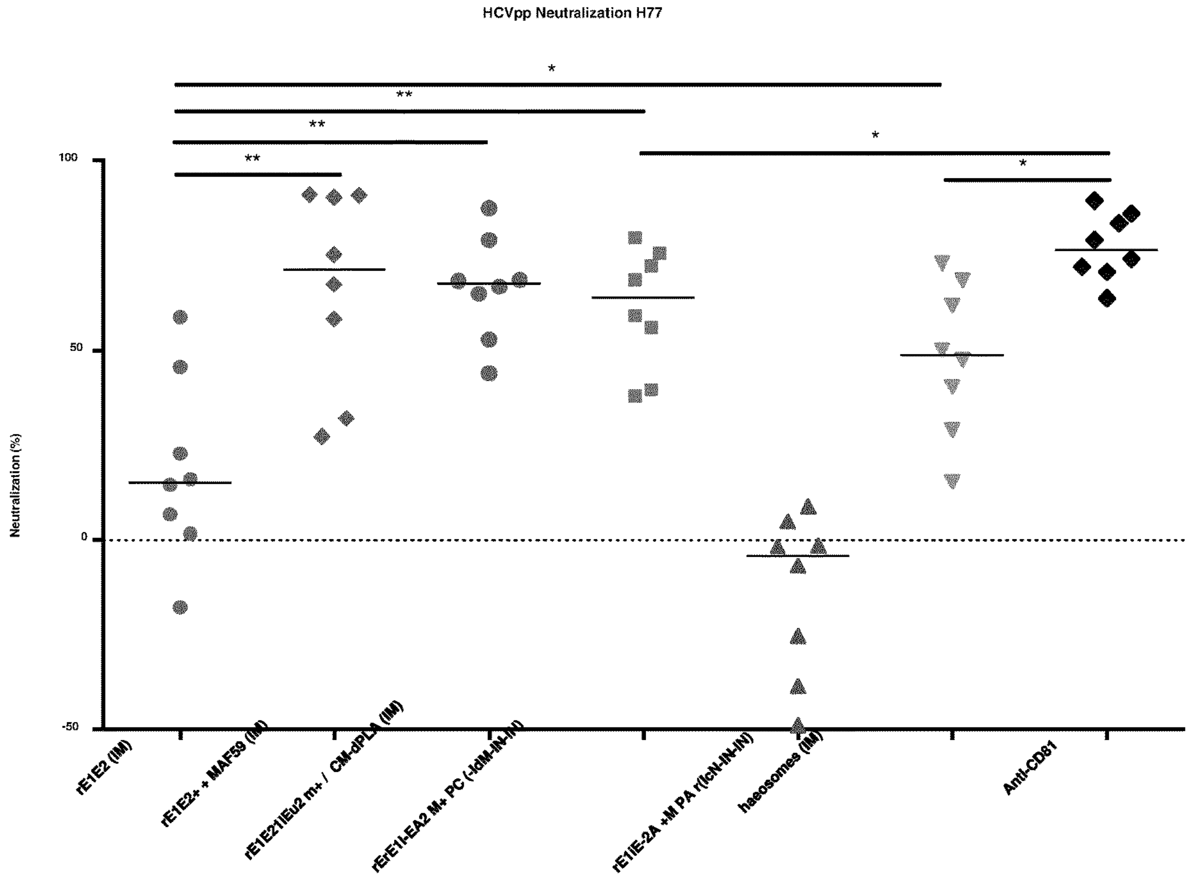

FIG. 14 depicts neutralization activity of recombinant E1E2 (rE1E2), in combination with adjuvant, in mice.

Figure 15:
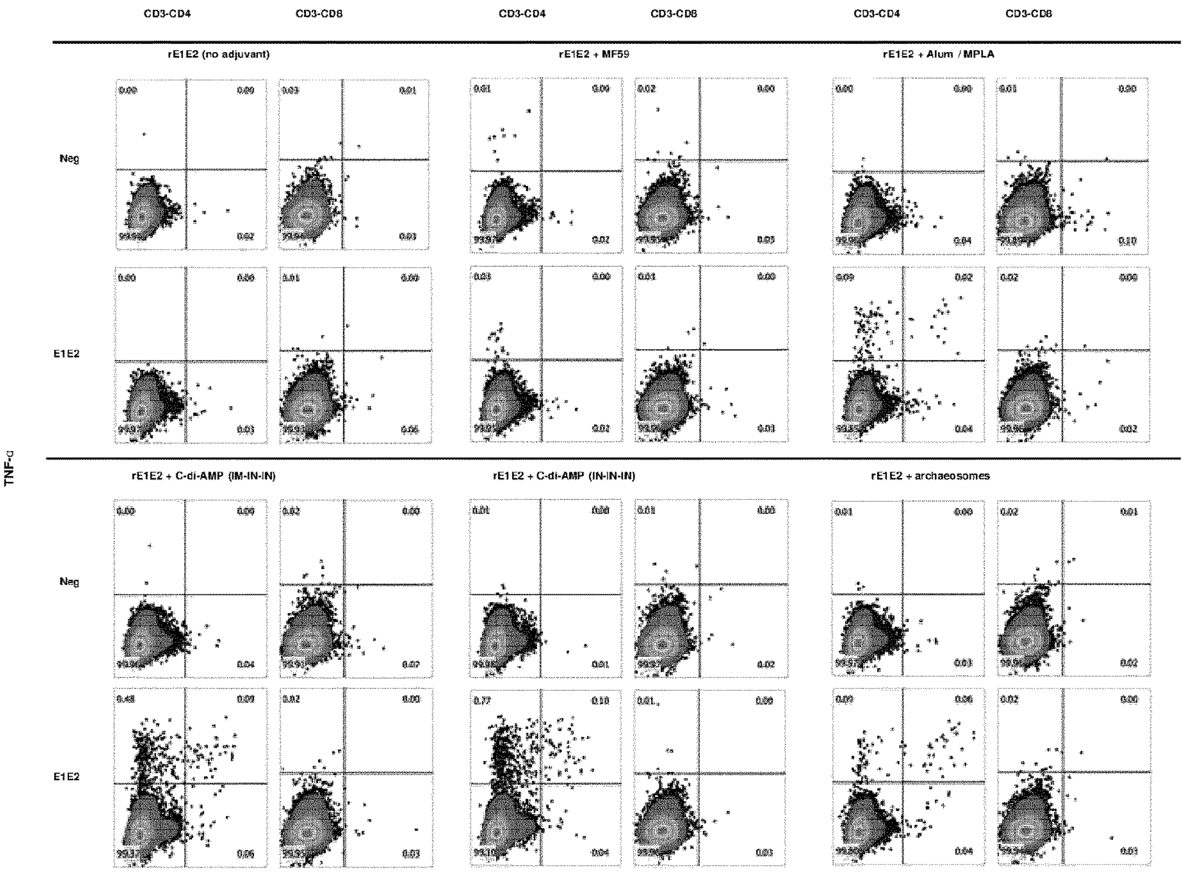

FIG. 15 depicts differential detection of T cell immune responses in mice.

DEFINITIONS

The term "hepatitis C virus" ("HCV"), as used herein, refers to any one of a number of different genotypes and isolates of hepatitis C virus. Thus, "HCV" encompasses any of a number of genotypes, subtypes, or quasispecies, of HCV, including, e.g., genotype 1, 2, 3, 4, 6, 7, etc. and subtypes (e.g., 1a, 1b, 2a, 2b, 3a, 4a, 4c, etc.), and quasispecies. Representative HCV genotypes and isolates include: the "Chiron" isolate HCV-1, H77, J6, Con1, isolate 1, BK, EC1, EC10, HC-J2, HC-J5; HC-J6, HC-J7, HC-J8, HC-JT, HCT18, HCT27, HCV-476, HCV-KF, "Hunan", "Japanese", "Taiwan", TH, type 1, type 1a, H77 type 1b, type 1c, type 1d, type 1e, type 1f, type 10, type 2, type 2a, type 2b, type 2c, type 2d, type 2f, type 3, type 3a, type 3b, type 3g, type 4, type 4a, type 4c, type 4d, type 4f, type 4h, type 4k, type 5, type 5a, type 6 and type 6a.

The terms "individual," "host," "subject," and "patient" are used interchangeably herein, and refer to a mammal, including, but not limited to, non-human primates (e.g., simians), equines (e.g., horses), rodents (e.g., rats; mice), and humans.

As used herein, the term "isolated," in reference to a polypeptide, refers to a polypeptide that is in an environment different from that in which the polypeptide naturally occurs. An isolated polypeptide can be purified. By "purified" is meant a compound of interest (e.g., a polypeptide) has been separated from components that accompany it in nature. "Purified" can also be used to refer to a polypeptide separated from components that can accompany it during production of the polypeptide (e.g., during synthesis in vitro, etc.). In some embodiments, a polypeptide (or a mixture of polypeptides) is substantially pure when the polypeptide (or mixture of polypeptides) is at least 60% or at least 75% by weight free from organic molecules with which it is naturally associated or with which it is associated during production. In some embodiments, the polypeptide is from 30% to 60% pure. In some embodiments, the polypeptide (or mixture of polypeptides) is at least 60%, at least 75%, at least 80%, at least 85%, at least 90%, at least 95%, or at least 99%, by weight, pure. For example, in some embodiments, an E1 or an E2 polypeptide (or a mixture of E1 and E2 polypeptides, e.g., an E1/E2 heterodimer) is substantially pure when the E1 or E2 polypeptide (or mixture of E1 and E2 polypeptides) is at least 60% or at least 75% by weight free from organic molecules with which the polypeptide(s) is naturally associated or with which it is associated during production. In some embodiments, the E1 or E2 polypeptide (or mixture of E1 and E2 polypeptides) is at least 60%, at least 75%, at least 80%, at least 85%, at least 90%, at least 95%, or at least 99%, by weight, pure. In some embodiments, where a composition comprises an E2 polypeptide, the E2 polypeptide is at least 60%, at least 75%, at least 80%, at least 85%, at least 90%, at least 95%, or at least 99%, by weight, pure. In some embodiments, where a composition comprises an E1/E2 heterodimeric complex polypeptide, the E1/E2 heterodimeric complex polypeptide is at least 60%, at least 75%, at least 80%, at least 85%, at least 90%, at least 95%, or at least 99%, by weight, pure. In some embodiments, where a composition comprises a T-cell epitope polypeptide, the T-cell epitope polypeptide is at least 60%, at least 75%, at least 80%, at least 85%, at least 90%, at least 95%, or at least 99%, by weight, pure.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. In some cases, a polynucleotide is RNA. In some cases, a polynucleotide is DNA. A "polynucleotide" includes a nucleic acid that is incorporated into a viral vector or a bacterial vector.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term "polypeptide" includes glycosylated polypeptides.

The term "heterologous" refers to two components that are defined by structures derived from different sources. For example, where "heterologous" is used in the context of a polypeptide, where the polypeptide includes operably linked amino acid sequences that can be derived from one or more different polypeptides, e.g., amino acid sequences that are not operably linked to the polypeptide in nature. As another example, where a composition comprises an HCV E1/E2 heterodimer and a "heterologous" polypeptide, the "heterologous polypeptide is a polypeptide other than HCV E1 or HCV E2. As another example, where a composition comprises an HCV E1 polypeptide and a "heterologous" polypeptide, the "heterologous polypeptide is a polypeptide other than HCV E1. As another example, where a composition comprises an HCV E2 polypeptide and a "heterologous" polypeptide, the "heterologous polypeptide is a polypeptide other than HCV E2.

The term "archaeal lipid" refer to a polar lipid common to the Domain Archaea typified by isoprenoid chains in ether linkage to the sn-2,3 carbons of the glycerol backbone.

Archaeal core lipids are most commonly 2,3-di-O-sn-diphytanylglycerol (archaeol), and 2,2',3,3'-tetra-O-dibiphytanyl-sn-diglycerol (caldarchaeol).

Synthetic archaeal lipids or polar synthetic lipids refer to core lipid precursors either derived from Archaeal lipids by hydrolysis or made by chemical synthesis, conjugated to at least one new head group.

Archaeol phospholipids are referred herein to using archaetidyl, for example, AG, archaetidylglycerol; AS, archaetidylserine.

The term "conventional lipids" refers to the lipids common to the Domains Bacteria and Eukarya. This includes polar lipids typified by fatty acyl chains in ester linkage to the sn-1,2 carbons of the glycerol backbone, and neutral lipids such as cholesterol. Conventional phospholipids are referred to in the usual way, for example, DPPG, dipalmitoylphosphatidylglycerol; DPPS, dipalmitoylphosphatidylserine.

The term "archaeosome" refers to a closed lipid vesicle that contains any amount of synthetic archaeal lipid(s).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an HCV E1E2 heterodimer" includes a plurality of such heterodimer and reference to "the cyclic dinucleotide" includes reference to one or more cyclic dinucleotides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides immunogenic compositions comprising: a) hepatitis C virus (HCV) E1E2 heterodimers, HCV E2, or HCV E1; and b) an adjuvant, where the adjuvant is a cyclic dinucleotide or an archaeosome. The present disclosure provides methods of inducing an immune response in an individual to HCV, the methods comprising administering to an individual an effective amount of an immunogenic composition of the present disclosure.

Immunogenic Compositions Comprising HCV E1E2, E2, or E1 Polypeptide+Cyclic Dinucleotide The present disclosure provides an immunogenic composition comprising: a) an HCV E1E2 heterodimer; and b) a cyclic dinucleotide (CDN). The present disclosure provides an immunogenic composition comprising: a) an HCV E2 polypeptide; and b) a CDN. The present disclosure provides an immunogenic composition comprising: a) an HCV E1 polypeptide; and b) a CDN.

In some cases, an immunogenic composition of the present disclosure, when administered to an individual in need thereof, induces an immune response in the individual to one or more HCV genotypes. In some cases, an immunogenic composition of the present disclosure, when administered to an individual in need thereof, induces an immune response in the individual to one or more HCV genotypes, where the immune response is greater than the immune response induced by administration of a control composition comprising the HCV E1/E2 heterodimer (or E1 polypeptide, or E2 polypeptide) but lacking the CDN.

In some cases, an immunogenic composition of the present disclosure, when administered to an individual in need thereof, induces $CD8^+$ CTLs specific for HCV, where the number of HCV-specific $CD8^+$ CTLs induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific $CD8^+$ CTLs induced by administration of a control composition (e.g., a composition comprising the HCV E1/E2 heterodimer but lacking the CDN; a composition comprising an E1 polypeptide but lacking the CDN; a composition comprising an E2 polypeptide but lacking the CDN).

In some cases, an immunogenic composition of the present disclosure, when administered to an individual in need thereof, induces $CD4^+$ T cells specific for HCV, where the number of HCV-specific $CD4^+$ T cells induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific $CD4^+$ T cells induced by administration of a control composition (e.g., a composition comprising the HCV E1/E2 heterodimer but lacking the CDN; a composition comprising an E1 polypeptide but lacking the CDN; a composition comprising an E2 polypeptide but lacking the CDN).

In some cases, an immunogenic composition of the present disclosure, when administered to an individual in need thereof, induces production of HCV-specific $CD4^+$ T cells and $CD8^+$ T cells in the individual, where the number of HCV-specific $CD4^+$ T cells and/or $CD8^+$ T cells is increased, such that the percent of total peripheral $CD4^+$ and/or $CD8^+$ T cells that is HCV-specific is from 0.01% to 0.05%, from 0.05% to 0.10%, from 0.10% to 0.125%, from 0.125% to 0.25%, from 0.25% to from 0.50%, or 0.5% to 10% (e.g., from 0.5% to 1%, from 1% to 2%, from 2% to 5%, or from 5% to 10%). The number of HCV-specific $CD4^+$ T cells and $CD8^+$ T cells in a control individual (e.g., an individual not infected with HCV) not treated with the immunogenic composition would be undetectable.

In some cases, an immunogenic composition of the present disclosure, when administered to an individual in need thereof, increases the number of HCV E1/E2-specific $CD4^+$ T cells and $CD8^+$ T cells in the individual by at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, compared to the number of HCV E1/E2-specific $CD4^+$ T cells and $CD8^+$ T cells in the individual induced by administration of a control composition comprising the HCV E1/E2 heterodimer (or HCV E2 polypeptide, or HCV E1 polypeptide) but lacking the CDN, or compared to the number of HCV E1/E2-specific CD4 T cells and $CD8^+$ T cells in the individual before administration of the immunogenic composition.

In some cases, an immunogenic composition of the present disclosure, when administered to an individual in need thereof, induces helper T lymphocytes (e.g., $CD4^+$ T cells) specific for HCV, where the number of HCV-specific helper T lymphocytes induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific helper T cells induced by administration of a control composition comprising the HCV E1/E2 heterodimer (or HCV E2 polypeptide, or HCV E1 polypeptide) but lacking the CDN, or compared to the number of HCV-specific $CD4^+$ T cells in the individual before administration of the immunogenic composition.

In some cases, an immunogenic composition of the present disclosure, when administered to an individual in need thereof, induces antibody specific for HCV, where the level of HCV-specific antibody induced is at least at high as the level of HCV-specific antibody induced by administration of a control composition comprising the HCV E1/E2 heterodimer (or HCV E2 polypeptide, or HCV E1 polypeptide) but lacking the CDN.

In some cases, an immunogenic composition of the present disclosure, when administered to an individual in need thereof, induces antibody specific for HCV, where the level of HCV-specific antibody induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the level of HCV-specific antibody induced by administration of a control composition comprising the HCV E1/E2 heterodimer (or HCV E2 polypeptide, or HCV E1 polypeptide) but lacking the CDN, or compared the level of HCV-specific antibody in the individual before administration of the immunogenic composition.

An immunogenic composition of the present disclosure, when administered to an individual in need thereof, induces an immune response (e.g., a cellular immune response) in the individual to one or more HCV genotypes. In some cases, an immunogenic composition of the present disclosure, when administered to an individual in need thereof, induces an immune response in the individual to HCV genotype 1. In some cases, an immunogenic composition of the present disclosure, when administered to an individual in need thereof, induces an immune response in the individual to HCV genotype 2. In some cases, an immunogenic composition of the present disclosure when administered to an individual in need thereof, induces an immune response in the individual to HCV genotype 3. In some cases, an immunogenic composition of the present disclosure, when administered to an individual in need thereof, induces an immune response in the individual to HCV genotype 1 and HCV genotype 3. In some cases, an immunogenic composition of the present disclosure, when administered to an individual in need thereof, induces an immune response in the individual to HCV genotype 1, HCV genotype 2, and HCV genotype 3. In some cases, an immunogenic composition of the present disclosure, when administered to an individual in need thereof, induces an immune response in the individual to HCV genotype 1, HCV genotype 2, HCV genotype 3, and HCV genotype 7. In some cases, an immunogenic composition of the present disclosure, when administered to an individual in need thereof, induces an immune response in the individual to HCV genotype 1, HCV genotype 2, HCV genotype 3, HCB genotype 4, HCV genotype 5, HCV genotype 6, and HCV genotype 7.

HCV E1/E2 Heterodimers: HCV E2 Polypeptides: HCV E1 Polypeptides

HCV E1/E2 heterodimers suitable for use in an immunogenic composition of the present disclosure include HCV E1/E2 heterodimers comprising wild-type HCV E1 polypeptides; HCV E1/E2 heterodimers comprising wild-type HCV E2 polypeptides; HCV E1/E2 heterodimers comprising variant HCV E1 polypeptides; and HCV E1/E2 heterodimers comprising variant HCV E2 polypeptides. HCV E2 polypeptides suitable for use in an immunogenic composition of the present disclosure include wild-type E2 polypeptides and variant E2 polypeptides. HCV E1 polypeptides suitable for use in an immunogenic composition of the present disclosure include wild-type E1 polypeptides and variant E1 polypeptides.

E2 polypeptides

An E2 polypeptide suitable for inclusion in an E1/E2 heterodimer for inclusion in an immunogenic composition of the present disclosure, or for inclusion by itself in an immunogenic composition of the present disclosure, can have a length of from about 200 amino acids (aa) to about 250 aa, from about 250 aa to about 275 aa, from about 275 aa to about 300 aa, from about 300 aa to about 325 aa, from about 325 aa to about 350 aa, or from about 350 aa to about 365 aa. In some cases, an HCV E2 polypeptide suitable for inclusion in an immunogenic composition of the present disclosure is an HCV E2 ectodomain polypeptide. In some cases, an HCV E2 polypeptide suitable for inclusion in an immunogenic composition of the present disclosure is a full-length HCV E2 polypeptide.

Figure 1A:
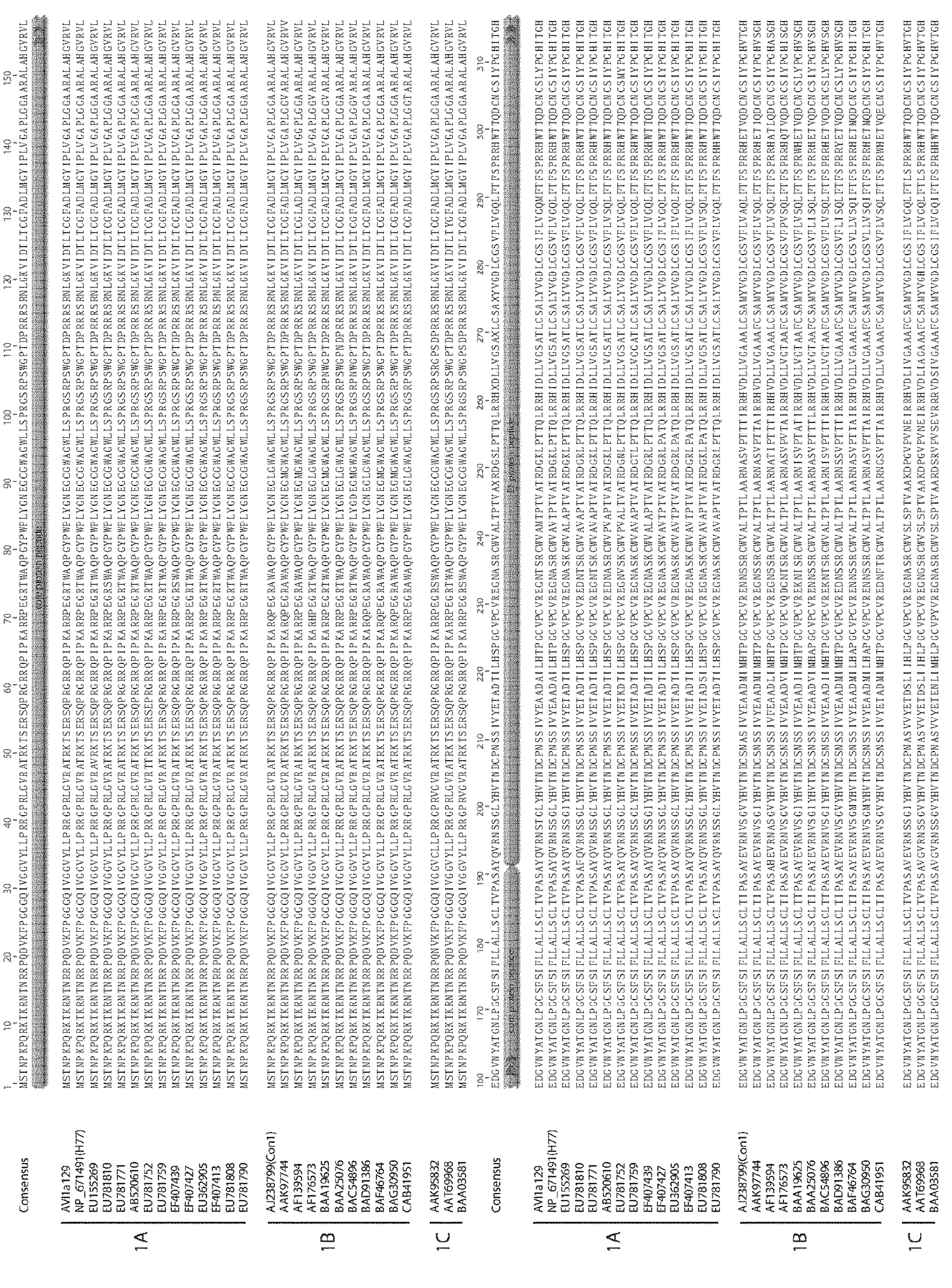
Figure 2A:
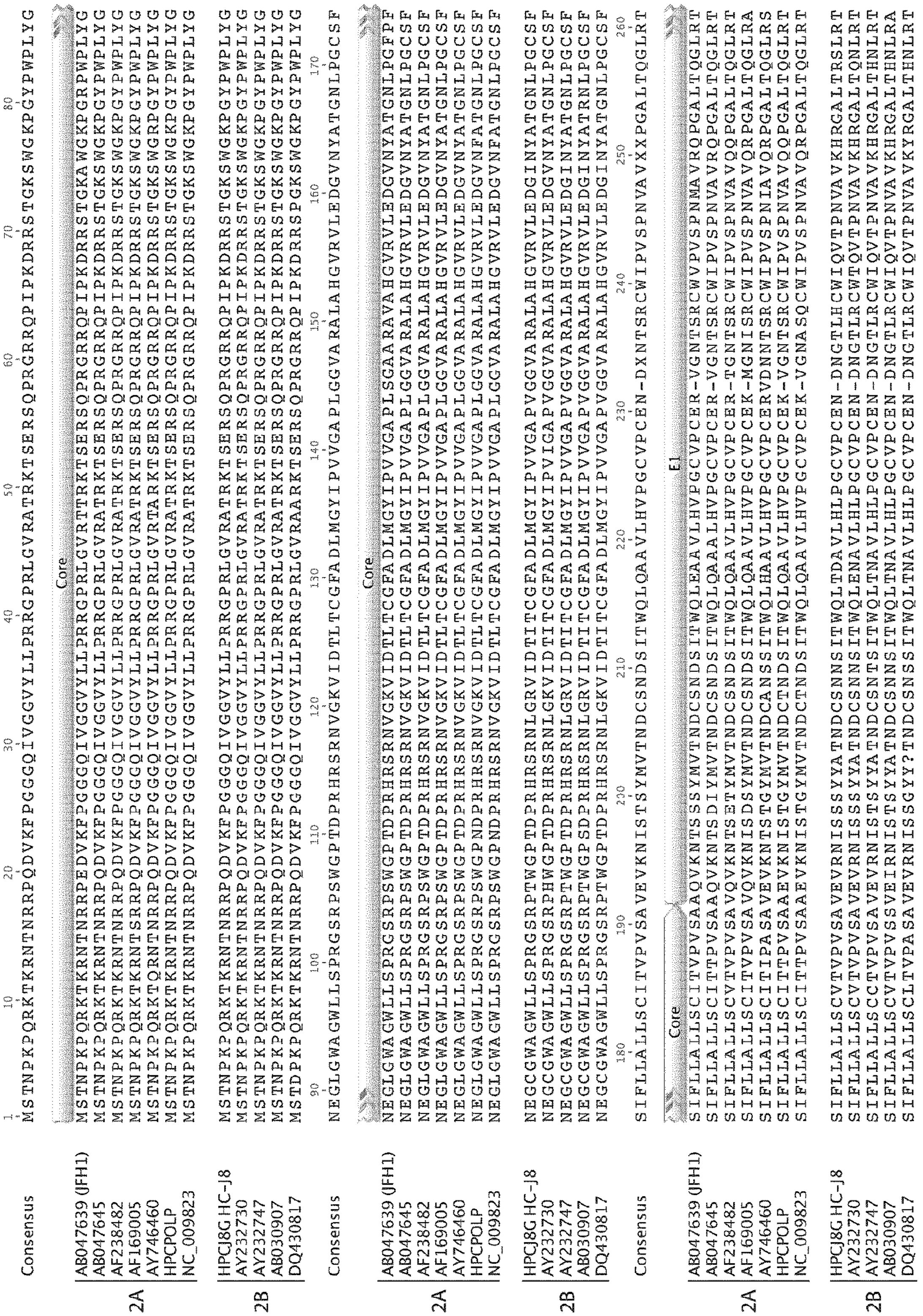
Figure 3A:
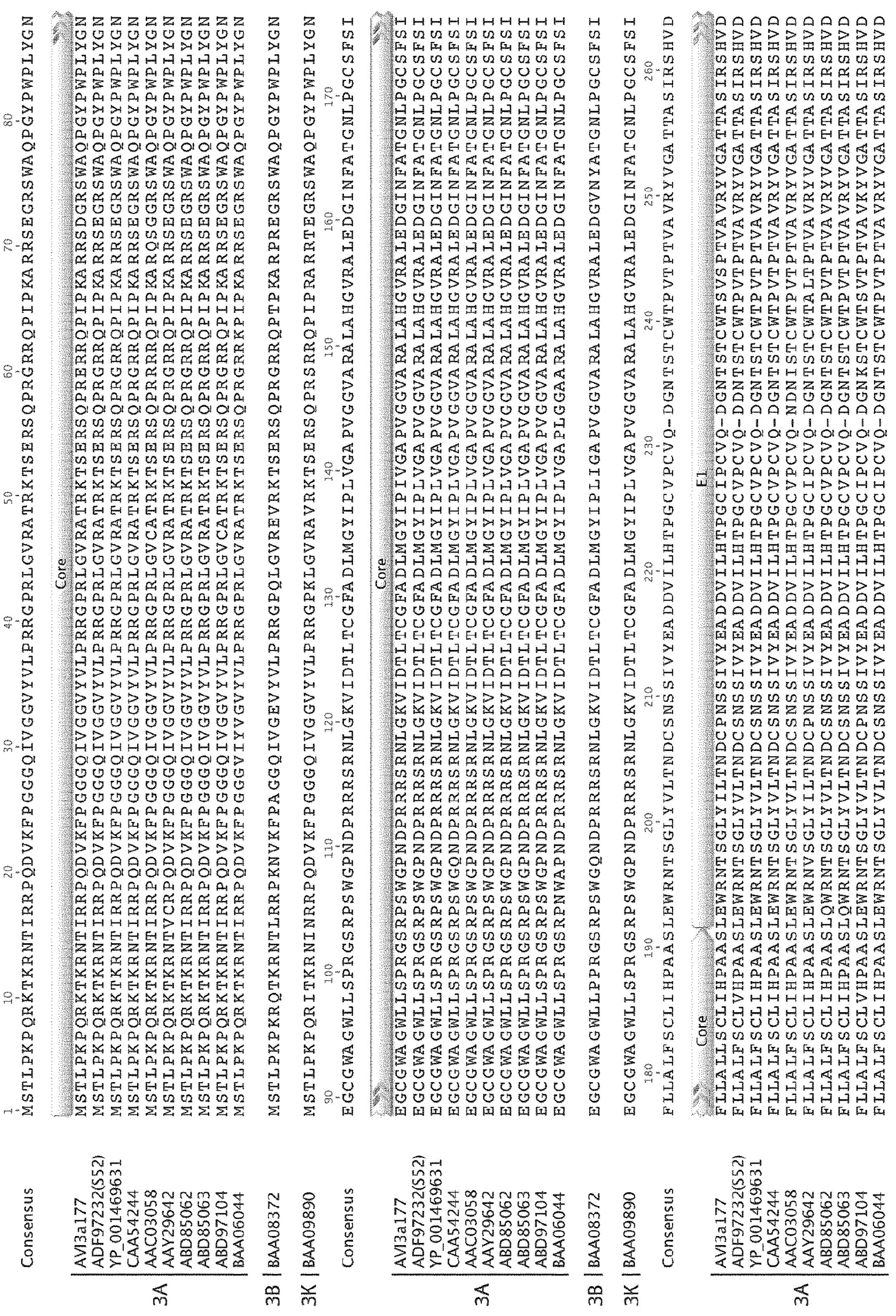
Figure 4A:
FIG. 4A-4B provide an amino acid sequence of the core-E1-E2 coding region for HCV genotype 7a. Amino acid sequence for the coding region core-E1-E2 of genotype 7a (isolate QC69; Genbank: ABN05226.1; SEQ ID NO:55) is shown according to the numbering scheme of the reference strain, NP_671941 (H77).
Figure 4B:
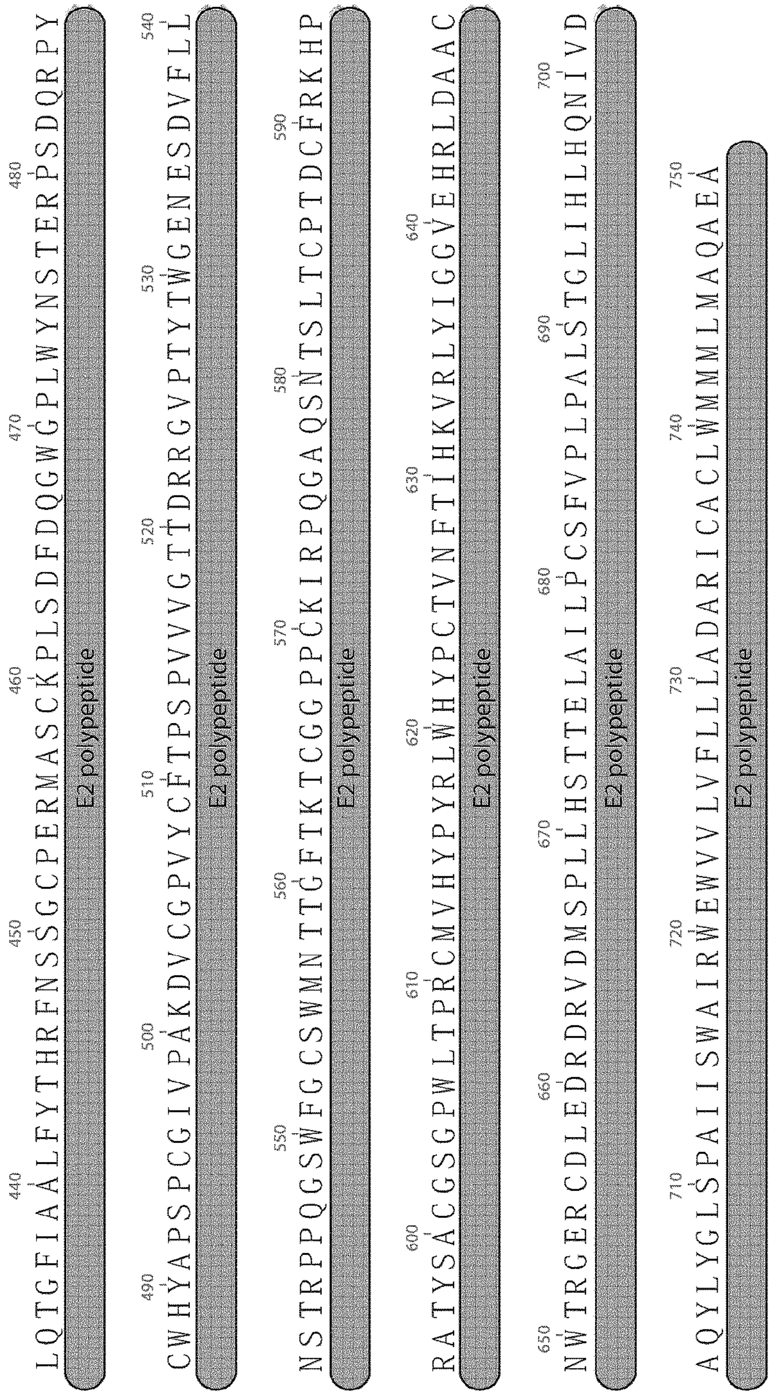

In FIG. 1A-AC, the amino acid sequence of E2 is amino acid 384 to amino acid 746. In FIG. 2A-2B, the amino acid sequence of E2 is amino acid 384 to amino acid 751. In FIG. 3A-3C, the amino acid sequence of E2 is amino acid 385 to amino acid 754. In FIG. 4A-4B, the amino acid sequence of E2 is amino acid 384 to amino acid 750. As used herein, an "E2 polypeptide" includes a precursor E2 protein, including the signal sequence; includes a mature E2 polypeptide which lacks this sequence; and includes an E2 polypeptide with a heterologous signal sequence. An E2 polypeptide can include a C-terminal membrane anchor sequence which occurs at approximately amino acid positions 715-730 and may extend as far as approximately amino acid residue 746 (see, Lin et al., J. Virol. (1994) 68:5063-5073).

Figure 1B:
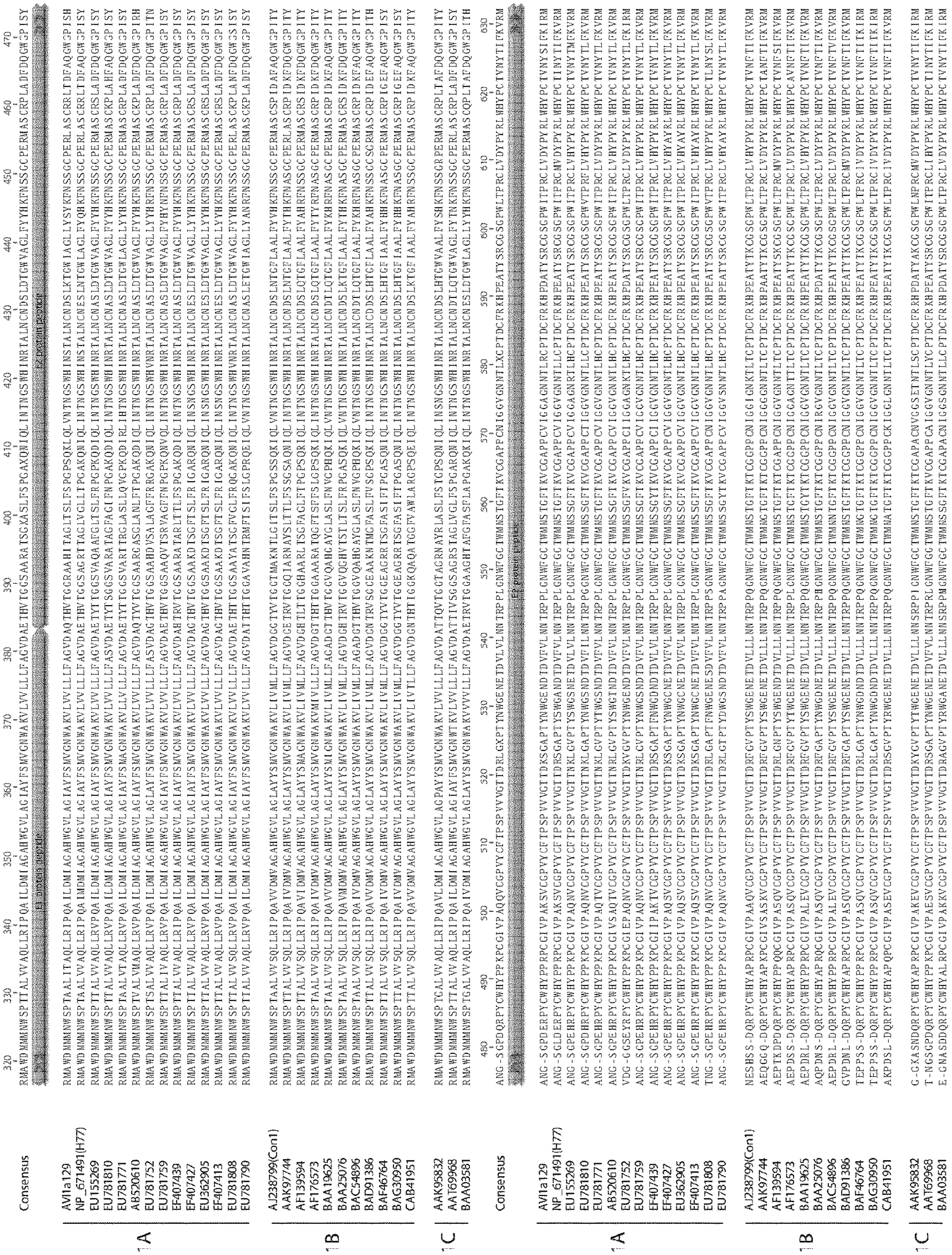

In some cases, a E2 polypeptide suitable for inclusion in an immunogenic composition of the present disclosure lacks a portion of its C-terminal region, e.g., from about amino acid 715 to the C-terminus; from about amino acid 625 to the C-terminus; from about amino acid 661 to the C-terminus; from about amino acid 655 to the C-terminus; from about amino acid 500 to the C-terminus, where the amino acid numbering is with reference to the numbering in FIG. 1A-1C. See, e.g., U.S. Pat. No. 6,521,423.

An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 1A-1C, FIG. 2A-2C, FIG. 3A-3C, or FIG. 4A-4B. An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, or at least about 75%, amino acid sequence identity to an amino acid sequence of an E2 polypeptide depicted in FIG. 1A-1C, FIG. 2A-2C, FIG. 3A-3C, or FIG. 4A-4B.

An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 1A-1C. For example, an E2 polypeptide of genotype 1 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence depicted in FIG. 1A-IC. For example, an E2 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1A and depicted in FIG. 1A-1C. For example, an E2 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1B and depicted in FIG. 1A-1C. For example, an E2 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1C and depicted in FIG. 1A-IC.

An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 2A-2C. For example, an E2 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of an amino acid sequence depicted in FIG. 2A-2C. For example, an E2 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIG. 2A-2C. For example, an E2 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIG. 2A-2C.

An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 3A-3C. For example, an E2 polypeptide of genotype 3 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence depicted in FIG. 3A-3C. For example, an E2 polypeptide of genotype 3A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence identified as 3A and depicted in FIG. 3A-3C. For example, an E2 polypeptide of genotype 3B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3B and depicted in FIG. 3A-3C. For example, an E2 polypeptide of genotype 3K can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3K and depicted in FIG. 3A-3C.

An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the amino acid sequence of the E2 polypeptide depicted in FIG. 4A-4B. For example, an E2 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-750 of the amino acid sequence depicted in FIG. 4A-4B.

E1 Polypeptides

An HCV E1 polypeptide suitable for inclusion in an E1/E2 heterodimer for inclusion in an immunogenic composition of the present disclosure, or for inclusion by itself in an immunogenic composition of the present disclosure, can have a length of from about 100 amino acids (aa) to about 150 aa, from about 150 aa to about 175 aa, from about 175 aa to about 195 aa, from about 131 aa to about 175 aa, or from about 175 aa to about 193 aa. In some cases, an HCV E1 polypeptide suitable for inclusion in an E1/E2 heterodimer present in an immunogenic composition of the present disclosure is an HCV E1 ectodomain polypeptide. In some cases, an HCV E1 polypeptide suitable for inclusion in an E1/E2 heterodimer present in an immunogenic composition of the present disclosure is a full-length HCV E1 polypeptide.

In FIG. 1A-IC, the amino acid sequence of E1 is amino acid 192 to amino acid 383. In FIG. 2A-2C, the amino acid sequence of E1 is amino acid 192 to amino acid 383. In FIG. 3A-3C, the amino acid sequence of E1 is amino acid 192 to amino acid 384. In FIG. 4A-4B, the amino acid sequence of E1 is amino acid 192 to amino acid 383. Amino acids at around 170 through approximately 191 serve as a signal sequence for E1. As used herein, "E1 polypeptide" includes a precursor E1 protein, including the signal sequence; includes a mature E1 polypeptide which lacks this sequence; and includes an E1 polypeptide with a heterologous signal sequence. An E1 polypeptide can include a C-terminal membrane anchor sequence which occurs at approximately amino acid positions 360-383 (see, e.g., WO 96/04301). In some cases, a suitable E1 polypeptide lacks a C-terminal portion that includes a transmembrane region. For example, in some cases, a suitable E1 polypeptide lacks the C-terminal portion from amino acid 330 to amino acid 384, or from amino acid 360 to amino acid 384. E1 polypeptides can be an E1 polypeptide of any genotype, subtype or isolate of HCV. E1 polypeptides of genotype 1 and E1 polypeptides of genotype 3 are included in an E1/E2 heterodimer of the present disclosure.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 1A-1C, FIG. 2A-2C, FIG. 3A-3C, or FIG. 4A-4B.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 1A-1C. For example, an E1 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1A and depicted in FIG. 1A-1C. For example, an E1 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1B and depicted in FIG. 1A-1C. For example, an E1 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1C and depicted in FIG. 1A-1C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 2A-2C. For example, an E1 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2A and depicted in FIG. 2A-2C. For example, an E1 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2B and depicted in FIG. 2A-2C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the consensus E1 polypeptide amino acid sequence depicted in FIG. 3A-3C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 4A-4B. For example, an E1 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of the amino acid sequence depicted in FIGS. 4A-4B.

HCV E1 and E2 Polypeptides Comprising Amino Acids from a Proteolytically Cleavable Linker As described in more detail below, an HCV E1/E2 heterodimer can be generated using a method that involves an HCV E1 or an HCV E2 polypeptide comprising a heterologous proteolytically cleavable linker. Following enzymatic cleavage of the proteolytically cleavable linker, from 1 to 6 (e.g., 1, 2, 3, 4, 5, or 6) heterologous amino acids can remain on the HCV E1 or E2 polypeptide. For example, from 1 to 6 (e.g., 1, 2, 3, 4, 5, or 6) heterologous amino acids can remain at the N-terminus of an HCV E2 polypeptide. As another example, from 1 to 6 (e.g., 1, 2, 3, 4, 5, or 6) heterologous amino acids can remain at the C-terminus of an HCV E2 polypeptide. As another example, from 1 to 6 (e.g., 1, 2, 3, 4, 5, or 6) heterologous amino acids can remain at the N-terminus of an HCV E1 polypeptide. As another example, from 1 to 6 (e.g., 1, 2, 3, 4, 5, or 6) heterologous amino acids can remain at the C-terminus of an HCV E1 polypeptide.

In some cases, amino acids C-terminal to the proteolytic cleavage site in a proteolytically cleavable linker are Gly-Pro, Ser, Gly, or Gly-Ser. Thus, in some cases, a modified HCV E1 polypeptide comprises, appended to the N-terminus of an HCV E1 polypeptide: Gly-Pro, Ser, Gly, or Gly-Ser. In other words, in some cases, a modified HCV E1 polypeptide comprises, in order from N-terminus to C-terminus: a) Gly-Pro, Ser, Gly, or Gly-Ser; and b) an HCV E1 polypeptide.

In some cases, amino acids C-terminal to the proteolytic cleavage site in a proteolytically cleavable linker are Gly-Pro, Ser, Gly, or Gly-Ser. Thus, in some cases, a modified HCV E2 polypeptide comprises, appended to the N-terminus of an HCV E2 polypeptide: Gly-Pro, Ser, Gly, or Gly-Ser. In other words, in some cases, a modified HCV E2 polypeptide comprises, in order from N-terminus to C-terminus: a) Gly-Pro, Ser, Gly, or Gly-Ser; and b) an HCV E2 polypeptide.

In some cases, amino acids N-terminal to the proteolytic cleavage site in a proteolytically cleavable linker are LEVLFQ (SEQ ID NO:122), ENLYYFQ (SEQ ID NO:150), LVPR (SEQ ID NO:124), I(E/D)GR (SEQ ID NO:125), or DDDDK (SEQ ID NO:123). Thus, in some cases, a modified HCV E1 polypeptide comprises, appended to the C-terminus of an HCV E1 polypeptide: LEVLFQ (SEQ ID NO:122), ENLYYFQ (SEQ ID NO:150), LVPR (SEQ ID NO:124), I(E/D)GR (SEQ ID NO:125), or DDDDK (SEQ ID NO:123). In other words, in some cases, a modified HCV E1 polypeptide comprises, in order from N-terminus to C-terminus: a) an HCV E1 polypeptide; and b) LEVLFQ (SEQ ID NO:122), ENLYYFQ (SEQ ID NO:150), LVPR (SEQ ID NO:124), I(E/D)GR (SEQ ID NO:125), or DDDDK (SEQ ID NO:123).

In some cases, amino acids N-terminal to the proteolytic cleavage site in a proteolytically cleavable linker are LEVLFQ (SEQ ID NO:122), ENLYYFQ (SEQ ID NO:150), LVPR (SEQ ID NO:124), I(E/D)GR (SEQ ID NO:125), or DDDDK (SEQ ID NO:123). Thus, in some cases, a modified HCV E2 polypeptide comprises, appended to the C-terminus of an HCV E2 polypeptide: LEVLFQ (SEQ ID NO:122), ENLYYFQ (SEQ ID NO:150), LVPR (SEQ ID NO:124), I(E/D)GR (SEQ ID NO:125), or DDDDK (SEQ ID NO:123). In other words, in some cases, a modified HCV E2 polypeptide comprises, in order from N-terminus to C-terminus: a) an HCV E2 polypeptide; and b) LEVLFQ (SEQ ID NO:122), ENLYYFQ (SEQ ID NO:150), LVPR (SEQ ID NO:124), I(E/D)GR (SEQ ID NO:125), or DDDDK (SEQ ID NO:123).

In some cases, a flexible linker of from 1 to 10 amino acids is interposed between the proteolytically cleavable linker and the HCV E1 or E2 polypeptide. Flexible linkers are intrinsically disordered flexible linker domains or loops that vary in length and can be rich in polar uncharged amino acids. Flexible linkers include, e.g., glycine polymers $(G)_n$, glycine-serine polymers (including, for example, $(GS)_n$, $GSGGS_n$ (SEQ ID NO:108), $GGSGGS_n$ (SEQ ID NO:109), and $GGGS_n$ (SEQ ID NO: 110), where n is an integer of at least one, e.g., where n is 1, 2, 3, 4, 5, or 6); glycine-alanine polymers, such as GAGAGAGA and the like; and alanine-serine polymers, e.g., SASASASA and the like. Exemplary linkers can comprise amino acid sequences including, but not limited to, GGSG (SEQ ID NO:111), GGSGG (SEQ ID NO:112), GSGSG (SEQ ID NO:113), GSGGG (SEQ ID NO:114), GGGSG (SEQ ID NO:115), GSSSG (SEQ ID NO:116), and the like.

For example, in some cases, a modified E1 polypeptide comprises, in order from N-terminus to C-terminus: a) Gly-Pro, Ser, Gly, or Gly-Ser; b) a flexible linker of from 1 to 10 amino acids; and c) an HCV E1 polypeptide.

As another example, in some cases, a modified E2 polypeptide comprises, in order from N-terminus to C-terminus: a) Gly-Pro, Ser, Gly, or Gly-Ser; b) a flexible linker of from 1 to 10 amino acids; and c) an HCV E2 polypeptide.

As another in some cases, a modified E1 polypeptide comprises, from N-terminus to C-terminus: a) an HCV E1 polypeptide; b) a flexible linker of from 1 to 10 amino acids; and c) LEVLFQ (SEQ ID NO:122), ENLYYFQ (SEQ ID NO:150), LVPR (SEQ ID NO:124), I(E/D)GR (SEQ ID NO:125), or DDDDK (SEQ ID NO:123).

As another in some cases, a modified E2 polypeptide comprises, from N-terminus to C-terminus: a) an HCV E2 polypeptide; b) a flexible linker of from 1 to 10 amino acids; and c) LEVLFQ (SEQ ID NO:122), ENLYYFQ (SEQ ID NO:150), LVPR (SEQ ID NO:124), I(E/D)GR (SEQ ID NO:125), or DDDDK (SEQ ID NO:123).

E2 with N-Terminal Heterologous Amino Acids

In some cases, an HCV E1/E2 heterodimer suitable for inclusion in an immunogenic composition of the present disclosure comprises a modified HCV E2 polypeptide with from 1 to 6 amino acids from the proteolytically cleavable linker on the N-terminus of the E2 polypeptide. In some cases, an HCV E1/E2 heterodimer suitable for inclusion in an immunogenic composition of the present disclosure comprises: a) an HCV E1 polypeptide; and b) a modified E2 polypeptide comprising, in order from N-terminus to C-terminus: i) from 1 to 6 heterologous amino acids wherein the from 1 to 6 heterologous amino acids are C-terminal to a site of proteolytic cleavage in a proteolytically cleavable linker; and ii) an HCV E2 polypeptide.

Proteolytically cleavable linkers are described elsewhere herein. Following proteolytic cleavage of a precursor polypeptide, as described herein, a modified E2 polypeptide is generated, which modified E2 polypeptide comprises, at its N-terminus, amino acids C-terminal to the protease cleavage site within the proteolytically cleavable linker.

For example, where the proteolytically cleavable linker comprises a PreScission cleavage site (LEVLFQGP; SEQ ID NO:117), where cleavage occurs between the glutamine and the glycine, a modified E2 polypeptide present in a heterodimeric E1/E2 polypeptide suitable for inclusion in an immunogenic composition of the present disclosure comprises, in order from N-terminus to C-terminus: a) Gly-Pro; and b) an HCV E2 polypeptide. As another example, where the proteolytically cleavable linker comprises a TEV cleavage site (ENLYFQS; SEQ ID NO:118), where cleavage occurs between the glutamine and the serine, a modified E2 polypeptide present in a heterodimeric E1/E2 polypeptide suitable for inclusion in an immunogenic composition of the present disclosure comprises, in order from N-terminus to C-terminus: a) Ser; and b) an HCV E2 polypeptide.

As another example, where the proteolytically cleavable linker comprises a TEV cleavage site (ENLYFQG; SEQ ID NO:119), where cleavage occurs between the glutamine and the glycine, a modified E2 polypeptide present in a heterodimeric E1/E2 polypeptide suitable for inclusion in an immunogenic composition of the present disclosure comprises, in order from N-terminus to C-terminus: a) Gly; and b) an HCV E2 polypeptide.

As another example, where the proteolytically cleavable linker comprises a thrombin cleavage site (LVPRGS; SEQ ID NO:120), where cleavage occurs between the arginine and the glycine, a modified E2 polypeptide present in a heterodimeric E1/E2 polypeptide suitable for inclusion in an immunogenic composition of the present disclosure comprises, in order from N-terminus to C-terminus: a) Gly-Ser; and an HCV E2 polypeptide.

As another example, where the proteolytically cleavable linker comprises a Factor Xa cleavage site (I(E/D)GRX, where X is any amino acid except arginine or proline; SEQ ID NO:121), where cleavage occurs between the arginine and the X, a modified E2 polypeptide present in a heterodimeric E1/E2 polypeptide suitable for inclusion in an immunogenic composition of the present disclosure comprises, in order from N-terminus to C-terminus: a) X (where X is any amino acid except arginine or proline); and an HCV E2 polypeptide.

Thus, for example, in some cases, an HCV E1/E2 heterodimer suitable for inclusion in an immunogenic composition of the present disclosure comprises: a) an HCV E1 polypeptide; and b) a modified E2 polypeptide comprising, in order from N-terminus to C-terminus: i) from 1 to 6 heterologous amino acids, wherein the from 1 to 6 (e.g., 1, 2, 3, 4, 5, or 6) heterologous amino acids are C-terminal to a site of proteolytic cleavage in a proteolytically cleavable linker; and ii) an HCV E2 polypeptide. In some cases, the 1 to 6 heterologous amino acids are Gly-Pro. In some cases, the 1 to 6 heterologous amino acids is Ser. In some cases, the 1 to 6 heterologous amino acids is Gly. In some cases, the 1 to 6 heterologous amino acids are Gly-Ser.

As another example, in some cases, an HCV E1/E2 heterodimer suitable for inclusion in an immunogenic composition of the present disclosure comprises: a) an HCV E2 polypeptide; and b) a modified E1 polypeptide comprising, in order from N-terminus to C-terminus: i) from 1 to 6 heterologous amino acids, wherein the from 1 to 6 (e.g., 1, 2, 3, 4, 5, or 6) heterologous amino acids are C-terminal to a site of proteolytic cleavage in a proteolytically cleavable linker; and ii) an HCV E1 polypeptide. In some cases, the 1 to 6 heterologous amino acids are Gly-Pro. In some cases, the 1 to 6 heterologous amino acids is Ser. In some cases, the 1 to 6 heterologous amino acids is Gly. In some cases, the 1 to 6 heterologous amino acids are Gly-Ser.

E1 with N-Terminal Heterologous Amino Acids

In some cases, an HCV E1/E2 heterodimer suitable for inclusion in an immunogenic composition of the present disclosure comprises a modified HCV E1 polypeptide with from 1 to 6 amino acids from a proteolytically cleavable linker on the N-terminus of the E1 polypeptide. In some cases, an HCV E1/E2 heterodimer suitable for inclusion in an immunogenic composition of the present disclosure comprises: a) an HCV E2 polypeptide; and b) a modified E1 polypeptide comprising, in order from N-terminus to C-terminus: i) from 1 to 6 heterologous amino acids wherein the from 1 to 6 heterologous amino acids are C-terminal to a site of proteolytic cleavage in a proteolytically cleavable linker; and ii) an HCV E1 polypeptide.

Proteolytically cleavable linkers are described elsewhere herein. Following proteolytic cleavage of a precursor polypeptide (e.g., a precursor polypeptide comprising, in order from N-terminus to C-terminus: a) an Fc polypeptide or an HCV E2 polypeptide; b) a proteolytically cleavable linker; and c) an HCV E1 polypeptide), a modified E1 polypeptide is generated, which modified E1 polypeptide comprises, at its N-terminus, amino acids C-terminal to the protease cleavage site within the proteolytically cleavable linker.

For example, where the proteolytically cleavable linker comprises a PreScission cleavage site (LEVLFQGP; SEQ ID NO:117), where cleavage occurs between the glutamine and the glycine, a modified E1 polypeptide present in an HCV E1/E2 heterodimer suitable for inclusion in an immunogenic composition of the present disclosure comprises, in order from N-terminus to C-terminus: a) Gly-Pro; and b) an HCV E1 polypeptide.

As another example, where the proteolytically cleavable linker comprises a TEV cleavage site (ENLYFQS; SEQ ID NO:118), where cleavage occurs between the glutamine and the serine, a modified E1 polypeptide present in an HCV E1/E2 heterodimer suitable for inclusion in an immunogenic composition of the present disclosure comprises, in order from N-terminus to C-terminus: a) Ser; and b) an HCV E1 polypeptide.

As another example, where the proteolytically cleavable linker comprises a TEV cleavage site (ENLYFQG; SEQ ID NO:119), where cleavage occurs between the glutamine and the glycine, a modified E1 polypeptide present in an HCV E1/E2 heterodimer suitable for inclusion in an immunogenic composition of the present disclosure comprises, in order from N-terminus to C-terminus: a) Gly; and b) an HCV E1 polypeptide.

As another example, where the proteolytically cleavable linker comprises a thrombin cleavage site (LVPRGS; SEQ ID NO:120), where cleavage occurs between the arginine and the glycine, a modified E1 polypeptide present in an HCV E1/E2 heterodimer suitable for inclusion in an immunogenic composition of the present disclosure comprises, in order from N-terminus to C-terminus: a) Gly-Ser; and an HCV E1 polypeptide.

As another example, where the proteolytically cleavable linker comprises a Factor Xa cleavage site (I(E/D)GRX, where X is any amino acid except arginine or proline; SEQ ID NO:121), where cleavage occurs between the arginine and the X, a modified E1 polypeptide present in an HCV E1/E2 heterodimer suitable for inclusion in an immunogenic composition of the present disclosure comprises, in order from N-terminus to C-terminus: a) X (where X is any amino acid except arginine or proline); and an HCV E1 polypeptide.

E2 with C-Terminal Heterologous Amino Acids

In some cases, an HCV E1/E2 heterodimer suitable for inclusion in an immunogenic composition of the present disclosure comprises a modified HCV E2 polypeptide with from 1 to 6 amino acids from a proteolytically cleavable linker on the C-terminus of the E2 polypeptide. In some cases, an HCV E1/E2 heterodimer suitable for inclusion in an immunogenic composition of the present disclosure comprises: a) an HCV E1 polypeptide; and b) a modified E2 polypeptide comprising, in order from N-terminus to C-terminus: i) an HCV E2 polypeptide; and ii) from 1 to 6 heterologous amino acids wherein the from 1 to 6 heterologous amino acids are N-terminal to a site of proteolytic cleavage in a proteolytically cleavable linker.

Proteolytically cleavable linkers are described elsewhere herein. Following proteolytic cleavage of a precursor polypeptide (e.g., a precursor polypeptide comprising, in order from N-terminus to C-terminus: a) HCV E2 polypeptide; b) a proteolytically cleavable linker; and c) an Fc polypeptide or an HCV E1 polypeptide), a modified E2 polypeptide is generated, which modified E2 polypeptide comprises, at its C-terminus, amino acids N-terminal to the protease cleavage site within the proteolytically cleavable linker.

For example, where the proteolytically cleavable linker comprises a PreScission cleavage site (LEVLFQGP; SEQ ID NO:117), where cleavage occurs between the glutamine and the glycine, a modified E2 polypeptide present in an HCV E1/E2 heterodimer suitable for inclusion in an immunogenic composition of the present disclosure comprises, in order from N-terminus to C-terminus: a) an HCV E2 polypeptide; and b) LEVLFQ (SEQ ID NO:122).

As another example, where the proteolytically cleavable linker comprises an enterokinase cleavage site (DDDDK; SEQ ID NO:123), where cleavage occurs C-terminal to the Lys, a modified E2 polypeptide present in an HCV E1/E2 heterodimer suitable for inclusion in an immunogenic composition of the present disclosure comprises, in order from N-terminus to C-terminus: a) an HCV E2 polypeptide; and b) DDDDK (SEQ ID NO:123).

As another example, where the proteolytically cleavable linker comprises a TEV cleavage site (ENLYFQG; SEQ ID NO:119), where cleavage occurs between the glutamine and the glycine, a modified E2 polypeptide present in an HCV E1/E2 heterodimer suitable for inclusion in an immunogenic composition of the present disclosure comprises, in order from N-terminus to C-terminus: a) an HCV E2 polypeptide; and b) ENLYFQ (SEQ ID NO:151).

As another example, where the proteolytically cleavable linker comprises a thrombin cleavage site (LVPRGS; SEQ ID NO:120), where cleavage occurs between the arginine and the glycine, a modified E2 polypeptide present in an HCV E1/E2 heterodimer suitable for inclusion in an immunogenic composition of the present disclosure comprises, in order from N-terminus to C-terminus: a) an HCV E2 polypeptide; and LVPR (SEQ ID NO:124).

As another example, where the proteolytically cleavable linker comprises a Factor Xa cleavage site (I(E/D)GRX, where X is any amino acid except arginine or proline; SEQ ID NO:121), where cleavage occurs between the arginine and the X, a modified E2 polypeptide present in an HCV E1/E2 heterodimer suitable for inclusion in an immunogenic composition of the present disclosure comprises, in order from N-terminus to C-terminus: a) an HCV E2 polypeptide; and I(E/D)GR (SEQ ID NO:125).

E1 with C-Terminal Heterologous Amino Acids

In some cases, an HCV E1/E2 heterodimer suitable for inclusion in an immunogenic composition of the present disclosure comprises a modified HCV E1 polypeptide with from 1 to 6 amino acids from a proteolytically cleavable linker on the C-terminus of the E1 polypeptide. In some cases, an HCV E1/E2 heterodimer suitable for inclusion in an immunogenic composition of the present disclosure comprises: a) an HCV E2 polypeptide; and b) a modified E1 polypeptide comprising, in order from N-terminus to C-terminus: i) an HCV E1 polypeptide; and ii) from 1 to 6 heterologous amino acids wherein the from 1 to 6 heterologous amino acids are N-terminal to a site of proteolytic cleavage in a proteolytically cleavable linker.

Proteolytically cleavable linkers are described elsewhere herein. Following proteolytic cleavage of a precursor polypeptide (e.g., a precursor polypeptide comprising, in order from N-terminus to C-terminus: a) HCV E1 polypeptide; b) a proteolytically cleavable linker; and c) an Fc polypeptide or an HCV E2 polypeptide), a modified E1 polypeptide is generated, which modified E1 polypeptide comprises, at its C-terminus, amino acids N-terminal to the protease cleavage site within the proteolytically cleavable linker.

For example, where the proteolytically cleavable linker comprises a PreScission cleavage site (LEVLFQGP; SEQ ID NO:117), where cleavage occurs between the glutamine and the glycine, a modified E1 polypeptide present in an HCV E1/E2 heterodimer suitable for inclusion in an immunogenic composition of the present disclosure comprises, in order from N-terminus to C-terminus: a) an HCV E1 polypeptide; and b) LEVLFQ (SEQ ID NO:122).

As another example, where the proteolytically cleavable linker comprises an enterokinase cleavage site (DDDDK; SEQ ID NO:123), where cleavage occurs C-terminal to the Lys, a modified E1 polypeptide present in an HCV E1/E2 heterodimer suitable for inclusion in an immunogenic composition of the present disclosure comprises, in order from N-terminus to C-terminus: a) an HCV E1 polypeptide; and b) DDDDK (SEQ ID NO:123).

As another example, where the proteolytically cleavable linker comprises a TEV cleavage site (ENLYFQG; SEQ ID NO:119), where cleavage occurs between the glutamine and the glycine, a modified E1 polypeptide present in an HCV E1/E2 heterodimer suitable for inclusion in an immunogenic composition of the present disclosure comprises, in order from N-terminus to C-terminus: a) an HCV E1 polypeptide; and b) ENLYFQ (SEQ ID NO:151).

As another example, where the proteolytically cleavable linker comprises a thrombin cleavage site (LVPRGS; SEQ ID NO:120), where cleavage occurs between the arginine and the glycine, a modified E1 polypeptide present in an HCV E1/E2 heterodimer suitable for inclusion in an immunogenic composition of the present disclosure comprises, in order from N-terminus to C-terminus: a) an HCV E1 polypeptide; and LVPR (SEQ ID NO:124).

As another example, where the proteolytically cleavable linker comprises a Factor Xa cleavage site (I(E/D)GRX, where X is any amino acid except arginine or proline; SEQ ID NO:121), where cleavage occurs between the arginine and the X, a modified E1 polypeptide present in an HCV E1/E2 heterodimer suitable for inclusion in an immunogenic composition of the present disclosure comprises, in order from N-terminus to C-terminus: a) an HCV E1 polypeptide; and I(E/D)GR (SEQ ID NO:125).

Additional Polypeptides

In any of the above-described embodiments, one or both of the polypeptide chains of the E1/E2 heterodimer can include one or more additional polypeptides. For example, the E1 polypeptide, the E2 polypeptide, or both the E1 and the E2 polypeptide, can include an affinity tag. Suitable affinity tags include, e.g., immunoglobulin Fc polypeptides, a poly(histidine) tag (e.g., $His_6$), a maltose binding protein (MBP), a glutathione-S-transferase (GST) polypeptide, calmodulin-binding peptide (CBP), Streptavidin-binding peptide (SBP), Strep-tag II, FLAG (e.g., DYKDDDDK (SEQ ID NO:126), hemagglutinin (HA) (e.g., YPYDVPDYA (SEQ ID NO:127), c-myc T7 ((e.g., EQKLISEEDL; SEQ ID NO:128), Glu-Glu, starch-binding domain (SBD), and Flag-Acidic-Target Tag (FATT), and the like.

In some cases, an E1/E2 heterodimer included in a composition of the present disclosure includes a variant E2 polypeptide. In some cases, the E1 polypeptide or the variant E2 polypeptide can include an Ig Fc polypeptide at the C-terminus of the E1 polypeptide or the variant E2 polypeptide. As another example, in some cases, the E1 polypeptide or the variant E2 polypeptide can include an Ig Fc polypeptide at the N-terminus of the E1 polypeptide or the variant E2 polypeptide. Ig Fc polypeptides are known in the art, and are described elsewhere herein.

T-Cell Epitope Polypeptides

In some cases, one or both of the polypeptide chains of the E1/E2 heterodimer present in an immunogenic composition of the present disclosure can include a T-cell epitope polypeptide. In some cases, an E2 polypeptide present in an E1/E2 heterodimer present in an immunogenic composition of the present disclosure includes a T-cell epitope polypeptide. In some cases, an E1 polypeptide present in an E1/E2 heterodimer present in an immunogenic composition of the present disclosure includes a T-cell epitope polypeptide. In some cases, an HCV E2 polypeptide present in an immunogenic composition of the present disclosure includes a T-cell epitope polypeptide. In some cases, an HCV E1 polypeptide present in an immunogenic composition of the present disclosure includes a T-cell epitope polypeptide. In these embodiments, the T-cell epitope is covalently linked to the E1 and/or E2 polypeptide. For example, in some cases, the T-cell epitope is covalently linked to the amino terminus (N-terminus) of the HCV E1 polypeptide. In some cases, the T-cell epitope is covalently linked to the carboxyl terminus (C-terminus) of the HCV E1 polypeptide. Thus, e.g., in some cases, an immunogenic composition of the present disclosure comprises: a) a fusion polypeptide comprising, in order from N-terminus to C-terminus: i) an HCV E1 polypeptide; and ii) a T-cell epitope polypeptide; and b) a CDN. In some cases, an immunogenic composition of the present disclosure comprises: a) a fusion polypeptide comprising, in order from N-terminus to C-terminus: i) an HCV E2 polypeptide; and ii) a T-cell epitope polypeptide; and b) a CDN. In some cases, an immunogenic composition of the present disclosure comprises: a) a fusion polypeptide comprising, in order from N-terminus to C-terminus: i) a T-cell epitope polypeptide; and ii) an HCV E1 polypeptide; and b) a CDN. In some cases, an immunogenic composition of the present disclosure comprises: a) a fusion polypeptide comprising, in order from N-terminus to C-terminus: i) a T-cell epitope polypeptide; and ii) an HCV E2 polypeptide; and b) a CDN. In some cases, an immunogenic composition of the present disclosure comprises: a) an HCV E1E2 heterodimer comprising i) a fusion polypeptide comprising, in order from N-terminus to C-terminus: an HCV E1 polypeptide; and a T-cell epitope polypeptide; and ii) an HCV E2 polypeptide; and b) a CDN. In some cases, an immunogenic composition of the present disclosure comprises: a) an HCV E1E2 heterodimer comprising i) a fusion polypeptide comprising, in order from N-terminus to C-terminus: an HCV E2 polypeptide; and a T-cell epitope polypeptide; and ii) an HCV E2 polypeptide; and b) a CDN. In some cases, an immunogenic composition of the present disclosure comprises: a) an HCV E1E2 heterodimer comprising i) a fusion polypeptide comprising, in order from N-terminus to C-terminus: a T-cell epitope polypeptide; and an HCV E1 polypeptide; and ii) an HCV E2 polypeptide; and b) a CDN. In some cases, an immunogenic composition of the present disclosure comprises: a) an HCV E1E2 heterodimer comprising i) a fusion polypeptide comprising, in order from N-terminus to C-terminus: a T-cell epitope polypeptide; and an HCV E2 polypeptide; and ii) an HCV E1 polypeptide; and b) a CDN.

In some cases, an immunogenic composition of the present disclosure comprises a T-cell epitope polypeptide, where the T-cell epitope polypeptide is not covalently linked to the HCV E1/E2 heterodimer, the HCV E1 polypeptide or the HCV E2 polypeptide. For example, in some cases, an immunogenic composition of the present disclosure comprises: a) an HCV E1/E2 heterodimer; b) a CDN; and c) a T-cell epitope polypeptide. In some cases, an immunogenic composition of the present disclosure comprises: a) an HCV E2 polypeptide; b) a CDN; and c) a T-cell epitope polypeptide. In some cases, an immunogenic composition of the present disclosure comprises: a) an HCV E1 polypeptide; b) a CDN; and c) a T-cell epitope polypeptide.

A T-cell epitope polypeptide suitable for inclusion in an immunogenic composition of the present disclosure comprises a T-cell epitope present in an HCV protein other than E1 and E2. T-cell epitope polypeptides suitable for inclusion in an immunogenic composition of the present disclosure comprise T cell epitopes that are conserved among different HCV genotypes leading to cross-reactive cellular immune responses. In some cases, the T-cell epitope polypeptide does not include a neotope; for example, in some cases, the T-cell epitope polypeptide does not include a junction formed by amino acid sequences that do not naturally occur adjacent to one another in a naturally-occurring HCV polypeptide.

In some cases, the T-cell epitope polypeptide comprises 1, 2, 3, 4, 5, 6, 7, 8, 9, or 10, or more than 10 (e.g., from 10 to 15, from 15 to 20, from 20 to 25, or from 25 to 30, or more than 30), T cell epitopes. T-cell epitopes are epitopes that, when presented with a major histocompatibility complex (MHC) (e.g., a human leukocyte antigen (HLA)) Class I or MHC Class II molecule, are recognized and bound by a T-cell receptor (TCR) present on a T cell surface. T-cell epitopes include epitopes recognized by cytotoxic T cells (e.g., $CD8^+$ T cells), and epitopes recognized by helper T cells (e.g., $CD4^+$ T cells).

The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the T-cell epitope polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. A suitable source of T-cell epitopes includes non-toxic mutants of toxins, where the mutants are referred to as "cross-reactive material (CRM)." Other examples of strong T helper epitopes are diphtheria toxoid, tetanus toxoid, meningococcal outer membrane protein, or mutant diphtheria protein CRM197 (see, e.g.: world-wide-website: Medscape.com/viewarticle/431127).

In some cases, the T-cell epitope polypeptide comprises a single T-cell epitope. In some cases, the heterologous polypeptide comprises a single HCV-NS3 T-cell epitope. In some cases, the T-cell epitope polypeptide comprises 2 or more T-cell epitopes. In some cases, the T-cell epitope polypeptide comprises 2 or more HCV-NS3 T-cell epitopes. In some cases, the T-cell epitope polypeptide comprises 3 or more HCV-NS3 T-cell epitopes. In some cases, the T-cell epitope polypeptide comprises 4 or more HCV-NS3 T-cell epitopes. In some cases, the T-cell epitope polypeptide comprises a single HCV-NS3 $CD4^+$ T-cell epitope. In some cases, the T-cell epitope polypeptide comprises 2 or more HCV-NS3 $CD4^+$ T-cell epitopes. In some cases, the T-cell epitope polypeptide comprises one or more HCV $CD8^+$ T cell epitopes. In some cases, the T-cell epitope polypeptide comprises a single HCV-NS3 $CD8^+$ T-cell epitope. In some cases, the T-cell epitope polypeptide comprises 2 or more HCV-NS3 $CD8^+$ T-cell epitopes. In some cases, the T-cell epitope polypeptide comprises at least one HCV $CD4^+$ T cell epitope and at least one HCV $CD8^+$ T cell epitope. In some cases, the T-cell epitope polypeptide comprises at least one HCV-NS3 $CD4^+$ T cell epitope and at least one HCV-NS3 $CD8^+$ T cell epitope. In some cases, T-cell epitope polypeptide comprises 2 or more HCV-NS3 $CD4^+$ T-cell epitopes and 2 or more HCV-NS3 $CD8^+$ T-cell epitopes. In some cases, the T-cell epitope polypeptide comprises 2, 3, 4, or 5 HCV-NS3 $CD4^+$ T-cell epitopes and 2, 3, 4, or 5 HCV-NS3 $CD8^+$ T-cell epitopes.

In some cases, the T-cell epitope polypeptide comprises a single T-cell epitope. In some cases, the T-cell epitope polypeptide comprises a single HCV-NS2 T-cell epitope. In some cases, the T-cell epitope polypeptide comprises 2 or more T-cell epitopes. In some cases, the T-cell epitope polypeptide comprises 2 or more HCV-NS2 T-cell epitopes. In some cases, the T-cell epitope polypeptide comprises 3 or more HCV-NS2 T-cell epitopes. In some cases, the T-cell epitope polypeptide comprises 4 or more HCV-NS2 T-cell epitopes. In some cases, the T-cell epitope polypeptide comprises a single HCV-NS2 $CD4^+$ T-cell epitope. In some cases, the T-cell epitope polypeptide comprises 2 or more HCV-NS2 $CD4^+$ T-cell epitopes. In some cases, the T-cell epitope polypeptide comprises one or more HCV $CD8^+$ T cell epitopes. In some cases, the T-cell epitope polypeptide comprises a single HCV-NS2 $CD8^+$ T-cell epitope. In some cases, the T-cell epitope polypeptide comprises 2 or more HCV-NS2 $CD8^+$ T-cell epitopes. In some cases, the T-cell epitope polypeptide comprises at least one HCV $CD4^+$ T cell epitope and at least one HCV $CD8^+$ T cell epitope. In some cases, the T-cell epitope polypeptide comprises at least one HCV-NS2 $CD4^+$ T cell epitope and at least one HCV-NS2 $CD8^+$ T cell epitope. In some cases, T-cell epitope polypeptide comprises 2 or more HCV-NS2 $CD4^+$ T-cell epitopes and 2 or more HCV-NS2 $CD8^+$ T-cell epitopes. In some cases, the T-cell epitope polypeptide comprises 2, 3, 4, or 5 HCV-NS2 $CD4^+$ T-cell epitopes and 2, 3, 4, or 5 HCV-NS2 $CD8^+$ T-cell epitopes.

In some cases, the T cell epitope polypeptide comprises a single T-cell epitope. In some cases, the T cell epitope polypeptide comprises a single HCV-NS4A T-cell epitope. In some cases, the T cell epitope polypeptide comprises 2 or more T-cell epitopes. In some cases, the T cell epitope polypeptide comprises 2 or more HCV-NS4A T-cell epitopes. In some cases, the T cell epitope polypeptide comprises 3 or more HCV-NS4A T-cell epitopes. In some cases, the T cell epitope polypeptide comprises 4 or more HCV-NS4A T-cell epitopes. In some cases, the T cell epitope polypeptide comprises a single HCV-NS4A $CD4^+$ T-cell epitope. In some cases, the T cell epitope polypeptide comprises 2 or more HCV-NS4A $CD4^+$ T-cell epitopes. In some cases, the T cell epitope polypeptide comprises one or more HCV $CD8^+$ T cell epitopes. In some cases, the T cell epitope polypeptide comprises a single HCV-NS4A $CD8^+$ T-cell epitope. In some cases, the T cell epitope polypeptide comprises 2 or more HCV-NS4A $CD8^+$ T-cell epitopes. In some cases, the T cell epitope polypeptide comprises at least one HCV $CD4^+$ T cell epitope and at least one HCV $CD8^+$ T cell epitope. In some cases, the T cell epitope polypeptide comprises at least one HCV-NS4A $CD4^+$ T cell epitope and at least one HCV-NS4A $CD8^+$ T cell epitope. In some cases, T cell epitope polypeptide comprises 2 or more HCV-NS4A $CD4^+$ T-cell epitopes and 2 or more HCV-NS4A $CD8^+$ T-cell epitopes. In some cases, the T cell epitope polypeptide comprises 2, 3, 4, or 5 HCV-NS4A $CD4^+$ T-cell epitopes and 2, 3, 4, or 5 HCV-NS4A $CD8^+$ T-cell epitopes.

In some cases, the T cell epitope polypeptide comprises a single T-cell epitope. In some cases, the T cell epitope polypeptide comprises a single HCV-NS5A T-cell epitope. In some cases, the T cell epitope polypeptide comprises 2 or more T-cell epitopes. In some cases, the T cell epitope polypeptide comprises 2 or more HCV-NS5A T-cell epitopes. In some cases, the T cell epitope polypeptide comprises 3 or more HCV-NS5A T-cell epitopes. In some cases, the T cell epitope polypeptide comprises 4 or more HCV-NS5A T-cell epitopes. In some cases, the T cell epitope polypeptide comprises a single HCV-NS5A $CD4^+$ T-cell epitope. In some cases, the T cell epitope polypeptide comprises 2 or more HCV-NS5A $CD4^+$ T-cell epitopes. In some cases, the T cell epitope polypeptide comprises one or more HCV $CD8^+$ T cell epitopes. In some cases, the T cell epitope polypeptide comprises a single HCV-NS5A $CD8^+$ T-cell epitope. In some cases, the T cell epitope polypeptide comprises 2 or more HCV-NS5A $CD8^+$ T-cell epitopes. In some cases, the T cell epitope polypeptide comprises at least one HCV $CD4^+$ T cell epitope and at least one HCV $CD8^+$ T cell epitope. In some cases, the T cell epitope polypeptide comprises at least one HCV-NS5A $CD4^+$ T cell epitope and at least one HCV-NS5A $CD8^+$ T cell epitope. In some cases, T cell epitope polypeptide comprises 2 or more HCV-NS5A $CD4^+$ T-cell epitopes and 2 or more HCV-NS5A $CD8^+$ T-cell epitopes. In some cases, the T cell epitope polypeptide comprises 2, 3, 4, or 5 HCV-NS5A $CD4^+$ T-cell epitopes and 2, 3, 4, or 5 HCV-NS5A $CD8^+$ T-cell epitopes.

In some cases, the T cell epitope polypeptide comprises a single T-cell epitope. In some cases, the T cell epitope polypeptide comprises a single HCV-NS5B T-cell epitope. In some cases, the T cell epitope polypeptide comprises 2 or more T-cell epitopes. In some cases, the T cell epitope polypeptide comprises 2 or more HCV-NS5B T-cell epitopes. In some cases, the T cell epitope polypeptide comprises 3 or more HCV-NS5B T-cell epitopes. In some cases, the T cell epitope polypeptide comprises 4 or more HCV-NS5B T-cell epitopes. In some cases, the T cell epitope polypeptide comprises a single HCV-NS5B $CD4^+$ T-cell epitope. In some cases, the T cell epitope polypeptide comprises 2 or more HCV-NS5B $CD4^+$ T-cell epitopes. In some cases, the T cell epitope polypeptide comprises one or more HCV $CD8^+$ T cell epitopes. In some cases, the T cell epitope polypeptide comprises a single HCV-NS5B $CD8^+$ T-cell epitope. In some cases, the T cell epitope polypeptide comprises 2 or more HCV-NS5B $CD8^+$ T-cell epitopes. In some cases, the T cell epitope polypeptide comprises at least one HCV $CD4^+$ T cell epitope and at least one HCV $CD8^+$ T cell epitope. In some cases, the T cell epitope polypeptide comprises at least one HCV-NS5B $CD4^+$ T cell epitope and at least one HCV-NS5B $CD8^+$ T cell epitope. In some cases, T cell epitope polypeptide comprises 2 or more HCV-NS5B $CD4^+$ T-cell epitopes and 2 or more HCV-NS5B $CD8^+$ T-cell epitopes. In some cases, the T cell epitope polypeptide comprises 2, 3, 4, or 5 HCV-NS5B $CD4^+$ T-cell epitopes and 2, 3, 4, or 5 HCV-NS5B $CD8^+$ T-cell epitopes.

In some cases, the T cell epitope polypeptide comprises a single T-cell epitope. In some cases, the T cell epitope polypeptide comprises a single HCV-core T-cell epitope. In some cases, the T cell epitope polypeptide comprises 2 or more T-cell epitopes. In some cases, the T cell epitope polypeptide comprises 2 or more HCV-core T-cell epitopes. In some cases, the T cell epitope polypeptide comprises 3 or more HCV-core T-cell epitopes. In some cases, the T cell epitope polypeptide comprises 4 or more HCV-core T-cell epitopes. In some cases, the T cell epitope polypeptide comprises a single HCV-core $CD4^+$ T-cell epitope. In some cases, the T cell epitope polypeptide comprises 2 or more HCV-core $CD4^+$ T-cell epitopes. In some cases, the T cell epitope polypeptide comprises one or more HCV $CD8^+$ T cell epitopes. In some cases, the T cell epitope polypeptide comprises a single HCV-core $CD8^+$ T-cell epitope. In some cases, the T cell epitope polypeptide comprises 2 or more HCV-core $CD8^+$ T-cell epitopes. In some cases, the T cell epitope polypeptide comprises at least one HCV $CD4^+$ T cell epitope and at least one HCV $CD8^+$ T cell epitope. In some cases, the T cell epitope polypeptide comprises at least one HCV-core $CD4^+$ T cell epitope and at least one HCV-core $CD8^+$ T cell epitope. In some cases, T cell epitope polypeptide comprises 2 or more HCV-core $CD4^+$ T-cell epitopes and 2 or more HCV-core $CD8^+$ T-cell epitopes. In some cases, the T cell epitope polypeptide comprises 2, 3, 4, or 5 HCV-core $CD4^+$ T-cell epitopes and 2, 3, 4, or 5 HCV-core $CD8^+$ T-cell epitopes.

In some cases, the T cell epitope polypeptide comprises a single T-cell epitope. In some cases, the T cell epitope polypeptide comprises a single HCV-p7 T-cell epitope. In some cases, the T cell epitope polypeptide comprises 2 or more T-cell epitopes. In some cases, the T cell epitope polypeptide comprises 2 or more HCV-p7 T-cell epitopes. In some cases, the T cell epitope polypeptide comprises 3 or more HCV-p7 T-cell epitopes. In some cases, the T cell epitope polypeptide comprises 4 or more HCV-p7 T-cell epitopes. In some cases, the T cell epitope polypeptide comprises a single HCV-p7 $CD4^+$ T-cell epitope. In some cases, the T cell epitope polypeptide comprises 2 or more HCV-core $CD4^+$ T-cell epitopes. In some cases, the T cell epitope polypeptide comprises one or more HCV $CD8^+$ T cell epitopes. In some cases, the T cell epitope polypeptide comprises a single HCV-p7 $CD8^+$ T-cell epitope. In some cases, the T cell epitope polypeptide comprises 2 or more HCV-p7 $CD8^+$ T-cell epitopes. In some cases, the T cell epitope polypeptide comprises at least one HCV $CD4^+$ T cell epitope and at least one HCV $CD8^+$ T cell epitope. In some cases, the T cell epitope polypeptide comprises at least one HCV-p7 $CD4^+$ T cell epitope and at least one HCV-p7 $CD8^+$ T cell epitope. In some cases, T cell epitope polypeptide comprises 2 or more HCV-p7 $CD4^+$ T-cell epitopes and 2 or more HCV-p7 $CD8^+$ T-cell epitopes. In some cases, the T-cell epitope polypeptide comprises 2, 3, 4, or 5 HCV-p7 $CD4^+$ T-cell epitopes and 2, 3, 4, or 5 HCV-p7 $CD8^+$ T-cell epitopes.

In some cases, the T cell epitope polypeptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63, of the T-cell epitopes set out in FIGS. 9A-9B. In some cases, the T cell epitope polypeptide comprises from 1 to 3, from 3 to 5, from 5 to 10, from 10 to 15, from 15 to 20, from 20 to 25, or from 25 to 30 of the T-cell epitopes set out in FIGS. 9A-9B. For example, in some cases, the T cell epitope polypeptide comprises the T-cell epitopes designated NS3-3, NS3-4, and NS3-11 in FIGS. 9A-9B and FIGS. 11A-11N. As another example, in some cases, the T cell epitope polypeptide comprises the T-cell epitopes designated NS2-1, NS2-2, NS2-3, NS2-7, and NS2-8 in FIGS. 9A-9B and FIGS. 11A-11N. As another example, in some cases, the T cell epitope polypeptide comprises the T-cell epitopes designated NS3-3, NS3-4, NS3-5, and NS3-11 in FIG. 9A-9B and FIGS. 11A-11N. As another example, in some cases, the T cell epitope polypeptide comprises the T-cell epitopes designated NS3-3, NS3-4, NS3-5, NS3-6, NS3-7, NS3-11, NS3-12, and NS3-13 in FIGS. 9A-9B and FIGS. 11A-11N. As another example, in some cases, the T cell epitope polypeptide comprises the T-cell epitopes designated NS3-3, NS3-4, NS3-5, NS3-6, NS3-7, NS3-10, NS3-11, NS3-12, and NS3-13 in FIGS. 9A-9B and FIGS. 11A-11N. As another example, in some cases, the T cell epitope polypeptide comprises the T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, and Core-22 in FIGS. 9A-9B and FIGS. 11A-11N. As another example, in some cases, the T cell epitope polypeptide comprises the T-cell epitopes designated NS3-1, NS3-2, NS3-3, NS3-4, NS3-5, NS3-6, NS3-7, NS3-9, NS3-10, NS3-11, NS3-12, and NS3-13 in FIGS. 9A-9B and FIGS. 11A-11N. As another example, in some cases, the T cell epitope polypeptide comprises the T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIG. 9A-9B and FIGS. 11A-11N. As another example, in some cases, the T cell epitope polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, and NS4b-10 in FIGS. 9A-9B and FIG. 11A-11N. As another example, in some cases, the T cell epitope polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, and NS5b-2 in FIG. 9A-9B and FIGS. 11A-11N. In some cases, the T-cell epitopes are contiguous. In some cases, any two T-cell epitopes are separated by linkers (e.g., a linker having a length of from 1 amino acid to about 50 amino acids, e.g., from 1 amino acid to 5 amino acids (aa), from 5 aa to 10 aa, from 10 aa to 15 aa, from 15 aa to 20 aa, from 20 aa to 25 aa, from 25 aa to 30 aa, from 30 aa to 40 aa, or from 40 aa to 50 aa).

In some cases, the T cell epitope polypeptide comprises at least one HCV $CD4^+$ T cell epitope and at least one HCV $CD8^+$ T cell epitope, where epitopes are conserved among HCV genotypes 1 and 2. In some cases, the T cell epitope polypeptide comprises at least one HCV $CD4^+$ T cell epitope and at least one HCV $CD8^+$ T cell epitope, where epitopes are conserved among HCV genotypes 1 and 3. In some cases, the T cell epitope polypeptide comprises at least one HCV $CD4^+$ T cell epitope and at least one HCV $CD8^+$ T cell epitope, where epitopes are conserved among HCV genotypes 1, 2, and 3. In some cases, the T cell epitope polypeptide comprises at least one HCV $CD4^+$ T cell epitope and at least one HCV $CD8^+$ T cell epitope, where epitopes are conserved among HCV genotypes 1, 2, 3, and 7. In some cases, the T cell epitope polypeptide comprises at least one HCV $CD4^+$ T cell epitope and at least one HCV $CD8^+$ T cell epitope, where epitopes are conserved among HCV genotypes 1-7.

The T cell epitope polypeptide can have a length of from about 10 amino acids to about 2000 amino acids; e.g., the T cell epitope polypeptide can have a length of from 10 amino acids (aa) to 15 aa, from 15 aa to 20 aa, from 20 aa to 25 aa, from 25 aa to 50 aa, from 50 aa to 75 aa, from 75 an to 100 aa, from 100 an to 150 aa, from 150 aa to 200 aa, from 200 aa to 250 aa, from 250 aa to 300 aa, from 300 an to 350 aa, from 350 aa to 400 aa, from 450 an to 500 aa, from 500 an to 550 aa, from 550 an to 600 aa, from 600 an to 650 aa, from 650 aa to 700 aa, from 700 aa to 750 aa, or from 750 aa to 800 aa. The T-cell epitope polypeptide can have a length of from about 25 amino acids to about 2000 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 an to 300 aa, from 300 aa to 350 aa, from 350 an to 400 aa, from 400 an to 500 aa, from 500 aa to 600 aa, from 600 an to 700 aa, from 700 an to 800 aa, from 800 aa to 900 aa, from 900 an to 1000 aa, from 1000 aa to 1100 aa, from 1100 aa to 1200 aa, from 1200 an to 1300 aa, from 1300 aa to 1400 aa, from 1400 aa to 1500 aa, from 1500 aa to 1600 aa, from 1600 aa to 1700 aa, from 1700 an to 1800 aa, from 1800 an to 1900 aa, or from 1900 aa to 2000 aa. The T-cell epitope polypeptide can have a length of from about 25 amino acids to about 3000 amino acids, e.g., from about 25 amino acids (aa) to 50 aa, from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 an to 400 aa, from 400 an to 500 aa, from 500 an to 600 aa, from 600 an to 700 aa, from 700 an to 800 aa, from 800 an to 900 aa, from 900 aa to 1000 aa, from 1000 aa to 1100 aa, from 1100 an to 1200 aa, from 1200 aa to 1300 aa, from 1300 an to 1400 aa, from 1400 aa to 1500 aa, from 1500 an to 1600 aa, from 1600 aa to 1700 aa, from 1700 an to 1800 aa, from 1800 an to 1900 aa, from 1900 aa to 2000 aa, from 2000 an to 2250 aa, from 2250 an to 2500 aa, from 2500 an to 2750 aa, or from 2750 an to 3000 aa.

The T cell epitope polypeptide can have a length of from about 25 amino acids to about 800 amino acids, e.g., from about 25 amino acids (aa) to 50 aa, from 50 an to 75 aa, from 75 an to 100 aa, from 100 an to 150 aa, from 150 an to 200 aa, from 200 an to 250 aa, from 250 aa to 300 aa, from 300 an to 350 aa, from 350 aa to 400 aa, from 450 an to 500 aa, from 500 an to 550 aa, from 550 aa to 600 aa, from 600 an to 650 aa, from 650 an to 700 aa, from 700 aa to 750 aa, or from 750 an to 800 aa. The T-cell epitope polypeptide can have a length of from about 25 amino acids to about 400 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 aa to 300 aa, from 300 an to 350 aa, or from 350 aa to 400 aa. The T-cell epitope polypeptide can have a length of 25 amino acids (aa), 26 aa, 27 aa, 28 aa, 29 aa, 30 aa, 31 aa, 32 aa, 33 aa, 34 aa, 35 aa, 36 aa, 37 aa, 38 aa, 39 aa, 40 aa, 41 aa, 42 aa, 43 aa, 44 aa, 45 aa, 46 aa, 47 aa, 48 aa, 49 aa, or 50 aa. The T cell epitope polypeptide can have a length of from about 100 amino acids (aa) to 800 aa, e.g., from 100 aa to 150 aa, from 150 aa to 200 aa, from 200 aa to 250 aa, from 250 aa to 300 aa, from 300 aa to 350 aa, from 350 aa to 400 aa, from 450 aa to 500 aa, from 500 aa to 550 aa, from 550 aa to 600 aa, from 600 an to 650 aa, from 650 aa to 700 aa, from 700 an to 750 aa, or from 750 aa to 800 aa. The T cell epitope polypeptide can have a length of from 25 an to 30 aa. The T cell epitope polypeptide can have a length of from 30 aa to 40 aa. The T cell epitope polypeptide can have a length of from 40 aa to 50 aa. The T-cell epitope polypeptide can have a length of from 50 an to 60 aa (e.g., 50 aa, 51 aa, 52, aa, 53 aa, 54 aa, 55 aa, 56 aa, 57 aa, 58 aa, 59 aa, or 60 aa). The T cell epitope polypeptide can have a length of from 60 an to 70 aa. The T cell epitope polypeptide can have a length of from 65 an to 75 an (e.g., 65, 66, 67, 68, 69, 70, 71, 72, 7, 74, or 75 aa). The T cell epitope polypeptide can have a length of 70 aa. The T cell epitope polypeptide can have a length of from 70 an to 80 aa. The T cell epitope polypeptide can have a length of from 80 an to 90 aa. The T cell epitope polypeptide can have a length of from 90 aa to 100 aa. The T cell epitope polypeptide can have a length of from 100 an to 105 aa (e.g., 100, 101, 102, 103, 104, 105, 106, 107, 108, 109, or 110 aa). The T cell epitope polypeptide can have a length of 100 aa. The T cell epitope polypeptide can have a length of from 10 amino acids (aa) to 50 aa; e.g., from 10 an to 15 aa, from 15 an to 20 aa, from 20 aa to 25 aa, from 25 aa to 30 aa, from 30 aa to 35 aa, from 35 aa to 40 aa, from 40 aa to 45 aa, or from 45 an to 50 aa. The T cell epitope polypeptide can have a length of from 10 amino acids (aa) to 20 aa, e.g., 10, 11, 12, 13, 14, 15, 16, 17, 18, 19, or 20 aa. HCV NS3 T-cell epitopes In some cases, the T cell epitope polypeptide present in an immunogenic composition of the present disclosure includes one or more T-cell epitopes present in an HCV NS3 polypeptide. Examples of T-cell epitopes present in NS3 polypeptides are depicted in FIGS. 11A-11N, FIG. 9B, and FIG. 10A-10B.

The T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 85)
AIPLEVIKGGRHLIFCHSKKKCDELAAKL.

(SEQ ID NO: 85)
AIPLEVIKGGRHLIFCHSKKKCDELAAKL is referred to in FIG. 10A as "TP29." In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 85)
AIPLEVIKGGRHLIFCHSKKKCDELAAKL;

and has a length of from 25 aa to 35 aa (e.g., 25 aa, 26 aa, 27 aa, 28 aa, 29 aa, 30 aa, 31 aa, 32 aa, 33 aa, 34 aa, or 35 aa). In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence (SEQ ID NO: 85)
AIPLEVIKGGRHLIFCHSKKKCDELAAKL;

and has a length of 29 amino acids. Such a polypeptide can include NS3 T-cell epitopes designated NS3-3, NS3-4, and NS3-11 in FIG. 9B and FIGS. 11A-11N.

The T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 87)
AIPLEVIKGGRHLIFCHSKKKCDELAAKLVALGINAVAYYRGLDVSVIPT
SG.

(SEQ ID NO: 87)
AIPLEVIKGGRHLIFCHSKKKCDELAAKLVALGINAVAYYRGLDVSVIPT
SG is referred to in FIG. 10A as "TP52." In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 87)
AIPLEVIKGGRHLIFCHSKKKCDELAAKLVALGINAVAYYRGLDVSVIP
TSG;

and has a length of from 45 amino acids to 60 amino acids (e.g., 45 aa, 46 aa, 47 aa, 48 aa, 49 aa, 50 aa, 51 aa, 52 aa, 53 aa, 54 aa, 55 aa, 56 aa, 57 aa, 58 aa, 59 aa, or 60 aa). In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 87)
AIPLEVIKGGRHLIFCHSKKKCDELAAKLVALGINAVAYYRGLDVSVIP

TSG;

and has a length of 52 amino acids. Such a polypeptide can include NS3 T-cell epitopes designated NS3-3, NS3-4, NS3-5, and NS3-11 in FIG. 9B and FIGS. 11A-11N.

The T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, least about 99%, or 100%, amino acid sequence identity to the following amino acid sequence:

(SEQ ID NO: 88)
KGGRHLIFCHSKKKCDELAAKLVALGINAVAYYRGLDVSVIPTSGDVVVV

ATDALMTGFTGDFDSVIDCN;

and has a length of from 65 amino acids to 80 amino acids (e.g., 65 aa, 66 aa, 67 aa, 68 aa, 69 aa, 7 aa, 71 aa, 72 aa, 73 aa, 74 aa, 75 aa, 76 aa, 77 aa, 78 aa, 79 aa, or 80 aa).

(SEQ ID NO: 88)
KGGRHLIFCHSKKKCDELAAKLVALGINAVAYYRGLDVSVIPTSGDVVV

VATDALMTGFTGDFDSVIDCN is referred to in FIG. 10A as "TP70."

In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 88)
KGGRHLIFCHSKKKCDELAAKLVALGINAVAYYRGLDVSVIPTSGDVVV

VATDALMTGFTGDFDSVIDCN;

and has a length of 70 amino acids. Such a polypeptide can include NS3 T-cell epitopes designated NS3-3, NS3-4, NS3-5, NS3-6, NS3-7, NS3-11, NS3-12, and NS3-13 in FIG. 9B and FIGS. 11A-11N.

The T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 89)
VALSTTGEIPFYGKAIPLEVIKGGRHLIFCHSKKKCDELAAKLVALGIN

AVAYYRGLDVSVIPTSGDVVVVATDALMTGFTGDFDSVIDCNTCVTQTV

DF;

and has a length of from 95 amino acids (aa) to 105 an (e.g., 95 aa, 96 aa, 97 aa, 98 aa, 99 aa, 100 aa, 101 aa, 102 aa, 103 aa, 104 aa, or 105 aa).

(SEQ ID NO: 89)
VALSTTGEIPFYGKAIPLEVIKGGRHLIFCHSKKKCDELAAKLVALGIN

AVAYYRGLDVSVIPTSGDVVVVATDALMTGFTGDFDSVIDCNTCVTQTV

DF in FIG. 10A as "TP100."

In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 89)
VALSTTGEIPFYGKAIPLEVIKGGRHLIFCHSKKKCDELAAKLVALGIN

AVAYYRGLDVSVIPTSGDVVVVATDALMTGFTGDFDSVIDCNTCVTQTV

DF;

and has a length of 100 amino acids. Such a polypeptide can include NS3 T-cell epitopes designated NS3-3, NS3-4, NS3-5, NS3-6, NS3-7, NS3-10, NS3-11, NS3-12, and NS3-13 in FIG. 9B and FIG. 11A-11N.

The T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 90)
MSTNPKPQRKTKRNTNRRPQDVKFPGGGQIVGGVYLLPRRGPRLGVRATR

KTSERSQPRGRRQPIPKARRPEGRTWAQPGYPWPLYGNEGCGWAGWLLSP

RGSRPSWGPTDPRRRSRNLGKVIDTLTCGFADLMGYIPLVGAPLGGAARA

LAHGVRVLEDGVNYATGNLPG;

and has a length of from 171 amino acids (aa) to 180 aa (e.g., 171 aa, 172 aa, 173 aa, 174 aa, 175 aa, 176 aa, 177 aa, 178 aa, 179 aa, or 180 aa.

(SEQ ID NO: 90)
MSTNPKPQRKTKRNTNRRPQDVKFPGGGQIVGGVYLLPRRGPRLGVRATR

KTSERSQPRGRRQPIPKARRPEGRTWAQPGYPWPLYGNEGCGWAGWLLSP

RGSRPSWGPTDPRRRSRNLGKVIDTLTCGFADLMGYIPLVGAPLGGAARA

LAHGVRVLEDGVNYATGNLPG is referred to in FIG. 10A as "TP171."

In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 90)
MSTNPKPQRKTKRNTNRRPQDVKFPGGGQIVGGVYLLPRRGPRLGVRATR

KTSERSQPRGRRQPIPKARRPEGRTWAQPGYPWPLYGNEGCGWAGWLLSP

RGSRPSWGPTDPRRRSRNLGKVIDTLTCGFADLMGYIPLVGAPLGGAARA

LAHGVRVLEDGVNYATGNLPG;

and has a length of 171 amino acids.

The T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 129)
MSTNPKPQRKTKRNTNRRPQDVKFPGGGQIVGGVYLLPRRGPRLGVRAT

RKTSERSQPRGRRQPIPKARRPEGRTWAQPGYPWPLYGNEGCGWAGWLL

SPRGSRPSWGPTDPRRRSRNLGKVIDTLTCGFADLMGYIPLVGAPLGGA

ARALAHGVRVLEDGVNYATGNLPGCSFSIFLLALLSCLTVPASA;

and has a length of from 190 amino acids (aa) to 200 aa (e.g., 190 aa, 191 aa, 192 aa, 193 aa, 197 aa, 196 aa, 197 aa, 198 aa, 199 aa, or 200 aa.

In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 129)
MSTNPKPQRKTKRNTNRRPQDVKFPGGGQIVGGVYLLPRRGPRLGVRAT

RKTSERSQPRGRRQPIPKARRPEGRTWAQPGYPWPLYGNEGCGWAGWLL

SPRGSRPSWGPTDPRRRSRNLGKVIDTLTCGFADLMGYIPLVGAPLGGA

ARALAHGVRVLEDGVNYATGNLPGCSFSIFLLALLSCLTVPASA;

and has a length of 191 amino acids.

The T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 91)
LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN;

and has a length of from 215 amino acids (aa) to 235 an (e.g., 215 aa, 216 aa, 217 11, 218 aa, 219 aa, 220 aa, 221 aa, 222 aa, 223 aa, 224 aa, 225 aa, 226 aa, 227 aa, 228 aa, 229 aa, 230 aa, 231 aa, 232 aa, 233 aa, 234 aa, or 235 aa).

(SEQ ID NO: 91)
LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN is referred to in FIG. 10A as "TP228."

In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 91)
LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN;

and has a length of 228 amino acids. Such a polypeptide can include NS3 T-cell epitopes designated NS3-1, NS3-2, NS3-3, NS3-4, NS3-5, NS3-6, NS3-7, NS3-9, NS3-10, NS3-11, NS3-12, and NS3-13 in FIG. 9B and FIGS. 11A-11N.

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1265-1279 of the amino acid sequence designated "Consensus" in FIG. 12A-12L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1309-1323 of the amino acid sequence designated "Consensus" in FIG. 12A-12L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1401-1415 of the amino acid sequence designated "Consensus" in FIG. 12A-12L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1402-1412 of the amino acid sequence designated "Consensus" in FIG. 12A-12L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1429-1439 of the amino acid sequence designated "Consensus" in FIG. 12A-12L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1464 of the amino acid sequence designated "Consensus" in FIG. 12A-12L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1453-1467 of the amino acid sequence designated "Consensus" in FIG. 12A-12L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1577-1591 of the amino acid sequence designated "Consensus" in FIG. 12A-12L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1306-1314 of the amino acid sequence designated "Consensus" in FIG. 12A-12L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1387-1394 of the amino acid sequence designated "Consensus" in FIG. 12A-12L, or a corresponding HCV NS3 amino acid sequence of any HCV genotype; and the HCV NS3 T-cell epitope can have a length of from 1 amino acids (aa) to 15 amino acids (e.g., 8 aa, 9 aa, 10 aa, 11 aa, 12 aa, 13 aa, 14 aa, or 15 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1405-1413 of the amino acid sequence designated "Consensus" in FIG. 12A-12L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1458 of the amino acid sequence designated "Consensus" in FIG. 12A-12L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1457-1465 of the amino acid sequence designated "Consensus" in FIG. 12A-12L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1610-1618 of the amino acid sequence designated "Consensus" in FIG. 12A-12L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

HCV NS2 T-Cell Epitopes

In some cases, the T cell epitope polypeptide present in an immunogenic composition of the present disclosure includes one or more T-cell epitopes present in an HCV NS2 polypeptide. Examples of T-cell epitopes present in NS2 polypeptides are depicted in FIGS. 11A-11N, and FIG. 9A.

For example, the T cell epitope polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-974 of the amino acid sequence designated "Consensus" in FIG. 12A-12L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 975-994 of the amino acid sequence designated "Consensus" in FIG. 12A-12L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 985-1004 of the amino acid sequence designated "Consensus" in FIG. 12A-12L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1015-1034 of the amino acid sequence designated "Consensus" in FIG. 12A-12L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1035-1054 of the amino acid sequence designated "Consensus" in FIG. 12A-12L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 924-933 of the amino acid sequence designated "Consensus" in FIG. 12A-12L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the T cell epitope polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 961-970 of the amino acid sequence designated "Consensus" in FIG. 12A-12L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the T cell epitope polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 989-997 of the amino acid sequence designated "Consensus" in FIG. 12A-12L, or a corresponding HCV NS2 amino acid sequence of any HCV genotype; and the NS2 T cell epitope can have a length of from 9 amino acids (aa) to 15 amino acids (e.g., 9 aa, 10 aa, 11 aa, 12 aa, 13 aa, 14 aa, or 15 aa).

In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 50 an (e.g., from 10 aa to 25 aa, or from 25 an to 50 aa) of amino acids 955-1004 of the amino acid sequence designated "Consensus" in FIG. 12A-12L, or a corresponding HCV NS2 amino acid sequence of any HCV genotype; and has a length of from 10 amino acids (aa) to 25 aa, or from 25 aa to 50 aa. In some cases, the T-cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-1004 of the amino acid sequence designated "Consensus" in FIG. 12A-12L, or a corresponding HCV NS2 amino acid sequence of any HCV genotype; and has a length of about 50 amino acids.

In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 553 an (e.g., from 10 aa to 25 aa, from 25 aa to 50 aa, from 50 aa to 100 aa, from 100 aa to 200 aa, from 200 aa to 300 aa, from 300 aa to 400 aa, from 400 aa to 500 aa, or from 500 an to 553 aa) of amino acids 917-1469 of the amino acid sequence designated "Consensus" in FIG. 12A-12L, or a corresponding HCV NS2 and NS3 amino acid sequence of any HCV genotype; and has a length of from 10 amino acids (aa) to 25 aa, from 25 aa to 50 aa, from 50 aa to 100 aa, from 100 aa to 200 aa, from 200 aa to 300 aa, from 300 aa to 400 aa, from 400 aa to 500 aa, or from 500 aa to 553 aa. In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 917-1469 of the amino acid sequence designated "Consensus" in FIG. 12A-12L, or a corresponding HCV NS2 and NS3 amino acid sequence of any HCV genotype; and has a length of about 553 amino acids.

The T cell epitope polypeptide can comprise an amino acid sequence having at least about 20%, at least about 25%, at least about 30%, at least about 35%, at least about 40%, at least about 45%, at least about 50%, at least about 60%, at least about 0%, at least about 75%, at least about 80%, at least about 85%, at least about 90%, at least about 95%, at least about 98%, at least about 99%, or 100%, amino acid sequence identity to the following amino acid sequence:

```
                                         (SEQ ID NO: 86)
LGALTGTYVYNHLTPLRDWAHNGLRDLAVAVEPVVFSQMETKLITWGADT.
```

```
                                         (SEQ ID NO: 86)
LGALTGTYVYNHLTPLRDWAHNGLRDLAVAVEPVVFSQMETKLITWGADT
```

is referred to in FIG. 10A as "TP50." In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

```
                                         (SEQ ID NO: 86)
LGALTGTYVYNHLTPLRDWAHNGLRDLAVAVEPVVFSQMETKLITWGADT;
```

and has a length of from 50 amino acids to 60 amino acids (e.g., 50 aa, 51 aa, 52 aa, 53 aa, 54 aa, 55 aa, 56 aa, 57 aa, 58 aa, 59 aa, or 60 aa). In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

```
                                         (SEQ ID NO: 86)
LGALTGTYVYNHLTPLRDWAHNGLRDLAVAVEPVVFSQMETKLITWGAD

T;
```

and has a length of 50 amino acids. Such a polypeptide can include NS2 T-cell epitopes designated NS2-1, NS2-2, NS2-3, NS2-7, and NS2-8 in FIG. 9A and FIGS. 11A-11N.

HCV NS4A T-Cell Epitopes

In some cases, the T cell epitope polypeptide present in an immunogenic composition of the present disclosure includes one or more T-cell epitopes present in an HCV NS4A polypeptide. Examples of T-cell epitopes present in NS4A polypeptides are depicted in FIG. 11A-11N and FIG. 9B.

The T cell epitope polypeptide can comprise an NS4A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1683-1692 of the amino acid sequence designated "Consensus" in FIG. 12A-12L, or a corresponding HCV NS4A amino acid sequence of any HCV genotype; and the NS4A T-cell epitope can have a length of from 10 amino acids (aa) to 15 amino acids (e.g., 10 aa, 11 aa, 12 aa, 13 aa, 14 aa, or 15 aa).

HCV NS4B T-Cell Epitopes

In some cases, the T cell epitope polypeptide present in an immunogenic composition of the present disclosure includes one or more T-cell epitopes present in an HCV NS4B polypeptide. Examples of T-cell epitopes present in NS4B polypeptides are depicted in FIG. 11A-11N and FIG. 9B.

As one example, the T cell epitope polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1790-1801 of the amino acid sequence designated "Consensus" in FIG. 12A-12L, or a corresponding HCV NS4B amino acid sequence of any HCV genotype; and the NS4B T-cell epitope can have a length of from 12 amino acids (aa) to 20 amino acids (e.g., 12 aa, 13 aa, 14 aa, 15 aa, 16 aa, 17 aa, 18 aa, 19 aa, or 20 aa).

As another example, the T cell epitope polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1792-1802 of the amino acid sequence designated "Consensus" in FIG. 12A-12L, or a corresponding HCV NS4B amino acid sequence of any HCV genotype; and the NS4B T-cell epitope can have a length of from 11 amino acids (aa) to 20 amino acids (e.g., 11 aa, 12 aa, 13 aa, 14 aa, 15 aa, 16 aa, 17 aa, 18 aa, 19 aa, or 20 aa).

As another example, the T cell epitope polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1898-1905 of the amino acid sequence designated "Consensus" in FIG. 12A-12L, or a corresponding HCV NS4B amino acid sequence of any HCV genotype; and the NS4B T-cell epitope can have a length of from 8 amino acids (aa) to 15 amino acids (e.g., 8 aa, 9 aa, 10 aa, 11 aa, 12 aa, 13 aa, 14 aa, or 15 aa).

As another example, the T cell epitope polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1921-1935 of the amino acid sequence designated "Consensus" in FIG. 12A-12L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

As another example, the T cell epitope polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1922-1941 of the amino acid sequence designated "Consensus" in FIG. 12A-12L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1928-1947 of the amino acid sequence designated "Consensus" in FIG. 12A-12L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1868-1876 of the amino acid sequence designated "Consensus" in FIG. 12A-12L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1927-1942 of the amino acid sequence designated "Consensus" in FIG. 12A-12L, or a corresponding HCV NS4B amino acid sequence of any HCV genotype; and the NS4B T-cell epitope can have a length of from 16 amino acids (aa) to 20 amino acids (e.g., 16 aa, 17 aa, 18 aa, 19 aa, or 20 aa).

As another example, the T cell epitope polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1932-1940 of the amino acid sequence designated "Consensus" in FIG. 12A-12L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1948-1962 of the amino acid sequence designated "Consensus" in FIG. 12A-12L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

HCV NS5A T-Cell Epitopes

In some cases, the T cell epitope polypeptide present in an immunogenic composition of the present disclosure includes one or more T-cell epitopes present in an HCV NS5A polypeptide. Examples of T-cell epitopes present in NS5A polypeptides are depicted in FIG. 11A-11N and FIG. 9B.

As one example, the T cell epitope polypeptide can comprise an NS5A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2218-2232 of the amino acid sequence designated "Consensus" in FIG. 12A-12L, or a corresponding HCV NS5A amino acid sequence of any HCV genotype; and the NS5A T-cell epitope can have a length of from 15 amino acids (aa) to 20 amino acids (e.g., 15 aa, 16 aa, 17 aa, 18 aa, 19 aa, or 20 aa).

As another example, the T cell epitope polypeptide can comprise an NS5A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2309-2317 of the amino acid sequence designated "Consensus" in FIG. 12A-12L, or a corresponding HCV NS5A amino acid sequence of any HCV genotype; and the NS5A T-cell epitope can have a length of from 9 amino acids (aa) to 15 amino acids (e.g., 9 aa, 10 aa, 11 aa, 12 aa, 13 aa, 14 aa, or 15 aa).

HCV NS5B T-Cell Epitopes

In some cases, the T cell epitope polypeptide present in an immunogenic composition of the present disclosure includes one or more T-cell epitopes present in an HCV NS5B polypeptide. Examples of T-cell epitopes present in NS5B polypeptides are depicted in FIG. 11A-11N and FIG. 9B.

As one example, the T cell epitope polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2847-2851 of the amino acid sequence designated "Consensus" in FIG. 12A-12L, or a corresponding HCV NS5B amino acid sequence of any HCV genotype; and the NS5B T-cell epitope can have a length of from 5 amino acids (aa) to 10 amino acids (e.g., 5 aa, 6 aa, 7 aa, 8 aa, 9 aa, or 10 aa).

As another example, the T cell epitope polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2602-2610 of the amino acid sequence designated "Consensus" in FIG. 12A-12L, or a corresponding HCV NS5B amino acid sequence of any HCV genotype; and the NS5B T-cell epitope can have a length of from 9 amino acids (aa) to 15 amino acids (e.g., 9 aa, 10 aa, 11 aa, 12 aa, 13 aa, 14 aa, or 15 aa).

HCV Core T-Cell Epitopes

In some cases, the T cell epitope polypeptide present in an immunogenic composition of the present disclosure includes one or more T-cell epitopes present in an HCV core polypeptide. Examples of T-cell epitopes present in HCV Core polypeptides are depicted in FIGS. 11A-11N and FIG. 9A.

As one example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-20 of the amino acid sequence designated "Consensus" in FIG. 12A-12L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 11-30 of the amino acid sequence designated "Consensus" in FIG. 12A-12L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 21-40 of the amino acid sequence designated "Consensus" in FIG. 12A-12L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 39-63 of the amino acid sequence designated "Consensus" in FIG. 12A-12L, or a corresponding HCV core amino acid sequence of any HCV genotype; and the HCV core T-cell epitope can have a length of from 23 amino acids (aa) to 28 amino acids (e.g., 23 aa, 24 aa, 25 aa, 26 aa, 27 aa, or 28 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 47-70 of the amino acid sequence designated "Consensus" in FIG. 12A-12L, or a corresponding HCV core amino acid sequence of any HCV genotype; and the HCV core T-cell epitope can have a length of from 24 amino acids (aa) to 29 amino acids (e.g., 24 aa, 25 aa, 26 aa, 27 aa, 28 aa, or 29 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 61-80 of the amino acid sequence designated "Consensus" in FIG. 12A-12L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 71-90 of the amino acid sequence designated "Consensus" in FIG. 12A-12L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 81-100 of the amino acid sequence designated "Consensus" in FIG. 12A-12L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 91-110 of the amino acid sequence designated "Consensus" in FIG. 12A-12L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 101-115 of the amino acid sequence designated "Consensus" in FIG. 12A-12L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 111-130 of the amino acid sequence designated "Consensus" in FIG. 12A-12L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 125-139 of the amino acid sequence designated "Consensus" in FIG. 12A-12L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-150 of the amino acid sequence designated "Consensus" in FIG. 12A-12L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 151-170 of the amino acid sequence designated "Consensus" in FIG. 12A-12L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 161-180 of the amino acid sequence designated "Consensus" in FIG. 12A-12L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 35-44 of the amino acid sequence designated "Consensus" in FIG. 12A-12L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 43-51 of the amino acid sequence designated "Consensus" in FIG. 12A-12L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 51-59 of the amino acid sequence designated "Consensus" in FIG. 12A-12L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 129-137 of the amino acid sequence designated "Consensus" in FIG. 12A-12L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-140 of the amino acid sequence designated "Consensus" in FIG. 12A-12L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 150-158 of the amino acid sequence designated "Consensus" in FIG. 12A-12L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 154-162 of the amino acid sequence designated "Consensus" in FIG. 12A-12L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 168-176 of the amino acid sequence designated "Consensus" in FIG. 12A-12L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 177-187 of the amino acid sequence designated "Consensus" in FIG. 12A-12L, or a corresponding HCV core amino acid sequence of any HCV genotype; and the HCV core T-cell epitope can have a length of from 11 amino acids (aa) to 16 amino acids (e.g., 11 aa, 12 aa, 13 aa, 14 aa, 15 aa, or 16 aa).

As another example, the T cell epitope polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 178-187 of the amino acid sequence designated "Consensus" in FIG. 12A-12L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 191 aa (e.g., from 10 aa to 25 aa, from 25 aa to 50 aa, from 50 aa to 75 aa, from 75 aa to 100 aa, from 100 aa to 150 aa, or from 150 aa to 191aa) of amino acids 1-191 of the amino acid sequence designated "Consensus" in FIG. 12A-12L, or a corresponding HCV core amino acid sequence of any HCV genotype; and has a length of from 10 amino acids (aa) to 25 aa, from 25 an to 50 aa, from 50 an to 100 aa, or from 100 aa to 150 aa, or from 150 an to 191 aa. In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-191 of the amino acid sequence designated "Consensus" in FIG. 12A-12L, or a corresponding HCV core amino acid sequence of any HCV genotype; and has a length of about 191 amino acids.

The T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 90)
MSTNPKPQRKTKRNTNRRPQDVKFPGGGQIVGGVYLLPRRGPRLGVRATR

KTSERSQPRGRRQPIPKARRPEGRTWAQPGYPWPLYGNEGCGWAGWLLSP

RGSRPSWGPTDPRRRSRNLGKVIDTLTCGFADLMGYIPLVGAPLGGAARA

LAHGVRVLEDGVNYATGNLPG;

and has a length of from 171 amino acids (aa) to 180 aa (e.g., 171 aa, 172 aa, 173 aa, 174 aa, 175 aa, 176 aa, 177 aa, 178 aa, 179 aa, or 180 aa. In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 90)
MSTNPKPQRKTKRNTNRRPQDVKFPGGGQIVGGVYLLPRRGPRLGVRATR

KTSERSQPRGRRQPIPKARRPEGRTWAQPGYPWPLYGNEGCGWAGWLLSP

RGSRPSWGPTDPRRRSRNLGKVIDTLTCGFADLMGYIPLVGAPLGGAARA

LAHGVRVLEDGVNYATGNLPG;

and has a length of 171 amino acids. Such a polypeptide can include core T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, Core-22 in FIG. 9A and FIGS. 11A-11N.

HCV p7 T-Cell Epitopes

In some cases, the T cell epitope polypeptide present in an immunogenic composition of the present disclosure includes one or more T-cell epitopes present in an HCV p7 polypeptide. Examples of T-cell epitopes present in HCV p7 polypeptides are depicted in FIGS. 11A-11N or FIG. 9A.

As another example, the T cell epitope polypeptide can comprise an HCV p7 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 803-811 of the amino acid sequence designated "Consensus" in FIG. 12A-12L, or a corresponding HCV p7 amino acid sequence of any HCV genotype; and the HCV p7 T-cell epitope can have a length of from 9 amino acids (aa) to 15 amino acids (e.g., 9 aa, 10 aa, 11 aa, 12 aa, 13 aa, 14 aa, or 15 aa).

T-Cell Epitope Polypeptides Including HCV T-Cell Epitopes from More than One HCV Polypeptide Other than E1 and E2

As noted above, a T-cell epitope polypeptide can include T-cell epitopes from more than one HCV polypeptide other than E1 and E2.

As one example, a T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

```
                                             (SEQ ID NO: 92)
QASLLKVPYFVRVQGLLRICALARKMAGGHYVQMAIIKLGALTGTYVYNA
LTPLRDWAHNGLRDLAVAVEPVVFSQMETKLITWGADTAACGDIINGLPV
SARRGREILLGPADGMVSKGWRLLAPITAYAQQTRGLLGCIITSLTGRDK
NQVEGEVQIVSTAAQTFLATCINGVCWTVYHGAGTRTIASPKGPVIQMYT
NVDQDLVGWPAPQGARSLTPCTCGSSDLYLVTRHADVIPVRRRGDSRGSL
LSPRPISYLKGSAGGPLLCPAGHAVGIFRAAVCTRGVAKAVDFIPVENLE
TTMRSPVFTDNSSPPAVPQSFQVAHLHAPTGSGKSTKVPAAYAAQGYKVL
VLNPSVAATLGFGAYMSKAHGIDPNIRTGVRTITTGSPITYSTYGKFLAD
GGCSGGAYDIIICDECHSTDATSILGIGTVLDQAETAGARLVVLATATPP
GSVTVPHPNIEEVALSTTGEIPFYGKAIPLEVIKGGRHLIFCHSKKKCDE
LAAKLVALGINAVAYYRGLDVSVIPTSGDVVVVATDALMTGFTGDFDSVI
DCN;
```

and has a length of from 550 amino acids (aa) to 560 aa (e.g., 550 aa, 551 aa, 552 aa, 553 aa, 554 aa, 555 aa, 556 aa, 557 aa, 558 aa, 559 aa, or 560 aa).

```
                                             (SEQ ID NO: 92)
QASLLKVPYFVRVQGLLRICALARKMAGGHYVQMAIIKLGALTGTYVYNA
LTPLRDWAHNGLRDLAVAVEPVVFSQMETKLITWGADTAACGDIINGLPV
SARRGREILLGPADGMVSKGWRLLAPITAYAQQTRGLLGCIITSLTGRDK
NQVEGEVQIVSTAAQTFLATCINGVCWTVYHGAGTRTIASPKGPVIQMYT
NVDQDLVGWPAPQGARSLTPCTCGSSDLYLVTRHADVIPVRRRGDSRGSL
LSPRPISYLKGSAGGPLLCPAGHAVGIFRAAVCTRGVAKAVDFIPVENLE
TTMRSPVFTDNSSPPAVPQSFQVAHLHAPTGSGKSTKVPAAYAAQGYKVL
VLNPSVAATLGFGAYMSKAHGIDPNIRTGVRTITTGSPITYSTYGKFLAD
```

-continued

```
GGCSGGAYDIIICDECHSTDATSILGIGTVLDQAETAGARLVVLATATPP
GSVTVPHPNIEEVALSTTGEIPFYGKAIPLEVIKGGRHLIFCHSKKKCDE
LAAKLVALGINAVAYYRGLDVSVIPTSGDVVVVATDALMTGFTGDFDSVI
DCN
```

is referred to in FIG. 10A-10B as "TP553."

In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

```
                                             (SEQ ID NO: 92)
QASLLKVPYFVRVQGLLRICALARKMAGGHYVQMAIIKLGALTGTYVYNA
LTPLRDWAHNGLRDLAVAVEPVVFSQMETKLITWGADTAACGDIINGLPV
SARRGREILLGPADGMVSKGWRLLAPITAYAQQTRGLLGCIITSLTGRDK
NQVEGEVQIVSTAAQTFLATCINGVCWTVYHGAGTRTIASPKGPVIQMYT
NVDQDLVGWPAPQGARSLTPCTCGSSDLYLVTRHADVIPVRRRGDSRGSL
LSPRPISYLKGSAGGPLLCPAGHAVGIFRAAVCTRGVAKAVDFIPVENLE
TTMRSPVFTDNSSPPAVPQSFQVAHLHAPTGSGKSTKVPAAYAAQGYKVL
VLNPSVAATLGFGAYMSKAHGIDPNIRTGVRTITTGSPITYSTYGKFLAD
GGCSGGAYDIIICDECHSTDATSILGIGTVLDQAETAGARLVVLATATPP
GSVTVPHPNIEEVALSTTGEIPFYGKAIPLEVIKGGRHLIFCHSKKKCDE
LAAKLVALGINAVAYYRGLDVSVIPTSGDVVVVATDALMTGFTGDFDSVI
DCN;
```

and has a length of 553 amino acids. Such a polypeptide can include T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIGS. 9A-9B and FIGS. 11A-11N. This polypeptide is also referred to as "TP553" (FIG. 12A-12D). In order to prevent self cleavage of the TP553 polypeptide (amino acids 917-1469) (FIG. 11E-11G) at the NS2-NS3 junction that is mediated by the catalytic domain of the NS2 protease (amino acids 917-1040), the histidine at position 966 (H966), a critical residue for NS2 protease activity, is mutated to alanine (H966A) (FIG. 11E). See, e.g., Grakoui, A. et al. A second hepatitis C virus-encoded proteinase. Proc. Natl Acad. Sci. USA 90, 10583-10587 (1993); Hijikata, M. et al. Two distinct proteinase activities required for the processing of a putative nonstructural precursor protein of hepatitis C virus. J. Virol. 67, 4665-4675 (1993); and Lorenz. I C. Structure of the catalytic domain of the hepatitis C virus NS2-3 protease. Nature. August 17; 442(7104):831-5 (2006).

As another example, the T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 778 aa (e.g., from 25 aa to 50 aa, from 50 aa to 75 aa, from 75 aa to 100 aa, from 100 an to 150 aa, from 150 an to 200 aa, from 200 an to 250 aa, from 250 aa to 300 aa, from 300 aa to 350 aa, from 350 aa to 400 aa, from 400 aa to 450 aa, from 450 aa to 500 aa, from 500 an to 550 aa, from 550 aa to 600 aa, from 600 an to 650 aa, from 650 an to 700 aa, from 700 an to 750 aa, or from 750 aa to 778 aa) the following amino acid sequence:

(SEQ ID NO: 93)
```
LHAPTGSGKSTKVPAAYAAQGYKVLVLNPSVAATLGFGAYMSKAHGIDPN
IRTGVRTITTGSPITYSTYGKFLADGGCSGGAYDIIICDECHSTDATSIL
GIGTVLDQAETAGARLVVLATATPPGSVTVPHPNIEEVALSTTGEIPFYG
KAIPLEVIKGGRHLIFCHSKKKCDELAAKLVALGINAVAYYRGLDVSVIP
TSGDVVVVATDALMTGFTGDFDSVIDCNTCVTQTVDFSLDPTFTIETTTL
PQDAVSRTQRRGRTGRGKPGIYRFVAPGERPSGMFDSSVLCECYDAGCAW
YELTPAETTVRLRAYMNTPGLPVCQDHLEFWEGVFTGLTHIDAHFLSQTK
QSGENLPYLVAYQATVCARAQAPPPSWDQMWKCLIRLKPTLHGPTPLLYR
LGAVQNEVTLTHPITKYIMTCMSADLEVVTSTWVLVGGVLAALAAYCLST
GCVVIVGRIVLSGKPAIIPDREVLYREFDEMEECSQHLPYIEQGMMLAEQ
FKQKALGLLQTASRQAEVIAPAVQTNWQKLEAFWAKHMWNFISGIQYLAG
LSTLPGNPAIASLMAFTAAVTSPLTTSQTLLFNILGGWVAAQLAAPGAAT
AFVGAGLAGAAIGSVGLGKVLVDILAGYGAGVAGALVAFKIMSGEVPSTE
DLVNLLPAILSPGALVVGVVCAAILRRHVGPGEGAVQWMNRLIAFASRGN
HVSPTHYVPESDAAARVTAILSSLTVTQLLRRLHQWISSECTTPCSGSWL
RDIWDWICEVLSDFKTWLKAKLMPQLPG;
```

and has a length of from 778 amino acids (aa) to 790 aa (e.g., 778 aa, 779 aa, 780 aa, 781 aa, 782 aa, 783 aa, 784 aa, 785 aa, 786 aa, 787 an, 788 aa, or 790 as).

(SEQ ID NO: 93)
```
LHAPTGSGKSTKVPAAYAAQGYKVLVLNPSVAATLGFGAYMSKAHGIDPN
IRTGVRTITTGSPITYSTYGKFLADGGCSGGAYDIIICDECHSTDATSIL
GIGTVLDQAETAGARLVVLATATPPGSVTVPHPNIEEVALSTTGEIPFYG
KAIPLEVIKGGRHLIFCHSKKKCDELAAKLVALGINAVAYYRGLDVSVIP
TSGDVVVVATDALMTGFTGDFDSVIDCNTCVTQTVDFSLDPTFTIETTTL
PQDAVSRTQRRGRTGRGKPGIYRFVAPGERPSGMFDSSVLCECYDAGCAW
YELTPAETTVRLRAYMNTPGLPVCQDHLEFWEGVFTGLTHIDAHFLSQTK
QSGENLPYLVAYQATVCARAQAPPPSWDQMWKCLIRLKPTLHGPTPLLYR
LGAVQNEVTLTHPITKYIMTCMSADLEVVTSTWVLVGGVLAALAAYCLST
GCVVIVGRIVLSGKPAIIPDREVLYREFDEMEECSQHLPYIEQGMMLAEQ
FKQKALGLLQTASRQAEVIAPAVQTNWQKLEAFWAKHMWNFISGIQYLAG
LSTLPGNPAIASLMAFTAAVTSPLTTSQTLLFNILGGWVAAQLAAPGAAT
AFVGAGLAGAAIGSVGLGKVLVDILAGYGAGVAGALVAFKIMSGEVPSTE
DLVNLLPAILSPGALVVGVVCAAILRRHVGPGEGAVQWMNRLIAFASRGN
```

-continued

```
HVSPTHYVPESDAAARVTAILSSLTVTQLLRRLHQWISSECTTPCSGSWL
RDIWDWICEVLSDFKTWLKAKLMPQLPG
```

is referred to in FIG. 10B as "TP778."

In some cases, the T cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (an) to 778 an (e.g., from 25 aa to 50 aa, from 50 aa to 75 aa, from 75 aa to 100 aa, from 100 an to 150 aa, from 150 aa to 200 aa, from 200 an to 250 an, from 250 an to 300 aa, from 300 aa to 350 aa, from 350 an to 400 an, from 400 an to 450 aa, from 450 aa to 500 aa, from 500 as to 550 aa, from 550 as to 600 aa, from 600 as to 650 aa, from 650 as to 700 aa, from 700 aa to 750 aa, or from 750 an to 778 aa) of the following amino acid sequence:

(SEQ ID NO: 93)
```
LHAPTGSGKSTKVPAAYAAQGYKVLVLNPSVAATLGFGAYMSKAHGIDPN
IRTGVRTITTGSPITYSTYGKFLADGGCSGGAYDIIICDECHSTDATSIL
GIGTVLDQAETAGARLVVLATATPPGSVTVPHPNIEEVALSTTGEIPFYG
KAIPLEVIKGGRHLIFCHSKKKCDELAAKLVALGINAVAYYRGLDVSVIP
TSGDVVVVATDALMTGFTGDFDSVIDCNTCVTQTVDFSLDPTFTIETTTL
PQDAVSRTQRRGRTGRGKPGIYRFVAPGERPSGMFDSSVLCECYDAGCAW
YELTPAETTVRLRAYMNTPGLPVCQDHLEFWEGVFTGLTHIDAHFLSQTK
QSGENLPYLVAYQATVCARAQAPPPSWDQMWKCLIRLKPTLHGPTPLLYR
LGAVQNEVTLTHPITKYIMTCMSADLEVVTSTWVLVGGVLAALAAYCLST
GCVVIVGRIVLSGKPAIIPDREVLYREFDEMEECSQHLPYIEQGMMLAEQ
FKQKALGLLQTASRQAEVIAPAVQTNWQKLEAFWAKHMWNFISGIQYLAG
LSTLPGNPAIASLMAFTAAVTSPLTTSQTLLFNILGGWVAAQLAAPGAAT
AFVGAGLAGAAIGSVGLGKVLVDILAGYGAGVAGALVAFKIMSGEVPSTE
DLVNLLPAILSPGALVVGVVCAAILRRHVGPGEGAVQWMNRLIAFASRGN
HVSPTHYVPESDAAARVTAILSSLTVTQLLRRLHQWISSECTTPCSGSWL
RDIWDWICEVLSDFKTWLKAKLMPQLPG;
```

and has a length of from 25 amino acids (aa) to 50 aa, from 50 aa to 100 aa, from 100 aa to 200 aa, from 200 aa to 300 aa, from 300 aa to 400 aa, from 400 aa to 500 aa, from 500 aa to 600 aa, from 600 aa to 700 aa, or from 700 an to 778 aa. In some cases, the T-cell epitope polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 93)
LHAPTGSGKSTKVPAAYAAQGYKVLVLNPSVAATLGFGAYMSKAHGIDPN
IRTGVRTITTGSPITYSTYGKFLADGGCSGGAYDIIICDECHSTDATSIL
GIGTVLDQAETAGARLVVLATATPPGSVTVPHPNIEEVALSTTGEIPFYG
KAIPLEVIKGGRHLIFCHSKKKCDELAAKLVALGINAVAYYRGLDVSVIP
TSGDVVVVATDALMTGFTGDFDSVIDCNTCVTQTVDFSLDPTFTIETTTL
PQDAVSRTQRRGRTGRGKPGIYRFVAPGERPSGMFDSSVLCECYDAGCAW
YELTPAETTVRLRAYMNTPGLPVCQDHLEFWEGVFTGLTHIDAHFLSQTK
QSGENLPYLVAYQATVCARAQAPPPSWDQMWKCLIRLKPTLHGPTPLLYR
LGAVQNEVTLTHPITKYIMTCMSADLEVVTSTWVLVGGVLAALAAYCLST
GCVVIVGRIVLSGKPAIIPDREVLYREFDEMEECSQHLPYIEQGMMLAEQ
FKQKALGLLQTASRQAEVIAPAVQTNWQKLEAFWAKHMWNFISGIQYLAG
LSTLPGNPAIASLMAFTAAVTSPLTTSQTLLFNILGGWVAAQLAAPGAAT
AFVGAGLAGAAIGSVGLGKVLVDILAGYGAGVAGALVAFKIMSGEVPSTE
DLVNLLPAILSPGALVVGVVCAAILRRHVGPGEGAVQWMNRLIAFASRGN
HVSPTHYVPESDAAARVTAILSSLTVTQLLRRLHQWISSECTTPCSGSWL
RDIWDWICEVLSDFKTWLKAKLMPQLPG;

and has a length of 778 amino acids. Such a polypeptide can include T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS2-14, NS4a-1, NS4b-1, NS4b-2, NS4b-3, NS4b-4, NS4b-5, NS4b-6, NS4b-7, NS4b-8, NS4b-9, and NS4b-10 in FIG. 9B and FIGS. 11A-11N.

As another example, the T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 1985 aa (e.g., from 25 an to 50 aa, from 50 an to 75 an, from 75 an to 100 an, from 100 an to 150 an, from 150 an to 200 aa, from 200 aa to 250 an, from 250 aa to 500 an, from 500 an to 750 an, from 750 an to 1000 aa, from 1000 aa to 1500 an, or from 1500 an to 1985 aa) of the following amino acid sequence:

(SEQ ID NO: 94)
APITAYAQQTRGLLGCIITSLTGRDKNQVEGEVQIVSTAAQTFLATCIN
GVCWTVYHGAGTRTIASPKGPVIQMYTNVDQDLVGWPAPQGARSLTPCT
CGSSDLYLVTRHADVIPVRRRGDSRGSLLSPRPISYLKGS<u>A</u>GGPLLCPA
GHAVGIFRAAVCTRGVAKAVDFIPVENLETTMRSPVFTDNSSPPAVPQS
FQVAHLHAPTGSGKSTKVPAAYAAQGYKVLVLNPSVAATLGFGAYMSKA
HGIDPNIRTGVRTITTGSPITYSTYGKFLADGGCSGGAYDIIICDECHS
TDATSILGIGTVLDQAETAGARLVVLATATPPGSVTVPHPNIEEVALST
TGEIPFYGKAIPLEVIKGGRHLIFCHSKKKCDELAAKLVALGINAVAYY
RGLDVSVIPTSGDVVVVATDALMTGFTGDFDSVIDCNTCVTQTVDFSLD
PTFTIETTTLPQDAVSRTQRRGRTGRGKPGIYRFVAPGERPSGMFDSSV

-continued

LCECYDAGCAWYELTPAETTVRLRAYMNTPGLPVCQDHLEFWEGVFTGL
THIDAHFLSQTKQSGENLPYLVAYQATVCARAQAPPPSWDQMWKCLIRL
KPTLHGPTPLLYRLGAVQNEVTLTHPITKYIMTCMSADLEVVTSTWVLV
GGVLAALAAYCLSTGCVVIVGRIVLSGKPAIIPDREVLYREFDEMEECS
QHLPYIEQGMMLAEQFKQKALGLLQTASRQAEVIAPAVQTNWQKLEAFW
AKHMWNFISGIQYLAGLSTLPGNPAIASLMAFTAAVTSPLTTSQTLLFN
ILGGWVAAQLAAPGAATAFVGAGLAGAAIGSVGLGKVLVDILAGYGAGV
AGALVAFKIMSGEVPSTEDLVNLLPAILSPGALVVGVVCAAILRRHVGP
GEGAVQWMNRLIAFASRGNHVSPTHYVPESDAAARVTAILSSLTVTQLL
RRLHQWISSECTTPCSGSWLRDIWDWICEVLSDFKTWLKAKLMPQLPGI
PFVSCQRGYRGVWRGDGIMHTRCHCGAEITGHVKNGTMRIVGPRTCRNM
WSGTFPINAYTTGPCTPLPAPNYTFALWRVSAEEYVEIRQVGDFHYVTG
MTTDNLKCPCQVPSPEFFTELDGVRLHRFAPPCKPLLREEVSFRVGLHE
YPVGSQLPCEPEPDVAVLTSMLTDPSHITAEAAGRRLARGSPPSVASSS
ASQLSAPSLKATCTANHDSPDAELIEANLLWRQEMGGNITRVESENKVV
ILDSFDPLVAEEDEREISVPAEILRKSRRFAPALPIWARPDYNPPLLET
WKKPDYEPPVVHGCPLPPPQSPPVPPPRKKRTVVLTESTVSTALAELAT
KSFGSSSTSGITGDNTTTSSEPAPSGCPPDSDAESYSSMPPLEGEPGDP
DLSDGSWSTVSSEADTEDVVCCSMSYSWTGALVTPCAAEEQKLPINALS
NSLLRHHNLVYSTTSRSACQRQKKVTFDRLQVLDSHYQDVLKEVKAAAS
KVKANLLSVEEACSLTPPHSAKSKFGYGAKDVRCHARKAVNHINSVWKD
LLEDSVTPIDTTIMAKNEVFCVQPEKGGRKPARLIVFPDLGVRVCEKMA
LYDVVSKLPLAVMGSSYGFQYSPGQRVEFLVQAWKSKKTPMGFSYDTRC
FDSTVTESDIRTEEAIYQCCDLDPQARVAIKSLTERLYVGGPLTNSRGE
NCGYRRCRASGVLTTSCGNTLTCYIKARAACRAAGLQDCTMLVCG<u>NN</u>LV
VICESAGVQEDAASLRAFTEAMTRYSAPPGDPPQPEYDLELITSCSSNV
SVAHDGAGKRVYYLTRDPTTPLARAAWETARHTPVNSWLGNIIMFAPTL
WARMILMTHFFSVLIARDQLEQALDCEIYGACYSIEPLDLPPIIQRLHG
LSAFSLHSYSPGEINRVAACLRKLGVPPLRAWRHRARSVRARLLSRGGR
AAICGKYLFNWAVRTKLKLTPIAAAGQLDLSGWFTAGYSGGDIYHSVSH
ARPRWFWFCLLLLAAGVGIYLLPNR;

this polypeptide is also referred to as "TP1985" and is depicted in FIG. 10C.

In some cases, the T cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 94)

APITAYAQQTRGLLGCIITSLTGRDKNQVEGEVQIVSTAAQTFLATCIN

GVCWTVYHGAGTRTIASPKGPVIQMYTNVDQDLVGWPAPQGARSLTPCT

CGSSDLYLVTRHADVIPVRRRGDSRGSLLSPRPISYLKGSAGGPLLCPA

GHAVGIFRAAVCTRGVAKAVDFIPVENLETTMRSPVFTDNSSPPAVPQS

FQVAHLHAPTGSGKSTKVPAAYAAQGYKVLVLNPSVAATLGFGAYMSKA

HGIDPNIRTGVRTITTGSPITYSTYGKFLADGGCSGGAYDIIICDECHS

TDATSILGIGTVLDQAETAGARLVVLATATPPGSVTVPHPNIEEVALST

TGEIPFYGKAIPLEVIKGGRHLIFCHSKKKCDELAAKLVALGINAVAYY

RGLDVSVIPTSGDVVVVATDALMTGFTGDFDSVIDCNTCVTQTVDFSLD

PTFTIETTTLPQDAVSRTQRRGRTGRGKPGIYRFVAPGERPSGMFDSSV

LCECYDAGCAWYELTPAETTVRLRAYMNTPGLPVCQDHLEFWEGVFTGL

THIDAHFLSQTKQSGENLPYLVAYQATVCARAQAPPPSWDQMWKCLIRL

KPTLHGPTPLLYRLGAVQNEVTLTHPITKYIMTCMSADLEVVTSTWVLV

GGVLAALAAYCLSTGCVVIVGRIVLSGKPAIIPDREVLYREFDEMEECS

QHLPYIEQGMMLAEQFKQKALGLLQTASRQAEVIAPAVQTNWQKLEAFW

AKHMWNFISGIQYLAGLSTLPGNPAIASLMAFTAAVTSPLTTSQTLLFN

ILGGWVAAQLAAPGAATAFVGAGLAGAAIGSVGLGKVLVDILAGYGAGV

AGALVAFKIMSGEVPSTEDLVNLLPAILSPGALVVGVVCAAILRRHVGP

GEGAVQWMNRLIAFASRGNHVSPTHYVPESDAAARVTAILSSLTVTQLL

RRLHQWISSECTTPCSGSWLRDIWDWICEVLSDFKTWLKAKLMPQLPGI

PFVSCQRGYRGVWRGDGIMHTRCHCGAEITGHVKNGTMRIVGPRTCRNM

WSGTFPINAYTTGPCTPLPAPNYTFALWRVSAEEYVEIRQVGDFHYVTG

MTTDNLKCPCQVPSPEFFTELDGVRLHRFAPPCKPLLREEVSFRVGLHE

YPVGSQLPCEPEPDVAVLTSMLTDPSHITAEAAGRRLARGSPPSVASSS

ASQLSAPSLKATCTANHDSPDAELIEANLLWRQEMGGNITRVESENKVV

ILDSFDPLVAEEDEREISVPAEILRKSRRFAPALPIWARPDYNPPLLET

WKKPDYEPPVVHGCPLPPPQSPPVPPPRKKRTVVLTESTVSTALAELAT

KSFGSSSTSGITGDNTTTSSEPAPSGCPPDSDAESYSSMPPLEGEPGDP

DLSDGSWSTVSSEADTEDVVCCSMSYSWTGALVTPCAAEEQKLPINALS

NSLLRHHNLVYSTTSRSACQRQKKVTFDRLQVLDSHYQDVLKEVKAAAS

KVKANLLSVEEACSLTPPHSAKSKFGYGAKDVRCHARKAVNHINSVWKD

LLEDSVTPIDTTIMAKNEVFCVQPEKGGRKPARLIVFPDLGVRVCEKMA

LYDVVSKLPLAVMGSSYGFQYSPGQRVEFLVQAWKSKKTPMGFSYDTRC

FDSTVTESDIRTEEAIYQCCDLDPQARVAIKSLTERLYVGGPLTNSRGE

NCGYRRCRASGVLTTSCGNTLTCYIKARAACRAAGLQDCTMLVCGNNLV

VICESAGVQEDAASLRAFTEAMTRYSAPPGDPPQPEYDLELITSCSSNV

SVAHDGAGKRVYYLTRDPTTPLARAAWETARHTPVNSWLGNIIMFAPTL

WARMILMTHFFSVLIARDQLEQALDCEIYGACYSIEPLDLPPIIQRLHG

LSAFSLHSYSPGEINRVAACLRKLGVPPLRAWRHRARSVRARLLSRGGR

-continued

AAICGKYLFNWAVRTKLKLTPIAAAGQLDLSGWFTAGYSGGDIYHSVSH

ARPRWFWFCLLLLAAGVGIYLLPNR;

and has a length of 1985 amino acids. Such a polypeptide can include T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, NS5b-2 in FIGS. 9A-9B and FIGS. 11A-11N.

Additional T-Cell Epitopes

As discussed above, an immunogenic composition of the present disclosure includes: a) an HCV E1/E2 heterodimer; b) a T cell epitope polypeptide that comprises one or more T-cell epitopes (e.g., one or more T cell epitopes present in an HCV polypeptide other than an HCV E1 polypeptide or an HCV E2 polypeptide); and c) a CDN. The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the T cell epitope polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein.

Thus, in some cases, an immunogenic composition of the present disclosure includes: a) an HCV E1/E2 heterodimer; b) a T-cell epitope polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein; and c) a CND.

A T helper tetanus toxin epitope or other bacterial T-cell epitope could be fused (e.g., by recombinant expression) or chemically conjugated to the T cell epitope polypeptide, or can be unconjugated (e.g., provided as a separate polypeptide), to further enhance both T and B cell responses to both the T-cell epitopes present in the T cell epitope polypeptide and in the E1/E2 polypeptides. Alternatively, the whole or part of the detoxified toxin ("toxoid") can be used, wherein specific amino acids of the toxins are mutated to render the toxins inactive, thereby generating toxoids. Methods of generating toxoids are well known in the art. Examples of bacterial epitopes include the use of diphtheria toxoid, meningococcal outer membrane protein, or mutant diphtheria protein CRM197 (see, e.g.: world-wide-website: Medscape.com/viewarticle/431127).

In some cases, a suitable tetanus toxoid polypeptide comprises the amino acid sequence QYIKANSKFIGIFE (SEQ ID NO:130). In some cases, a suitable tetanus toxoid polypeptide comprises the amino acid sequence QYIKANSKFIGITE (SEQ ID NO:131).

In some cases, a T cell epitope polypeptide can comprise cholera toxin (or toxoid) epitope. In some cases, a suitable T-cell epitope polypeptide comprising a cholera toxoid epitope comprises a fragment of cholera toxin-B subunit (CT-B), e.g., a fragment of from 5 amino acids to 25 amino acids, or from 25 amino acids to 50 amino acids, of the following amino acid sequence:

(SEQ ID NO: 132)
MIKLKFGVFF TVLLSSAYAH GTPQNITDLC AEYHNTQIHT

LNDKIFSYTE SLAGKREMAI ITFKNGATFQ VEVPGSQHID

SQKKAIERMK DTLRIAYLTE AKVEKLCVWN NKTPHAIAAI

SMAN.

In some cases, a T cell epitope polypeptide can comprise a tetanus toxin (or toxoid) T-cell epitope. In some cases, a suitable T cell epitope polypeptide comprising a tetanus toxin T-cell epitope comprises the amino acid sequence:

(SEQ ID NO: 133)
ILMQYIKANSKFIGI;

and has a length of from 15 amino acids to 20 amino acids. In some cases, a suitable T cell epitope polypeptide comprising a tetanus toxin T-cell epitope comprises the amino acid sequence:

(SEQ ID NO: 134)
VNNESSE.

In some cases, a suitable T cell epitope polypeptide comprising a tetanus toxin T-cell epitope comprises the amino acid sequence:

(SEQ ID NO: 135)
PGINGKAIHLVNNESSE.

In some cases, a suitable T cell epitope polypeptide comprising a tetanus toxin T-cell epitope comprises the amino acid sequence:

(SEQ ID NO: 136)
PNRDIL.

In some cases, a suitable T cell epitope polypeptide comprising a tetanus toxin T-cell epitope comprises the amino acid sequence:

(SEQ ID NO: 137)
FIGITEL.

In some cases, a suitable tetanus toxin T-cell epitope comprises the amino acid sequence:

(SEQ ID NO: 138)
SYFPSV

In some cases, a suitable T cell epitope polypeptide comprising a tetanus toxin T-cell epitope comprises the amino acid sequence:

(SEQ ID NO: 139)
NSVDDALINSTKIYSYFPSV.

In some cases, a suitable T cell epitope polypeptide comprising a tetanus toxin T-cell epitope comprises the amino acid sequence:

(SEQ ID NO: 140)
IDKISDVSTIVPYIGPALNI.

In some cases, a T cell epitope polypeptide can comprise a diphtheria toxin T-cell epitope In some cases, a suitable T-cell epitope polypeptide comprising a diphtheria toxin T-cell epitope comprises the amino acid sequence:

(SEQ ID NO: 141)
QSIALSSLMVAQAIP;

and has a length of from 15 amino acids to 20 amino acids. In some cases, a suitable T cell epitope polypeptide comprising a diphtheria toxin T-cell epitope comprises the amino acid sequence:

(SEQ ID NO: 142)
PVFAGANYAAWAVNVAQVI.

In some cases, a suitable T cell epitope polypeptide comprising a diphtheria toxin T-cell epitope comprises the amino acid sequence:

(SEQ ID NO: 143)
VHHNTEEIVAQSIALSSLMV.

In some cases, a suitable T cell epitope polypeptide comprising a diphtheria toxin T-cell epitope comprises the amino acid sequence:

(SEQ ID NO: 144)
QSIALSSLMVAQAIPLVGEL.

In some cases, a suitable T cell epitope polypeptide comprising a diphtheria toxin T-cell epitope comprises the amino acid sequence:

(SEQ ID NO: 145)
VDIGFAAYNFVESIINLFQV.

In some cases, a suitable T cell epitope polypeptide comprising a diphtheria toxin T-cell epitope comprises the amino acid sequence:

(SEQ ID NO: 146)
QGESGHDIKITAENTPLPIA.

In some cases, a suitable T cell epitope polypeptide comprising a diphtheria toxin T-cell epitope comprises the amino acid sequence:

(SEQ ID NO: 147)
GVLLPTIPGKLDVNKSKTHI.

In some cases, a suitable T cell epitope polypeptide comprising a diphtheria toxin T-cell epitope comprises the amino acid sequence of CRM197 (see, e.g., Giannini et al. (1984) *Nucl. Acids. Res.* 12:4063).

The amino acid sequence of CRM197 is as follows:

(SEQ ID NO: 148)
laddvvdssksfvmenfssyhgtkpgyvdsiqkgiqkpksgtqgnydddw kefystdnkydaagysydnenplsgkaggvvkvtypgltkvlalkvdnae -continued

```
tikkelglslteplmeqvgteefikrfgdgasrvvlslpfaegsssveyi

nnweqakalsveleinfetrgkrgqdamyeymaqacagnrvasvgsslsc

inldwdvirdktktkieslkehgpiknkmsespnktvseekakqyleefh

qtalehpelselktvtgtnpvfaganyaawavnvaqvidsetadnlektt

aalsilpgigsvmgiadgavhhnteeivaqsialsslmvaqaiplvgelv

digfanynfvesiinlfqvvhnsynrpayspghktqpflhdgyavswntv

edsiirtgfqgesghdikitaentplpiagvllptipgkldvnkskthis

yngrkirmrcraidgdvtfcrpkspvyvgngvhanlhvafhrsssekihs

neissdsigvlgyqktvdhtkvnsklslffeiks .
```

In some cases, a T cell epitope polypeptide can comprise a tetanus toxin T-cell epitope and a diphtheria toxin T-cell epitope. In some of these cases, the T cell epitope polypeptide can comprise the amino acid sequence:

```
                                        (SEQ ID NO: 149)
        IMQYIKANSKFIGIQSIALSSLMVAQ;
```

and can have a length of from 26 amino acids to 30 amino acids.

Mixtures of T-Cell Epitope Polypeptides (T-Cell Epitope Polypeptides)

In some cases, an immunogenic composition of the present disclosure comprises two or more different T-cell epitope polypeptides comprising a T-cell epitope present in an HCV protein other than E1 and E2 (e.g., a mixture of two or more different T-cell epitope polypeptides comprising a T-cell epitope present in an HCV protein other than E1 and E2).

For example, in some cases, an immunogenic composition of the present disclosure comprises: a) an HCV E1/E2 heterodimeric polypeptide; b) two or more different T-cell epitope polypeptides comprising a T-cell epitope present in an HCV protein other than E1 and E2; and c) a CDN. In some cases, an immunogenic composition of the present disclosure comprises: a) an HCV E2 polypeptide; b) two or more different T-cell epitope polypeptides comprising a T-cell epitope present in an HCV protein other than E1 and E2; and c) a CDNs.

For example, the two or more different T cell epitope polypeptides can include: i) a first T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP29, and having a length of from 29 amino acids to 35 amino acids; and ii) a second T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP50, and having a length of from 50 amino acids to 55 amino acids.

As another example, the two or more different T cell epitope polypeptides can include: i) a first T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP29, and having a length of from 29 amino acids to 35 amino acids; and ii) a second T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP52, and having a length of from 52 amino acids to 60 amino acids.

As another example, the two or more different T cell epitope polypeptides can include: i) a first T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP29, and having a length of from 29 amino acids to 35 amino acids; and ii) a T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP70, and having a length of from 70 amino acids to 75 amino acids.

As another example, the two or more different T cell epitope polypeptides can include: i) a first T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP29, and having a length of from 29 amino acids to 35 amino acids; and ii) a second T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP100, and having a length of from 100 amino acids to 110 amino acids.

As another example, the two or more different T cell epitope polypeptides can include: i) a first T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP29, and having a length of from 29 amino acids to 35 amino acids; and ii) a second T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP171, and having a length of from 171 amino acids to 180 amino acids.

As another example, the two or more different T cell epitope polypeptides can include: i) a first T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP29, and having a length of from 29 amino acids to 35 amino acids; and ii) a T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP228, and having a length of from 228 amino acids to 235 amino acids.

As another example, the two or more different T cell epitope polypeptides can include: i) a first T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP29, and having a length of from 29 amino acids to 35 amino acids; and ii) a second T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP553, and having a length of from 553 amino acids to 565 amino acids.

As another example, the two or more different T cell epitope polypeptides can include: i) a first T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP29, and having a length of from 29 amino acids to 35 amino acids; and ii) a second T cell epitope polypeptide comprising an amino acid sequence having at least 20%, at least 30%, at least 40%, at least 50%, at least 60%, at least 70%, at least 80%, at least 90%, at least 95%, at least 98%, or 100%, amino acid sequence identity to TP778, and having a length of from 778 amino acids to 785 amino acids.

Pharmaceutically Acceptable Excipients

An immunogenic composition of the present disclosure can include a pharmaceutically acceptable excipient. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

In some cases, a pharmaceutically acceptable excipient is an aqueous buffer. Thus, an immunogenic composition of the present disclosure can include an aqueous buffer. Suitable aqueous buffers include, but are not limited to, acetate, succinate, citrate, and phosphate buffers varying in strengths from about 5 mM to about 100 mM. In some cases, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 (TWEEN®20) or polysorbate 80 (TWEEN®80). For example, an immunogenic composition of the present disclosure in an aqueous buffer can include, e.g., from about 0.01% to about 0.05% polysorbate-20 (TWEEN®20) non-ionic detergent. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some cases, the aqueous buffer further includes a non-ionic surfactant. In some cases, the aqueous buffer includes the non-ionic surfactant Triton™ X-100, e.g., 0.1% Triton™ X-100.

Cyclic Dinucleotides

In some cases, a CDN suitable for use in an immunogenic composition of the present disclosure is of Formula (I):

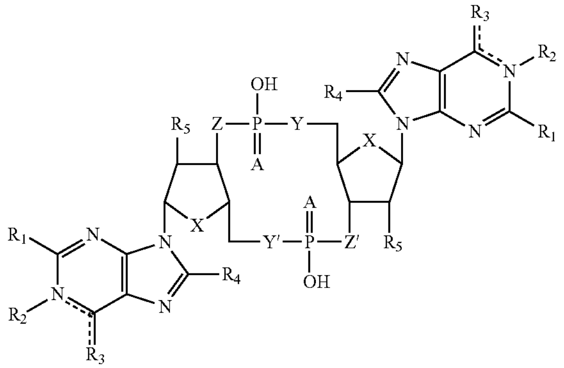

wherein:

A is S or O;

X is S, N, O, $CH_2$;

Y, Y' is NH, $CH_2$, O;

Z, Z' is NH, $CH_2$, O;

R1 represents hydrogen or $NH_2$ which may be substituted;

R2 is hydrogen or absent;

R3 represents $NH_2$, O, OH, H, or a halogen;

R4 represents hydrogen, halogen, or a straight or branched $C_1$-$C_6$ alkyl group which may optionally be substituted;

R5 represents hydrogen, OH or a straight or branched $C_1$-$C_6$ alkyl chain or $C_1$-$C_6$ straight or branched alkoxy chain which may optionally be substituted;

 is a single or double bond;

or conjugates thereof, and salts or solvates thereof. See, e.g., US 2008/0286296.

In formula (I), the purine residue is in some cases a guanine (G), adenine (A), xanthine or hypoxanthine (X), or inosine (I) residue. The compound can have identical purine residues, e.g. c-diGMP, c-diAMP, c-dilMP, or c-dXMP, or can contain different purine residues, e.g. c-GpAp, c-Gplp, c-GpXp, c-Aplp, c-ApXp, or c-lpXp. Further, R5 is in some cases an OH group. In addition, X is in some cases an oxygen atom. In one embodiment, Y, Y', Z, and Z' are an oxygen atom, O. Thus, in one embodiment, the compound of formula (I) is a cyclic bis(3'-5')diguanylic acid (c-diGMP) or conjugates thereof or a cyclic bis(3'-5')diadenylic acid (c-di-AMP) or conjugates thereof, or salts or solvates thereof. In one embodiment, the compound of formula (I) is cyclic Bis(3'-5')adenylic acid, which is also referred to as c-di-AMP; or the pegylated conjugate. With the term "which may be substituted" is meant the substitution with a straight or branched C1-C6 alkyl group or a straight or branched C1-C6 alkoxy group and/or with a halogen, hydroxyl group or carboxyl group.

In some cases, a CDN suitable for use in an immunogenic composition of the present disclosure is selected from the group consisting of cyclic di-adenosine monophosphate (c-di-AMP), cyclic di-guanosine monophosphate (c-di-GMP), and cyclic guanosine monophosphate-adenosine monophosphate (cGAMP). In some cases, a CDN suitable for use in an immunogenic composition of the present disclosure is cGAMP (2'-3'-cyclic GMP-AMP) or cGAMP (3'-3'-cyclic GMP-AMP). In some cases, a CDN suitable for use in an immunogenic composition of the present disclosure is cGAMP (2'-3'-cyclic GMP-AMP). In some cases, a CDN suitable for use in an immunogenic composition of the present disclosure is cGAMP (3'-3'-cyclic GMP-AMP).

In some cases, a CDN suitable for use in an immunogenic composition of the present disclosure is of Formula (II):

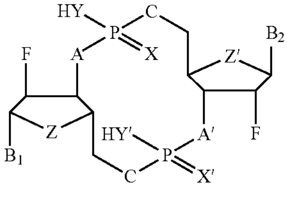

where:

A, C, A' and C' are independently selected from NH, O, and S;

X, Y, X', and Y' are independently selected from O or S;

Z and Z' are independently selected from O, S, NH, and $CH_2$; and $B_1$ and $B_2$ are independently a purine selected from:

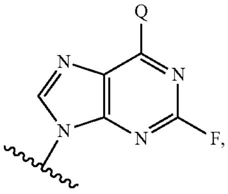

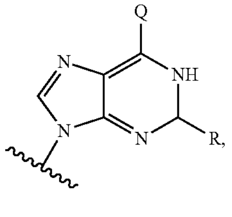

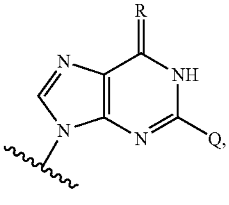

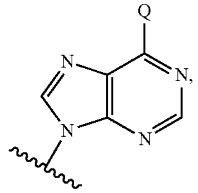

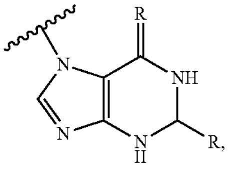

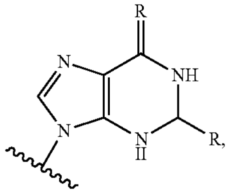

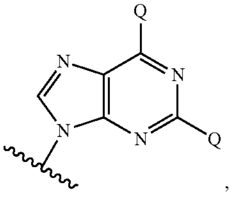

, or

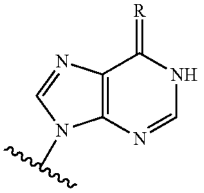

where:

Q is hydrogen or $NH_2$;

Nitrogen is optionally substituted with a $C_1$-$C_6$ alkyl or a $C_1$-$C_6$ acyl group; and R is O or S.

In some cases, a CDN suitable for inclusion in an immunogenic composition of the present disclosure is a fluorinated CND. In some cases, the fluorinated CDN is 2'-F-c-diGMP having the following structure:

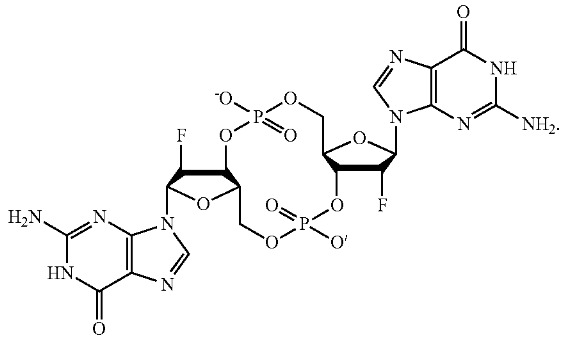

Immunogenic Composition Comprising HCV E1E2, HCV E2, or HCV E1 and an Archaeal Glycolipid The present disclosure provides an immunogenic composition comprising: a) an HCV E1E2 heterodimer; and b) an archaeosome. The present disclosure provides an immunogenic composition comprising: a) an HCV E2 polypeptide; and b) an archaeosome. The present disclosure provides an immunogenic composition comprising: a) an HCV E1 polypeptide; and b) an archaeosome.

In some cases, an immunogenic composition of the present disclosure, when administered to an individual in need thereof, induces an immune response in the individual to one or more HCV genotypes. In some cases, an immunogenic composition of the present disclosure, when administered to an individual in need thereof, induces an immune response in the individual to one or more HCV genotypes, where the immune response is greater than the immune response induced by administration of a control composition comprising the HCV E1/E2 heterodimer (or E1 polypeptide, or E2 polypeptide) but lacking the archaeosome.

In some cases, an immunogenic composition of the present disclosure, when administered to an individual in need thereof, induces $CD8^+$ CTLs specific for HCV, where the number of HCV-specific $CD8^+$ CTLs induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific $CD8^+$ CTLs induced by administration of a control composition (e.g., a composition comprising the HCV E1/E2 heterodimer but lacking the archaeosome; a composition comprising an E1 polypeptide but lacking the archaeosome; a composition comprising an E2 polypeptide but lacking the archaeosome).

In some cases, an immunogenic composition of the present disclosure, when administered to an individual in need thereof, induces $CD4^+$ T cells specific for HCV, where the number of HCV-specific $CD4^+$ T cells induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific $CD4^+$ T cells induced by administration of a control composition (e.g., a composition comprising the HCV E1/E2 heterodimer but lacking the archaeosome; a composition comprising an E1 polypeptide but lacking the archaeosome; a composition comprising an E2 polypeptide but lacking the archaeosome).

In some cases, an immunogenic composition of the present disclosure, when administered to an individual in need thereof, induces production of HCV-specific $CD4^+$ T cells and $CD8^+$ T cells in the individual, where the number of HCV-specific $CD4^+$ T cells and/or $CD8^+$ T cells is increased, such that the percent of total peripheral $CD4^+$ and/or $CD8^+$ T cells that is HCV-specific is from 0.01% to 0.05%, from 0.05% to 0.10%, from 0.10% to 0.125%, from 0.125% to 0.25%, from 0.25% to from 0.50%, or 0.5% to 10% (e.g., from 0.5% to 1%, from 1% to 2%, from 2% to 5%, or from 5% to 10%). The number of HCV-specific $CD4^+$ T cells and $CD8^+$ T cells in a control individual (e.g., an individual not infected with HCV) not treated with the immunogenic composition would be undetectable.

In some cases, an immunogenic composition of the present disclosure, when administered to an individual in need thereof, increases the number of HCV E1/E2-specific $CD4^+$ T cells and $CD8^+$ T cells in the individual by at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, compared to the number of HCV E1/E2-specific $CD4^+$ T cells and $CD8^+$ T cells in the individual induced by administration of a control composition comprising the HCV E1/E2 heterodimer (or HCV E2 polypeptide, or HCV E1 polypeptide) but lacking the archaeosome, or compared to the number of HCV E1/E2-specific $CD4^+$ T cells and $CD8^+$ T cells in the individual before administration of the immunogenic composition.

In some cases, an immunogenic composition of the present disclosure, when administered to an individual in need thereof, induces helper T lymphocytes (e.g., $CD4^+$ T cells) specific for HCV, where the number of HCV-specific helper T lymphocytes induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific helper T cells induced by administration of a control composition comprising the HCV E1/E2 heterodimer (or HCV E2 polypeptide, or HCV E1 polypeptide) but lacking the archaeosome, or compared to the number of HCV-specific $CD4^+$ T cells in the individual before administration of the immunogenic composition.

In some cases, an immunogenic composition of the present disclosure, when administered to an individual in need thereof, induces antibody specific for HCV, where the level of HCV-specific antibody induced is at least at high as the level of HCV-specific antibody induced by administration of a control composition comprising the HCV E1/E2 heterodimer (or HCV E2 polypeptide, or HCV E1 polypeptide) but lacking the archaeosome.

In some cases, an immunogenic composition of the present disclosure, when administered to an individual in need thereof, induces antibody specific for HCV, where the level of HCV-specific antibody induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the level of HCV-specific antibody induced by administration of a control composition comprising the HCV E1/E2 heterodimer (or HCV E2 polypeptide, or HCV E1 polypeptide) but lacking the archaeosome, or compared the level of HCV-specific antibody in the individual before administration of the immunogenic composition.

An immunogenic composition of the present disclosure, when administered to an individual in need thereof, induces an immune response (e.g., a cellular immune response) in the individual to one or more HCV genotypes. In some cases, an immunogenic composition of the present disclosure, when administered to an individual in need thereof, induces an immune response in the individual to HCV genotype 1. In some cases, an immunogenic composition of the present disclosure, when administered to an individual in need thereof, induces an immune response in the individual to HCV genotype 2. In some cases, an immunogenic composition of the present disclosure when administered to an individual in need thereof, induces an immune response in the individual to HCV genotype 3. In some cases, an immunogenic composition of the present disclosure, when administered to an individual in need thereof, induces an immune response in the individual to HCV genotype 1 and HCV genotype 3. In some cases, an immunogenic composition of the present disclosure, when administered to an individual in need thereof, induces an immune response in the individual to HCV genotype 1, HCV genotype 2, and HCV genotype 3. In some cases, an immunogenic composition of the present disclosure, when administered to an individual in need thereof, induces an immune response in the individual to HCV genotype 1, HCV genotype 2, HCV genotype 3, and HCV genotype 7. In some cases, an immunogenic composition of the present disclosure, when administered to an individual in need thereof, induces an immune response in the individual to HCV genotype 1, HCV genotype 2, HCV genotype 3, HCB genotype 4, HCV genotype 5, HCV genotype 6, and HCV genotype 7.

HCV E1E2 Heterodimers, HCV E2 Polypeptides, and HCV E1 Polypeptides.

The present disclosure provides an immunogenic composition comprising: a) an HCV E1E2 heterodimer; and b) an archaeosome. The present disclosure provides an immunogenic composition comprising: a) an HCV E2 polypeptide; and b) an archaeosome. The present disclosure provides an immunogenic composition comprising: a) an HCV E1 polypeptide; and b) an archaeosome. Suitable HCV E1E2 heterodimers, HCV E2 polypeptides, and HCV E1 polypeptides are as described above.

Archaeal Lipids and Archaeosomes

An archaeal lipid suitable for use in an immunogenic composition of the present disclosure comprises a polar lipid based on a 2,3-dialkylglycerol skeleton. These 2,3-dialkylglycerol groups are isoprenoid and the simplest molecules are derivatives or 2,3-dibiphytanyl-O-sn-glycerol (archeol); for instance, two isoprenoid units of 20 carbons joined at positions sn-2 and sn-3 of glycerol. These alkyl chains are generally saturated; nevertheless, some forms have double bonds in different positions. These lipids have one or two groups of polar head, which may be different with units 2,3-sn-glycerol joined by C40 alkyl components which are also isoprenoid molecules. For instance, calarcheol (so called because it is the predominant form in some thermophile archaebacteria), has two C40 isoprenoid units bonded from positions 2 to 3' and from position 3 to 2'.

In some cases, an archaeal adjuvant suitable for use in an immunogenic composition of the present disclosure comprises multivalent cations in association with aggregates of a plurality of spherical archaeal polar lipid structures containing aqueous compartments (e.g., an "AMVAD structure"), where the archaeal polar lipid is a total polar lipids extract or archaetidyl glycerophosphate-O-methyl, obtained from an archaeal species. The multivalent cations can be divalent or trivalent cations. The multivalent cations can be divalent $Ca^{2+}$ or $Mg^{2+}$, or trivalent $Al^{3+}$. The $Ca^{2+}$ can be provided as $CaCl_2$. The $Al^{3+}$ can be provided as $AiCl_3$ or $AlK(SO_4)_2$. In some cases, the total polar lipids extract from an archaeal species is mixed with neutral lipids from the archaeal species. See, e.g., U.S. Patent Publication No. 2013/0195932.

In some cases, lipids suitable for use in an immunogenic composition of the present disclosure comprises 1,2-di-O-hexadecyl-sn-glycero-3-phosphatidylcholine and 1,2-di-O-phytanyl-sn-glycero-3-phosphatidylethanolamine. In some cases, the 1,2-di-O-hexadecyl-sn-glycero-3-phosphatidylcholine and 1,2-di-O-phytanyl-sn-glycero-3-phosphatidylethanolamine form uniformly sized particles; for example, the particles can comprise: liposomes, nanoliposomes, niosomes, microspheres, nanospheres, nanoparticles, micelles or archaeosomes.

In some cases, an archaeosome comprises at least one polar synthetic lipid, where the at least one polar synthetic lipid comprises at least one carbohydrate or anionic group linked by covalent bonding to at least one free hydroxyl group of an archaeal core lipid. In some cases, the archaeal core lipid is archaeol (2,3-di-O-diphytanyl-sn-glycerol). In some cases, the archaeal core lipid is caldarchaeol (2,2',3,3'-tetra-O-dibiphytanyl-sn-diglycerol). In some cases, the carbohydrate group is selected from the group consisting of: β-D-Glc-(1,6)-β-D-Glc-; β-D-Glc-(1,6)-α-D-Glc-; α-D-Glc-(1,6)-β-D-Glc-; β-D-Glc-(1,4)-β-D-Glc-; α-D-Glc-(1,4)-β-D-Glc-; β-D-Gal-(1,4)-β-D-Glc-; α-D-Gal-(1,6)-β-D-Glc-; β-D-Glc-(1,6)-β-D-Glc-(1,6)-β-D-Glc-; α-D-Glc-(1,4)-α-D-Glc-(1,4)-β-D-Glc-; α-D-Man-(1,2)-α-D-Man-(1,2)-α-D-Man-; and α-D-Man-(1,2)-α-D-Man-(1,2)-α-D-Man-(1,2)-α-D-Man-. In some cases, the carbohydrate group comprises two or three β-D-Glc-units in (1,6) linkage. In some cases, the carbohydrate group is a Galactose-Glucose (gal-glc) group. In some cases, the anionic group is selected from the group consisting of phosphoserine, phosphoethanolamine, phosphoinositol and phosphoglycerol. In some cases, the at least one anionic lipid is selected from the group consisting of archaetidylglycerol, archaetidylglycerolphosphate-methyl, archaetidylserine, and archaetidylinositol. In some cases, the archaeosome comprises at least one conventional lipid. In some cases, the at least one conventional lipid is selected from a group consisting of phosphatidylglycerol, phosphatidylserine, sulfoquinovosyl diacylglycerol (SQDG), and cholesterol. In some cases, the at least one conventional lipid comprises cholesterol, and wherein cholesterol is present in an amount of between 10 and 45 mol % of the total lipid composition. In some cases, the phosphatidylglycerol is present in an amount of between 20 and 80 mol % of the lipid composition. In some cases, the phosphatidylserine is present in an amount of between 10 and 30 mol % of the lipid composition. In some cases, the at least one polar synthetic lipid comprises at least one synthetic immunoactive glycolipid and at least one anionic lipid, and the archaeosome further comprises at least one stabilizing lipid. In some cases, the at least one polar synthetic lipid comprises caldarchaeol having one carbohydrate head group and one anionic head group. In some cases, the carbohydrate head group comprises gentiobiose and the anionic head group comprises phosphoinositol. In some cases, the at least one polar synthetic lipid comprises a first caldarchaeol having two carbohydrate head groups and a second caldarchaeol having two anionic head groups, and wherein the at least one stabilizing lipid is the first and/or second caldarchaeol. In some cases, the at least one polar synthetic lipid comprises gentiotriose-archaeol and wherein the at least one stabilizing lipid comprises cholesterol and at least one of phosphatidylethanolamine, archaetidylglycerol, archaetidylserine or archaetidylglycerolphosphate-methyl.

Caldarchaeol is also known as dibiphytanyldiglycerol tetraether. Two glycerol units are linked together by two strains that consist of two phytanes linked together to form a linear chain of 32 carbon atoms. Caldarchaeol has the following structure:

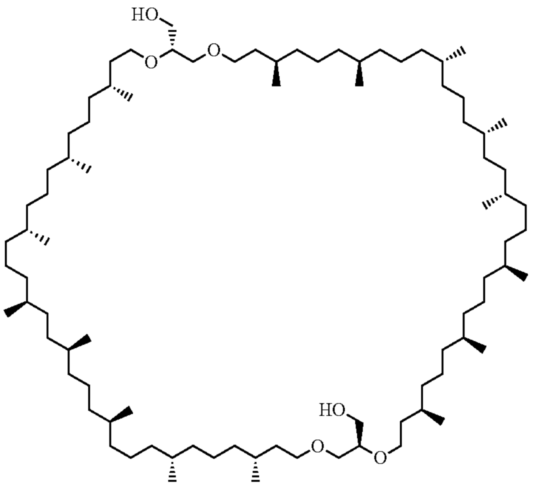 [SMILES: C[C@@H]1CCC[C@H](C)CCC[C@H](C)CC[C@@H](C)CCC[C@@H](C)CCC[C@@H](C)CCC[C@@H](C)CCO[C@H](CO)COCC[C@H](C)CCC[C@H](C)CCC[C@H](C)CCC[C@H](C)CC[C@@H](C)CCC[C@@H](C)CCC[C@@H](C)CCC[C@@H](C)CCO[C@H](CO)COCC[C@H](C)CCC1]

Archaeal lipids can be obtained from any archaea of the phyla Euryarchaeota, Crenarchaeota, Korarchaeota, or, Nanoarchaea. Archaeal lipids can be obtained from any archaea of the genus *Thermococcus, Sulfolobus. Halobacterium. Methanococcus. Ferroglobus, Thermoplasma, Archaeoglobus. Haloquadratum*, or *Halorubrum*. Suitable sources of archaeal lipids include, but are not limited to, *Thermus aquaticus, Thermus thermophilus*; Methanobrevibacter *smithii; Thermoplasma acidophilum*; a *Sulfolobus* species, e.g. *Sulfolobus acidocaldarius, Sulfolobus solfataricus, Sulfolobus islandicus, Sulfolobus tokodaii*, etc.; a *Pyrobaculum* species, e.g. *Pyrobaculum islandicum* or *Pyrobaculum aerophilum*; a *Methanococcus* species, e.g., *Methanocaldococcus vulcanius, Methanocaldococcus jannaschii, Methanococcus acolicus, Methanococcus voltae*; or a *Halobacterium* species such as *Halobacterium salinarum; Methanopyrus kandleri; Methanobacterium espanolae; Methanosphaera stadtmanae; Methanosarcina mazei; Natronobacterium magadii*; etc.

Total polar lipids (TPL) can be extracted from archaea and collected as the acetone-insoluble fraction. Choquet et al. (1994) *Appl. Microbiol. Biotechnol.* 42:375; Bligh and Dyer (1959) *Can. J. Biochem. Physiol.* 37:911. The polar lipids consist of regularly branched, and usually fully saturated, phytanyl chains of 20, 25, or 40 carbon length, with the 20 and 40 being most common. Archaeosomes can be prepared by hydrating TPL in a buffer (e.g., phosphate-buffered saline). The TPL-buffer solution can be sonicated (e.g., at 60 Hz for 10 min).

TPL can be extracted from archaea by stirring the cells (which may be lyophilized) with chloroform-methanol (2:1, v/v) for 1 hour at room temperature. The suspension is passed through a sintered glass filter, and the residue reextracted for an additional hour. Combined filtrates are evaporated, taken up in chloroform-methanol-water (60:30:4.5, v/v/v), and passed through Sephadex G-25 for removal of nonlipid contaminations. Langworthy et al. (1977) *J. Bacteriol.* 130:1326.

The mean diameter of archaeosomes in an archaeosomal formulation can range from about 50 nm to 600 nm, e.g., from 50 nm to 100 nm, from 100 nm to 150 nm, from 150 nm to 200 nm, from 200 nm to 250 nm, from 250 nm to 300 nm, from 300 nm to 400 nm, from 400 nm to 450 nm, from 450 nm to 500 nm, from 500 nm to 550 nm, or from 550 nm to 600 nm.

T-Cell Epitope Polypeptides

In some cases, one or both of the polypeptide chains of the E1/E2 heterodimer present in an immunogenic composition of the present disclosure can include a T-cell epitope polypeptide. In some cases, an E2 polypeptide present in an E1/E2 heterodimer present in an immunogenic composition of the present disclosure includes a T-cell epitope polypeptide. In some cases, an E1 polypeptide present in an E1/E2 heterodimer present in an immunogenic composition of the present disclosure includes a T-cell epitope polypeptide. In some cases, an HCV E2 polypeptide present in an immunogenic composition of the present disclosure includes a T-cell epitope polypeptide. In some cases, an HCV E1 polypeptide present in an immunogenic composition of the present disclosure includes a T-cell epitope polypeptide. In these embodiments, the T-cell epitope is covalently linked to the E1 and/or E2 polypeptide. For example, in some cases, the T-cell epitope is covalently linked to the amino terminus (N-terminus) of the HCV E1 polypeptide. In some cases, the T-cell epitope is covalently linked to the carboxyl terminus (C-terminus) of the HCV E1 polypeptide. Thus, e.g., in some cases, an immunogenic composition of the present disclosure comprises: a) a fusion polypeptide comprising, in order from N-terminus to C-terminus: i) an HCV E1 polypeptide; and ii) a T-cell epitope polypeptide; and b) an archaeosome. In some cases, an immunogenic composition of the present disclosure comprises: a) a fusion polypeptide comprising, in order from N-terminus to C-terminus: i) an HCV E2 polypeptide; and ii) a T-cell epitope polypeptide; and b) an archaeosome. In some cases, an immunogenic composition of the present disclosure comprises: a) a fusion polypeptide comprising, in order from N-terminus to C-terminus: i) a T-cell epitope polypeptide; and ii) an HCV E1 polypeptide; and b) an archaeosome. In some cases, an immunogenic composition of the present disclosure comprises: a) a fusion polypeptide comprising, in order from N-terminus to C-terminus: i) a T-cell epitope polypeptide; and ii) an HCV E2 polypeptide; and b) an archaeosome. In some cases, an immunogenic composition of the present disclosure comprises: a) an HCV E1E2 heterodimer comprising i) a fusion polypeptide comprising, in order from N-terminus to C-terminus: an HCV E1 polypeptide; and a T-cell epitope polypeptide; and ii) an HCV E2 polypeptide; and b) an archaeosome. In some cases, an immunogenic composition of the present disclosure comprises: a) an HCV E1E2 heterodimer comprising i) a fusion polypeptide comprising, in order from N-terminus to C-terminus: an HCV E2 polypeptide; and a T-cell epitope polypeptide; and ii) an HCV E2 polypeptide; and b) an archaeosome. In some cases, an immunogenic composition of the present disclosure comprises: a) an HCV E1E2 heterodimer comprising i) a fusion polypeptide comprising, in order from N-terminus to C-terminus: a T-cell epitope polypeptide; and an HCV E1 polypeptide; and ii) an HCV E2 polypeptide; and b) an archaeosome. In some cases, an immunogenic composition of the present disclosure comprises: a) an HCV E1E2 heterodimer comprising i) a fusion polypeptide comprising, in order from N-terminus to C-terminus: a T-cell epitope polypeptide; and an HCV E2 polypeptide; and ii) an HCV E1 polypeptide; and b) an archaeosome.

In some cases, an immunogenic composition of the present disclosure comprises a T-cell epitope polypeptide, where the T-cell epitope polypeptide is not covalently linked to the HCV E1/E2 heterodimer, the HCV E1 polypeptide or the HCV E2 polypeptide. For example, in some cases, an immunogenic composition of the present disclosure comprises: a) an HCV E1/E2 heterodimer; b) an archaeosome; and c) a T-cell epitope polypeptide. In some cases, an immunogenic composition of the present disclosure comprises: a) an HCV E2 polypeptide; b) an archaeosome; and c) a T-cell epitope polypeptide. In some cases, an immunogenic composition of the present disclosure comprises: a) an HCV E1 polypeptide; b) an archaeosome; and c) a T-cell epitope polypeptide.

Suitable T-cell epitope polypeptides are as described above.

Compositions Comprising a T-Cell Epitope Polypeptide Comprising T-Cell Epitopes Present in an HCV Polypeptide Other than E1 and E2

The present disclosure provides an immunogenic composition comprising: a) a T-cell epitope polypeptide comprising T-cell epitopes present in an HCV polypeptide other than E1 and E2; and b) a CDN. The present disclosure provides an immunogenic composition comprising: a) a T-cell epitope polypeptide comprising T-cell epitopes present in an HCV polypeptide other than E1 and E2; and b) an archaeosome.

Suitable T-cell epitope polypeptides are as described above. Suitable CDNs are as described above. Suitable archaeosomes are as described above.

Nucleic Acid Immunogenic Compositions

The present disclosure provides nucleic acid compositions comprising: a) one or more nucleic acids comprising a nucleotide sequence(s) encoding polypeptides (e.g., HCV E1/E2; HCV E1; HCV E2; T-cell epitope polypeptide) as described above; and b) a CDN. The present disclosure provides nucleic acid compositions comprising: a) one or more nucleic acids comprising a nucleotide sequence(s) encoding polypeptides (e.g., HCV E1/E2; HCV E1; HCV E2; T-cell epitope polypeptide) as described above; and b) an archaeosome. The present disclosure provides an immunogenic composition comprising: a) a nucleic acid (e.g., a recombinant viral expression vector(s)) comprising nucleotide sequence(s) encoding one or more of: an HCV E1/E2 heterodimer; an HCV E1 polypeptide; an HCV E2 polypeptide; and a T-cell epitope polypeptide, where such polypeptides are described above; and b) a CDN. The present disclosure provides an immunogenic composition comprising: a) a nucleic acid (e.g., a recombinant viral expression vector(s)) comprising nucleotide sequence(s) encoding one or more of: an HCV E1/E2 heterodimer; an HCV E1 polypeptide; an HCV E2 polypeptide; and a T-cell epitope polypeptide, where such polypeptides are described above; and b) an archaeosome. The polypeptides can be encoded in the same nucleic acid, or on separate nucleic acids. For example, where the nucleic acid(s) are recombinant expression vectors, the polypeptides can be encoded in the same or separate recombinant expression vectors.

In some cases, the nucleic acid(s) is/are DNA. In some cases, the nucleic acid(s) is/are RNA. In some cases, the nucleic acid(s) is/are present in expression vector(s), generating recombinant expression vector(s) comprising the nucleic acid(s). In some cases, the recombinant expression vector(s) is/are recombinant bacterial vectors. In some cases, the recombinant expression vector(s) is/are recombinant viral vector(s). In some cases, the recombinant viral vector(s) are packaged into viral particles. In some cases, the nucleic acid(s) are present in bacteria (e.g., non-pathogenic bacteria (e.g., attenuated bacteria) suitable for delivery of nucleic acids to an individual). Where the recombinant expression vector is a bacterial vector or a viral vector, the vector is suitably attenuated so as not to cause significant pathology in an individual.

In some cases, the nucleic acid is present in an expression vector. Suitable expression vectors include, but are not limited to, a replication-defective adenovirus vector; a replication-defective vaccinia virus vector; a lentivirus vector (e.g., a self-inactivating lentivirus vector); a retroviral vector (e.g., a self-inactivating retroviral vector); an adeno-associated virus vector; and the like. In some cases, the vector is a modified vaccinia Ankara (MVA) vector, or an MVA-based vector (see, e.g., Verheust et al. (2012) *Vaccine* 30:2623). In some cases, the vector is a replication-defective adenovirus vector. In some cases, the vector is a replication-defective adenovirus 6 (Ad6) vector. In some cases, the vector is a replication-defective simian adenovirus vector (e.g., ChAd3). Suitable viral vectors are described in, e.g., Zhou et al. (2012) *Invest. Ophthalmol. Vis. Sci.* 53:2804; Swadling et al. (2014) *Sci. Transl. Med.* 6:261ra153; and Choi and Chang (2013) *Clin. Exp. Vaccine Res.* 2:97. In many cases, the recombinant viral vectors are packaged into viral particles; and the viral particles are formulated in an immunogenic composition along with a pharmaceutically acceptable carrier. Suitable pharmaceutically acceptable carriers are described above.

In some cases, an immunogenic composition of the present disclosure comprises: a) a recombinant viral vector comprising nucleotide sequences encoding one or more of: an HCV E1/E2 heterodimer; an HCV E1 polypeptide; an HCV E2 polypeptide; and a T-cell epitope polypeptide; and b) a CDN or an archaeosome. In some cases, an immunogenic composition of the present disclosure comprises: a) a recombinant viral vector comprising nucleotide sequences encoding: an HCV E1/E2 heterodimer; and a T-cell epitope polypeptide; and b) a CDN or an archaeosome. In some cases, an immunogenic composition of the present disclosure comprises: a) a recombinant viral vector comprising nucleotide sequences encoding: an HCV E1 polypeptide; and a T-cell epitope polypeptide; and b) a CDN or an archaeosome. In some cases, an immunogenic composition of the present disclosure comprises: a) a recombinant viral vector comprising nucleotide sequences encoding: an HCV E2 polypeptide; and a T-cell epitope polypeptide; and b) a CDN or an archaeosome. In some cases, an immunogenic composition of the present disclosure comprises: a) a recombinant viral vector comprising nucleotide sequences encoding an HCV E1/E2 heterodimer; and b) a CDN or an archaeosome. In some cases, an immunogenic composition of the present disclosure comprises: a) a recombinant viral vector comprising nucleotide sequences encoding an HCV E2 polypeptide; and b) a CDN or an archaeosome. In some cases, an immunogenic composition of the present disclosure comprises: a) a recombinant viral vector comprising nucleotide sequences encoding an HCV E1 polypeptide; and b) a CDN or an archaeosome.

In some cases, the present disclosure provides: a) a first immunogenic composition comprising: i) a recombinant viral vector comprising nucleotide sequences encoding one or more of: an HCV E1/E2 heterodimer; an HCV E1 polypeptide; an HCV E2 polypeptide; and a T-cell epitope polypeptide; and ii) a CDN; and b) a second immunogenic composition comprising: i) a recombinant viral vector comprising nucleotide sequences encoding one or more of: an HCV E1/E2 heterodimer; an HCV E1 polypeptide; an HCV E2 polypeptide; and a T-cell epitope polypeptide; and ii) a CDN. In some cases, the present disclosure provides: a) a first immunogenic composition comprising: i) a recombinant viral vector comprising nucleotide sequences encoding one or more of: an HCV E1/E2 heterodimer; an HCV E1 polypeptide; an HCV E2 polypeptide; and a T-cell epitope polypeptide; and ii) an archaeosome; and b) a second immunogenic composition comprising: i) a recombinant viral vector comprising nucleotide sequences encoding one or more of: an HCV E1/E2 heterodimer; an HCV E1 polypeptide; an HCV E2 polypeptide; and a T-cell epitope polypeptide; and ii) an archaeosome.

In some cases, the present disclosure provides: a) a first immunogenic composition comprising: i) a first recombinant viral vector comprising nucleotide sequences encoding one or more of: an HCV E1/E2 heterodimer; an HCV E1 polypeptide; an HCV E2 polypeptide; and a T-cell epitope polypeptide; and ii) a CDN or an archaeosome; and b) a second immunogenic composition comprising: i) a second recombinant viral vector comprising nucleotide sequences encoding one or more of: an HCV E1/E2 heterodimer; an HCV E1 polypeptide; an HCV E2 polypeptide; and a T-cell epitope polypeptide; and ii) a CDN or an archaeosome. In some cases, the first recombinant viral vector is a replication-defective adenovirus-based recombinant viral vector; and the second recombinant viral vector is an MVA-based recombinant viral vector. In some cases, the first recombinant viral vector is a chimpanzee adenovirus-based recombinant viral vector; and the second recombinant viral vector is an MVA-based recombinant viral vector.

In some cases, the nucleic acid(s) are present in bacteria (e.g., non-pathogenic bacteria suitable for delivery of nucleic acids to an individual). In some cases, the nucleic acid(s) are present in recombinant expression vector(s) present in bacteria (e.g., non-pathogenic bacteria suitable for delivery of nucleic acids to an individual). Thus, the present disclosure provides an immunogenic composition comprising a non-pathogenic, bacterium that harbors a nucleic acid(s) comprising nucleotide sequences encoding one or more of: an HCV E1/E2 heterodimer; an HCV E1 polypeptide; an HCV E2 polypeptide; and a T-cell epitope polypeptide, where such polypeptides are described above. The present disclosure provides an immunogenic composition comprising a non-pathogenic bacterium that harbors a recombinant expression vector(s) comprising nucleotide sequences encoding one or more of: an HCV E1/E2 heterodimer; an HCV E1 polypeptide; an HCV E2 polypeptide; and a T-cell epitope polypeptide, where such polypeptides are described above. In some cases, the bacteria are live. In some cases, the bacteria are live attenuated bacteria. In some cases, the bacteria are killed.

Bacteria suitable for delivery of nucleic acid(s) (which nucleic acid(s) may be present in expression vector(s)) include, but are not limited to, *Lactobacillus; Lactococcus* (e.g., *Lactococcus lactis*); *Salmonella*, e.g., attenuated, non-pathogenic *Salmonella*, e.g., *Salmonella enterica* serovar *Typhi, Salmonella enterica* serovar *Typhimurium*; non-pathogenic strains of *Francisella*; non-pathogenic strains of *Escherichia coli*; non-pathogenic strains of *Bordetella pertussis*; non-pathogenic strains of *Listeria*; non-pathogenic strains of *Shigella*; non-pathogenic strains of *Vibrio* (e.g., *Vibrio cholera*); *Streptococcus gordonii*; non-pathogenic strains of *Yersinia enterocolitica*; non-pathogenic strains of

*Shigella flexneri*; non-pathogenic strains of *Pseudomonas aeruginosa*; non-pathogenic strains of *Bacillus subtilis*; and the like.

In some cases, one or more virulence genes in the bacterium is all or partially deleted. For example, for *Salmonella enterica* serovar *Typhi* and *Salmonella enterica* serovar *Typhimurium*, an aroA, aroC, and aroD mutation can be made. Other mutations that can attenuate pathogenicity affect biosynthesis of the nucleotides adenine (pur) and guanine (guaBA), and outer membrane proteins C and F (ompC, ompF), as well as expression of the cAMP receptor (cya/crp), the conversion of UDP-galactose to UDP-glucose (galE), DNA recombination and repair (recA, recBC), and regulation of virulence genes (phoP, phoQ). For *Listeria monocytogenes*, attenuation can be achieved with auxotrophic mutants, or deletion of virulence factors such as the genes actA and internalin B (intB).

Methods of Inducing an Immune Response to HCV

The present disclosure provides a method of inducing an immune response (e.g., a protective immune response) to at least one HCV genotype in a mammalian subject (e.g., a human). In some cases, a method of the present disclosure for inducing an immune response in an individual to at least one HCV genotype comprises administering an immunogenic composition of the present disclosure, where the immunogenic composition comprises polypeptides (e.g., HCV E1/E2, HCV E1, or HCV E2; and optionally a T-cell epitope polypeptide). In some cases, a method of the present disclosure for inducing an immune response in an individual to at least one HCV genotype comprises administering an immunogenic composition of the present disclosure, where the immunogenic composition comprises one or more nucleic acids comprising nucleotide sequences encoding polypeptides (e.g., e.g., HCV E1/E2, HCV E1, or HCV E2; and optionally a T-cell epitope polypeptide).

Administering an Immunogenic Composition Comprising Polypeptides

In some cases, the methods comprise administering to an individual in need thereof an effective amount of an immunogenic composition of the present disclosure, where the immunogenic composition comprises: a) an HCV E1/E2 heterodimer; and b) a CDN; or where the immunogenic composition comprises: a) an HCV E2 polypeptide; and b) a CDN; or where the immunogenic composition comprises: a) an HCV E1 polypeptide; and b) a CDN. In some cases, the methods comprise administering to an individual in need thereof an effective amount of an immunogenic composition of the present disclosure, where the immunogenic composition comprises: a) an HCV E1/E2 heterodimer; and b) an archaeosome; or where the immunogenic composition comprises: a) an HCV E2 polypeptide; and b) an archaeosome; or where the immunogenic composition comprises: a) an HCV E1 polypeptide; and b) an archaeosome.

In some cases, the methods comprise administering to an individual in need thereof an effective amount of an immunogenic composition of the present disclosure, where the immunogenic composition comprises: a) an HCV E1/E2 heterodimer; b) a T-cell epitope polypeptide comprising a T-cell epitope present in an HCV polypeptide other than E1 and E2; and c) a CDN; or where the immunogenic composition comprises: a) an HCV E2 polypeptide; b) a T-cell epitope polypeptide comprising a T-cell epitope present in an HCV polypeptide other than E1 and E2; and c) a CDN; or where the immunogenic composition comprises: a) an HCV E1 polypeptide; b) a T-cell epitope polypeptide comprising a T-cell epitope present in an HCV polypeptide other than E1 and E2; and c) a CDN.

In some cases, the methods comprise administering to an individual in need thereof an effective amount of an immunogenic composition of the present disclosure, where the immunogenic composition comprises: a) an HCV E1/E2 heterodimer; b) a T-cell epitope polypeptide comprising a T-cell epitope present in an HCV polypeptide other than E1 and E2; and c) an archaeosome; or where the immunogenic composition comprises: a) an HCV E2 polypeptide; b) a T-cell epitope polypeptide comprising a T-cell epitope present in an HCV polypeptide other than E1 and E2; and c) an archaeosome; or where the immunogenic composition comprises: a) an HCV E1 polypeptide; b) a T-cell epitope polypeptide comprising a T-cell epitope present in an HCV polypeptide other than E1 and E2; and c) an archaeosome.

In some cases, an immunogenic composition of the present disclosure comprising an HCV E1/E2 heterodimer and a CDN is administered via intramuscular administration. In some cases, an immunogenic composition of the present disclosure comprising an HCV E1/E2 heterodimer and a CDN is administered via intranasal administration. In some cases, an immunogenic composition of the present disclosure comprising an HCV E1/E2 heterodimer and a CDN is administered: a) first via intramuscular administration; b) followed by a second administration via intranasal administration; c) followed by a third administration via intranasal administration.

In some cases, an immunogenic composition of the present disclosure comprising an HCV E1/E2 heterodimer and an archaeosome is administered via intramuscular administration.

Administering an Immunogenic Composition Comprising Nucleic Acid(s)

In some cases, a method of the present disclosure for inducing an immune response to HCV in an individual comprises administering to the individual an effective amount of an immunogenic composition comprising: a) nucleic acid(s) comprising nucleotide sequences encoding: 1) an HCV E1/E2 heterodimer and a T-cell epitope polypeptide; 2) an HCV E2 polypeptide and a T-cell epitope polypeptide; 3) an HCV E1 polypeptide and a T-cell epitope polypeptide; 4) an HCV E1/E2 heterodimer; 5) an HCV E2 polypeptide; or 6) an HCV E1 polypeptide; and b) a CDN or an archaeosome. The polypeptides can be encoded in the same nucleic acid, or on separate nucleic acids. For example, where the nucleic acid(s) are recombinant expression vectors, the polypeptides can be encoded in the same or separate recombinant expression vectors.

In some cases, the nucleic acid(s) is/are DNA. In some cases, the nucleic acid(s) is/are RNA. In some cases, the nucleic acid(s) is/are present in expression vector(s) such that a recombinant expression vector(s) comprising the nucleic acid(s) are administered. In some cases, the recombinant expression vector(s) is/are recombinant viral vector(s). In some cases, the recombinant viral vector(s) are packaged into viral particles. In some cases, the nucleic acid(s) are present in bacteria (e.g., non-pathogenic bacteria (e.g., attenuated bacteria) suitable for delivery of nucleic acids to an individual).

In some cases, the nucleic acid is present in an expression vector, thereby generating a recombinant expression vector. Suitable expression vectors include, but are not limited to, a replication-defective adenovirus vector; a replication-defective vaccinia virus vector; a lentivirus vector (e.g., a self-inactivating lentivirus vector); a retroviral vector (e.g., a self-inactivating retroviral vector); an adeno-associated virus vector; and the like. In some cases, the vector is a modified vaccinia Ankara (MVA) vector, or an MVA-based vector (see, e.g., Verheust et al. (2012) *Vaccine* 30:2623). In some cases, the vector is a replication-defective adenovirus vector. In some cases, the vector is a replication-defective adenovirus 6 (Ad6) vector. In some cases, the vector is a replication-defective simian adenovirus vector (e.g., ChAd3). Suitable viral vectors are described in, e.g., Zhou et al. (2012) *Invest. Ophthalmol. Vis. Sci.* 53:2804; Swadling et al. (2014) *Sci. Transl. Med.* 6:261ra153; and Choi and Chang (2013) *Clin. Exp. Vaccine Res.* 2:97. In many cases, the recombinant viral vectors are packaged into viral particles; and the viral particles are formulated in an immunogenic composition along with a pharmaceutically acceptable carrier.

In some cases, an HCV E1/E2 heterodimer is encoded by nucleotide sequences present in a first recombinant viral vector, e.g., an adenovirus vector, a vaccinia virus vector, an MVA vector or MVA-based vector; and a T-cell epitope polypeptide is encoded by nucleotide sequences present in a second recombinant viral vector, e.g., an adenovirus vector, a vaccinia virus vector, an MVA vector or MVA-based vector.

In some cases, a prime-boost vaccine protocol is used. In some cases, a first (priming) immunogenic composition is administered, where the first immunogenic composition comprises a recombinant viral vector comprising nucleotide sequences encoding one or more of: a) an HCV E1/E2 heterodimer; b) an HCV E2 polypeptide; c) an HCV E1 polypeptide; and d) a T-cell epitope polypeptide; and, after a time, a second (booster) immunogenic composition is administered, where the second immunogenic composition comprises a recombinant viral vector comprising nucleotide sequences encoding one or more of: a) an HCV E1/E2 heterodimer; b) an HCV E2 polypeptide; c) an HCV E1 polypeptide; and d) a T-cell epitope polypeptide. In some cases, the first recombinant viral vector and the second recombinant viral vector are the same. In some cases, the first recombinant viral vector and the second recombinant viral vector are different. For example, in some cases, the first recombinant viral vector is a vaccinia-based recombinant viral vector; and the second recombinant viral vector is an adenovirus-based recombinant viral vector. In general, the recombinant viral vectors are packaged into viral particles. A second immunogenic composition can be administered at a time period of from 1 day to 1 year following administration of the first immunogenic composition. For example, a second immunogenic composition can be administered at a time period of from 1 day to 1 week, from 1 week to 2 weeks, from 2 weeks to 1 month, from 1 month to 2 months, from 2 months to 6 months, or from 6 months to 1 year following administration of the first immunogenic composition.

For example, in some cases, a first (priming) vaccine comprising a recombinant adenovirus (e.g., Ad6 or chimpanzee Ad (e.g., ChAd3)) that comprises a nucleotide sequence encoding an HCV E1/E2 heterodimer is followed by a second (booster) vaccine comprising a recombinant MVA vector that comprises a nucleotide sequence encoding a T-cell epitope polypeptide. Other prime-boost protocols can be used. For example, multiple primes and/or multiple boosts can be administered.

In some cases, a first (priming) immunogenic composition is administered, where the first immunogenic composition comprises one or more of: a) an HCV E1/E2 heterodimer; b) an HCV E2 polypeptide; c) an HCV E1 polypeptide; and d) a T-cell epitope polypeptide, as described above; and a second (boosting) immunogenic composition is administered, where the second immunogenic composition comprises a recombinant viral vector comprising nucleotide sequence(s) encoding one or more of: a) an HCV E1/E2 heterodimer; b) an HCV E2 polypeptide; c) an HCV E1 polypeptide; and d) a T-cell epitope polypeptide, as described above.

In some cases, a first (priming) immunogenic composition is administered, where the first immunogenic composition comprises a recombinant viral vector comprising nucleotide sequence(s) encoding one or more of: a) an HCV E1/E2 heterodimer; b) an HCV E2 polypeptide; c) an HCV E1 polypeptide; and d) a T-cell epitope polypeptide, as described above; and a second (boosting) immunogenic composition is administered, where the second immunogenic composition comprises one or more of: a) an HCV E1/E2 heterodimer; b) an HCV E2 polypeptide; c) an HCV E1 polypeptide; and d) a T-cell epitope polypeptide, as described above.

In some cases, a co-immunization regimen is carried out, in which a polypeptide(s) per se is administered substantially concomitantly with a nucleic acid(s) encoding the polypeptide(s). For example, in some cases, a method of the present disclosure for inducing an immune response to an HCV polypeptide can comprise administering: a) a first immunogenic composition of the present disclosure, as described above, where the immunogenic composition comprises: i) an HCV E1/E2 heterodimer; ii) a T-cell epitope polypeptide; and iii) a pharmaceutically acceptable carrier; or i) an HCV E1 polypeptide; ii) a T-cell epitope polypeptide; and iii) a pharmaceutically acceptable carrier; or i) an HCV E2 polypeptide; ii) a T-cell epitope polypeptide; and iii) a pharmaceutically acceptable carrier; and b) a second immunogenic composition of the present disclosure, as described above, where the immunogenic composition comprises: i) one or more nucleic acids comprising nucleotide sequence encoding one or more of: an HCV E1/E2 heterodimer, an HCV E1 polypeptide, an HCV E2 polypeptide, and a T-cell epitope polypeptide; and ii) a pharmaceutically acceptable carrier. In some cases, the first and the second immunogenic compositions are in a single formulation. In some cases, the first and the second immunogenic compositions are in separate formulations. In some cases, the first and the second immunogenic compositions are administered via the same route of administration. In some cases, the first and the second immunogenic compositions are administered via different routes of administration. In some cases, the first and the second immunogenic compositions are in separate formulations that are administered substantially simultaneously, e.g., within 1 minute, within 1 minute to 5 minutes, within 5 minutes to 15 minutes, or within 15 minutes to 30 minutes, of one another. In some cases, the first and the second immunogenic compositions are administered multiple times to an individual.

In some cases, a co-immunization regimen is carried out, in which a polypeptide(s) per se is administered substantially concomitantly with a nucleic acid(s) encoding the polypeptide(s). For example, in some cases, a method of the present disclosure for inducing an immune response to an HCV polypeptide can comprise administering: a) a first immunogenic composition of the present disclosure, as described above, where the immunogenic composition comprises: i) an HCV E1/E2 heterodimer; ii) a T-cell epitope polypeptide; and iii) a CDN; and b) a second immunogenic composition of the present disclosure, as described above, where the immunogenic composition comprises: i) one or more nucleic acids comprising nucleotide sequences encoding an HCV E1/E2 heterodimer and a T-cell epitope polypeptide; and ii) a CDN. In some cases, the first and the second immunogenic compositions are in a single formulation. In some cases, the first and the second immunogenic compositions are in separate formulations. In some cases, the first and the second immunogenic compositions are administered via the same route of administration. In some cases, the first and the second immunogenic compositions are administered via different routes of administration. In some cases, the first and the second immunogenic compositions are in separate formulations that are administered substantially simultaneously, e.g., within 1 minute, within 1 minute to 5 minutes, within 5 minutes to 15 minutes, or within 15 minutes to 30 minutes, of one another. In some cases, the first and the second immunogenic compositions are administered multiple times to an individual. In some cases, the one or more nucleic acids are recombinant viral vectors.

In some cases, a method of the present disclosure for inducing an immune response to HCV in an individual comprises administering to the individual an effective amount of an immunogenic composition comprising: a) nucleic acid(s) comprising nucleotide sequences encoding 1) an HCV E1/E2 heterodimer and a T-cell epitope polypeptide; 2) an HCV E2 polypeptide and a T-cell epitope polypeptide; 3) an HCV E1 polypeptide and a T-cell epitope polypeptide; 4) an HCV E1/E2 polypeptide; 5) an HCV E2 polypeptide; or 6) an HCV E1 polypeptide; and b) a CDN or an archaeosome. In some cases, the nucleic acid is an RNA comprising nucleotide sequences encoding a polypeptide of the present disclosure (e.g., an HCV E1/E2 heterodimer; an HCV E1 polypeptide; an HCV E2 polypeptide; a T-cell epitope polypeptide, as described herein. See, e.g., Weiner (2013) *Molec. Therapy* 21:506; and Ulmer et al. (2012) *Vaccine* 30:4414. In some cases, an RNA (e.g., a single mRNA molecule; or 2 mRNA molecules; or 3 mRNA molecules) comprising nucleotide sequences encoding a polypeptide of the present disclosure is formulated with a liposome. In some cases, an RNA (e.g., a single mRNA molecule; or 2 mRNA molecules) comprising nucleotide sequences encoding a polypeptide of the present disclosure is complexed with protamine. In some cases, an RNA (e.g., a single mRNA molecule; or 2 mRNA molecules) comprising nucleotide sequences encoding a polypeptide of the present disclosure is complexed with 1,2-dioleoyl-3-trimethylammonium-propane/1,2-dioleoyl-sn-glycero-3-phosphoethanolamine (DOTAP/DOPE).

In some cases, the nucleic acid(s) are present in bacteria (e.g., non-pathogenic bacteria suitable for delivery of nucleic acids to an individual). In some cases, the nucleic acid(s) are present in recombinant expression vector(s) present in bacteria (e.g., non-pathogenic bacteria suitable for delivery of nucleic acids to an individual). In some cases, the bacteria are live. In some cases, the bacteria are live attenuated bacteria. In some cases, the bacteria are killed. Bacteria suitable for delivery of nucleic acid(s) (which may be present in expression vectors) include, but are not limited to, *Lactobacillus; Lactococcus* (e.g., *Lactococcus lactis*); *Salmonella*, e.g., attenuated, non-pathogenic *Salmonella*, e.g., *Salmonella enterica* serovar *Typhi, Salmonella enterica* serovar *Typhimurium*; non-pathogenic strains of *Escherichia coli*; non-pathogenic strains of *Bordetella pertussis*; non-pathogenic strains of *Listeria*; non-pathogenic strains of *Shigella*; non-pathogenic strains of *Vibrio* (e.g., *Vibrio cholera*); *Streptococcus gordonii*; non-pathogenic strains of *Yersinia enterocolitica*; non-pathogenic strains of *Shigella flexneri*; non-pathogenic strains of *Pseudomonas aeruginosa*; non-pathogenic strains of *Bacillus subtilis*; and the like. In some cases, one or more virulence genes in the bacterium is all or partially deleted. For example, for *Salmonella enterica* serovar *Typhi* and *Salmonella enterica* serovar *Typhimurium*, an aroA, aroC, and aroD mutation can be made. Other mutations that can attenuate pathogenicity affect biosynthesis of the nucleotides adenine (pur) and guanine (guaBA), and outer membrane proteins C and F (ompC, ompF), as well as expression of the cAMP receptor (cya/crp), the conversion of UDP-galactose to UDP-glucose (galE), DNA recombination and repair (recA, recBC), and regulation of virulence genes (phoP, phoQ). For *Listeria monocytogenes*, attenuation can be achieved with auxotrophic mutants, or deletion of virulence factors such as the genes actA and internalin B (intB).

General Considerations

An immunogenic composition of the present disclosure is generally administered to a human subject who has an HCV infection or who is at risk of acquiring an HCV infection (e.g., is at greater risk than the general population of acquiring an HCV infection) so as to prevent or at least partially arrest the development of disease and its complications. An amount adequate to accomplish this is defined as a "therapeutically effective dose" or a "therapeutically effective amount." "Prophylactic" use of a subject immunogenic composition generally refers to administration to an individual who has not been infected with HCV. "Therapeutic" use of a subject immunogenic composition can refer to "prophylactic" use (administration to an individual who has not been infected with HCV) and/or to administration to an individual who has an HCV infection. A "therapeutically effective amount" of an immunogenic composition of the present disclosure, can be an amount that, when administered in one or more doses to an individual who is not infected with HCV, is effective to induce an immune response in the individual to HCV. A "therapeutically effective amount" of an immunogenic composition of the present disclosure, can be an amount that, when administered in one or more doses to an individual who is infected with HCV, is effective to enhance an immune response in the individual to HCV.

Amounts effective for therapeutic use will depend on, e.g., the manner of administration, the weight and general state of health of the patient, and the judgment of the prescribing physician. Single or multiple doses of a subject immunogenic composition can be administered depending on the dosage and frequency required and tolerated by the patient, and route of administration.

In some cases, an effective amount of an immunogenic composition of the present disclosure is an amount that, when administered to an individual in one or more doses, is effective to induce an antibody response (e.g., a neutralizing antibody response) to HCV in the individual. For example, antibody to HCV (e.g., extracellular HCV), and/or to an HCV-infected cell, can be induced.

An effective amount of an immunogenic composition of the present disclosure can be an amount that, when administered to an individual in one or more doses, is effective to induce a neutralizing antibody response to HCV of a variety of genotypes (e.g., genotype 1; genotype 3; etc.). A neutralizing antibody response reduces binding of HCV to one or more host receptors for HCV and inhibits entry of HCV into a cell.

In some cases, an effective amount (e.g., a therapeutically effective amount) of an immunogenic composition of the present disclosure is an amount that, when administered to an individual in one or more doses, is effective to induce a cytotoxic T lymphocyte (CTL) response to HCV. For example, a CTL response to an HCV-infected cell can be induced.

In some cases, an effective amount (e.g., a therapeutically effective amount) of an immunogenic composition of the present disclosure is an amount that, when administered to an individual in one or more doses, is effective to induce a helper T lymphocyte (e.g., $CD4^+$ T cell) to HCV in an individual.

In some cases, an effective amount (e.g., a therapeutically effective amount) of an immunogenic composition of the present disclosure is an amount that, when administered to an individual in one or more doses, is effective to induce an antibody response (e.g., a neutralizing antibody response) and/or a CTL response and/or a helper T cell response to HCV genotype 1. In some cases, an effective amount (e.g., a therapeutically effective amount) of an immunogenic composition of the present disclosure is an amount that, when administered to an individual in one or more doses, is effective to induce an antibody response (e.g., a neutralizing antibody response) and/or a CTL response and/or a helper T cell response to HCV genotype 3. In some cases, an effective amount (e.g., a therapeutically effective amount) of an immunogenic composition of the present disclosure is an amount that, when administered to an individual in one or more doses, is effective to induce an antibody response (e.g., a neutralizing antibody response) and/or a CTL response and/or a helper T cell response to HCV genotype 1 and HCV genotype 3. In some cases, an effective amount (e.g., a therapeutically effective amount) of an immunogenic composition of the present disclosure is an amount that, when administered to an individual in one or more doses, is effective to induce an antibody response (e.g., a neutralizing antibody response) and/or a CTL response and/or a helper T cell response to HCV of any genotype.

An immunogenic composition of the present disclosure is generally administered in an amount effective to elicit an immune response, e.g., a humoral immune response (e.g., an antibody response) and/or a CTL response, in the mammalian subject. Effective amounts for immunization will vary, and can generally range from about 1 pg to 100 μg per 70 kg patient, e.g., from about 5 μg/70 kg to about 50 μg/70 kg. Substantially higher dosages (e.g. 10 mg to 100 mg or more) may be suitable in oral, nasal, or topical administration routes. The initial administration can be followed by booster immunization of the same immunogenic composition or a different immunogenic composition. In some instances, a subject method of inducing an immune response involves an initial administration of an immunogenic composition of the present disclosure, followed by at least one booster, and in some instances involves two or more (e.g., three, four, or five) boosters. The interval between an initial administration and a booster, or between a give booster and a subsequent booster, can be from about 1 week to about 12 weeks, e.g., from about 1 week to about 2 weeks, from about 2 weeks to about 4 weeks, from about 4 weeks to about 6 weeks, from about 6 weeks to about 8 weeks, from about 8 weeks to about 10 weeks, or from about 10 weeks to about 12 weeks. The interval between an initial administration and a booster, or between a give booster and a subsequent booster, can be from 4 months to 6 months, or from 6 months to 1 year.

In general, immunization can be accomplished by administration of an immunogenic composition of the present disclosure by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980). In some instances, immunization is accomplished by intramuscular injection of an immunogenic composition of the present disclosure.

Individuals Suitable for Administration

Individuals who are suitable for administration with an immunogenic composition of the present disclosure include immunologically naïve individuals (e.g., individuals who have not been infected with HCV and/or who have not been administered with an HCV vaccine). Individuals suitable for administration include humans. Individuals who are suitable for administration with an immunogenic composition of the present disclosure are also referred to as "an individual in need thereof."

Individuals who are suitable for administration with an immunogenic composition of the present disclosure composition of the present disclosure include individuals who are at greater risk than the general population of becoming infected with HCV, where such individuals include, e.g., intravenous drug users; individuals who are the recipients, or the prospective recipients, of blood or blood products from another (donor) individual(s); individuals who are the recipients, or the prospective recipients, of non-autologous cells, tissues, or organs from another (donor) individual; health care workers; emergency medical and non-medical personnel (e.g., first responders; fire fighters; emergency medical team personnel; etc.) and the like.

Individuals who are suitable for administration with an immunogenic composition of the present disclosure composition of the present disclosure include individuals who recently became exposed to HCV or who recently became infected with HCV. For example, a subject immunogenic composition can be administered to an individual within from about 24 hours to about 48 hours, from about 48 hours to about 1 week, or from about 1 week to about 4 weeks, following possible or suspected exposure to HCV or following infection with HCV.

Individuals who are suitable for administration with an immunogenic composition of the present disclosure composition of the present disclosure include individuals who have been diagnosed as having an HCV infection, and include chronically infected individuals. In some cases, an individual who has been diagnosed as having an HCV infection is treated with an anti-viral agent and an immunogenic composition of the present disclosure. Suitable anti-viral agents for treating HCV infection include, e.g., ribavirin (1-β-D-ribofuranosyl-1H-1,2,4-triazole-3-carboxamide); interferon-alpha (IFN-α) (where "IFN-α" includes IFN-α2a; IFN-α2b; IFN-α that is conjugated with poly (ethylene glycol) ("pegylated IFN-α), where the pegylated IFN-α can be pegylated IFN-α2a or pegylated IFN-α 2b); an HCV NS3 protease inhibitor (e.g., boceprevir; telaprevir); and an HCV NS5 protease inhibitor. In some cases, an individual who has been diagnosed as having an HCV infection is treated with, e.g.: 1) IFN-α+ribavirin; and an immunogenic composition of the present disclosure; or 2) IFN-α+ribavirin+an HCV protease inhibitor (e.g., boceprevir or telaprevir); and an immunogenic composition of the present disclosure. Suitable anti-viral agents for treating HCV infection include Sovaldi (Sofosbuvir; a nucleotide analog that functions as an NS5B polymerase inhibitor), alone or in combination with pegylated IFN-α and ribavirin.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-136 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. An immunogenic composition comprising: a) an HCV E1/E2 heterodimer; and b) a cyclic dinucleotide (CDN); or a) an HCV E2 polypeptide; and b) a CDN; or a) an HCV E1 polypeptide; and b) a CDN.

Aspect 2. The immunogenic composition of aspect 1A, aspect 1B, or aspect 1C, wherein the CDN is fluorinated.

Aspect 3. The immunogenic composition of aspect 2, wherein the CDN is 2'-F-c-di-GMP.

Aspect 4. The immunogenic composition of aspect 1A, aspect 1B, or aspect 1C, wherein the CDN is of Formula (I):

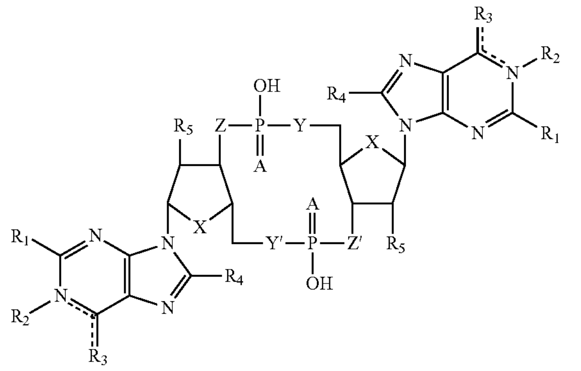

wherein:

A is S or O;

X is S, N, O, $CH_2$;

Y, Y' is NH, $CH_2$, O;

Z, Z' is NH, $CH_2$, O;

R1 represents hydrogen or $NH_2$ which may be substituted;

R2 is hydrogen or absent;

R3 represents $NH_2$, O, OH, H, or a halogen;

R4 represents hydrogen, halogen, or a straight or branched $C_1$-$C_6$ alkyl group which may optionally be substituted;

R5 represents hydrogen, OH or a straight or branched $C_1$-$C_6$ alkyl chain or $C_1$-$C_6$ straight or branched alkoxy chain which may optionally be substituted;

----- is a single or double bond;

or conjugates thereof, and salts or solvates thereof.

Aspect 5. The immunogenic composition of aspect 4, wherein the CDN is c-diGMP, c-diAMP, c-dilMP, or c-dXMP.

Aspect 6. The immunogenic composition of aspect 4, wherein the CDN is c-GpAp, c-Gplp, c-GpXp, c-Aplp, c-ApXp, or c-lpXp.

Aspect 7. The immunogenic composition of aspect 1, wherein the CDN is cyclic-GMP-AMP (cGAMP).

Aspect 8. The immunogenic composition of aspect 7, wherein the cGAMP is 2'3'-cGAMP, 2'2-cGAMP, 3'2'-cGAMP or 3'3'-GAMP.

Aspect 9. The immunogenic composition of any one of aspect aspects 1-8, wherein the composition comprises an HCV E1/E2 heterodimer.

Aspect 10. The immunogenic composition of aspect 9, wherein:

a) the HCV E2 polypeptide is derived from an HCV of major genotype 1, 2, 3, 4, 5, 6, or 7; and b) the HCV E1 polypeptide is derived from an HCV of major genotype 1, 2, 3, 4, 5, 6, or 7.

Aspect 11. The immunogenic composition of any one of aspects 1-10, wherein the HCV E2 polypeptide comprises an amino acid sequence having at least 20% amino acid sequence identity to an E2 polypeptide depicted in one of FIG. 1A-1C, FIG. 2A-2C, FIG. 3A-3C, and FIG. 4A-4B.

Aspect 12. The immunogenic composition of any one of aspects 1-10, wherein the HCV E1 polypeptide comprises an amino acid sequence having at least 20% amino acid sequence identity to an E1 polypeptide depicted in FIG. 1A-1C, FIG. 2A-2C, FIG. 3A-3C, and FIG. 4A-4B.

Aspect 13. The immunogenic composition of any one of aspects 1-12, wherein the E2 polypeptide and/or the E1 polypeptide lacks a C-terminal transmembrane domain.

Aspect 14. The immunogenic composition of any one of aspects 1-13, wherein the HCV E2 polypeptide and the HCV E1 polypeptide are derived from an HCV of the same genotype.

Aspect 15. The immunogenic composition of any one of aspects 1-13, wherein the HCV E2 polypeptide and the HCV E1 polypeptide are derived from an HCV of different genotypes.

Aspect 16. The immunogenic composition of any one of aspects 1-15, wherein the HCV E1/E2 heterodimeric polypeptide comprises:

a) an HCV E1 polypeptide; and b) a modified E2 polypeptide comprising, in order from N-terminus to C-terminus:

i) from 1 to 6 heterologous amino acids, wherein the from 1 to 6 heterologous amino acids are C-terminal to a site of proteolytic cleavage in a proteolytically cleavable linker; and ii) an HCV E2 polypeptide; or a) an HCV E2 polypeptide; and b) a modified E1 polypeptide comprising, in order from N-terminus to C-terminus:

i) from 1 to 6 heterologous amino acids, wherein the from 1 to 6 heterologous amino acids are C-terminal to a site of proteolytic cleavage in a proteolytically cleavable linker; and ii) an HCV E1 polypeptide; or a) an HCV E1 polypeptide; and b) a modified E2 polypeptide comprising, in order from N-terminus to C-terminus:

i) an HCV E2 polypeptide; and ii) from 1 to 6 heterologous amino acids, wherein the from 1 to 6 heterologous amino acids are N-terminal to a site of proteolytic cleavage in a proteolytically cleavable linker; or a) an HCV E2 polypeptide; and b) a modified E1 polypeptide comprising, in order from N-terminus to C-terminus:

i) an HCV E1 polypeptide; and ii) from 1 to 6 heterologous amino acids, wherein the from 1 to 6 heterologous amino acids are N-terminal to a site of proteolytic cleavage in a proteolytically cleavable linker.

Aspect 17. The immunogenic composition of aspect 16, wherein:

a) the from 1 to 6 heterologous amino acids at the N-terminus of the modified E2 polypeptide or the modified E1 polypeptide are Gly-Pro, Ser, Gly, or Gly-Ser; or b) the from 1 to 6 heterologous amino acids at the C-terminus of the modified E2 polypeptide or the modified E1 polypeptide are LEVLFQGP (SEQ ID NO:117), ENLYYFQ (SEQ ID NO:150), LVPR (SEQ ID NO:124), I(E/D)GR (SEQ ID NO:125), or DDDDK.

Aspect 18. The immunogenic composition of any one of aspects 1-17, wherein the HCV E1 polypeptide, the HCV E2 polypeptide, or one or both chains of the HCV E1/E2 heterodimer comprises a covalently linked T-cell epitope polypeptide comprising a T-cell epitope present in an HCV protein other than E1 and E2.

Aspect 19. The immunogenic composition of any one of aspects 1-18, comprising a T-cell epitope polypeptide comprising a T-cell epitope present in an HCV protein other than E1 and E2, wherein the T-cell epitope polypeptide is not covalently linked to the HCV E1E2 heterodimer, the HCV E1 polypeptide, or the HCV E2 polypeptide.

Aspect 20. The immunogenic composition of aspect 18 or aspect 19, wherein the T-cell epitope polypeptide comprises one or more T cell epitopes present in one or more of:

a) an HCV non-structural polypeptide-3 (NS3) polypeptide;

b) an HCV non-structural polypeptide-2 (NS2) polypeptide;

c) an HCV non-structural polypeptide-4A (NS4A) polypeptide;

d) an HCV non-structural polypeptide-4B (NS4B) polypeptide;

e) an HCV non-structural polypeptide-5A (NS5A) polypeptide;

f) an HCV non-structural polypeptide-5B (NS5B) polypeptide;

g) an HCV core polypeptide; and h) an HCV p7 polypeptide.

Aspect 21. The immunogenic composition of any one of aspects 18-20, wherein the T-cell epitope polypeptide has a length of from about 10 amino acids to about 3000 amino acids.

Aspect 22. The immunogenic composition of any one of aspects 18-20, wherein the T-cell epitope polypeptide has a length of from about 10 amino acids to about 50 amino acids, from about 100 amino acids to about 230 amino acids, from about 230 amino acids to about 550 amino acids, from about 550 amino acids to about 780 amino acids, or from about 780 amino acids to about 2000 amino acids.

Aspect 23. The immunogenic composition of any one of aspects 18-22, wherein the T-cell epitope polypeptide comprises one or more T cell epitopes present in an HCV NS3 polypeptide.

Aspect 24. The immunogenic composition of any one of aspects 18-23, wherein the T-cell epitope polypeptide comprises an amino acid sequence having at least 20% amino acid sequence identity to the amino acid sequence of one of TP29, TP50, TP52, TP70, TP100, TP171, TP228, TP553, TP778, and TP1985.

Aspect 25. The immunogenic composition of aspect any one of aspects 18-24, wherein the T-cell epitope polypeptide comprises an amino acid sequence having at least 20% amino acid sequence identity to a polypeptide depicted in any one of FIGS. 9A, 9B, 10A-10D, and 11A-11N.

Aspect 26. The immunogenic composition of any one of 18-25, wherein the T-cell epitope polypeptide comprises one or more T cell epitopes present in:

a) cholera toxin or toxoid; and/or b) tetanus toxin or toxoid; and/or c) diphtheria toxin or toxoid; and/or d) CRM197.

Aspect 27. The immunogenic composition of any one of aspects 1-25, wherein the composition comprises a polypeptide comprising one or more T cell epitopes present in:

a) cholera toxin or toxoid; and/or b) tetanus toxin or toxoid; and/or c) diphtheria toxin or toxoid; and/or d) CRM197.

Aspect 28. A method of inducing an immune response to HCV in an individual, the method comprising administering to the individual an effective amount of the immunogenic composition of any one of aspects 1-27.

Aspect 29. The method of aspect 28, wherein said administering is via intramuscular administration, intranasal administration, subcutaneous administration, or a combination thereof.

Aspect 30. The method of aspect 28, wherein said administering comprises a prime and a boost.

Aspect 31. An immunogenic composition comprising:

a) one or more nucleic acids comprising nucleotide sequences encoding the hepatitis C virus (HCV) E1 polypeptide, the HCV E2 polypeptide, or the HCV E1/E2 heterodimer as recited in any one of aspects 1-28; and b) a cyclic dinucleotide as recited in any one of aspects 1-28.

Aspect 32. The immunogenic composition of aspect 31, wherein the one or more nucleic acids are recombinant expression vectors.

Aspect 33. The immunogenic composition of aspect 32, wherein the one or more recombinant expression vectors are recombinant viral vectors.

Aspect 34. The immunogenic composition of aspect 32, wherein the one or more recombinant viral vectors are packaged into viral particles.

Aspect 35. The immunogenic composition of any one of aspects 31-34, wherein the one or more nucleic acids are present within non-pathogenic bacteria.

Aspect 36. A method of inducing an immune response to HCV in an individual, the method comprising administering to the individual an effective amount of any one of aspects 31-35.

Aspect 37. The method of aspect 36, wherein said administering is via intramuscular administration, intranasal administration, subcutaneous administration, or a combination thereof.

Aspect 38. The method of aspect 36, wherein said administering comprises a prime and a boost.

Aspect 39. The method of any one of aspects 28-30 or aspects 36-38, wherein the immune response comprises one or more of a $CD4^+$ response, a $CD8^+$ response, and a neutralizing antibody response.

Aspect 40. The method of any one of aspects 28-30 or aspects 36-38, wherein the immune response induced is to more than one HCV genotype.

Aspect 41. An immunogenic composition comprising: a) an HCV E1/E2 heterodimer; and b) an archaeosome comprising at least one polar synthetic lipid, wherein the at least one polar synthetic lipid comprises at least one carbohydrate or anionic group linked by covalent bonding to at least one free hydroxyl group of an archaeal core lipid; or a) an HCV E2 polypeptide; and b) an archaeosome comprising at least one polar synthetic lipid, wherein the at least one polar synthetic lipid comprises at least one carbohydrate or anionic group linked by covalent bonding to at least one free hydroxyl group of an archaeal core lipid; or a) an HCV E1 polypeptide; and b) an archaeosome comprising at least one polar synthetic lipid, wherein the at least one polar synthetic lipid comprises at least one carbohydrate or anionic group linked by covalent bonding to at least one free hydroxyl group of an archaeal core lipid.

Aspect 42. The immunogenic composition of aspect 41, wherein the archaeal core lipid is archaeol (2,3-di-O-diphytanyl-sn-glycerol).

Aspect 43. The immunogenic composition of aspect 41, wherein the archaeal core lipid is caldarchaeol (2,2',3,3'-tetra-O-dibiphytanyl-sn-diglycerol).

Aspect 44. The immunogenic composition of aspect 41, wherein the carbohydrate group is selected from the group consisting of: β-D-Glc-(1,6)-β-D-Glc-; β-D-Glc-(1,6)-.alpha.-D-Glc-; .alpha.-D-Glc-(1,6)-β-D-Glc-; β-D-Glc-(1,4)-β-D-Glc-; α-D-Glc-(1,4)-β-D-Glc-; β-D-Gal-(1,4)-β-D-Glc-; α-D-Gal-(1,6)-β-D-Glc-; β-D-Glc-(1,6)-β-D-Glc-(1,6)-β-D-Glc-; α-D-Glc-(1,4)-α-D-Glc-(1,4)-β-D-Glc-; α-D-Man-(1,2)-α-D-Man-(1,2)-α-D-Man-; and α-D-Man-(1,2)-α-D-Man-(1,2)-α-D-Man-(1,2)-α-D-Man-.

Aspect 45. The immunogenic composition of aspect 41, wherein the carbohydrate group comprises two or three β-D-Glc-units in (1,6) linkage.

Aspect 46. The immunogenic composition of aspect 41, wherein the carbohydrate group is a gal-glc-group.

Aspect 47. The immunogenic composition of aspect 41, wherein the anionic group is selected from the group consisting of phosphoserine, phosphoethanolamine, phosphoinositol and phosphoglycerol.

Aspect 48. The immunogenic composition of aspect 41, wherein the at least one polar synthetic lipid comprises at least one anionic lipid.

Aspect 49. The immunogenic composition of aspect 48, wherein the at least one anionic lipid is selected from the group consisting of archaetidylglycerol, archaetidylglycerolphosphate-methyl, archaetidylserine, and archaetidylinositol.

Aspect 50. The immunogenic composition of aspect 48, wherein the archaeosome comprises at least one conventional lipid.

Aspect 51. The immunogenic composition of aspect 50, wherein the at least one conventional lipid is selected from a group consisting of phosphatidylglycerol, phosphatidylserine, SQDG, and cholesterol.

Aspect 52. The immunogenic composition of aspect 51, wherein the at least one conventional lipid comprises cholesterol, and wherein cholesterol is present in an amount of between 10 and 45 mol % of the total lipid composition.

Aspect 53. The immunogenic composition of aspect 51, wherein the phosphatidylglycerol is present in an amount of between 20 and 80 mol % of the lipid composition.

Aspect 54. The immunogenic composition of aspect 51, wherein the phosphatidylserine is present in an amount of between 10 and 30 mol % of the lipid composition.

Aspect 55. The immunogenic composition of aspect 51, wherein the at least one polar synthetic lipid comprises at least one synthetic immunoactive glycolipid and at least one anionic lipid, and the archaeosome further comprises at least one stabilizing lipid.

Aspect 56. The immunogenic composition of aspect 55, wherein the at least one polar synthetic lipid comprises caldarchaeol having one carbohydrate head group and one anionic head group.

Aspect 57. The immunogenic composition of aspect 56, wherein the carbohydrate head group comprises gentiobiose and the anionic head group comprises phosphoinositol.

Aspect 58. The immunogenic composition of aspect 55, wherein the at least one polar synthetic lipid comprises a first caldarchaeol having two carbohydrate head groups and a second caldarchaeol having two anionic head groups, and wherein the at least one stabilizing lipid is the first and/or second caldarchaeol.

Aspect 59. The immunogenic composition of aspect 55, wherein the at least one polar synthetic lipid comprises gentiotriose-archaeol and wherein the at least one stabilizing lipid comprises cholesterol and at least one of phosphatidylethanolamine, archaetidylglycerol, archaetidylserine or archaetidylglycerolphosphate-methyl.

Aspect 60. The immunogenic composition of any one of aspects 41-59, wherein the composition comprises an HCV E1/E2 heterodimer.

Aspect 61. The immunogenic composition of aspect 60, wherein:

a) the HCV E2 polypeptide is derived from an HCV of major genotype 1, 2, 3, 4, 5, 6, or 7; and
b) the HCV E1 polypeptide is derived from an HCV of major genotype 1, 2, 3, 4, 5, 6, or 7.

Aspect 62. The immunogenic composition of any one of aspects 41-61, wherein the HCV E2 polypeptide comprises an amino acid sequence having at least 20% amino acid sequence identity to an E2 polypeptide depicted in one of FIG. 1A-1C, FIG. 2A-2C, FIG. 3A-3C, and FIG. 4A-4B.

Aspect 63. The immunogenic composition of any one of aspects 41-61, wherein the HCV E1 polypeptide comprises an amino acid sequence having at least 20% amino acid sequence identity to an E1 polypeptide depicted in FIG. 1A-1C, FIG. 2A-2C, FIG. 3A-3C, and FIG. 4A-4B.

Aspect 64. The immunogenic composition of any one of aspects 41-63, wherein the E2 polypeptide and/or the E1 polypeptide lacks a C-terminal transmembrane domain.

Aspect 65. The immunogenic composition of any one of aspects 41-64, wherein the HCV E2 polypeptide and the HCV E1 polypeptide are derived from an HCV of the same genotype.

Aspect 66. The immunogenic composition of any one of aspects 41-64, wherein the HCV E2 polypeptide and the HCV E1 polypeptide are derived from an HCV of different genotypes.

Aspect 67. The immunogenic composition of any one of aspects 41-66, wherein the HCV E1/E2 heterodimeric polypeptide comprises:

a) an HCV E1 polypeptide; and
b) a modified E2 polypeptide comprising, in order from N-terminus to C-terminus:
i) from 1 to 6 heterologous amino acids, wherein the from 1 to 6 heterologous amino acids are C-terminal to a site of proteolytic cleavage in a proteolytically cleavable linker; and
ii) an HCV E2 polypeptide; or
a) an HCV E2 polypeptide; and
b) a modified E1 polypeptide comprising, in order from N-terminus to C-terminus:
i) from 1 to 6 heterologous amino acids, wherein the from 1 to 6 heterologous amino acids are C-terminal to a site of proteolytic cleavage in a proteolytically cleavable linker; and ii) an HCV E1 polypeptide; or a) an HCV E1 polypeptide; and b) a modified E2 polypeptide comprising, in order from N-terminus to C-terminus:

i) an HCV E2 polypeptide; and ii) from 1 to 6 heterologous amino acids, wherein the from 1 to 6 heterologous amino acids are N-terminal to a site of proteolytic cleavage in a proteolytically cleavable linker; or a) an HCV E2 polypeptide; and b) a modified E1 polypeptide comprising, in order from N-terminus to C-terminus:

i) an HCV E1 polypeptide; and ii) from 1 to 6 heterologous amino acids, wherein the from 1 to 6 heterologous amino acids are N-terminal to a site of proteolytic cleavage in a proteolytically cleavable linker.

Aspect 68. The immunogenic composition of aspect 67, wherein:

a) the from 1 to 6 heterologous amino acids at the N-terminus of the modified E2 polypeptide or the modified E1 polypeptide are Gly-Pro, Ser, Gly, or Gly-Ser; or b) the from 1 to 6 heterologous amino acids at the C-terminus of the modified E2 polypeptide or the modified E1 polypeptide are LEVLFQGP (SEQ ID NO:117), ENLYYFQ (SEQ ID NO:150), LVPR (SEQ ID NO:124), I(E/D)GR (SEQ ID NO:125), or DDDDK.

Aspect 69. The immunogenic composition of any one of aspects 41-68, wherein the HCV E1 polypeptide, the HCV E2 polypeptide, or one or both chains of the HCV E1/E2 heterodimer comprises a covalently linked T-cell epitope polypeptide comprising a T-cell epitope present in an HCV protein other than E1 and E2.

Aspect 70. The immunogenic composition of any one of aspects 41-68, comprising a T-cell epitope polypeptide comprising a T-cell epitope present in an HCV protein other than E1 and E2, wherein the T-cell epitope polypeptide is not covalently linked to the HCV E1E2 heterodimer, the HCV E1 polypeptide, or the HCV E2 polypeptide.

Aspect 71. The immunogenic composition of aspect 69 or aspect 70, wherein the T-cell epitope polypeptide comprises one or more T cell epitopes present in one or more of:

a) an HCV non-structural polypeptide-3 (NS3) polypeptide;

b) an HCV non-structural polypeptide-2 (NS2) polypeptide;

c) an HCV non-structural polypeptide-4A (NS4A) polypeptide;

d) an HCV non-structural polypeptide-4B (NS4B) polypeptide;

e) an HCV non-structural polypeptide-5A (NS5A) polypeptide;

f) an HCV non-structural polypeptide-5B (NS5B) polypeptide;

g) an HCV core polypeptide; and h) an HCV p7 polypeptide.

Aspect 72. The immunogenic composition of any one of aspects 69-71, wherein the T-cell epitope polypeptide has a length of from about 10 amino acids to about 3000 amino acids.

Aspect 73. The immunogenic composition of any one of aspects 69-71, wherein the T-cell epitope polypeptide has a length of from about 10 amino acids to about 50 amino acids, from about 100 amino acids to about 230 amino acids, from about 230 amino acids to about 550 amino acids, from about 550 amino acids to about 780 amino acids, or from about 780 amino acids to about 2000 amino acids.

Aspect 74. The immunogenic composition of any one of aspects 69-73, wherein the T-cell epitope polypeptide comprises one or more T cell epitopes present in an HCV NS3 polypeptide.

Aspect 75. The immunogenic composition of aspect any one of aspects 69-74, wherein the T-cell epitope polypeptide comprises an amino acid sequence having at least 20% amino acid sequence identity to the amino acid sequence of one of TP29, TP50, TP52, TP70, TP100, TP171, TP228, TP553, TP778, and TP1985.

Aspect 76. The immunogenic composition of aspect any one of aspects 69-74, wherein the T-cell epitope polypeptide comprises an amino acid sequence having at least 20% amino acid sequence identity to a polypeptide depicted in any one of FIGS. 9A, 9B, 10A-10D, and 11A-11N.

Aspect 77. The immunogenic composition of any one of 69-76, wherein the T-cell epitope polypeptide comprises one or more T cell epitopes present in:

a) cholera toxin or toxoid; and/or b) tetanus toxin or toxoid; and/or c) diphtheria toxin or toxoid; and/or d) CRM197.

Aspect 78. The immunogenic composition of any one of aspects 41-76, wherein the composition comprises a polypeptide comprising one or more T cell epitopes present in:

a) cholera toxin or toxoid; and/or b) tetanus toxin or toxoid; and/or c) diphtheria toxin or toxoid; and/or d) CRM197.

Aspect 79. A method of inducing an immune response to HCV in an individual, the method comprising administering to the individual an effective amount of the immunogenic composition of any one of aspects 41-78.

Aspect 80. The method of aspect 79, wherein said administering is via intramuscular administration, intranasal administration, subcutaneous administration, or a combination thereof.

Aspect 81. The method of aspect 79, wherein said administering comprises a prime and a boost.

Aspect 82. An immunogenic composition comprising:

a) one or more nucleic acids comprising nucleotide sequences encoding the hepatitis C virus (HCV) E1 polypeptide, the HCV E2 polypeptide, or the HCV E1/E2 heterodimer as recited in any one of aspects 41-78; and b) an archaeosome as recited in any one of aspects 41-78.

Aspect 83. The immunogenic composition of aspect 82, wherein the one or more nucleic acids are recombinant expression vectors.

Aspect 84. The immunogenic composition of aspect 83, wherein the one or more recombinant expression vectors are recombinant viral vectors.

Aspect 85. The immunogenic composition of aspect 84, wherein the one or more recombinant viral vectors are packaged into viral particles.

Aspect 86. The immunogenic composition of any one of aspects 82-84, wherein the one or more nucleic acids are present within non-pathogenic bacteria.

Aspect 87. A method of inducing an immune response to HCV in an individual, the method comprising administering to the individual an effective amount of any one of aspects 82-86.

Aspect 88. The method of aspect 87, wherein said administering is via intramuscular administration, intranasal administration, subcutaneous administration, or a combination thereof.

Aspect 89. The method of aspect 87, wherein said administering comprises a prime and a boost.

Aspect 90. The method of any one of aspects 79-81 or aspects 87-89, wherein the immune response comprises one or more of a $CD4^+$ response, a $CD8^+$ response, and a neutralizing antibody response.

Aspect 91. The method of any one of aspects 79-81 or aspects 87-89, wherein the immune response induced is to more than one HCV genotype.

Aspect 92. An immunogenic composition comprising:

a) a T-cell epitope polypeptide comprising a T-cell epitope present in a hepatitis C virus (HCV) protein other than E1 and E2; and b) a cyclic dinucleotide (CDN).

Aspect 93. The immunogenic composition of aspect 92, wherein the CDN is fluorinated.

Aspect 94. The immunogenic composition of aspect 93, wherein the CDN is 2'-F-c-di-GMP.

Aspect 95. The immunogenic composition of aspect 92, wherein the CDN is of Formula

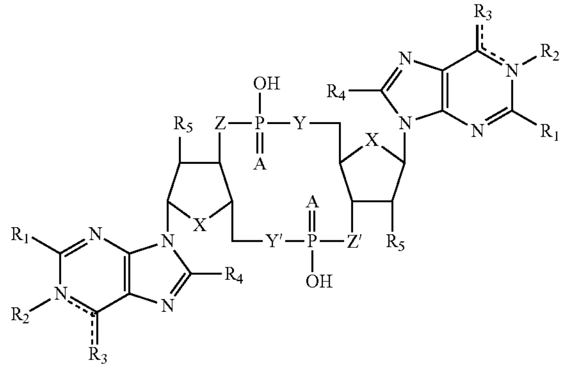

(I):

wherein:

A is or O;

X is S, N, O, $CH_2$;

Y, Y' is NH, $CH_2$, O;

Z, Z' is NH, $CH_2$, O;

R1 represents hydrogen or $NH_2$ which may be substituted;

R2 is hydrogen or absent;

R3 represents $NH_2$, O, OH, H, or a halogen;

R4 represents hydrogen, halogen, or a straight or branched $C_1$-$C_6$ alkyl group which may optionally be substituted;

R5 represents hydrogen, OH or a straight or branched $C_1$-$C_6$ alkyl chain or $C_1$-$C_6$ straight or branched alkoxy chain which may optionally be substituted;

⎓ is a single or double bond;

or conjugates thereof, and salts or solvates thereof.

Aspect 96. The immunogenic composition of aspect 95, wherein the CDN is c-diGMP, c-diAMP, c-dilMP, or c-dXMP.

Aspect 97. The immunogenic composition of aspect 95, wherein the CDN is c-GpAp, c-Gplp, c-GpXp, c-Aplp, c-ApXp, or c-lpXp.

Aspect 98. The immunogenic composition of aspect 92, wherein the CDN is cyclic-GMP-AMP (cGAMP).

Aspect 99. The immunogenic composition of aspect 98, wherein the cGAMP is 2'3'-cGAMP, 2'2-cGAMP, 3'2'-cGAMP or 3'3'-GAMP.

Aspect 100. The immunogenic composition of any one of aspects 92-99, wherein the T-cell epitope polypeptide comprises one or more T cell epitopes present in one or more of:

a) an HCV non-structural polypeptide-3 (NS3) polypeptide;

b) an HCV non-structural polypeptide-2 (NS2) polypeptide;

c) an HCV non-structural polypeptide-4A (NS4A) polypeptide;

d) an HCV non-structural polypeptide-4B (NS4B) polypeptide;

e) an HCV non-structural polypeptide-5A (NS5A) polypeptide;

f) an HCV non-structural polypeptide-5B (NS5B) polypeptide;

g) an HCV core polypeptide; and h) an HCV p7 polypeptide.

Aspect 101. The immunogenic composition of any one of aspects 92-100, wherein the T-cell epitope polypeptide has a length of from about 10 amino acids to about 3000 amino acids.

Aspect 102. The immunogenic composition of any one of aspects 92-100, wherein the T-cell epitope polypeptide has a length of from about 10 amino acids to about 50 amino acids, from about 100 amino acids to about 230 amino acids, from about 230 amino acids to about 550 amino acids, from about 550 amino acids to about 780 amino acids, or from about 780 amino acids to about 2000 amino acids.

Aspect 103. The immunogenic composition of any one of aspects 92-102, wherein the T-cell epitope polypeptide comprises one or more T cell epitopes present in an HCV NS3 polypeptide.

Aspect 104. The immunogenic composition of aspect any one of aspects 92-103, wherein the T-cell epitope polypeptide comprises an amino acid sequence having at least 20% amino acid sequence identity to the amino acid sequence of one of TP29, TP50, TP52, TP70, TP100, TP171, TP228, TP553, TP778, and TP1985.

Aspect 105. The immunogenic composition of aspect any one of aspects 1-20, wherein the T-cell epitope polypeptide comprises an amino acid sequence having at least 20% amino acid sequence identity to a polypeptide depicted in any one of FIGS. 9A, 9B, 10A-10D, and 11A-11N.

Aspect 106. The immunogenic composition of any one of 92-105, wherein the T-cell epitope polypeptide comprises one or more T cell epitopes present in:

a) cholera toxin or toxoid; and/or b) tetanus toxin or toxoid; and/or c) diphtheria toxin or toxoid; and/or d) CRM197.

Aspect 107. The immunogenic composition of any one of aspects 92-105, wherein the composition comprises a polypeptide comprising one or more T cell epitopes present in:

a) cholera toxin or toxoid; and/or b) tetanus toxin or toxoid; and/or c) diphtheria toxin or toxoid; and/or d) CRM197.

Aspect 108. A method of inducing an immune response to an antigen in an individual, the method comprising administering to the individual an effective amount of:

a) the composition of any one of aspects 92-107; and b) the antigen.

Aspect 109. An immunogenic composition comprising:

a) a T-cell epitope polypeptide comprising a T-cell epitope present in a hepatitis C virus (HCV) protein other than E1 and E2; and b) an archaeosome comprising at least one polar synthetic lipid, wherein the at least one polar synthetic lipid comprises at least one carbohydrate or anionic group linked by covalent bonding to at least one free hydroxyl group of an archaeal core lipid.

Aspect 110. The immunogenic composition of aspect 109, wherein the archaeal core lipid is archaeol (2,3-di-O-diphytanyl-sn-glycerol).

Aspect 111. The immunogenic composition of aspect 109, wherein the archaeal core lipid is caldarchaeol (2,2',3,3'-tetra-O-dibiphytanyl-sn-diglycerol).

Aspect 112. The immunogenic composition of aspect 109, wherein the carbohydrate group is selected from the group consisting of: β-D-Glc-(1,6)-β-D-Glc-; β-D-Glc-(1,6)-.alpha.-D-Glc-; .alpha.-D-Glc-(1,6)-β-D-Glc-; β-D-Glc-(1,4)-β-D-Glc-; α-D-Glc-(1,4)-β-D-Glc-; β-D-Gal-(1,4)-β-D-Glc-; α-D-Gal-(1,6)-β-D-Glc-; β-D-Glc-(1,6)-β-D-Glc-(1,6)-β-D-Glc-; α-D-Glc-(1,4)-α-D-Glc-(1,4)-β-D-Glc-; α-D-Man-(1,2)-α-D-Man-(1,2)-α-D-Man-; and α-D-Man-(1,2)-α-D-Man-(1,2)-α-D-Man-(1,2)-α-D-Man-.

Aspect 113. The immunogenic composition of aspect 109, wherein the carbohydrate group comprises two or three β-D-Glc-units in (1,6) linkage.

Aspect 114. The immunogenic composition of aspect 109, wherein the carbohydrate group is a gal-glc-group.

Aspect 115. The immunogenic composition of aspect 109, wherein the anionic group is selected from the group consisting of phosphoserine, phosphoethanolamine, phosphoinositol and phosphoglycerol.

Aspect 116. The immunogenic composition of aspect 109, wherein the at least one polar synthetic lipid comprises at least one anionic lipid.

Aspect 117. The immunogenic composition of aspect 116, wherein the at least one anionic lipid is selected from the group consisting of archaetidylglycerol, archaetidylglycerolphosphate-methyl, archaetidylserine, and archaetidylinositol.

Aspect 118. The immunogenic composition of aspect 116, wherein the archaeosome comprises at least one conventional lipid.

Aspect 119. The immunogenic composition of aspect 118, wherein the at least one conventional lipid is selected from a group consisting of phosphatidylglycerol, phosphatidylserine, SQDG, and cholesterol.

Aspect 120. The immunogenic composition of aspect 119, wherein the at least one conventional lipid comprises cholesterol, and wherein cholesterol is present in an amount of between 10 and 45 mol % of the total lipid composition.

Aspect 121. The immunogenic composition of aspect 119, wherein phosphatidylglycerol is present in an amount of between 20 and 80 mol % of the lipid composition.

Aspect 122. The immunogenic composition of aspect 119, wherein phosphatidylserine is present in an amount of between 10 and 30 mol % of the lipid composition.

Aspect 123. The immunogenic composition of aspect 109, wherein the at least one polar synthetic lipid comprises at least one synthetic immunoactive glycolipid and at least one anionic lipid, and the archaeosome further comprises at least one stabilizing lipid.

Aspect 124. The immunogenic composition of aspect 123, wherein the at least one polar synthetic lipid comprises caldarchaeol having one carbohydrate head group and one anionic head group.

Aspect 125. The immunogenic composition of aspect 124, wherein the carbohydrate head group comprises gentiobiose and the anionic head group comprises phosphoinositol.

Aspect 126. The immunogenic composition of aspect 123, wherein the at least one polar synthetic lipid comprises a first caldarchaeol having two carbohydrate head groups and a second caldarchaeol having two anionic head groups, and wherein the at least one stabilizing lipid is the first and/or second caldarchaeol.

Aspect 127. The immunogenic composition of aspect 123, wherein the at least one polar synthetic lipid comprises gentiotriose-archaeol and wherein the at least one stabilizing lipid comprises cholesterol and at least one of phosphatidylethanolamine, archaetidylglycerol, archaetidylserine or archaetidylglycerolphosphate-methyl.

Aspect 128. The immunogenic composition of any one of aspects 109-127, wherein the T-cell epitope polypeptide comprises one or more T cell epitopes present in one or more of:

a) an HCV non-structural polypeptide-3 (NS3) polypeptide;

b) an HCV non-structural polypeptide-2 (NS2) polypeptide;

c) an HCV non-structural polypeptide-4A (NS4A) polypeptide;

d) an HCV non-structural polypeptide-4B (NS4B) polypeptide;

e) an HCV non-structural polypeptide-5A (NS5A) polypeptide;

f) an HCV non-structural polypeptide-5B (NS5B) polypeptide;

g) an HCV core polypeptide; and h) an HCV p7 polypeptide.

Aspect 129. The immunogenic composition of any one of aspects 109-128, wherein the T-cell epitope polypeptide has a length of from about 10 amino acids to about 3000 amino acids.

Aspect 130. The immunogenic composition of any one of aspects 109-128, wherein the T-cell epitope polypeptide has a length of from about 10 amino acids to about 50 amino acids, from about 100 amino acids to about 230 amino acids, from about 230 amino acids to about 550 amino acids, from about 550 amino acids to about 780 amino acids, or from about 780 amino acids to about 2000 amino acids.

Aspect 131. The immunogenic composition of any one of aspects 109-130, wherein the T-cell epitope polypeptide comprises one or more T cell epitopes present in an HCV NS3 polypeptide.

Aspect 132. The immunogenic composition of aspect any one of aspects 109-131, wherein the T-cell epitope polypeptide comprises an amino acid sequence having at least 20% amino acid sequence identity to the amino acid sequence of one of TP29, TP50, TP52, TP70, TP100, TP171, TP228, TP553, TP778, and TP1985.

Aspect 133. The immunogenic composition of aspect any one of aspects 109-132, wherein the T-cell epitope polypeptide comprises an amino acid sequence having at least 20% amino acid sequence identity to a polypeptide depicted in any one of FIGS. 9A, 9B, 10A-10D, and 11A-11N.

Aspect 134. The immunogenic composition of any one of 109-133, wherein the T-cell epitope polypeptide comprises one or more T cell epitopes present in:

a) cholera toxin or toxoid; and/or b) tetanus toxin or toxoid; and/or c) diphtheria toxin or toxoid; and/or d) CRM197.

Aspect 135. The immunogenic composition of any one of aspects 109-133, wherein the composition comprises a polypeptide comprising one or more T cell epitopes present in:

a) cholera toxin or toxoid; and/or b) tetanus toxin or toxoid; and/or c) diphtheria toxin or toxoid; and/or d) CRM197.

Aspect 136. A method of inducing an immune response to an antigen in an individual, the method comprising administering to the individual an effective amount of:

a) the composition of any one of aspects 109-135; and b) the antigen.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Induction of an Immune Response with HCV E1/E2 and a CDN or an Archaeosome Various adjuvants including MF59, aluminum hydroxide/monophosphoryl lipid A (Alum/MPLA), cyclic di-adenosine monophosphate (C-di-AMP) and archaeosomes, were formulated with rE1E2 to immunize mice. 6-8 weeks mice were immunized three times on day 0, day 14, and day 35 and sera was collected two weeks after last immunization (FIG. 13). The ability of the antibodies to neutralize HCV was evaluated using HCV pseudo-particle (HCVpp) carrying a luciferase reported gene, where the particles were incubated with serum before culturing and the level of luciferase expression was used to measure the neutralization activity of the given serum. Spleens were also collected, and isolated splenocytes were restimulated ex vivo with short peptides to evaluate cellular immunity using multicolor flow cytometry to detect intracellular production of cytokines. Different groups of mice received rE1E2 formulated with MF59, Alum/MPLA, C-di-AMP, or archaeosomes along with appropriate controls FIG. 13 depicts the immunization protocol.

Results

The sera collected from immunized mice is able to neutralize and prevent the entry of HCV pseudo-particles in vitro: As compared to the controls, the sera collected from immunized mice with adjuvanted rE1E2, showed significant increase in preventing the entry of HCVpp in an in vitro neutralization assay (FIG. 14). When the antigen was formulated with MF59 or Alum-MPLA, this effect was highly comparable to neutralization activity of anti-CD81 against HCVpp. However, this effect was lower than that of anti-CD81 in the case of C-di-AMP and archaeosomes formulations. The route seemed to be playing a significant role for C-di-AMP, since the sera from mice with three intranasal administration (IN-IN-IN) of rE1E2+C-di-AMP did not neutralize HCVpp, as opposed to an intramuscular immunization followed by two intranasal boost (IM-IN-IN) regimen.

FIG. 14. Neutralization activity of rE1E2 in combination with adjuvant in mice. The sera from mice immunized with rE1E2 were able to neutralize the entry of HCV pseudo particle in vitro. Percentage of neutralization was calculated based on the neutralizing activity for post-vaccination bleed divided by neutralization activity of pre-vaccination bleed.

Horizontal lines are the medians in each group.

**=p value<0.01; *=p value<0.05.

Robust T cell immune response in C-di-AMP and archaeosomes groups: In vitro stimulation of mice splenocytes with a pool of 55 peptides that span the whole length of HCV E1E2 induced a strong memory T cell response in the groups, where the antigen was formulated with C-di-AMP and archaeosomes (p value<0.005). A moderate response was also detected in Alum/MPLA group (p value<0.05). The data show that while C-di-AMP and archaesomes elicit strong neutralizing antibodies comparable to MF59 and Alum/MPLA, both induced a more robust cellular immune response which was confirmed by the detection of vaccine-specific poly-functional CD4+ T cells (FIG. 15).

FIG. 15. Differential detection of T cell immune response in mice. The splenocytes from vaccinated mice with rE1E2 in combination with different adjuvants were stimulated in vitro and intracellular production of cytokine was detected by multi-color flow cytometry. IM=Intramuscular; IN=Intranasal; Neg=Negative control splenocytes; E1E2=Splenocytes that are stimulated with a pool of 55 peptides spanning E1E2.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

```
Sequence total quantity: 151
SEQ ID NO: 1            moltype = AA  length = 746
FEATURE                 Location/Qualifiers
VARIANT                 248
                        note = X can be any amino acid
VARIANT                 262
                        note = X can be any amino acid
VARIANT                 270
```

-continued

```
                        note = X can be any amino acid
VARIANT                 275
                        note = X can be any amino acid
VARIANT                 399
                        note = X can be any amino acid
VARIANT                 408
                        note = X can be any amino acid
VARIANT                 524
                        note = X can be any amino acid
VARIANT                 580
                        note = X can be any amino acid
VARIANT                 641
                        note = X can be any amino acid
VARIANT                 709
                        note = X can be any amino acid
VARIANT                 733
                        note = X can be any amino acid
source                  1..746
                        mol_type = protein
                        organism = Hepatitis C virus
SEQUENCE: 1
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASRCWV  240
ALTPTVAXRD GSLPTTQLRR HXDLLVGSAX LCSAXYVGDL CGSVFLVGQL FTFSPRRHWT  300
TQDCNCSIYP GHITGHRMAW DMMMNWSPTT ALVVAQLLRI PQAILDMIAG AHWGVLAGIA  360
YFSMVGNWAK VLVVLLLFAG VDAETHVTGG SAARATSGXA SLFSPGAXQN IQLINTNGSW  420
HINRTALNCN DSLDTGWVAG LFYYHKFNSS GCPERMASCR PLADFDQGWG PISYANGSGP  480
DQRPYCWHYP PKPCGIVPAQ QVCGPVYCFT PSPVVVGTTD RLGXPTYNWG ENETDVLVLN  540
NTRPPLGNWF GCTWMNSTGF TKVCGAPPCN IGGVGNNTLX CPTDCFRKHP EATYSRCGSG  600
PWLTPRCLVD YPYRLWHYPC TVNYTIFKVR MYVGGVEHRL XAACNWTRGE RCDLDDRDRS  660
ELSPLLLSTT QWQVLPCSFT TLPALSTGLI HLHQNIVDVQ YLYGVGSSXV SWAIKWEYVI  720
LLFLLLADAR ICXCLWMMLL ISQAEA                                      746

SEQ ID NO: 2            moltype = AA  length = 746
FEATURE                 Location/Qualifiers
source                  1..746
                        mol_type = protein
                        organism = Hepatitis C virus
SEQUENCE: 2
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYEAADAI LHTPGCVPCV REGNTSRCWV  240
AMTPTVATRD GKLPTTQLRR HIDLLVGSAT LCSALYVGDL CGSIFLVGQM FTFSPRRHWT  300
TQDCNCSLYP GHITGHRMAW DMMMNWSPTA ALITAQLLRI PQAILDMIAG AHWGVLAGIA  360
YFSMVGNWAK VLVVLLLFAG VDAQTHVTGG RAAHITAGLT SLFSPGPSQK LQLVNTNGSW  420
HINSTALNCN DSLKTGWIAG LLYSYKFNSS GCPERLASCR RLTDFAQGWG PISHANGSGP  480
DERPYCWHYP PRPCGIVPAK SVCGPVYCFT PSPVVVGTTD KSGAPTYNWG ENDTDVFVLN  540
NTRPPLGNWF GCTWMNSTGF TKVCGAPPCV IGGAGNNTLR CPTDCFRKHP DATYSRCGSG  600
PWITPRCLVD YPYRLWHYPC TVNYSIFKIR MYLGGVEHRL EAACNWTRGE RCDLEDRDRS  660
ELSPLLLSTT QWQVLPCSFT TLPALSTGLI HLHQNIVDVQ YLYGVGSSVA SWAIKWDYVV  720
LLFLLLADAR ICSCLWMMLL ISQAEA                                      746

SEQ ID NO: 3            moltype = AA  length = 746
FEATURE                 Location/Qualifiers
source                  1..746
                        mol_type = protein
                        organism = Hepatitis C virus
SEQUENCE: 3
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYEAADAI LHTPGCVPCV REGNASRCWV  240
AVTPTVATRD GKLPTTQLRR HIDLLVGSAT LCSALYVGDL CGSVFLVGQL FTFSPRRHWT  300
TQDCNCSIYP GHITGHRMAW DMMMNWSPTA ALVVAQLLRI PQAIMDMIAG AHWGVLAGIA  360
YFSMVGNWAK VLVVLLLFAG VDAETHVTGG SAGRTTAGLV GLLTPGAKQN IQLINTNGSW  420
HINSTALNCN ESLNTGWLAG LFYQHKFNSS GCPERLASCR RLTDFAQGWG PISYANGSGL  480
DERPYCWHYP PRPCGIVPAK SVCGPVYCFT PSPVVVGTTD RSGAPTYSWG ANDTDVFVLN  540
NTRPPLGNWF GCTWMNSTGF TKVCGAPPCV IGGVGNNTLL CPTDCFRKHP EATYSRCGSG  600
PWITPRCMVD YPYRLWHYPC TINYTIFKVR MYVGGVEHRL EAACNWTRGE RCDLEDRDRS  660
ELSPLLLSTT QWQVLPCSFT TLPALSTGLI HLHQNIVDVQ YLYGVGSSIA SWAIKWEYVV  720
LLFLLLADAR VCSCLWMMLL ISQAEA                                      746

SEQ ID NO: 4            moltype = AA  length = 746
FEATURE                 Location/Qualifiers
source                  1..746
                        mol_type = protein
```

-continued

```
                         organism = Hepatitis C virus
SEQUENCE: 4
MSTNPKPQRK TKRNTNRRPQ DVKFPGGGQI VGGVYLLPRR GPRLGVRAVR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGI YHVTNDCPNS SIVYETADTI LHSPGCVPCV REGNASKCWV  240
ALAPTVATRD GKLPTTQLRR HIDLLVGSAT LCSALYVGDL CGSVFLVGQL FTFSPRRHWT  300
TQDCNCSIYP GHITGHRMAW DMMMNWSPTT ALVVAQLLRV PQAILDMIAG AHWGVLAGIA  360
YFSMVGNWAK VLVVLLLFAG VDAETYTTGG SVAQAAFGLT SLFRPGPKQD IQLINTNGSW  420
HINRTALNCN ASLDTGWVAG LFYYHKFNSS GCPERMASCR SLADFDQGWG PISYANGSGP  480
EHRPYCWHYP PKPCGIVPAQ NVCGPVYCFT PSPVVVGTTN KLGVPTYSWG SNETDVLVLN  540
NTRPPLGNWF GCTWMNSSGF TKVCGAPPCV IGGAGNRTLH CPTDCFRKHP EATYSRCGSG  600
PWITPRCLVH YPYRLWHYPC TVNYTMFKVR MYVGGVEHRL EVACNWTRGE RCDLDDRDRS  660
ELSPLLLSTT QWQVLPCSFT TLPALTTGLI HLHQNIVDVQ YLYGVGSSIV SWAIKWEYVI  720
LLFLLLADAR ICSCLWMMLL ISQAEA                                       746

SEQ ID NO: 5             moltype = AA  length = 746
FEATURE                  Location/Qualifiers
source                   1..746
                         mol_type = protein
                         organism = Hepatitis C virus
SEQUENCE: 5
MSTNPKPQRK TKRNTNRRPQ DVKFPGGGQI VGGVYLLPRR GPRLGVRATR KTSERSQPRG  60
RRQPIPKARR PEGRSWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AFQVRNSSGL YHVTNDCPNS SIVYETADTI LHSPGCVPCV REDNTSRCWV  240
AVAPTVATRD GRLPTTQLRR HIDLLVGSAT LCSALYVGDL CGSVFLVGQL FTFSPRRHWT  300
TQDCNCSIYP GHITGHRMAW DMMMNWSPTT ALVVAQLLRV PQAILDMIAG AHWGVLAGIA  360
YFSMVGNWAK VLVVLLLFAS VDAETYTSGG SVARATAGFA GIFNPGAKQD IQLINTNGSW  420
HINRTALNCN ASLDTGWVAG LFYYHKFNSS GCPERMASCK PLAHFAQGWG PISYANGSGP  480
DHRPYCWHYP PKPCGIVPAQ NVCGPVYCFT PSPVVVGTTN KLGAPTYNWG SNDTDVFILN  540
NTRPPGGNWF GCTWMNSSGF TKVCGAPPCT IGGVGNNTLL CPTDCFRKHP EATYSRCGSG  600
PWVTPRFLVH YPYRLWHYPC TVNYTLFKVR MYVGGVEHRL EVACNWTRGE RCDLDDRDRS  660
ELSPLLLSTT QWQVLPCSFT TLPALTTGLI HLHQNIVDVQ YLYGVGSSLV SWAIKWEYVI  720
LLFLLLADAR ICSCLWMMLL ISQAEA                                       746

SEQ ID NO: 6             moltype = AA  length = 746
FEATURE                  Location/Qualifiers
source                   1..746
                         mol_type = protein
                         organism = Hepatitis C virus
SEQUENCE: 6
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNTSKCWV  240
AVAPTVATRD GKLPTTQLRR HIDLLVGSAT LCSALYVGDL CGSVFLVGQL FTFSPRRHWT  300
TQDCNCSIYP GHITGHRMAW DMMMNWSPTA ALVTAQLLRV PQAILDMIAG AHWGVLAGIA  360
YFSMAGNWAK VLLVLLLFAG VDAETYTTGG SVARTTRGLA SLLQVGPKQD IRLIHTNGSW  420
HINRTALNCN ASLDTGWLAG LLYYHKFNSS GCPERMASCR PLADFDQGWG PISYANGSGP  480
EHRPYCWHYP PKPCGIVPAQ TVCGPVYCFT PSPVVVGTTN KLGVPTYTWG SNDTDVFVLN  540
NTRPPLGNWF GCTWMNSTGF TKVCGAPPCV IGGVGNNTLH CPTDCFRKHP EATYSRCGSG  600
PWITPRCLVD YPYRLWHYPC TVNYTLFKVR MYVGGVEHRL QAACNWTRGE RCDLDDRDRS  660
ELSPLLLSTT QWQVLPCSFT TLPALTTGLI HLHQNIVDVQ YLYGVGSSIV SWAIKWEYVI  720
LLFLLLADAR ICSCLWMMLL ISQAEA                                       746

SEQ ID NO: 7             moltype = AA  length = 746
FEATURE                  Location/Qualifiers
source                   1..746
                         mol_type = protein
                         organism = Hepatitis C virus
SEQUENCE: 7
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REDNASRCWV  240
PVAPTVATRD GKLPTTQLRR HIDLLVGSAT LCSALYVGDL CGSVFLVSQL FTFSPRRHWT  300
TQDCNCSIYP GHITGHRMAW DMMMNWSPTV ALVMAQLLRV PQAILDMIAG AHWGVLAGIA  360
YFSMVGNWAK VLVVLLLFAG VDAQTYVTGG SAARGASGLA NLFTPGAKQD IQLINTNGSW  420
HINRTALNCN ASLDTGWVAG LFYYHKFNSS GCPERMASCK PLADFDQGWG PIRHANGSGP  480
EHRPYCWHYP PKPCGIVSAQ TVCGPVYCFT PSPVVVGTTN RLGVPTYSWG TNDTDVFVLN  540
NTRPPLGNWF GCTWMNSSGF TKVCGAPPCV IGGVGNNTLH CPTDCFRKHP EATYSRCGSG  600
PWITPRCLVH YPYRLWHYPC TVNYTLFKVR MYVGGVEHRL EVACNWTRGE RCDLDDRDRS  660
ELSPLLLSTT QWQVLPCSFT TLPALTTGLI HLHQNIVDVQ YLYGVGSSIV SWAIKWEYVI  720
LLFLLLADAR ICSCLWMMLL ISQAEA                                       746

SEQ ID NO: 8             moltype = AA  length = 746
FEATURE                  Location/Qualifiers
source                   1..746
```

-continued

```
                         mol_type = protein
                         organism = Hepatitis C virus
SEQUENCE: 8
MSTNPKPQRK TKRNTNRRPQ DVKFPGGGQI VGGVYLLPRR GPRLGVRTTR KTSERSEPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETKDTI LHSPGCVPCV REGNVSKCWV  240
PVALTVATRD GNLPTTQLRR HIDLLVGSAT LCSALYVGDL CGSVFLVGQL FTFSPRRHWT  300
TQDCNCSMYP GHITGHRMAW DMMMNWSPTS ALVVAQLLRV PQAILDMIAG AHWGVLAGLA  360
YFSMVGNWAK VLVVLLLFAS VDAGTHVTGG SAAHDVSALA GFFRRGAKQN IQLINTNGSW  420
HVNRTALNCN ASLDTGWVAG LLYYHRFNSS GCPERMASCR PLADFDQGWG PITNVDGGGS  480
EYRPYCWHYP PKPCGIEPAQ NVCGPVYCFT PSPVVVGTTD KVGVPTYNWG ENDTDVFVLN  540
NTRPPLGNWF GCTWMNSSGF VKVCGAPPCI IGGAGNKTLH CPTDCFRKHP DATYSRCGSG  600
PWLTPRCLVD YPYRLWHYPC TVNYTLFKIR MYVGGVEHRL VAACNWTYGE RCNLDDRDRS  660
ELSPLLLSTT QWQVLPCSFT TLPALTTGLI HLHQNIVDVQ YLYGVGSSIV SWAIKWEYVI  720
LLFLLLADAR ICSCLWMMLL ISQAEA                                     746

SEQ ID NO: 9             moltype = AA  length = 746
FEATURE                  Location/Qualifiers
source                   1..746
                         mol_type = protein
                         organism = Hepatitis C virus
SEQUENCE: 9
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASKCWV  240
AVAPTVATRD GTLPTTQLRR HIDLLVGGAT LCSALYVGDL CGSVFLVGQL FTFSPRRHWT  300
TQDCNCSIYP GHITGHRMAW DMMMNWSPTT ALIVAQLLRV PQAILDMIAG AHWGVLAGIA  360
YFSMVGNWAK VLVVLLLFAG VDAETHVTGG SAAQVTSRVA GFFNPGPKQN VQLINTNGSW  420
HINRTALNCN ASLDTGWVAG LFYHYNFNSS GCPERMASCR PLADFDQGWG PISYANGSGP  480
EHRPYCWHYP PKPCGIVPAQ NVCGPVYCFT PSPVVVGTTN RLGVPTYNWG SNDTDVFVLN  540
NTRPPLGNWF GCTWMNSSGF TKVCGAPPCV IGGVGNNTLH CPTDCFRKHP EATYSRCGSG  600
PWITPRCLVH YPYRLWHYPC TVNYTLFKVR MYVGGVEHRL EAACNWTRGE RCDLDDRDRS  660
ELSPLLLSTT QWQVLPCSFT TLPALTTGLI HLHQNIVDVQ YLYGVGSSIV SWAIKWEYVI  720
LLFLLLADAR ICSCLWMMLL ISQAEA                                     746

SEQ ID NO: 10            moltype = AA  length = 746
FEATURE                  Location/Qualifiers
source                   1..746
                         mol_type = protein
                         organism = Hepatitis C virus
SEQUENCE: 10
MSTNPKPQRK TKRNTNRRPQ DVKFPGGGQI VGGVYLLPRR GPRLGVRATR KTSERSQPRG  60
RRQPIPKARR PEGRSWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGI YHVTNDCPNS SIVYETADTI LHSPGCVPCV REGNASKCWV  240
ALAPTVATRD GRLPTTQLRR HIDLLVGSAT LCSALYVGDL CGSVFLVGQL FTFSPRRHWT  300
TQDCNCSIYP GHITGHRMAW DMMMNWSPTT ALVVAQLLRI PQAILDMIAG AHWGVLAGIA  360
YFSMVGNWAK VLVVLLLFAG VDAHTRVTGG SAARATARLT TLFSPGAKQD IQLINTNGSW  420
HINRTALNCN ASLDTGWVAG LFYYHKFNSS GCPERMASCR PLADFDQGWG PISYANGSGP  480
EHRPYCWHYP PKPCGIIPAK TVCGPVYCFT PSPVVVGTTD RSGAPTFNWG DNDTDVLVLN  540
NTRPPLGNWF GCTWMNSSGY TKVCGAPPCI IGGVGNNTLH CPTDCFRKHP EATYSRCGSG  600
PWITPRCLVH YPYRLWHYPC TVNYTLFKVR MYVGGVEHRL EAACNWTRGE RCNLDDRDRS  660
ELSPLLLSTT QWQVLPCSFT TLPALTTGLI HLHQNIVDVQ YLYGVGSSIV SWAIKWEYVI  720
LLFLLLADAR VCSCLWMMLL ISQVEA                                     746

SEQ ID NO: 11            moltype = AA  length = 746
FEATURE                  Location/Qualifiers
source                   1..746
                         mol_type = protein
                         organism = Hepatitis C virus
SEQUENCE: 11
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASKCWV  240
AVTPTVATRD GRLPATQLRR HIDLLVGSAT LCSALYVGDL CGSIFLVGQL FTFSPRRHWT  300
TQDCNCSIYP GHITGHRMAW DMMMNWSPTT ALVVAQLLRV PQAILDMIAG AHWGVLAGIA  360
YFSMVGNWAK VLVVLLLFAG VDAGTHVTGG SAAKDTSGFT SLFRIGARQN IQLINSNGSW  420
HINRTALNCN ESLDTGWVAG LLYYHKFNSS GCPERMASCR SLADFDQGWG PISYANGSGP  480
EHRPYCWHYP PKPCGIVPAQ SVCGPVYCFT PSPVVVGTTD KSGAPTYNWG CNETDVFVLN  540
NTRPPLGNWF GCTWMNSSGF TKVCGAPPCV IGGVGNNTLH CPTDCFRKHP EATYSRCGSG  600
PWITPRCLVH YAYRLWHYPC TVNYTLFKVR MYVGGVEHRL DVACNWTRGE RCNLDDRDRS  660
ELSPLLLSTT QWQVLPCSFT TLPALSTGLI HLHQNIVDVQ YLYGVGSSIV SWAIKWEYVI  720
LLFLLLADAR ICSCLWMMLL ISQAEA                                     746

SEQ ID NO: 12            moltype = AA  length = 746
FEATURE                  Location/Qualifiers
```

-continued

```
source                  1..746
                        mol_type = protein
                        organism = Hepatitis C virus
SEQUENCE: 12
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASKCWV  240
AVTPTVATRD GRLPATQLRR HIDLLVGSAT LCSALYVGDL CGSIFLVGQL FTFSPRRHWT  300
TQDCNCSIYP GHITGHRMAW DMMMNWSPTT ALVVAQLLRV PQAILDMIAG AHWGVLAGIA  360
YFSMVGNWAK VLVVLLLFAG VDAGTHVTGG SAAKDTSGFT SLFRIGARQN IQLINSNGSW  420
HINRTALNCN ESLDTGWVAG LLYYHKFNSS GCPERMASCR SLADFDQGWG PISYANGSGP  480
EHRPYCWHYP PKPCGIVPAQ SVCGPVYCFT PSPVVVGTTD KSGAPTYNWG CNETDVFVLN  540
NTRPPLGNWF GCTWMNSSGF TKVCGAPPCV IGGVGNNTLH CPTDCFRKHP EATYSRCGSG  600
PWITPRCLVH YAYRLWHYPC TVNYTLFKVR MYVGGVEHRL DVACNWTRGE RCNLDDRDRS  660
ELSPLLLSTT QWQVLPCSFT TLPALSTGLI HLHQNIVDVQ YLYGVGSSIV SWAIKWEYVI  720
LLFLLLADAR ICSCLWMMLL ISQAEA                                     746

SEQ ID NO: 13           moltype = AA  length = 746
FEATURE                 Location/Qualifiers
source                  1..746
                        mol_type = protein
                        organism = Hepatitis C virus
SEQUENCE: 13
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASKCWV  240
AVTPTVATRD GRLPATQLRR HIDLLVGSAT LCSALYVGDL CGSIFLVGQL FTFSPRRHWT  300
TQDCNCSIYP GHITGHRMAW DMMMNWSPTT ALVVAQLLRV PQAILDMIAG AHWGVLAGIA  360
YFSMVGNWAK VLVVLLLFAG VDAGTHVTGG SAAKDTSGFT SLFRIGARQN IQLINSNGSW  420
HINRTALNCN ESLDTGWVAG LLYYHKFNSS GCPERMASCR SLADFDQGWG PISYANGSGP  480
EHRPYCWHYP PKPCGIVPAQ SVCGPVYCFT PSPVVVGTTD KSGAPTYNWG CNETDVFVLN  540
NTRPPLGNWF GCTWMNSSGF TKVCGAPPCV IGGVGNNTLH CPTDCFRKHP EATYSRCGSG  600
PWITPRCLVH YAYRLWHYPC TVNYTLFKVR MYVGGVEHRL DVACNWTRGE RCNLDDRDRS  660
ELSPLLLSTT QWQVLPCSFT TLPALSTGLI HLHQNIVDVQ YLYGVGSSIV SWAIKWEYVI  720
LLFLLLADAR ICSCLWMMLL ISQAEA                                     746

SEQ ID NO: 14           moltype = AA  length = 746
FEATURE                 Location/Qualifiers
source                  1..746
                        mol_type = protein
                        organism = Hepatitis C virus
SEQUENCE: 14
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADSI LHSPGCVPCV REGNASKCWV  240
AVAPTVATRD GKLPATQLRR HIDLLVGSAT LCSALYVGDL CGSVFLVSQL FTFSPRRHWT  300
TQDCNCSIYP GHITGHRMAW DMMMNWSPTT ALVVSQLLRV PQAILDMIAG AHWGVLAGIA  360
YFSMVGNWAK VLVVLLLFAG VDAETHTTGG SAAYATSGFV GLFRQGAKQN IQLINTNGSW  420
HVNRTALNCN ASLDTGWVAG LFYYHKFNSS GCPERLASCK PLANFDQGWG SISYTNGSGP  480
EHRPYCWHYP PKPCGIVPAQ NVCGPVYCFT PSPVVVGTTD RLGAPTFNWG ENESDVFVLN  540
NTRPPSGNWF GCTWMNSSGF TKVCGAPPCN IGGVGNNTLH CPTDCFRKHP EATYSRCGSG  600
PWVTPRCLVH YPYRLWHYPC TLNYSLFKVR MYVGGIEHRL EVACNWTRGE RCNLDDRDRS  660
ELSPLLLTTT QWQVLPCSFT TLPALTTGLI HLHQNVVDVQ YLYGVGSSIV SWAIKWEYVI  720
LLFLLLADAR ICSCLWMMLL ISQAEA                                     746

SEQ ID NO: 15           moltype = AA  length = 746
FEATURE                 Location/Qualifiers
source                  1..746
                        mol_type = protein
                        organism = Hepatitis C virus
SEQUENCE: 15
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASKCWV  240
AVAPTVATRD GRLPTTQLRR HIDLLVGSAT LCSALYVGDL CGSVFLVGQL FTFSPRHHWT  300
TQDCNCSIYP GHITGHRMAW DMMMNWSPTT ALVVAQLLRV PQAILDMIAG AHWGVLAGIA  360
YFSMVGNWAK VLVVLLLFAG VDATTHTTGG AVAHNTRMFT SIFSLGPRQE IQLVNTNGSW  420
HINRTALNCN ASLETGWIAG LLYANRFNSS GCPERMASCK PLADFDQGWG PISYANGSGP  480
EHRPYCWHYP PKPCGIVPAQ NVCGPVYCFT PSPVVVGTTD RLGTPTYDWG SNDTDVFVLN  540
NTRPPAGNWF GCTWMNSSGY TKVCGAPPCV IGGVSNNTLH CPTDCFRKHP EATYSRCGSG  600
PWITPRCLVH YAYRLWHYPC TVNYTLFKVR MYVGGVEHRL EVACNWTRGE RCNLDDRDRS  660
ELSPLLLSTT QWQVLPCSFT TLPALTTGLI HLHQNIVDVQ YLYGVGSSIV SWAVKWEYVI  720
LLFLLLADAR ICSCLWMMLL ISQAEA                                     746

SEQ ID NO: 16           moltype = AA  length = 746
```

```
FEATURE                 Location/Qualifiers
source                  1..746
                        mol_type = protein
                        organism = Hepatitis C virus
SEQUENCE: 16
MSTNPKPQRK TKRNTNRRPQ DVKFPGGGQI VGGVYLLPRR GPRLGVRATR KTSERSQPRG  60
RRQPIPKARQ PEGRAWAQPG YPWPLYGNEG LGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTIPAS AYEVRNVSGV YHVTNDCSNA SIVYEAADMI MHTPGCVPCV RENNSSRCWV  240
ALTPTLAARN ASVPTTTIRR HVDLLVGAAA LCSAMYVGDL CGSVFLVAQL FTFSPRRHET  300
VQDCNCSIYP GHVTGHRMAW DMMMNWSPTA ALVVSQLLRI PQAVVDMVAG AHWGVLAGLA  360
YYSMVGNWAK VLIVMLLFAG VDGGTYVTGG TMAKNTLGIT SLFSPGSSQK IQLVNTNGSW  420
HINRTALNCN DSLNTGFLAA LFYVHKFNSS GCPERMASCS PIDAFAQGWG PITYNESHSS  480
DQRPYCWHYA PRPCGIVPAA QVCGPVYCFT PSPVVVGTTD RFGVPTYSWG ENETDVLLLN  540
NTRPPQGNWF GCTWMNSTGF TKTCGGPPCN IGGIGNKTLT CPTDCFRKHP EATYTKCGSG  600
PWLTPRCLVH YPYRLWHYPC TVNFTIFKVR MYVGGVEHRL EAACNWTRGE RCNLEDRDRS  660
ELSPLLLSTT EWQVLPCSFT TLPALSTGLI HLHQNVVDVQ YLYGIGSAVV SFAIKWEYVL  720
LLFLLLADAR VCACLWMMLL IAQAEA                                     746

SEQ ID NO: 17           moltype = AA  length = 746
FEATURE                 Location/Qualifiers
source                  1..746
                        mol_type = protein
                        organism = Hepatitis C virus
SEQUENCE: 17
MSTNPKPQRK TKRNTNRRPQ DVKFPGGGQI VGGVYLLPRR GPRLGVRATR KTSERSQPRG  60
RRQPIPKARQ PEGRAWAQPG YPWPLYGNEG MGWAGWLLSP RGSRPSWGPT DPRRRSRNLG  120
KVIDTLTCGF ADLMGYIPLV GAPLGGVARA LAHGVRVVED GVNYATGNLP GCSFSIFLLA  180
LLSCLTIPAS AYEVRNVSGI YHVTNDCSNS SIVYEAADMI MHTPGCVPCV REGNSSRCWV  240
ALTPTLAARN ASVPTTAIRR HVDLLVGAAA FCSAMYVGDL CGSVFLVSQL FTFSPRRHET  300
IQDCNCSIYP GHVSGHRMAW DMMMNWSPTT ALVVSQLLRI PQAIVDMVAG AHWGVLAGLA  360
YYSMVGNWAK VLIVMLLFAG VDGETRVTGG QIARNAYSLT TLFSSGSAQN IQLINTNGSW  420
HINRTALNCN DSLNTGFLAA LFYTHKFNAS GCPERLASCR PIDKFDQGWG PITYAEQGGQ  480
DQRPYCWHYA PKPCGIVSAS KVCGPVYCFT PSPVVVGTTD RFGVPTYSWG ENETDVLLLN  540
NTRPPQGNWF GCTWMNGTGF TKTCGGPPCN IGGGGNNTLT CPTDCFRKHP AATYTKCGSG  600
PWLTPRCLVD YPYRLWHYPC TANFTIFKVR MYVGGVEHRL DAACNWTRGE RCNLEDRDRL  660
ELSPLLLSTT EWQVLPCSFT TLPALSTGLI HLHQNIVDVQ YLYGIGSAVV SFAIKWDYIV  720
ILFLLLADAR VCACLWMMLL IAQAEA                                     746

SEQ ID NO: 18           moltype = AA  length = 747
FEATURE                 Location/Qualifiers
source                  1..747
                        mol_type = protein
                        organism = Hepatitis C virus
SEQUENCE: 18
MSTNPKPQRK TKRNTNRRPQ DVKFPGGGQI VGGVYLLPRR GPRLGVRAIR KTSERSQPRG  60
RRQPIPKARR PEGRAWAQPG YPWPLYGNEG MGWAGWLLSP RGSRPSWGPT DPRRRSRNLG  120
KVIDTLTCGL ADLMGYIPLV GGPLGGAARA LAHGVRVLED GVNYATGNLP GCSFSIFLLA  180
LLSCLTVPAS AHEVRNASGV YHVTNDCSNS SIVFEAADLI MHTPGCVPCV REGNSSRCWV  240
ALTPTLAARN ATIPTTTIRH HVDLLVGAAA LCSAMYVGDL CGSVFLVSQL FTFSPRRHAT  300
LQDCNCSIYP GHASGHRMAW DMMMNWSPTT ALVVSQLLRI PQAVIDMVAG AHWGVLAGLA  360
YYSMAGNWAK VLIVMLLFAG VDGHTLTTGG HAARLTSGFA GLFTPGPSQR IQLINTNGSW  420
HINRTALNCN DSLQTGFLAA LFYAHRFNSS GCPERMASCR SIDKFDQGWG PITYAEPTKD  480
PDQRPYCWHY PPQQCGIVPA SQVCGPVYCF TPSPVVVGTT DRLGNPTYSW GENDTDVLLL  540
NNTRPPQGNW FGCTWMNSTG FTKTCGAPPC NIGGVGNNTL TCPTDCFRKH PEATYSKCGS  600
GPWLTPRCMV DYPYRLWHYP CTVNFSIFKV RMYVGGVEHR LNAACNWTRG ERCNLDDRDR  660
SELSPLLLST TEWQVLPCSF TTLPALSTGL IHLHQNIVDV QYLYGIGSAV VSFAIKWEYV  720
VLLFLLLADA RVCACLWMML LIAQAEA                                    747

SEQ ID NO: 19           moltype = AA  length = 746
FEATURE                 Location/Qualifiers
source                  1..746
                        mol_type = protein
                        organism = Hepatitis C virus
SEQUENCE: 19
MSTNPKPQRK TKRNTNRRPQ DVKFPGGGQI VGGVYLLPRR GPRLGVRATR KTSERSQPRG  60
RRQPIPKARH PEGRTWAQPG YPWPLYGNEG LGWAGWLLSP RGSRPSWGPT DPRRRSRNLG  120
KVIDTLTCGF ADLMGYIPLV GAPLGGVARA LAHGVRVLED GVNYATGNLP GCSFSIFLLA  180
LLSCLTIPAS AYEVRNVSGV YHVTNDCSNS SIVYEAADVI MHTPGCVPCV QDGNTSRCWV  240
ALTPTLAARN ASVPVTAIRR HVDLLVGTAA FCSAMYVGDL CGSVFPVSQL FTFSPRRHQT  300
VQDCNCSIYP GHISGHRMAW DMMMNWSPTA ALVVSQLLRI PQAIVDMVAG AHWGVLAGLA  360
YYSMVGNWAK VMIVLLLFAG VDGTTHTTGG AAARATQGFT SFFSLGPSQK IQLINTNGSW  420
HINRTALNCN DSLQTGFLAA LFYTYRFNAS GCPERMASCR PIDKFDQGWG PITYAEPDSS  480
DQRPYCWHYA PRPCGIVPAS QVCGPVYCFT PSPVVVGTTD RFGVPTYTWG ENETDVLLLN  540
NTRPPLGNWF GCTWMNSTGF TKTCGGPPCN IGGAGNTTLT CPTDCFRKHP EATYTKCGSG  600
PWLTPRCLVD YPYRLWHYPC AVNFTIFKVR MYVGGVEHRL NAACNWTRGE RCDLEDRDRS  660
ELSPLLLSTT EWQVLPCSFT TLPALSTGLI HLHQNIVDVQ YLYGIGSAVI PFAIKWEYVL  720
LLFLLLADAR VCACLWMMLL IAQAEA                                     746
```

-continued

```
SEQ ID NO: 20          moltype = AA  length = 746
FEATURE                Location/Qualifiers
source                 1..746
                       mol_type = protein
                       organism = Hepatitis C virus
SEQUENCE: 20
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG MGWAGWLLSP RGSRPNWGPT DPRRRSRNLG  120
KVIDTLTCGF ADLMGYIPLV GAPLGGVARA LAHGVRVLED GVNYATGNLP GCSFSIFLLA  180
LLSCLTTPAS AYEVRNVSGI YHVTNDCSNS SIVYEAADII MHTPGCVPCV REKNISRCWV  240
ALTPTLAARN ISVPTATIRR HVDLLVGTAA FCSAMYVGDL CGSVFLVSQL FTFSPRWHET  300
VQDCNCSLYP GHVSGHRMAW DMMMNWSPTA ALVVSQLLRI PQAVVDMVAG AHWGVLAGLA  360
YYSMIGNWAK VLIVMLLFAG ADGTTHVTGG VQAHGAYGLA SLFNVGPHQK IQLVNTNGSW  420
HINRTALNCN DTLQTGFLAA LFYKHRFNAS GCPERMASCR PIDKFAQGWG PITYAEPDRL  480
DQRPYCWHYP PRPCGIVPAL EVCGPVYCFT PSPVVVGTTD RFGVPTYSWG ENETDVLLLN  540
NTRPPQGNWF GCTWMNSTGY TKTCGGPPCN IGGVGNNTLT CPTDCFRKHP EATYTKCGSG  600
PWLTPRCLVH YPYRLWHYPC TVNFTIFKVR MYVGGIEHRL DAACNWTRGE RCDLEDRDRS  660
ELSPLLLSTT EWQILPCSFT TLPALSTGLI HLHRNIVDVQ YLYGIGSAVV SFAIKWEYVL  720
LLFLLLADAR VCACLWMMLL IAQAEA                                     746

SEQ ID NO: 21          moltype = AA  length = 746
FEATURE                Location/Qualifiers
source                 1..746
                       mol_type = protein
                       organism = Hepatitis C virus
SEQUENCE: 21
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG LGWAGWLLSP RGSRPSWGPN DPRRRSRNLG  120
KVIDTLTCGF ADLMGYIPLV GAPLGGAARA LAHGVRVLED GVNYATGNLP GCSFSIFLLA  180
LLSCLTIPAS AYEVRNVSGI YHVTNDCSNS SIVYEAADVI MHAPGCVPCV RENNSSRCWV  240
ALTPTLAARN ASVPTTTLRR HVDLLVGTAA FCSAMYVGDL CGSVFLISQL FTFSPRRHET  300
VQDCNCSIYP GHVSGHRMAW DMMMNWSPTA ALVVSQLLRI PQAVMDMVAG AHWGVLAGLA  360
YYSMVGNWAK VLIVMLLFAG VDGHTRVTGG VQGHVTSTLT SLFRPGASQK IQLVNTNGSW  420
HINRTALNCN DSLKTGFLAA LFYTHKFNAS GCPERMASCR SIDKFDQGWG PITYAQPDNS  480
DQRPYCWHYA PRQCGIVPAS QVCGPVYCFT PSPVVVGTTD RFGAPTYNWG DNETDVLLLN  540
NTRPPHGNWF GCTWMNSTGF TKTCGGPPCN IRGVGNNTLT CPTDCFRKHP DATYTKCGSG  600
PWLTPRCLVD YPYRLWHYPC TVNFTIFKVR MYVGGVEHRL DAACNWTRGE RCDLEDRDRA  660
ELSPLLLSTT EWQILPCSYT TLPALSTGLI HLHQNIVDIQ YLYGIGSAVV SIAIKWEYVV  720
LLFLLLADAR VCACLWMMLL IAQAEA                                     746

SEQ ID NO: 22          moltype = AA  length = 746
FEATURE                Location/Qualifiers
source                 1..746
                       mol_type = protein
                       organism = Hepatitis C virus
SEQUENCE: 22
MSTNPKPQRK TKRNTNRRPQ DVKFPGGGQI VGGVYLLPRR GPRLGVRATR KTSERSQPRG  60
RRQPIPKARR PEGRTWAQPG YPWPLYGDEG MGWAGWLLSP RGSRPNWGPT DPRRRSRNLG  120
KVIDTLTCGF ADLMGYIPLV GAPLGGVARA LAHGVRVLED GVNYATGNLP GCSFSIFLLA  180
LLSCLTTPAS AYEVRNVSGI YHVTNDCSNS SIVYEAADII MHTPGCVPCV REKNTSRCWV  240
ALTPTLAARN ISVPTTTIRR HVDLLVGTAA FCSAMYVGDL CGSVFLVSQL FTFSPRRHET  300
VQDCNCSLYP GHVSGHRMAW DMMMNWSPTA ALVVSQLLRI PQAIVDMVAG AHWGVLAGLA  360
YYSMVGNWAK VLIVMLLFAG ADGTTHVTGG VQAHGAYGLA SLFNVGPHQK IQLVNTNGSW  420
HINRTALNCN DTLQTGFLAA LFYKHRFNAS GCPERMASCR PIDKFAQGWG PITYAEPDRL  480
DQRPYCWHYP PRPCGIVPAL EVCGPVYCFT PSPVVVGTTD RFGVPTYSWG ENETDVLLLN  540
NTRPPQGNWF GCTWMNNTGF TKTCGGPPCN IGGVGNNTLT CPTDCFRKHP EATYTKCGSG  600
PWLTPRCLVD YPYRLWHYPC TVNFTVFKVR MYVGGIEHRL DAACNWTRGE RCDLEDRDRS  660
ELSPLLLSTT EWQILPCSFT TLPALSTGLI HLHRNIVDVQ YLYGIGSAVV SFAIKWEYIL  720
LLFLLLADAR VCACLWMMLL IAQAEA                                     746

SEQ ID NO: 23          moltype = AA  length = 746
FEATURE                Location/Qualifiers
source                 1..746
                       mol_type = protein
                       organism = Hepatitis C virus
SEQUENCE: 23
MSTNPKPQRK TKRNTNRRPQ DVKFPGGGQI VGGVYLLPRR GPRLGVRATR KTSERSQPRG  60
RRQPIPKARQ PEGRAWAQPG YPWPLYGNEG LGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTIPAS AYEVRNVSGV YHVTNDCSNS SIVYEAADMI MHTPGCVPCV REDNSSRCWV  240
ALTPTLAARN SSVPTTTIRR HVDLLVGAAA FCSAMYVGDL CGSVFLISQL FTFSPRRYET  300
VQDCNCSLYP GHVSGHRMAW DMMMNWSPTT ALVVSQLLRI PQAVVDMVAG AHWGVLAGLA  360
YYSMVGNWAK VLIVMLLFAG VDGNTRVSGG EAAKNTMGFA SLFVSGPSQK IQLINTNGSW  420
HINRTALNCD DSLHTGFLAA LFYAHKFNSS GCSGRMASCR PIDEFAQGWG PITHGVPDNL  480
DQRPYCWHYA PRPCGIVPAS QVCGPVYCFT PSPVVVGTTD RFGAPTYSWG ENETDVLLLN  540
NTRPPQGNWF GCTWMNSTGF TKTCGGPPCN IGGVGNNTLT CPTDCFRKHP EATYTKCGSG  600
PWLTPRCMVD YPYRLWHYPC TVNFTIFKVR MYVGGVEHRL DAACNWTRGE RCNVEDRDRS  660
ELSPLLLSTT EWQILPCSFT TLPALSTGLI HLHQNIVDVQ YLYGVGSVVV SVVIRWEYVV  720
LLFLLLADAR VCACLWMMLL IAQAEA                                     746
```

```
SEQ ID NO: 24          moltype = AA  length = 746
FEATURE                Location/Qualifiers
source                 1..746
                       mol_type = protein
                       organism = Hepatitis C virus
SEQUENCE: 24
MSTNPKPQRK TKRNTNRRPQ DVKFPGGGQI VGGVYLLPRR GPRLGVRATR KTSERSQPRG  60
RRQPIPKARQ PEGRAWAQPG YPWPLYGNEG MGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTIPAS AYEVRNVSGM YHVTNDCSNS SIVYEAADMI LHAPGCVPCV RENNSSRCWV  240
ALTPTLAARN ASVPTTAIRR HVDLLVGAAA FCSAMYVGDL CGSVLLVSQI FTFSPRRHET  300
MQDCNCSIYP GHITGHRMAW DMMMNWSPTT ALVVSQLLRI PQAIVDMVAG AHWGVLAGLA  360
YYSMVGNWAK VLIVMLLFAG VDGGTYVTGG EAGRRTSGFA SIFTPGASQN IQLINTNGSW  420
HINRTALNCN DSLHTGFIAA LFYHHKFNAS GCPERMASCR PIGEFAQGWG PISYTEPPSS  480
DQRPYCWHYP PRPCGIVPAS QVCGPVYCFT PSPVVVGTTD RLGAPTYNWG DNDTDVLLLN  540
NTRPPQGNWF GCTWMNGTGF TKTCGGPPCN IGGVGNNTLT CPTDCFRKHP EATYTKCGSG  600
PWLTPRCIVD YPYRLWHYPC TVNFTITKIR MYVGGVEHRL TAACNWTRGE RCDLEDRDRS  660
ELSPLLLSTT EWQIMPCSFT TLPALSTGLI HLHQNIVDIQ YLYGIGSAAV SFAIRWEYVL  720
LLFLLLADAR VCACLWMMLL IAQAEA                                      746

SEQ ID NO: 25          moltype = AA  length = 746
FEATURE                Location/Qualifiers
source                 1..746
                       mol_type = protein
                       organism = Hepatitis C virus
SEQUENCE: 25
MSTNPKPQRK TKRNTNRRPQ DVKFPGGGQI VGGVYLLPRR GPRLGVRATR KTSERSQPRG  60
RRQPIPKARQ PEGRAWAQPG YPWPLYGNEG MGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTIPAS AYEVRNVSGM YHVTNDCSNS SIVYEAADMI LHAPGCVPCV RENNSSRCWV  240
ALTPTLAARN ASVPTTAIRR HVDLLVGAAA FCSAMYVGDL CGSVLLVSQI FTFSPRRHET  300
MQDCNCSIYP GHITGHRMAW DMMMNWSPTT ALVVSQLLRI PQAIVDMVAG AHWGVLAGLA  360
YYSMVGNWAK VLIVMLLFAG VDGGTYVTGG EAGRRTSGFA SIFTPGASQN IQLINTNGSW  420
HINRTALNCN DSLHTGFIAA LFYHHKFNAS GCPERMASCR PIGEFAQGWG PISYTEPPSS  480
DQRPYCWHYP PRPCGIVPAS QVCGPVYCFT PSPVVVGTTD RLGAPTYNWG DNDTDVLLLN  540
NTRPPQGNWF GCTWMNGTGF TKTCGGPPCN IGGVGNNTLT CPTDCFRKHP EATYTKCGSG  600
PWLTPRCIVD YPYRLWHYPC TVNFTITKIR MYVGGVEHRL TAACNWTRGE RCDLEDRDRS  660
ELSPLLLSTT EWQIMPCSFT TLPALSTGLI HLHQNIVDIQ YLYGIGSAAV SFAIRWEYVL  720
LLFLLLADAR VCACLWMMLL IAQAEA                                      746

SEQ ID NO: 26          moltype = AA  length = 746
FEATURE                Location/Qualifiers
source                 1..746
                       mol_type = protein
                       organism = Hepatitis C virus
SEQUENCE: 26
MSTNPKPQRK TKRNTNRRPQ DVKFPGGGQI VGGVYLLPRR GPRLGVRATR KTSERSQPRG  60
RRQPIPKARR PEGRAWAQPG YPWPLYGNEG LGWAGWLLSP RGSRPSWGPT DPRRRSRNLG  120
KVIDTLTCGF ADLMGYIPLV GAPLGGTARA LAHGVRVLED GVNYATGNLP GCSFSIFLLA  180
LLSCLTIPAS AYEVRNVSGV YHVTNDCSNS SIVYETADMI MHTPGCVPCV REDNFTRCWV  240
ALTPTLAARN GSVPTTAIRR HVDLLVGAAA FCSAMYVGDL CGSVFLVSQL FTFSPRWHET  300
VQECNCSIYP GHVTGHRMAW DMMMNWSPTT ALVVSQLLRI PQAVVDMVAG AHWGVLAGLA  360
YYSMVGNWAK VLIVTLLFAG VDGNTHTIGG KQAQATGGFV AWLARGPSQE IQLINTNGSW  420
HINRTALNCN DSLKTGFIAA LFYAHRFNSS GCPERMASCR PIDKFAQGWG PITYAKPDSL  480
DQRPYCWHYA PQPCGIVPAS EVCGPVYCFT PSPVVVGTTD RSGVPTYRWG ENETDVLLLN  540
NTRPPQGNWF GCTWMNATGF TKTCGGPPCK IGGLGNNTLT CPTDCFRKHP EATYTKCGSG  600
PWLTPRCIVD YPYRLWHYPC TVNFTIFKVR MYVGGIEHRL SAACNWTRGE RCDLEDRDRS  660
ELSPLLLSTT EWQILPCSFT TLPALSTGLI HLHQNTVDVQ YLYGVGSVLV SFAIKWEYIL  720
LFFLLLADAR VCACLWMMLL IAQAEA                                      746

SEQ ID NO: 27          moltype = AA  length = 746
FEATURE                Location/Qualifiers
source                 1..746
                       mol_type = protein
                       organism = Hepatitis C virus
SEQUENCE: 27
MSTNPKPQRK TKRNTNRRPQ NVKFPGGGQI VGGVCLLPRR GPRVGVRATR KTSERSQPRG  60
RRQPIPKARR PEGRSWAQPG YPWPLYGNEG CGWAGWLLSP RGSRPSRGPS DPRRRSRNLG  120
KVIDTLTCGF ADLMGYIPLV GAPLGGAARA LAHGVRVLED GVNYATGNLP GCSFSIFLLA  180
LLSCLTVPAS AVEVRNSSGI YHVTNDCPNA SVVYETDSLI IHLPGCVPCV REGNASRCWV  240
SLSPTVAAKD PGVPVNEIRR HVDLIVGAAA FCSAMYVGDL CGSIFLVGQL FTLSPRRHWT  300
TQDCNCSIYP GHVTGHRMAW DMMMNWSPTG ALVVAQLLRI PQAVLDMIAG AHWGVLAGPA  360
YYSMVGNWAK VLVVLLLFAG VDATTQVTGG TAGRNAYRLA SLFSTGPSQN IQLINSNGSW  420
HINRTALNCN DSLHTGWVAA LFYSHKFNSS GRPERMASCR PLTAFDQGWG PITYGGKASN  480
DQRPYCWHYA PRPCGIVPAK EVCGPVYCFT PSPVVVGTTD KYGVPTYTWG ENETDVLLLN  540
NSRPPIGNWF GCTWMNSTGF TKTCGAPACN VGGSETNTLS CPTDCFRRHP DATYAKCGSG  600
PWLNPRCMVD YPYRLWHYPC TVNYTIFKIR MFVGGIEHRL TAACNWTRGE RCDLDDRDRA  660
ELSPLLLSTT QWQVLPCSFT TLPALSTGLI HLHQNIVDVQ YLYGLSSVVT SWAIRWEYVV  720
```

-continued

```
LLFLLLADAR ICACLWMMLL ISQVEA                                        746

SEQ ID NO: 28          moltype = AA  length = 746
FEATURE                Location/Qualifiers
source                 1..746
                       mol_type = protein
                       organism = Hepatitis C virus
SEQUENCE: 28
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTYGF ADLMGYIPLV GAPLGGAARA LAHGVRVLED GVNYATGNLP GCSFSIFLLA  180
LLSCLTVPAS AVGVRNSSGV YHVTNDCPNA SVVYETDSLI IHLPGCVPCV REGNGSRCWV  240
SLSPTVAAKD PGVPVNEIRR HVDLIAGAAA FCSAMYVGHL CGSIFLVGQL FTLSPRRHWT  300
TQDCNCSIYP GHVTGHRMAW DMMMNWSPTT ALVVAQLLRI PQAILDMIAG AHWGVLAGIA  360
YFSMVGNWTK VLVVLLLFAG VDATTIVSGG SAGRSTAGLV GLFSPGARQN IQLINTNGSW  420
HINRTALNCN DTLQTGWVAG LFYTNKFNSS GCPERLASCR PLADFDQGWG PISYTNGSGP  480
DQRPYCWHYP PKPCGIVPAE SVCGPVYCFT PSPVVVGTTD RSGAPTYNWG ENETDVFVLN  540
NTRPRLGNWF GGTWMNSTGF TKVCGAPPCA IGGVGNNTLY CPTDCFRKHP EATYSRCGSG  600
PWITPRCLIH YPYRLWHYPC TINYTIFKIR MFVGGVEHRL DAACNWTRGE RCDLDDRDRA  660
ELSPLLLSTT QWQVLPCSFT TLPALSTGLI HLHQNIVDVQ YLYGLSSAVT SWVIKWEYVV  720
LLFLLLADAR ICACLWMMLL ISQVEA                                        746

SEQ ID NO: 29          moltype = AA  length = 746
FEATURE                Location/Qualifiers
source                 1..746
                       mol_type = protein
                       organism = Hepatitis C virus
SEQUENCE: 29
MSTNPKPQRK TKRNTNRRPQ DVKFPGGGQI VGGVYLLPRR GPRVGVRATR KTSERSQPRG  60
RRQPIPKARR PEGRSWAQPG YPWPLYGNEG CGWAGWLLSP RGSRPSWGPS DPRRRSRNLG  120
KVIDTLTCGF ADLMGYIPLV GAPLGGAARA LAHGVRVLED GVNYATGNLP GCSFSIFLLA  180
LLSCLTVPAS AVGVRNSSGV YHVTNDCPNA SVVYETENLI MHLPGCVPYV REGNASRCWV  240
SLSPTVAARD SRVPVSEVRR RVDSIVGAAA FCSAMYVGDL CGSIFLVGQI FTFSPRHHWT  300
TQDCNCSIYP GHVTGHRMAW DMMMNWSPTG ALVVAQLLRI PQAIVDMIAG AHWGVLAGLA  360
YYSMVGNWAK VVVVLLLFAG VDAETRVTGG AAGHTAFGFA SFLAPGAKQK IQLINTNGSW  420
HINRTALNCN ESLDTGWLAG LLYYHKFNSS GCPERMASCQ PLTAFDQGWG PITHEGNASD  480
DQRPYCWHYA LRPCGIVPAK KVCGPVYCFT PSPVVVGTTD RAGVPTYRWG ANETDVLLLN  540
NSRPPMGNWF GCTWMNSSGF TKTCGAPACN IGGSGNNTLL CPTDCFRKHP DATYSRCGSG  600
PWLTPRCLVD YPYRLWHYPC TVNYTIFKIR MFVGGVEHRL DAACNWTRGE RCDLDDRDRA  660
ELSPLLLSTT QWQVLPCSFT TLPALSTGLI HLHQNIVDVQ YLYGLSSAVT SWVIKWEYVV  720
LLFLLLADAR ICACLWMMLL ISQVEA                                        746

SEQ ID NO: 30          moltype = AA  length = 750
FEATURE                Location/Qualifiers
VARIANT                233
                       note = X can be any amino acid
VARIANT                249..250
                       note = X can be any amino acid
VARIANT                290
                       note = X can be any amino acid
VARIANT                378
                       note = X can be any amino acid
VARIANT                392
                       note = X can be any amino acid
VARIANT                399
                       note = X can be any amino acid
VARIANT                445
                       note = X can be any amino acid
VARIANT                495
                       note = X can be any amino acid
VARIANT                599
                       note = X can be any amino acid
VARIANT                628
                       note = X can be any amino acid
VARIANT                664
                       note = X can be any amino acid
VARIANT                683
                       note = X can be any amino acid
source                 1..750
                       mol_type = protein
                       organism = synthetic construct
SEQUENCE: 30
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCITVPVS AVEVKNISTS YMVTNDCSND SITWQLQAAV LHVPGCVPCE NDXNTSRCWI  240
PVSPNVAVXX PGALTQGLRT HIDMVVMSAT LCSALYVGDL CGGVMLAAQX FIVSPQRHWF  300
VQECNCSIYP GTITGHRMAW DMMMNWSPTA TMILAYAMRV PEVIIDIIFG AHWGVMFGLA  360
YFSMQGAWAK VIVILLLXAG VDARTHTVGG SXGRTTSGXA GLFSSGPKQN IQLINTNGSW  420
```

```
HINRTALNCN DSLQTGFIAS LFYTXNFNSS GCPERLSACR GIEAFRIGWG TLQYEDNVTN  480
PEDMRPYCWH YPPKXCGIVP ARSVCGPVYC FTPSPVVVGT TDRLGVPTYT WGENETDVFL  540
LNSTRPPRGS WFGCTWMNST GFTKTCGAPP CRIRADFNAS TDLLCPTDCF RKHPDATYXK  600
CGSGPWLTPR CLVDYPYRLW HYPCTVNXTI FKIRMYVGGV EHRLTAACNF TRGDRCNLED  660
RDRXQLSPLL HSTTEWAILP CSXSDLPALS TGLLHLHQNI VDVQYMYGLS PALTKYIVRW  720
EWVVLLFLLL ADARVCACLW MLILLGQAEA                                   750

SEQ ID NO: 31          moltype = AA  length = 750
FEATURE                Location/Qualifiers
source                 1..750
                       mol_type = protein
                       organism = Hepatitis C virus
SEQUENCE: 31
MSTNPKPQRK TKRNTNRRPE DVKFPGGGQI VGGVYLLPRR GPRLGVRTTR KTSERSQPRG  60
RRQPIPKDRR STGKAWGKPG RPWPLYGNEG LGWAGWLLSP RGSRPSWGPT DPRHRSRNVG  120
KVIDTLTCGF ADLMGYIPVV GAPLSGAARA VAHGVRVLED GVNYATGNLP GFPFSIFLLA  180
LLSCITVPVS AAQVKNTSSS YMVTNDCSND SITWQLEAAV LHVPGCVPCE RVGNTSRCWV  240
PVSPNMAVRQ PGALTQGLRT HIDMVVMSAT FCSALYVGDL CGGVMLAAQV FIVSPQYHWF  300
VQECNCSIYP GTITGHRMAW DMMMNWSPTA TMILAYVMRV PEVIIDIVSG AHWGVMFGLA  360
YFSMQGAWAK VIVILLLAAG VDAGTTTVGG AVARSTNVIA GVFSHGPQQN IQLINTNGSW  420
HINRTALNCN DSLNTGFLAA LFYTNRFNSS GCPGRLSACR NIEAFRIGWG TLQYEDNVTN  480
PEDMRPYCWH YPPKPCGVVP ARSVCGPVYC FTPSPVVVGT TDRRGVPTYT WGENETDVFL  540
LNSTRPPQGS WFGCTWMNST GFTKTCGAPP CRTRADFNAS TDLLCPTDCF RKHPDATYIK  600
CGSGPWLTPK CLVHYPYRLW HYPCTVNFTI FKIRMYVGGV EHRLTAACNF TRGDRCDLED  660
RDRSQLSPLL HSTTEWAILP CTYSDLPALS TGLLHLHQNI VDVQYMYGLS PAITKYVVRW  720
EWVVLLFLLL ADARVCACLW MLILLGQAEA                                   750

SEQ ID NO: 32          moltype = AA  length = 749
FEATURE                Location/Qualifiers
source                 1..749
                       mol_type = protein
                       organism = Hepatitis C virus
SEQUENCE: 32
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCITTPVS AAQVKNTSDI YMVTNDCSND SITWQLQAAA LHVPGCVPCE RVGNTSRCWI  240
PVSPNVAVRQ PGALTQGLRT HIDMVVMSAT LCSALYVGDL CGGVMLAAQM FIISPQHHWF  300
VQECNCSIYP GTITGHRMAW DMMMNWSPTT TMILAYVMRV PEVIIDIIGG AHWGVMFGLA  360
YFSMQGAWAK VVVILLLAAG VDAHTRTGSS VGYATSGIVG LFTSGPKQNI QLINTNGSWH  420
INRTALNCND SLNTGFIVSL FYARNFNSTG CPERLSACRG IEGFRIGWGT LQYEDNVTNP  480
EDMRPYCWHY PPKQCGIVPA GSVCGPVYCF TPSPVVVGTT DRLGVPTYTW GENETDVFLL  540
NSTRPPVGSW FGCTWMNSTG FTKTCGAPPC RIRADFNAST DLLCPTDCFR KHPEATYIKC  600
GSGPWLTPRC LVDYPYRLWH YPCTVNYSIF KIRMYVGGVE HRLTAACNFT RGDRCNLEDR  660
DRSQLTPLLH STTEWAILPC TYSDLPALST GLLHLHQNIV DVQYMYGLSP ALTKYVVRWE  720
WVVLLFLLLA DARVCACVWM LILLGQAEA                                    749

SEQ ID NO: 33          moltype = AA  length = 750
FEATURE                Location/Qualifiers
VARIANT                458
                       note = X can be any amino acid
source                 1..750
                       mol_type = protein
                       organism = Hepatitis C virus
SEQUENCE: 33
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCVTVPVS AVQVKNTSET YMVTNDCSND SITWQLQAAV LHVPGCVPCE RTGNTSRCWI  240
PVSPNVAVQQ PGALTQGLRT HIDMVVMSAT LCSALYVGDL CGGVVLAAQL FIVSPRRHWF  300
VQECNCSIYP GAITGHRMAW DMMMNWSPTT TMVLAYAMRV PEVIIDIISG AHWGVMFGLA  360
YFSMQGAWAK VAVILLLTAG VEARTHTTGS VAGRTTSGFA GIFTSGPKQN IQLINTNGSW  420
HINRTALNCN DSLNTGFMAA LFYTKNFNSS GCPERLSXCR NIEAFRIGWG TLQYEDDVTN  480
PEDMRPYCWH YPPKQCGIFP AGSVCGPVYC FTPSPVVVGT TNKLGVPTYT WGENETDVFI  540
LNSTRPPRGS WFGCTWMNST GFTKTCGAPP CRIRADFNAS TDLLCPTDCF RKHPEATYIK  600
CGSGPWLTPR CLVDYPYRLW HYPCTVNYSI FKIRMYVGGV EHRLTAACNF SRGDRCNLED  660
RDRSQLTPLL HSTTEWAILP CSYSDLPALS TGLLHLHQNI VDVQYMYGLT PALTKYVVRW  720
EWVVLLFLLL ADARVCACLW MLILLGQAEA                                   750

SEQ ID NO: 34          moltype = AA  length = 750
FEATURE                Location/Qualifiers
source                 1..750
                       mol_type = protein
                       organism = Hepatitis C virus
SEQUENCE: 34
MSTNPKPQRK TKRNTSRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCITVPVS AVQVKNISDS YMVTNDCSND SITWQLQAAV LHVPGCVPCE KMGNISRCWI  240
```

```
PVSPNVAVQR PGALTQGLRA HIDMVVMSAT LCSALYVGDL CGGVMLAAQM FIVSPQHHHF  300
VQECNCSIYP GAITGHRMAW DMMMNWSPTA TMILAYAMRV PEVIIDIISG AHWGVMFGLA  360
YFSMQGAWAK VVVILLLTAG VDAHTRSIAG SVAHATSGLA GLFTSGAKQN IQLINTNGSW  420
HINRTALNCN DSLNTGFIAS LFYTYRFNSS GCPERLSACR GIQAFRIGWG TLRYEDNVTN  480
PEDMRPYCWH YPPKQCGIVS ARSVCGPVYC FTPSPVVVGT TDRLGVPTYT WGENETDVFI  540
LNSTRPPGGS WFGCTWMNST GFTKTCGAPP CRIRADFNAS MDLLCPTDCF RKHPDATYIK  600
CGSGPWLTPR CLVDYPYRLW HYPCTINYTI FKIRMYVGGV EHRLTAACNF TRGDPCNLED  660
RDRSQLSPLL HSTTEWAILP CSYSDLPALS TGLLHLHQNI VDVQYMYGLS PALTKYIVRW  720
EWVVLLFLLL ADARVCACLW MLILLGQAEA                                  750

SEQ ID NO: 35          moltype = AA  length = 751
FEATURE                Location/Qualifiers
source                 1..751
                       mol_type = protein
                       organism = Hepatitis C virus
SEQUENCE: 35
MSTNPKPQRK TQRNTNRRPQ DVKFPGGGQI VGGVYLLPRR GPRLGVRTAR KTSERSQPRG  60
RRQPIPKDRR STGKSWGRPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCITIPAS AVEVKNTSTG YMVTNDCANS SITWQLHAAV LHVPGCVPCE RVDNNTSRCW  240
IPVSPNIAVQ RPGALTQGLR SHIDIVVMSA TLCSALYVGD LCGGVMLAAQ MFVVSPEHHW  300
FVQECNCSIY PGTITGHRMA WDMMMNWSPT ATMILAYAMR VPEVIIDIIG GAHWGVMFGL  360
AYFSMQGAWA KVVVILLLAA GVDAYTHTVG GAAASTANSI AGLLSRGPRQ NLQLINSNGS  420
WHINRTALNC HDSLQTGFIT ALFYARHFNS SGCPERLAAC RNIEAFRVGW GALQYEDNVT  480
NPEDMRPYCW HYPPKQCGIV PARSVCGPVY CFTPSPVVVG TTDKLGVPTY TWGENETDVF  540
LLNSTRPPQG PWFGCTWMNS TGFTKTCGAP PCRTRADFNA STDLLCPTDC FRKHPDATYN  600
KCGSGPWLTP RCLIDYPYRL WHYPCTVNYT TFKIRMYVGG VEHRLMAACN FTRGDSCDLS  660
QRDRGQLSPL LHSTTEWAIL PCSFSDLPAL STGLLHLHQN IVDVQYMYGL SPALTKYIVR  720
WEWVVLLFLL LADARVCACI WMLILLGQAE A                                751

SEQ ID NO: 36          moltype = AA  length = 750
FEATURE                Location/Qualifiers
source                 1..750
                       mol_type = protein
                       organism = Hepatitis C virus
SEQUENCE: 36
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPN DPRHRSRNVG  120
KVIDTLTCGF ADLMGYIPVV GAPLGGVARA LAHGVRVLED GVNFATGNLP GCSFSIFLLA  180
LLSCITTPVS AAEVKNISTG YMVTNDCTND SITWQLQAAV LHVPGCVPCE KVGNTSRCWI  240
PVSPNVAVQQ PGALTQGLRT HIDMVVMSAT LCSALYVGDL CGGVMLAAQM FIVSPQHHWF  300
VQDCNCSIYP GTITGHRMAW DMMMNWSPTA TMILAYAMRV PEVIIDIIGG AHWGVMFGLA  360
YFSMQGAWAK VVVILLLAAG VDAQTHTVGG STAHNARTLT GMFSLGARQK IQLINTNGSW  420
HINRTALNCN DSLHTGFLAS LFYTHSFNSS GCPERMSACR SIEAFRVGWG ALQYEDNVTN  480
PEDMRPYCWH YPPRQCGVVS ASSVCGPVYC FTPSPVVVGT TDRLGAPTYT WGENETDVFL  540
LNSTRPPQGS WFGCTWMNST GYTKTCGAPP CRIRADFNAS MDLLCPTDCF RKHPDTTYIK  600
CGSGPWLTPR CLIDYPYRLW HYPCTVNYTI FKIRMYVGGV EHRLTAACNF TRGDRCNLED  660
RDRSQLSPLL HSTTEWAILP CTYSDLPALS TGLLHLHQNI VDVQFMYGLS PALTKYIVRW  720
EWVVLLFLLL ADARVCACLW MLILLGQAEA                                  750

SEQ ID NO: 37          moltype = AA  length = 750
FEATURE                Location/Qualifiers
source                 1..750
                       mol_type = protein
                       organism = Hepatitis C virus
SEQUENCE: 37
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPN DPRHRSRNVG  120
KVIDTLTCGF ADLMGYIPVV GAPLGGVARA LAHGVRVLED GVNFATGNLP GCSFSIFLLA  180
LLSCITTPVS AAEVKNISTG YMVTNDCTND SITWQLQAAV LHVPGCVPCE KVGNASQCWI  240
PVSPNVAVQR PGALTQGLRT HIDMVVMSAT LCSALYVGDL CGGVMLAAQM FIVSPQHHWF  300
VQDCNCSIYP GTITGHRMAW DMMMNWSPTA TMILAYAMRV PEVIIDIISG AHWGVMFGLA  360
YFSMQGAWAK VVVILLLAAG VDARTHTVGG SAAQTTGRLT SLFDMGPRQK IQLVNTNGSW  420
HINRTALNCN DSLHTGFIAS LFYTHSFNSS GCPERMSACR SIEAFRVGWG ALQYEDNVTN  480
PEDMRPYCWH YPPRQCGVVS AKTVCGPVYC FTPSPVVVGT TDRLGAPTYT WGENETDVFL  540
LNSTRPPLGS WFGCTWMNSS GYTKTCGAPP CRTRADFNAS TDLLCPTDCF RKHPDTTYLK  600
CGSGPWLTPR CLIDYPYRLW HYPCTVNYTI FKIRMYVGGV EHRLTAACNF TRGDRCNLED  660
RDRSQLSPLL HSTTEWAILP CSYSDLPALS TGLLHLHQNI VDVQFMYGLS PALTKYIVRW  720
EWVILLFLLL ADARVCACLW MLILLGQAEA                                  750

SEQ ID NO: 38          moltype = AA  length = 750
FEATURE                Location/Qualifiers
source                 1..750
                       mol_type = protein
                       organism = Hepatitis C virus
SEQUENCE: 38
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG CGWAGWLLSP RGSRPTWGPT DPRHRSRNLG  120
RVIDTITCGF ADLMGYIPVV GAPVGGVARA LAHGVRVLED GINYATGNLP GCSFSIFLLA  180
```

-continued

```
LLSCVTVPVS AVEVRNISSS YYATNDCSNN SITWQLTDAV LHLPGCVPCE NDNGTLHCWI  240
QVTPNVAVKH RGALTRSLRT HVDMIVMAAT ACSALYVGDV CGAVMILSQA FMVSPQRHNF  300
TQECNCSIYQ GHITGHRMAW DMMLSWSPTL TMILAYAARV PELVLEIIFG GHWGVVFGLA  360
YFSMQGAWAK VIAILLLVAG VDATTYSSGQ EAGRTVAGFA GLFTTGAKQN LYLINTNGSW  420
HINRTALNCN DSLQTGFLAS LFYTHKFNSS GCPERLSSCR GLDDFRIGWG TLEYETNVTN  480
DGDMRPYCWH YPPRPCGIVP ARTVCGPVYC FTPSPVVVGT TDKQGVPTYT WGENETDVFL  540
LNSTRPPRGA WFGCTWMNGT GFTKTCGAPP CRIRKDYNST IDLLCPTDCF RKHPDATYLK  600
CGAGPWLTPR CLVDYPYRLW HYPCTVNFTI FKARMYVGGV EHRFSAACNF TRGDRCRLED  660
RDRGQQSPLL HSTTEWAVLP CSFSDLPALS TGLLHLHQNI VDVQYLYGLS PALTRYIVKW  720
EWVILLFLLL ADARICACLW MLIILGQAEA                                  750

SEQ ID NO: 39          moltype = AA  length = 750
FEATURE                Location/Qualifiers
source                 1..750
                       mol_type = protein
                       organism = Hepatitis C virus
SEQUENCE: 39
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG CGWAGWLLSP RGSRPHWGPT DPRHRSRNLG  120
KVIDTITCGF ADLMGYIPVI GAPVGGVARA LAHGVRVLED GVNYATGNLP GCSFSIFLLA  180
LLSCVTVPVS AVEVRNISSS YYATNDCSNN SITWQLENAV LHLPGCVPCE NDNGTLRCWT  240
QVTPNVAVKH RGALTQNLRT HVDVIVVAAT VCSALYVGDV CGAVMIASQA LIVSPARHNF  300
TQECNCSIYQ GRITGHHMAW DMMLNWSPTI TMILAYAARI PELVLEVIFG GHWGVMFGLA  360
YFSMQGAWAK VIVILLLVAG VDARHHTTGL QAGKTLARVT SLFSIGAKQN IQLINTNGSW  420
HINRTALNCN DSLQTGFIAS LFYVNNINSS GCPERMSSCR ELDDFRIGWG TLEYETNVTN  480
DEDMRPYCWH YPPKPCGIVP ARTVCGPVYC FTPSPIVVGT TDKQGVPTYS WGENETDVFL  540
LNSTRPPRGS WFGCTWMNGT GFTKTCGAPP CRIRRDYNST LDLLCPTDCF RKHPDTTYLK  600
CGSGPWLTPK CLVEYPYRLW HYPCTVNFTI FKVRMYVGAV EHRFSAACNF TRGDRCRLED  660
RDRGQQSPLL HSTTEWAVLP CSFSDLPALS TGLLHLHQNI VDVQYLYGLS PAITRYIVKW  720
EWVVLLFLLL ADARVCACLW MLIILGQAEA                                  750

SEQ ID NO: 40          moltype = AA  length = 750
FEATURE                Location/Qualifiers
source                 1..750
                       mol_type = protein
                       organism = Hepatitis C virus
SEQUENCE: 40
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG CGWAGWLLSP RGSRPTWGPT DPRHRSRNLG  120
RVIDTITCGF ADLMGYIPVV GAPVGGVARA LAHGVRVLED GINYATGNLP GCSFSIFLLA  180
LLSCCTVPVS AVEVRNISTS YYATNDCSNT SITWQLTNAV LHLPGCVPCE NDNGTLRCWI  240
QVTPNVAVKH RGALTHNLRT HVDVIVMAAT VCSALYVGDI CGAVMIVSQA FIISPERHNF  300
TQECNCSMYQ GHITGHRMAW DMMLNWSPTL TMILAYAARV PELVLEVIFG GHWGVVFGLA  360
YFSMQGAWAK VIAILLLVAG VDANTYSSGV TVGHTTSTFA NIFSVGPSQK INLINTNGSW  420
HINRTALNCN DSLQTGFLAS LFYVRNFNSS GCRERLSSCR RLDDFRIGWG TLEYETNVTN  480
DEDMRPYCWH YPPKPCGIVS ARTVCGPVYC FTPSPVVVGT TDRQGVPTYS WGENETDVFL  540
LNSTRPPRGA WFGCTWMNGT GFTKTCGAPP CRIRRDYNST LDLLCPTDCF RKHPDTTYLK  600
CGAGPWLTPK CLVDYPYRLW HYPCTVNFTI FKVRMYVGGV EHRLSAACNF TRGDRCGLED  660
RDRGQQSPLL HSTTEWAVLP CSFSDLPALS TGLLHLHQNI VDVQYLYGLS PAITRYIVKW  720
EWVVLLFLLL ADARVCACLW MLIILGQAEA                                  750

SEQ ID NO: 41          moltype = AA  length = 750
FEATURE                Location/Qualifiers
source                 1..750
                       mol_type = protein
                       organism = Hepatitis C virus
SEQUENCE: 41
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG CGWAGWLLSP RGSRPTWGPS DPRHRSRNLG  120
RVIDTITCGF ADLMGYIPVV GAPVGGVARA LAHGVRVLED GINYATRNLP GCSFSIFLLA  180
LLSCVTVPVS SVEIRNISTS YYATNDCSNN SITWQLTNAV LHLPGCVPCE NDNGTLRCWI  240
QVTPNVAVKH RGALTHNLRA HVDVIVMAAT VCSALYVGDV CGAVMIVSQA LIVSPERHNF  300
TQECNCSIYQ GHITGQRMAW DMMLNWSPTL TMILAYAARV PELVLEIVFG GHWGVVFGLA  360
YFSMQGAWAK VIAILLLVAG VDATTYSTGA TVGRTVGSFA GLFKLGAQQN VQLINTNGSW  420
HINRTALNCN DSLHTGFMAA LFYANKFNSS GCPERLSSCR GLDDFRIGWG TLEYETNVTN  480
VEDMRPYCWH YPPKPCGIVP AQSVCGPVYC FTPSPVVVGT TDRQGVPTYN WGDNETDVFL  540
LNSTRPPRGA WFGCTWMNGT GFTKTCGAPP CRIRKDFNST LDLLCPTDCF RKHPDATYVK  600
CGAGPWLTPR CLIDYPYRLW HYPCTVNFTI FKVRMYVGGV EHRFSAACNF TRGDRCRLED  660
RDRGQQSPLL HSTTEWAVLP CSFSDLPALS TGLLHLHQNI VDVQYLYGLS PAVTKYIVKW  720
EWVVLLFLLL ADARICACLW MLIILGQAEA                                  750

SEQ ID NO: 42          moltype = AA  length = 750
FEATURE                Location/Qualifiers
VARIANT                203
                       note = X can be any amino acid
VARIANT                295
                       note = X can be any amino acid
VARIANT                343
                       note = X can be any amino acid
```

```
VARIANT                401
                       note = X can be any amino acid
VARIANT                426
                       note = X can be any amino acid
VARIANT                626
                       note = X can be any amino acid
source                 1..750
                       mol_type = protein
                       organism = Hepatitis C virus
SEQUENCE: 42
MSTDPKPQRK TKRNTNRRPQ DVKFPGGGQI VGGVYLLPRR GPRLGVRAAR KTSERSQPRG  60
RRQPIPKDRR SPGKSWGKPG YPWPLYGNEG CGWAGWLLSP RGSRPTWGPT DPRHRSRNLG  120
KVIDTITCGF ADLMGYIPVV GAPVGGVARA LAHGVRVLED GINYATGNLP GCSFSIFLLA  180
LLSCLTVPAS AVEVRNISSG YYXTNDCSNS SITWQLTNAV LHLPGCVPCE NDNGTLRCWI  240
QVTPNVAVKY RGALTHNLRT HVDMIVMAAT VCSALYVGDV CGAVMIVSQA FIMSXERHNF  300
TQECNCSIYQ GHITGHRMAW DMMLGWSPTL TMILAYAARV PEXVLEVVFG GHWGVVFGLA  360
YFSMQGAWAK VIAILLLVAG VDAGTYSSGA TIGQGTRGLV XLFSAGPSQK ISLINTNGSW  420
HINRTXLNCN DSLQTGFIAS LFYAKSFNSS GCPERLSSCR GLDDFRIGWG TLEYENNVTN  480
DEDMRPYCWH YPPKPCGIVP ARTVCGPVYC FTPSPVVVGT TDKQGVPTYS WGENETDVFL  540
LNSTRPPQGA WFGCTWMNGT GFTKTCGAPP CRIRRDHTST LDLLCPTDCF RKHPDTTYLK  600
CGAGPWLTPK CLVDYPYRLW HYPCTXNFTI FKVRMYVGGV EHRFSAACNF TRGDRCRLED  660
RDRGQQSPLL HSTTEWAVLP CSFSDLPALS TGLLHLHQNI VDVQYLYGLS PAITKYIVKW  720
EWVILLFLLL ADARVCACLW MLIILGQAEA                                  750

SEQ ID NO: 43          moltype = AA  length = 752
FEATURE                Location/Qualifiers
VARIANT                431
                       note = X can be any amino acid
VARIANT                466
                       note = X can be any amino acid
source                 1..752
                       mol_type = protein
                       organism = Hepatitis C virus
SEQUENCE: 43
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLEWRNTSGL YVLTNDCSNS SIVYEADDVI LHTPGCVPCV QDGNTSTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWSPAV GMVVAHVLRL PQTLFDIIAG AHWGILAGLA  360
YYSMQGNWAK VAIIMVMFSG VDATTYTTGG SAARGARGLT SLFSVGAKQK LQLVNTNGSW  420
HINSTALNCN XSINTGFIAG LFYYHKFNST GCPQRLSSCK PITFFXQGWG PLTDANITGP  480
SDDKPYCWHY APRPCDVVPA SSVCGPVYCF TPSPVVVGTT DAKGVPTYTW GENETDVFLL  540
ESLRPPSGRW FGCTWMNSTG FVKTCGAPPC NIYGGGGNPH NESDLFCPTD CFRKHPEATY  600
SRCGAGPWLT PRCMVDYPYR LWHYPCTVNF TLFKVRMFVG GFEHRFTAAC NWTRGERCDI  660
EDRDRSEQHP LLHSTTELAI LPCSFTPMPA LSTGLIHLHQ NIVDVQYLYG VGSGMVGWAL  720
KWEFVILVFL LLADARVCVA LWLMLMISQA EA                               752

SEQ ID NO: 44          moltype = AA  length = 752
FEATURE                Location/Qualifiers
source                 1..752
                       mol_type = protein
                       organism = Hepatitis C virus
SEQUENCE: 44
MSTLPKPQRK TKRNTIRRPQ DVKFPGGGQI VGGVYVLPRR GPRLGVRATR KTSERSQPRE  60
RRQPIPKARR SDGRSWAQPG YPWPLYGNEG CGWAGWLLSP RGSRPSWGPN DPRRRSRNLG  120
KVIDTLTCGF ADLMGYIPIV GAPVGGVARA LAHGVRALED GINFATGNLP GCSFSIFLLA  180
LLSCLIHPAA SLEWRNTSGL YILTNDCPNS SIVYEADDVI LHTPGCIPCV QDGNTSTCWT  240
SVSPTVAVRY VGATTASIRS HVDLLVGAAT LCSALYVGDM CGAVFLVGQA FTFRPRRHQT  300
VQTCNCSLYP GHLTGHRMAW DMMMNWSPAV GMVVAHVLRM PQTVFDIIAG AHWGILAGLA  360
YYSMQGNWAK VAIIMVMFSG VDAETHTTGG TAARNAFTLT GLFTQGARQK LELINTNGSW  420
HINRTALNCN ESLNTGFIAG LFYLHKFNST GCPERLSSCK PITFFRQGWG SLTDANITGP  480
SDDKPYCWHY APRPCEVVPA LNVCGPVYCF TPSPVVVGTT DRQGVPTYTW GENETDVFLL  540
RSLRPPSGQW FGCTWMNSTG FVKTCGAPPC DIYGGGGNRC NESDLFCPTD CFRKHPEATY  600
SRCGAGPWLT PRCLVDYPYR LWHYPCTVNF TLFKVRMFVG GFEHRFTAAC NWTRGERCNI  660
EDRDRSEQHP LLHSTTELAI LPCSFTPMPA LSTGLIHLHQ NIVDVQYLYG VGSGVVGWAL  720
RWEFVVLVFL LLADARVCVA LWLMLMISQA EA                               752

SEQ ID NO: 45          moltype = AA  length = 752
FEATURE                Location/Qualifiers
source                 1..752
                       mol_type = protein
                       organism = Hepatitis C virus
SEQUENCE: 45
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLVHPAA SLEWRNTSGL YVLTNDCSNS SIVYEADDVI LHTPGCVPCV QDDNTSTCWT  240
PVTPTVAVRY VGATTASIRS HVDLLVGAAT LCSALYVGDM CGAVFLVGQA FTFRPRRHQT  300
```

-continued

```
VQTCNCSLYP GHVSGHRMAW DMMMNWSPAV GMVVAHILRL PQTLFDILAG AHWGILAGLA  360
YYSMQGNWAK VAIVMIMFSG VDAETYVTGG SVAHSARGLT SLFSMGAKQK LQLVNTNGSW  420
HINSTALNCN ESINTGFIAG LFYYHKFNST GCPQRLSSCK PIISFRQGWG PLTDANITGP  480
SDDRPYCWHY APRPCSVVPA SSVCGPVYCF TPSPVVVGTT DIKGKPTYNW GENETDVFLL  540
ESLRPPSGRW FGCAWMNSTG FLKTCGAPPC NIYGGEGDPE NETDLFCPTD CFRKHPEATY  600
SRCGAGPWLT PRCMVDYPYR LWHYPCTVNF TLFKVRMFVG GFEHRFTAAC NWTRGERCNI  660
EDRDRSEQHP LLHSTTELAI LPCSFTPMPA LSTGLIHLHQ NIVDVQYLYG VGSDMVGWAL  720
KWEFVILVFL LLADARVCVA LWLMLMVSQA EA                                752

SEQ ID NO: 46           moltype = AA  length = 752
FEATURE                 Location/Qualifiers
source                  1..752
                        mol_type = protein
                        organism = Hepatitis C virus
SEQUENCE: 46
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLEWRNTSGL YVLTNDCSNS SIVYEADDVI LHTPGCVPCV QDGNTSTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWSPAV GMVVAHVLRL PQTLFDIMAG AHWGILAGLA  360
YYSMQGNWAK VAIIMVMFSG VDAHTYTTGG TASRHTQAFA GLFDIGPQQK LQLVNTNGSW  420
HINSTALNCN ESINTGFIAG LFYYHKFNST GCPQRLSSCK PITFFRQGWG PLTDANITGP  480
SDDRPYCWHY APRPCDIVPA SSVCGPVYCF TPSPVVVGTT DARGVPTYTW GENEKDVFLL  540
KSQRPPSGRW FGCSWMNSTG FLKTCGAPPC NIYGGEGNPH NESDLFCPTD CFRKHPETTY  600
SRCGAGPWLT PRCMVDYPYR LWHYPCTVDF RLFKVRMFVG GFEHRFTAAC NWTRGERCDI  660
EDRDRSEQHP LLHSTTELAI LPCSFTPMPA LSTGLIHLHQ NIVDVQYLYG VGSGMVGWAL  720
KWEFVILVFL LLADARVCVA LWLMLMISQT EA                                752

SEQ ID NO: 47           moltype = AA  length = 752
FEATURE                 Location/Qualifiers
source                  1..752
                        mol_type = protein
                        organism = Hepatitis C virus
SEQUENCE: 47
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGQN DPRRRSRNLG  120
KVIDTLTCGF ADLMGYIPLV GAPVGGVARA LAHGVRALED GINFATGNLP GCSFSIFLLA  180
LFSCLIHPAA SLEWRNTSGL YVLTNDCSNS SIVYEADDVI LHTPGCVPCV QDGNTSTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWSPAV GMVVSHVLRL PQTLFDIIAG AHWGILAGLA  360
YYSMQGNWAK VAVIMVMFSG VDAETYITGG SAAHGVSTLT SLFSSGPQQK LQLVKTNGSW  420
HINSTALNCN ESINTGFIAG LFYYHKFNST GCPQRLSSCK PITFFRQGWG SLTDANVTGA  480
SADKPYCWHY APRPCDVVPA LNVCGPVYCF TPSPVVVGTT DRKGVPTYNW GENESDVFLL  540
ESLRPPSGRW FGCAWMNSTG FLKTCGAPPC NIYGGGGNPN NESHLFCPTD CFRKHPDATY  600
SRCGAGPWLT PRCMVDYPYR LWHYPCTVNF TLFKVRMFVG GFEHRFTAAC NWTRGERCNI  660
EDRDRSEQHP LLHSTTELAI LPCSFTPMPA LSTGLIHLHQ NIVDVQYLYG VGSGMVGWAL  720
KWEFVILIFL LLADARVCVA LWLMLMISQA EA                                752

SEQ ID NO: 48           moltype = AA  length = 752
FEATURE                 Location/Qualifiers
source                  1..752
                        mol_type = protein
                        organism = Hepatitis C virus
SEQUENCE: 48
MSTLPKPQRK TKRNTIRRPQ DVKFPGGGQI VGGVYVLPRR GPRLGVCATR KTSERSQPRR  60
RRQPIPKARQ SGGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLEWRNTSGL YVLTNDCSNS SIVYEADDVI LHTPGCVPCV QNDNISTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWFPAL GMAVAHVLRV PQTLFDIIAG AHWGILAGLA  360
YYSMQGNWAK VAIIMVMFSG VDAVTYTTGG SAAHATRGLT SLFSVGAQQK LQLVNTNGSW  420
HINSTALNCN ESINTGFIAG LFYYHRFNST GCPQRLSSCK PITFFKQGWG PLTDANISGP  480
SDDKPYCWHY APRPCKVVPA SGVCGPVYCF TPSPVVVGTT DAKGVPTYTW GANDTDVFLL  540
ESLRPPGGRW FGCTWMNSTG FVKTCGASPC DIYGGGGNSG NESDLFCPTD CFRKHPEATY  600
SRCGAGPWLT PRCMVDYPYR LWHYPCTVNF TLFKVRMFVG GFEHRFTAAC NWTRGERCDI  660
EDRDRSEQHP LLHSTTELAI LPCSFTPMPA LSTGLIHLHQ NIVDVQYLYG VGSGMVGWAL  720
KWEFVILIFL LLADRRVCVA LWLMLMITQA EA                                752

SEQ ID NO: 49           moltype = AA  length = 752
FEATURE                 Location/Qualifiers
source                  1..752
                        mol_type = protein
                        organism = Hepatitis C virus
SEQUENCE: 49
MSTLPKPQRK TKRNTVCRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLEWRNVSGL YILTNDCPNS SIVYEADDVI LHTPGCIPCV QDGNTSTCWT  240
```

-continued

```
ALTPTVAVRY VGATTASIRS HVDLLVGAAT MCSALYVGDM CGAVFLVGQA FTFRPRRHQT  300
VQTCNCSLYP GHLTGHRMAW DMMMNWSPAV GMVVAHVLRL PQTLFDIIAG AHWGILAGLA  360
YYSMQGNWAK VIIIMVMFSG VDATTHVTGG TAGLTAFRLT GLFTVGPQQK LQLVNTNGSW  420
HINRTALNCN DSLNTGFIAG LFRFHKFNST GCPEMLSSCK PITSFKQGWG PLTDANITIP  480
SDDRPYCWHY PPRSCEVVPA LSVCGPVYCF TPSPVVVGTT DAKGVPTYTW GENETDVFLL  540
KSLRPPGGRW FGCTWMNSTG FVQTCGAPPC NIYGGGGDLK NESDLFCPTD CFRKHPEATY  600
SRCGAGPWLT PRCMVDYPYR LWHYPCTVNF TLFKVRMFVG GFEHRFTAAC NWTRGERCDI  660
EDRDRSELHP LLHSTTELAI LPCSFTPMPA LSTGLIHLHQ NIVDVQYLYG VGSGMVGWAV  720
KWEFVILVFL LLADARVCVA LWLMLMISQA EA                                752

SEQ ID NO: 50           moltype = AA  length = 752
FEATURE                 Location/Qualifiers
source                  1..752
                        mol_type = protein
                        organism = Hepatitis C virus
SEQUENCE: 50
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLQWRNTSGL YVLTNDCSNS SIVYEADDVI LHTPGCVPCV QDGNTSTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWSPAA GMVVAHILRL PQTLFDIIAG AHWGILAGLA  360
YYSMQGNWAK VAIIMVMFSG VDATTYTSGG SVAQQARGLA DLFSVGAKQN LQLVNTNGSW  420
HINSTALNCD DSINTGFIAG LFYYHKFNST GCPQRLSDCK PITFFKQGWG PLTDANITGP  480
SDDKPYCWHY APRRCGVVPA SSVCGPVYCF TPSPVVVGTT DAKGVPTYTW GANETDVFLL  540
ESLRPPSGRW FGCAWMNSTG FLKTCGAPPC NIYGGGGNPH NESDLFCPTD CFRKHPEATY  600
SRCGAGPWLT PRCMVDYPYR LWHYPCTVNF TLFKMRTFVG GFEHRFTAAC NWTRGERCDI  660
EDRDRSEQHP LLHSTTELAI LPCSFTPMPA LSTGLIHLHQ NIVDVQYLYG VGSGMVGWAL  720
KWEFVILVFL LLADARVCVA LWLMLMISQA EA                                752

SEQ ID NO: 51           moltype = AA  length = 752
FEATURE                 Location/Qualifiers
source                  1..752
                        mol_type = protein
                        organism = Hepatitis C virus
SEQUENCE: 51
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLQWRNTSGL YVLTNDCSNS SIVYEADDVI LHTPGCVPCV QDGNTSTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWSPAA GMVVAHILRL PQTLFDIIAG AHWGILAGLA  360
YYSMQGNWAK VAIIMVMFSG VDATTYTSGG SVAQQARGLA DLFSVGAKQN LQLVNTNGSW  420
HINSTALNCD DSINTGFIAG LFYYHKFNST GCPQRLSDCK PITFFKQGWG PLTDANITGP  480
SDDKPYCWHY APRRCGVVPA SSVCGPVYCF TPSPVVVGTT DAKGVPTYTW GANETDVFLL  540
ESLRPPSGRW FGCAWMNSTG FLKTCGAPPC NIYGGGGNPH NESDLFCPTD CFRKHPEATY  600
SRCGAGPWLT PRCMVDYPYR LWHYPCTVNF TLFKMRTFVG GFEHRFTAAC NWTRGERCDI  660
EDRDRSEQHP LLHSTTELAI LPCSFTPMPA LSTGLIHLHQ NIVDVQYLYG VGSGMVGWAL  720
KWEFVILVFL LLADARVCVA LWLMLMISQA EA                                752

SEQ ID NO: 52           moltype = AA  length = 752
FEATURE                 Location/Qualifiers
source                  1..752
                        mol_type = protein
                        organism = Hepatitis C virus
SEQUENCE: 52
MSTLPKPQRK TKRNTIRRPQ DVKFPGGGQI VGGVYVLPRR GPRLGVCATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLVHPAA SLEWRNTSGL YVLTNDCPNS SIVYEADDVI LHTPGCIPCV QDGNKSTCWT  240
SVTPTVAVKY VGATTASIRS HVDLLVGAAT MCSALYVGDM CGAVFLVGQA FTFRPRRHQT  300
VQTCNCSLYP GHLSGHRMAW DMMMNWSPAV GMVVAHVLRL PQTLFDIIAG AHWGILAGLA  360
YYSMQGNWAK VAIIMVMFSG VDATTYTTGG NAARGASGIV SLFTPGAKQN LQLVNTNGSW  420
HINRTALNCN DSINTGFIAG LIYYHKFNST GCPQRLSSCK PITFFRQGWG SLTDANITGP  480
SDDKPYCWHY PPRPCDTIRA SSVCGPVYCF TPSPVVVGTT DAKGAPTYNW GANETDMFLL  540
QSLRPPSGRW FGCTWMNSTG FTKTCGAPPC NIYGGGGNLN NESDLFCPTD CFRKHPEATY  600
SRCGAGPWLT PRCLVDYPYR LWHYPCTVNF TLFRMRTFVG GFEHRFTAAC NWTRGERCNI  660
EDRDRSEQHP LLHSTTELAI LPCSFTPMPA LSTGLIHLHQ NIVDVQYLYG IGSGVVGWAL  720
KWEFVILVFL LLADARVCVA LWLMLMISQA EA                                752

SEQ ID NO: 53           moltype = AA  length = 752
FEATURE                 Location/Qualifiers
source                  1..752
                        mol_type = protein
                        organism = Hepatitis C virus
SEQUENCE: 53
MSTLPKPQRK TKRNTIRRPQ DVKFPGGGVI YVGVYVLPRR GPRLGVRATR KTSERSQPRG  60
RRKPIPKARR SEGRSWAPG YPWPLYGNEG CGWAGWLLSP RGSRPNWAPN DPRRRSRNLG  120
KVIDTLTCGF ADLMGYIPLV GAPLGGAARA LAHGVRALED GINFATGNLP GCSFSIFLLA  180
```

-continued

```
LFSCLIHPAA SLEWRNTSGL YVLTNDCSNS SIVYEADDVI LHTPGCIPCV QDGNTSTCWT  240
PVTPTVAVRY VGATTASIRS HVDLLVGAGT MCSALYVGDM CGPVFLVGQA FTFRPRRHRT  300
VQTCNCSLYP GHLSGQRMAW DMMMNWSPAV GMVVAHILRL PQTLFDVVAG AHWGIIAGLA  360
YYSMQGNWAK VAIIMVMFSG VDASTHVTAG QAARNAYGIT SLFSVGAKQN LQLINTNGSW  420
HINRTALNCN ESINTGFIAG LFYYHKFNST GCPQRLSSCK PITFFKQGWG PLTDANITGP  480
SDDKPYCWHY APRPCGIVPA LNVCGPVYCF TPSPVVVGTT DAKGAPTYTW GANKTDVFLL  540
ESLRPPSGRW FGCTWMNSTG FVKTCGAPPC NIYGDGRDAQ NESDLFCPTD CFRKHPEATY  600
SRCGAGPWLT PRCLVDYPYR LWHYPCTVNF TLFKVRMFVG GFEHRFTAAC NWTRGERCDI  660
EDRDRSEQHP LLHSTTELAI LPCSFTPMPA LSTGLIHLHQ NIVDVQYLYG IGSGMVGWAL  720
KWEFVILIFL LLADARVCVA LWLILTISQA EA                                752

SEQ ID NO: 54          moltype = AA  length = 754
FEATURE                Location/Qualifiers
source                 1..754
                       mol_type = protein
                       organism = Hepatitis C virus
SEQUENCE: 54
MSTLPKPKRQ TKRNTLRRPK NVKFPAGGQI VGEVYVLPRR GPQLGVREVR KTSERSQPRG  60
RRQPTPKARP REGRSWAQPG YPWPLYGNEG CGWAGWLLPP RGSRPSWGQN DPRRRSRNLG  120
KVIDTLTCGF ADLMGYIPLI GAPVGGVARA LAHGVRALED GVNYATGNLP GCSFSIFLLA  180
LFSCLTCPAS SLEYRNASGL YLLTNDCSNR SIVYEADDVI LHLPGCVPCV ETDNNNTSCW  240
TPISPTVAVK HPGVTTASIR NHVNMLVAPP TLCSALYVED AFGAVSLVGQ AFTFRPRQHK  300
TVQTCNCSIY PGHVSGHRMA WDMMMNWSPA IGLVISHLMR LPQTFFDLVV GAHWGVMAGL  360
AYFSMQGNWA KVVIVLIMFS GVDATTHTTG GSAAQATAGF TSFFTRGPSQ NLQLVNSNGS  420
WHINSTALNC NDSLNTGFIA GLFYYHKFNS SGCPERMSSC KPITYFNQGW GPLTDANING  480
PSEDRPYCWH YPPRPCNITK PLNVCGPVYC FTPSPVVVGT TDIKGLPTYR FGVNESDVFL  540
LTSLRPPQGR WFGCVWMNST GFVKTCGAPP CNIYGGMKDI EANQTHLKCP TDCFRKHHDA  600
TFTRCGSGPW LTPRCLVDYP YRLWHYPCTV NFSIFKVRMF VGGHEHRFSA ACNWTRGERC  660
DLEDRDRSEQ QPLLHSTTDS LILPCSFTPM RRLSTGLIHL HQNIVDVQYL YGVGSAVVGW  720
ALKWEFVVLV FLLLADARVC VALWMMLLIS QAEA                              754

SEQ ID NO: 55          moltype = AA  length = 750
FEATURE                Location/Qualifiers
source                 1..750
                       mol_type = protein
                       organism = Hepatitis C virus
SEQUENCE: 55
MSTNPKPQRL TKRNTVRRPQ NVKFPGGGQI VGGVYLLPRR GPRLGVRGTR KSSERSQPRG  60
RRQRIPKAAS SQGKAWGKPG YPWPLYGNEG CGWAGWLLSP RGSRPTWGPT DPRHRSRNLG  120
KVIDTMTCGF ADLMGYIPVL GAPLGGVARA LAHGVRVLED GVNYATGNLP GCSFSIFLLA  180
LLSCLTVPAS AYEVRNSSGV YHLTNDCPNA SIVYETDNAI LHEPGCVPCV REGNTSRCWE  240
PVAPTLAVRY RGALTDDLRT HIDLVVASAT LCSALYVGDI CGAIFIASQA VLWKPGGGRI  300
VQDCNCSIYP GHVTGHRMAW DMMQNWAPAL SMVAAYAVRV PGVIITTVAG GHWGVLFGLA  360
YFGMAGNWAK VILIMLLMSG VDAETMAVGA RAAHTTGALV SLLNPGPSQR LQLINTNGSW  420
HINRTALNCN DSLQTGFIAA LFYTHRFNSS GCPERMASCK PLSDFDQGWG PLWYNSTERP  480
SDQRPYCWHY APSPCGIVPA KDVCGPVYCF TPSPVVVGTT DRRGVPTYTW GENESDVFLL  540
NSTRPPQGSW FGCSWMNTTG FTKTCGGPPC KIRPQGAQSN TSLTCPTDCF RKHPRATYSA  600
CGSGPWLTPR CMVHYPYRLW HYPCTVNFTI HKVRLYIGGV EHRLDAACNW TRGERCDLED  660
RDRVDMSPLL HSTTELAILP CSFVPLPALS TGLIHLHQNI VDAQYLYGLS PAIISWAIRW  720
EWVVLVFLLL ADARICACLW MMMLMAQAEA                                   750

SEQ ID NO: 56          moltype = AA  length = 227
FEATURE                Location/Qualifiers
source                 1..227
                       mol_type = protein
                       organism = Homo sapiens
SEQUENCE: 56
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 57          moltype = AA  length = 325
FEATURE                Location/Qualifiers
source                 1..325
                       mol_type = protein
                       organism = Homo sapiens
SEQUENCE: 57
STKGPSVFPL APCSRSTSES TAALGCLVKD YFPEPVTVSW NSGALTSGVH TFPAVLQSSG  60
LYSLSSVVTV PSSNFGTQTY TCNVDHKPSN TKVDKTVERK CCVECPPCPA PPVAGPSVFL  120
FPPKPKDTLM ISRTPEVTCV VVDVSHEDPE VQFNWYVDGV EVHNAKTKPR EEQFNSTFRV  180
VSVLTVVHQD WLNGKEYKCK VSNKGLPAPI EKTISKTKGQ PREPQVYTLP PSREEMTKNQ  240
VSLTCLVKGF YPSDIAVEWE SNGQPENNYK TTPPMLDSDG SFFLYSKLTV DKSRWQQGNV  300
FSCSVMHEAL HNHYTQKSLS LSPGK                                        325

SEQ ID NO: 58          moltype = AA  length = 246
FEATURE                Location/Qualifiers
source                 1..246
                       mol_type = protein
```

```
                          organism = Homo sapiens
SEQUENCE: 58
HKPSNTKVDK RVELKTPLGD TTHTCPPCPA PELLGGPSVF LFPPKPKDTL MISRTPEVTC  60
VVVDVSHEDP EVKFNWYVDG VEVHNAKTKP REEQYNSTYR VVSVLTVLHQ DWLNGKEYKC  120
KVSNKALPAP IEKTISKAKG QPREPQVYTL PPSRDELTKN QVSLTCLVKG FYPSDIAVEW  180
ESNGQPENNY KTTPPVLDSD GSFFLYSKLT VDKSRWQQGN VFSCSVMHEA LHNHYTQKSL  240
SLSPGK                                                             246

SEQ ID NO: 59             moltype = AA  length = 383
FEATURE                   Location/Qualifiers
source                    1..383
                          mol_type = protein
                          organism = Homo sapiens
SEQUENCE: 59
PTKAPDVFPI ISGCRHPKDN SPVVLACLIT GYHPTSVTVT WYMGTQSQPQ RTFPEIQRRD  60
SYYMTSSQLS TPLQQWRQGE YKCVVQHTAS KSKKEIFRWP ESPKAQASSV PTAQPQAEGS  120
LAKATTAPAT TRNTGRGGEE KKKEKEKEEQ EERETKTPEC PSHTQPLGVY LLTPAVQDLW  180
LRDKATFTCF VVGSDLKDAH LTWEVAGKVP TGGVEEGLLE RHSNGSQSQH SRLTLPRSLW  240
NAGTSVTCTL NHPSLPPQRL MALREPAAQA PVKLSLNLLA SSDPPEAASW LLCEVSGFSP  300
PNILLMWLED QREVNTSGFA PARPPPQPRS TTFWAWSVLR VPAPPSPQPA TYTCVVSHED  360
SRTLLNASRS LEVSYVTDHG PMK                                          383

SEQ ID NO: 60             moltype = AA  length = 276
FEATURE                   Location/Qualifiers
source                    1..276
                          mol_type = protein
                          organism = Homo sapiens
SEQUENCE: 60
VTSTLTIKZS DWLGESMFTC RVDHRGLTFQ QNASSMCVPD QDTAIRVFAI PPSFASIFLT  60
KSTKLTCLVT DLTTYBSVTI SWTREENGAV KTHTNISESH PNATFSAVGE ASICEDBDWS  120
GERFTCTVTH TDLPSPLKQT ISRPKGVALH RPBVYLLPPA RZZLNLRESA TITCLVTGFS  180
PADVFVEWMQ RGEPLSPQKY VTSAPMPEPQ APGRYFAHSI LTVSEEEWNT GGTYTCVVAH  240
EALPNRVTER TVDKSTGKPT LYNVSLVMSD TAGTCY                             276

SEQ ID NO: 61             moltype = AA  length = 353
FEATURE                   Location/Qualifiers
source                    1..353
                          mol_type = protein
                          organism = Homo sapiens
SEQUENCE: 61
ASPTSPKVFP LSLCSTQPDG NVVIACLVQG FFPQEPLSVT WSESGQGVTA RNFPPSQDAS  60
GDLYTTSSQL TLPATQCLAG KSVTCHVKHY TNPSQDVTVP CPVPSTPPTP SPSTPPTPSP  120
SCCHPRLSLH RPALEDLLLG SEANLTCTLT GLRDASGVTF TWTPSSGKSA VQGPPERDLC  180
GCYSVSSVLP GCAEPWNHGK TFTCTAAYPE SKTPLTATLS KSGNTFRPEV HLLPPPSEEL  240
ALNELVTLTC LARGFSPKDV LVRWLQGSQE LPREKYLTWA SRQEPSQGTT TFAVTSILRV  300
AAEDWKKGDT FSCMVGHEAL PLAFTQKTID RLAGKPTHVN VSVVMAEVDG TCY          353

SEQ ID NO: 62             moltype = AA  length = 222
FEATURE                   Location/Qualifiers
source                    1..222
                          mol_type = protein
                          organism = Homo sapiens
SEQUENCE: 62
ADPCDSNPRG VSAYLSRPSP FDLFIRKSPT ITCLVVDLAP SKGTVNLTWS RASGKPVNHS  60
TRKEEKQRNG TLTVTSTLPV GTRDWIEGET YQCRVTHPHL PRALMRSTTK TSGPRAAPEV  120
YAFATPEWPG SRDKRTLACL IQNFMPEDIS VQWLHNEVQL PDARHSTTQP RKTKGSGFFV  180
FSRLEVTRAE WEQKDEFICR AVHEAASPSQ TVQRAVSVNP GK                      222

SEQ ID NO: 63             moltype = AA  length = 327
FEATURE                   Location/Qualifiers
source                    1..327
                          mol_type = protein
                          organism = Homo sapiens
SEQUENCE: 63
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 64             moltype = AA  length = 15
FEATURE                   Location/Qualifiers
REGION                    1..15
                          note = Synthetic Sequence
source                    1..15
                          mol_type = protein
                          organism = synthetic construct
SEQUENCE: 64
```

-continued

```
VLVLNPSVAA TLGFG                                                  15

SEQ ID NO: 65          moltype = AA  length = 15
FEATURE                Location/Qualifiers
REGION                 1..15
                       note = Synthetic Sequence
source                 1..15
                       mol_type = protein
                       organism = synthetic construct
SEQUENCE: 65
TYGKFLADGG CSGGA                                                  15

SEQ ID NO: 66          moltype = AA  length = 15
FEATURE                Location/Qualifiers
REGION                 1..15
                       note = Synthetic Sequence
source                 1..15
                       mol_type = protein
                       organism = synthetic construct
SEQUENCE: 66
GGRHLIFCHS KKKCD                                                  15

SEQ ID NO: 67          moltype = AA  length = 11
FEATURE                Location/Qualifiers
REGION                 1..11
                       note = Synthetic Sequence
source                 1..11
                       mol_type = protein
                       organism = synthetic construct
SEQUENCE: 67
VAYYRGLDVS V                                                      11

SEQ ID NO: 68          moltype = AA  length = 18
FEATURE                Location/Qualifiers
REGION                 1..18
                       note = Synthetic Sequence
source                 1..18
                       mol_type = protein
                       organism = synthetic construct
SEQUENCE: 68
ATDALMTGFT GDFDSVID                                               18

SEQ ID NO: 69          moltype = AA  length = 15
FEATURE                Location/Qualifiers
REGION                 1..15
                       note = Synthetic Sequence
source                 1..15
                       mol_type = protein
                       organism = synthetic construct
SEQUENCE: 69
TGLTHIDAHF LSQTK                                                  15

SEQ ID NO: 70          moltype = AA  length = 13
FEATURE                Location/Qualifiers
REGION                 1..13
                       note = Synthetic Sequence
source                 1..13
                       mol_type = protein
                       organism = synthetic construct
SEQUENCE: 70
QYLAGLSTLP GNP                                                    13

SEQ ID NO: 71          moltype = AA  length = 8
FEATURE                Location/Qualifiers
REGION                 1..8
                       note = Synthetic Sequence
source                 1..8
                       mol_type = protein
                       organism = synthetic construct
SEQUENCE: 71
NLLPAILS                                                          8

SEQ ID NO: 72          moltype = AA  length = 27
FEATURE                Location/Qualifiers
REGION                 1..27
                       note = Synthetic Sequence
source                 1..27
                       mol_type = protein
                       organism = synthetic construct
```

-continued

```
SEQUENCE: 72
RHVGPGEGAV QWMNRLIAFA SRGNHVS                                   27

SEQ ID NO: 73          moltype = AA  length = 15
FEATURE                Location/Qualifiers
REGION                 1..15
                       note = Synthetic Sequence
source                 1..15
                       mol_type = protein
                       organism = synthetic construct
SEQUENCE: 73
SSASQLSAPS LKATC                                                15

SEQ ID NO: 74          moltype = AA  length = 5
FEATURE                Location/Qualifiers
REGION                 1..5
                       note = Synthetic Sequence
source                 1..5
                       mol_type = protein
                       organism = synthetic construct
SEQUENCE: 74
SNVSV                                                           5

SEQ ID NO: 75          moltype = AA  length = 9
FEATURE                Location/Qualifiers
REGION                 1..9
                       note = Synthetic Sequence
source                 1..9
                       mol_type = protein
                       organism = synthetic construct
SEQUENCE: 75
TYSTYGKFL                                                       9

SEQ ID NO: 76          moltype = AA  length = 9
FEATURE                Location/Qualifiers
REGION                 1..9
                       note = Synthetic Sequence
source                 1..9
                       mol_type = protein
                       organism = synthetic construct
SEQUENCE: 76
LIFCHSKKK                                                       9

SEQ ID NO: 77          moltype = AA  length = 16
FEATURE                Location/Qualifiers
REGION                 1..16
                       note = Synthetic Sequence
source                 1..16
                       mol_type = protein
                       organism = synthetic construct
SEQUENCE: 77
ATDALMTGFT GDFDSV                                               16

SEQ ID NO: 78          moltype = AA  length = 10
FEATURE                Location/Qualifiers
REGION                 1..10
                       note = Synthetic Sequence
source                 1..10
                       mol_type = protein
                       organism = synthetic construct
SEQUENCE: 78
VLAALAAYCL                                                      10

SEQ ID NO: 79          moltype = AA  length = 9
FEATURE                Location/Qualifiers
REGION                 1..9
                       note = Synthetic Sequence
source                 1..9
                       mol_type = protein
                       organism = synthetic construct
SEQUENCE: 79
ILAGYGAGV                                                       9

SEQ ID NO: 80          moltype = AA  length = 8
FEATURE                Location/Qualifiers
REGION                 1..8
                       note = Synthetic Sequence
source                 1..8
                       mol_type = protein
```

```
                         organism = synthetic construct
SEQUENCE: 80
IPFYGKAI                                                        8

SEQ ID NO: 81            moltype = AA  length = 9
FEATURE                  Location/Qualifiers
REGION                   1..9
                         note = Synthetic Sequence
source                   1..9
                         mol_type = protein
                         organism = synthetic construct
SEQUENCE: 81
RAQAPPPSW                                                       9

SEQ ID NO: 82            moltype = AA  length = 36
FEATURE                  Location/Qualifiers
REGION                   1..36
                         note = Synthetic Sequence
source                   1..36
                         mol_type = protein
                         organism = synthetic construct
SEQUENCE: 82
EGAVQWMNRL IAFASRGNHV SPTHYVPESD AAARVT                         36

SEQ ID NO: 83            moltype = AA  length = 9
FEATURE                  Location/Qualifiers
REGION                   1..9
                         note = Synthetic Sequence
source                   1..9
                         mol_type = protein
                         organism = synthetic construct
SEQUENCE: 83
RPDYNPPLL                                                       9

SEQ ID NO: 84            moltype = AA  length = 9
FEATURE                  Location/Qualifiers
REGION                   1..9
                         note = Synthetic Sequence
source                   1..9
                         mol_type = protein
                         organism = synthetic construct
SEQUENCE: 84
TIMAKNEVF                                                       9

SEQ ID NO: 85            moltype = AA  length = 29
FEATURE                  Location/Qualifiers
REGION                   1..29
                         note = Synthetic Sequence
source                   1..29
                         mol_type = protein
                         organism = synthetic construct
SEQUENCE: 85
AIPLEVIKGG RHLIFCHSKK KCDELAAKL                                 29

SEQ ID NO: 86            moltype = AA  length = 50
FEATURE                  Location/Qualifiers
REGION                   1..50
                         note = Synthetic Sequence
source                   1..50
                         mol_type = protein
                         organism = synthetic construct
SEQUENCE: 86
LGALTGTYVY NHLTPLRDWA HNGLRDLAVA VEPVVFSQME TKLITWGADT           50

SEQ ID NO: 87            moltype = AA  length = 52
FEATURE                  Location/Qualifiers
REGION                   1..52
                         note = Synthetic Sequence
source                   1..52
                         mol_type = protein
                         organism = synthetic construct
SEQUENCE: 87
AIPLEVIKGG RHLIFCHSKK KCDELAAKLV ALGINAVAYY RGLDVSVIPT SG        52

SEQ ID NO: 88            moltype = AA  length = 70
FEATURE                  Location/Qualifiers
REGION                   1..70
                         note = Synthetic Sequence
source                   1..70
```

```
                         mol_type = protein
                         organism = synthetic construct
SEQUENCE: 88
KGGRHLIFCH SKKKCDELAA KLVALGINAV AYYRGLDVSV IPTSGDVVVV ATDALMTGFT  60
GDFDSVIDCN                                                         70

SEQ ID NO: 89            moltype = AA  length = 100
FEATURE                  Location/Qualifiers
REGION                   1..100
                         note = Synthetic Sequence
source                   1..100
                         mol_type = protein
                         organism = synthetic construct
SEQUENCE: 89
VALSTTGEIP FYGKAIPLEV IKGGRHLIFC HSKKKCDELA AKLVALGINA VAYYRGLDVS  60
VIPTSGDVVV VATDALMTGF TGDFDSVIDC NTCVTQTVDF                        100

SEQ ID NO: 90            moltype = AA  length = 171
FEATURE                  Location/Qualifiers
REGION                   1..171
                         note = Synthetic Sequence
source                   1..171
                         mol_type = protein
                         organism = synthetic construct
SEQUENCE: 90
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP G            171

SEQ ID NO: 91            moltype = AA  length = 228
FEATURE                  Location/Qualifiers
REGION                   1..228
                         note = Synthetic Sequence
source                   1..228
                         mol_type = protein
                         organism = synthetic construct
SEQUENCE: 91
LHAPTGSGKS TKVPAAYAAQ GYKVLVLNPS VAATLGFGAY MSKAHGIDPN IRTGVRTITT  60
GSPITYSTYG KFLADGGCSG GAYDIIICDE CHSTDATSIL GIGTVLDQAE TAGARLVVLA  120
TATPPGSVTV PHPNIEEVAL STTGEIPFYG KAIPLEVIKG GRHLIFCHSK KKCDELAAKL  180
VALGINAVAY YRGLDVSVIP TSGDVVVVAT DALMTGFTGD FDSVIDCN                228

SEQ ID NO: 92            moltype = AA  length = 553
FEATURE                  Location/Qualifiers
REGION                   1..553
                         note = Synthetic Sequence
source                   1..553
                         mol_type = protein
                         organism = synthetic construct
SEQUENCE: 92
QASLLKVPYF VRVQGLLRIC ALARKMAGGH YVQMAIIKLG ALTGTYVYNA LTPLRDWAHN  60
GLRDLAVAVE PVVFSQMETK LITWGADTAA CGDIINGLPV SARRGREILL GPADGMVSKG  120
WRLLAPITAY AQQTRGLLGC IITSLTGRDK NQVEGEVQIV STAAQTFLAT CINGVCWTVY  180
HGAGTRTIAS PKGPVIQMYT NVDQDLVGWP APQGARSLTP CTCGSSDLYL VTRHADVIPV  240
RRRGDSRGSL LSPRPISYLK GSSAGGPLLCP AGHAVGIFRA AVCTRGVAKA VDFIPVENLE  300
TTMRSPVFTD NSSPPAVPQS FQVAHLHAPT GSGKSTKVPA AYAAQGYKVL VLNPSVAATL  360
GFGAYMSKAH GIDPNIRTGV RTITTGSPIT YSTYGKFLAD GGCSGGAYDI IICDECHSTD  420
ATSILGIGTV LDQAETAGAR LVVLATATPP GSVTVPHPNI EEVALSTTGE IPFYGKAIPL  480
EVIKGGRHLI FCHSKKKCDE LAAKLVALGI NAVAYYRGLD VSVIPTSGDV VVVATDALMT  540
GFTGDFDSVI DCN                                                      553

SEQ ID NO: 93            moltype = AA  length = 778
FEATURE                  Location/Qualifiers
REGION                   1..778
                         note = Synthetic Sequence
source                   1..778
                         mol_type = protein
                         organism = synthetic construct
SEQUENCE: 93
LHAPTGSGKS TKVPAAYAAQ GYKVLVLNPS VAATLGFGAY MSKAHGIDPN IRTGVRTITT  60
GSPITYSTYG KFLADGGCSG GAYDIIICDE CHSTDATSIL GIGTVLDQAE TAGARLVVLA  120
TATPPGSVTV PHPNIEEVAL STTGEIPFYG KAIPLEVIKG GRHLIFCHSK KKCDELAAKL  180
VALGINAVAY YRGLDVSVIP TSGDVVVVAT DALMTGFTGD FDSVIDCNTC VTQTVDFSLD  240
PTFTIETTTL PQDAVSRTQR RGRTGRGKPG IYRFVAPGER PSGMFDSSVL CECYDAGCAW  300
YELTPAETTV RLRAYMNTPG LPVCQDHLEF WEGVFTGLTH IDAHFLSQTK QSGENLPYLV  360
AYQATVCARA QAPPPSWDQM WKCLIRLKPT LHGPTPLLYR LGAVQNEVTL THPITKYIMT  420
CMSADLEVVT STWVLVGGVL AALAAYCLST GCVVIVGRIV LSGKPAIIPD REVLYREFDE  480
MEECSQHLPY IEQGMMLAEQ FKQKALGLLQ TASRQAEVIA PAVQTNWQKL EAFWAKHMWN  540
FISGIQYLAG LSTLPGNPAI ASLMAFTAAV TSPLTTSQTL LFNILGGWVA AQLAAPGAAT  600
```

-continued

```
AFVGAGLAGA AIGSVGLGKV LVDILAGYGA GVAGALVAFK IMSGEVPSTE DLVNLLPAIL  660
SPGALVVGVV CAAILRRHVG PGEGAVQWMN RLIAFASRGN HVSPTHYVPE SDAAARVTAI  720
LSSLTVTQLL RRLHQWISSE CTTPCSGSWL RDIWDWICEV LSDFKTWLKA KLMPQLPG    778

SEQ ID NO: 94          moltype = AA  length = 1985
FEATURE                Location/Qualifiers
REGION                 1..1985
                       note = Synthetic Sequence
source                 1..1985
                       mol_type = protein
                       organism = synthetic construct
SEQUENCE: 94
APITAYAQQT RGLLGCIITS LTGRDKNQVE GEVQIVSTAA QTFLATCING VCWTVYHGAG  60
TRTIASPKGP VIQMYTNVDQ DLVGWPAPQG ARSLTPCTCG SSDLYLVTRH ADVIPVRRRG  120
DSRGSLLSPR PISYLKGSAG GPLLCPAGHA VGIFRAAVCT RGVAKAVDFI PVENLETTMR  180
SPVFTDNSSP PAVPQSFQVA HLHAPTGSGK STKVPAAYAA QGYKVLVLNP SVAATLGFGA  240
YMSKAHGIDP NIRTGVRTIT TGSPITYSTY GKFLADGGCS GGAYDIIICD ECHSTDATSI  300
LGIGTVLDQA ETAGARLVVL ATATPPGSVT VPHPNIEEVA LSTTGEIPFY GKAIPLEVIK  360
GGRHLIFCHS KKKCDELAAK LVALGINAVA YYRGLDVSVI PTSGDVVVVA TDALMTGFTG  420
DFDSVIDCNT CVTQTVDFSL DPTFTIETTT LPQDAVSRTQ RRGRTGRGKP GIYRFVAPGE  480
RPSGMFDSSV LCECYDAGCA WYELTPAETT VRLRAYMNTP GLPVCQDHLE FWEGVFTGLT  540
HIDAHFLSQT KQSGENLPYL VAYQATVCAR AQAPPPSWDQ MWKCLIRLKP TLHGPTPLLY  600
RLGAVQNEVT LTHPITKYIM TCMSADLEVV TSTWVLVGGV LAALAAYCLS TGCVVIVGRI  660
VLSGKPAIIP DREVLYREFD EMEECSQHLP YIEQGMMLAE QFKQKALGLL QTASRQAEVI  720
APAVQTNWQK LEAFWAKHMW NFISGIQYLA GLSTLPGNPA IASLMAFTAA VTSPLTTSQT  780
LLFNILGGWV AAQLAAPGAA TAFVGAGLAG AAIGSVGLGK VLVDILAGYG AGVAGALVAF  840
KIMSGEVPST EDLVNLLPAI LSPGALVVGV VCAAILRRHV GPGEGAVQWM NRLIAFASRG  900
NHVSPTHYVP ESDAAARVTA ILSSLTVTQL LRRLHQWISS ECTTPCSGSW LRDIWDWICE  960
VLSDFKTWLK AKLMPQLPGI PFVSCQRGYR GVWRGDGIMH TRCHCGAEIT GHVKNGTMRI  1020
VGPRTCRNMW SGTFPINAYT TGPCTPLPAP NYTFALWRVS AEEYVEIRQV GDFHYVTGMT  1080
TDNLKCPCQV PSPEFFTELD GVRLHRFAPP CKPLLREEVS FRVGLHEYPV GSQLPCEPEP  1140
DVAVLTSMLT DPSHITAEAA GRRLARGSPP SVASSSASQL SAPSLKATCT ANHDSPDAEL  1200
IEANLLWRQE MGGNITRVES ENKVVILDSF DPLVAEEDER EISVPAEILR KSRRFAPALP  1260
IWARPDYNPP LLETWKKPDY EPPVVHGCPL PPPQSPPVPP PRKKRTVVLT ESTVSTALAE  1320
LATKSFGSSS TSGITGDNTT TSSEPAPSGC PPDSDAESYS SMPPLEGEPG DPDLSDGSWS  1380
TVSSEADTED VVCCSMSYSW TGALVTPCAA EEQKLPINAL SNSLLRHHNL VYSTTSRSAC  1440
QRQKKVTFDR LQVLDSHYQD VLKEVKAAAS KVKANLLSVE EACSLTPPHS AKSKFGYGAK  1500
DVRCHARKAV NHINSVWKDL LEDSVTPIDT TIMAKNEVFC VQPEKGGRKP ARLIVFPDLG  1560
VRVCEKMALY DVVSKLPLAV MGSSYGFQYS PGQRVEFLVQ AWKSKKTPMG FSYDTRCFDS  1620
TVTESDIRTE EAIYQCCDLD PQARVAIKSL TERLYVGGPL TNSRGENCGY RRCRASGVLT  1680
TSCGNTLTCY IKARAACRAA GLQDCTMLVC GNNLVVICES AGVQEDAASL RAFTEAMTRY  1740
SAPPGDPPQP EYDLELITSC SSNVSVAHDG AGKRVYYLTR DPTTPLARAA WETARHTPVN  1800
SWLGNIIMFA PTLWARMILM THFFSVLIAR DQLEQALDCE IYGACYSIEP LDLPPIIQRL  1860
HGLSAFSLHS YSPGEINRVA ACLRKLGVPP LRAWRHRARS VRARLLSRGG RAAICGKYLF  1920
NWAVRTKLKL TPIAAAGQLD LSGWFTAGYS GGDIYHSVSH ARPRWFWFCL LLLAAGVGIY  1980
LLPNR                                                              1985

SEQ ID NO: 95          moltype = AA  length = 3012
FEATURE                Location/Qualifiers
VARIANT                3012
                       note = X can be any amino acid
source                 1..3012
                       mol_type = protein
                       organism = synthetic construct
SEQUENCE: 95
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSTGL YHVTNDCPNS SIVYEAADAI LHTPGCVPCV REGNASRCWV  240
AVTPTVATRD GKLPTTQLRR HIDLLVGSAT LCSALYVGDL CGSVFLVGQL FTFSPRRHWT  300
TQDCNCSIYP GHITGHRMAW DMMMNWSPTT ALVVAQLLRI PQAILDMIAG AHWGVLAGIA  360
YFSMVGNWAK VLVVLLLFAG VDAETHVTGG SAARTTSGLA SLFTPGAKQN IQLINTNGSW  420
HINRTALNCN DSLNTGWLAG LFYYHKFNSS GCPERLASCR PLTDFDQGWG PISYANGSGP  480
DQRPYCWHYP PKPCGIVPAK SVCGPVYCFT PSPVVVGTTD RSGAPTYNWG ENDTDVFVLN  540
NTRPPLGNWF GCTWMNSTGF TKVCGAPPCV IGGVGNNTLH CPTDCFRKHP EATYSRCGSG  600
PWITPRCLVD YPYRLWHYPC TINYTIFKVR MYVGGVEHRL EAACNWTRGE RCDLEDRDRS  660
ELSPLLLSTT QWQVLPCSFT TLPALSTGLI HLHQNIVDVQ YLYGVGSSIA SWAIKWEYVV  720
LLFLLLADAR VCSCLWMMLL ISQAEAALEN LVVLNAASLA GTHGLVSFLV FFCFAWYLKG  780
RWVPGAAYAL YGMWPLLLLL LALPQRAYAL DTEVAASCGG VVLVGLMALT LSPYYKRYIS  840
WCLWWLQYFL TRVEAQLHVW VPPLNVRGGR DAVILLMCVV HPTLVFDITK LLLAVFGPLW  900
ILQASLLKVP YFVRVQGLLR ICALARKMAG GHYVQMAIIK LGALTGTYVY NHLTPLRDWA  960
HNGLRDLAVA VEPVVFSQME TKLITWGADT AACGDIINGL PVSARRGREI LLGPADGMVS  1020
KGWRLLAPIT AYAQQTRGLL GCIITSLTGR DKNQVEGEVQ IVSTAAQTFL ATCINGVCWT  1080
VYHGAGTRTI ASPKGPVIQM YTNVDQDLVG WPAPQGARSL TPCTCGSSDL YLVTRHADVI  1140
PVRRRGDSRG SLLSPRPISY LKGSSGGPLL CPAGHAVGIF RAAVCTRGVA KAVDFIPVEN  1200
LETTMRSPVF TDNSSPPAVP QSFQVAHLHA PTGSGKSTKV PAAYAAQGYK VLVLNPSVAA  1260
TLGFGAYMSK AHGIDPNIRT GVRTITTGSP ITYSTYGKFL ADGGCSGGAY DIIICDECHS  1320
TDATSILGIG TVLDQAETAG ARLVVLATAT PPGSVTVPHP NIEEVALSTT GEIPFYGKAI  1380
PLEVIKGGRH LIFCHSKKKC DELAAKLVAL GINAVAYYRG LDVSVIPTSG DVVVVATDAL  1440
```

-continued

```
MTGFTGDFDS VIDCNTCVTQ TVDFSLDPTF TIETTTLPQD AVSRTQRRGR TGRGKPGIYR  1500
FVAPGERPSG MFDSSVLCEC YDAGCAWYEL TPAETTVRLR AYMNTPGLPV CQDHLEFWEG  1560
VFTGLTHIDA HFLSQTKQSG ENLPYLVAYQ ATVCARAQAP PPSWDQMWKC LIRLKPTLHG  1620
PTPLLYRLGA VQNEVTLTHP ITKYIMTCMS ADLEVVTSTW VLVGGVLAAL AAYCLSTGCV  1680
VIVGRIVLSG KPAIIPDREV LYREFDEMEE CSQHLPYIEQ GMMLAEQFKQ KALGLLQTAS  1740
RQAEVIAPAV QTNWQKLEAF WAKHMWNFIS GIQYLAGLST LPGNPAIASL MAFTAAVTSP  1800
LTTSQTLLFN ILGGWVAAQL AAPGAATAFV GAGLAGAAIG SVGLGKVLVD ILAGYGAGVA  1860
GALVAFKIMS GEVPSTEDLV NLLPAILSPG ALVVGVVCAA ILRRHVGPGE GAVQWMNRLI  1920
AFASRGNHVS PTHYVPESDA AARVTAILSS LTVTQLLRRL HQWISSECTT PCSGSWLRDI  1980
WDWICEVLSD FKTWLKAKLM PQLPGIPFVS CQRGYRGVWR GDGIMHTRCH CGAEITGHVK  2040
NGTMRIVGPR TCRNMWSGTF PINAYTTGPC TPLPAPNYTF ALWRVSAEEY VEIRQVGDFH  2100
YVTGMTTDNL KCPCQVPSPE FFTELDGVRL HRFAPPCKPL LREEVSFRVG LHEYPVGSQL  2160
PCEPEPDVAV LTSMLTDPSH ITAEAAGRRL ARGSPPSVAS SSASQLSAPS LKATCTANHD  2220
SPDAELIEAN LLWRQEMGGN ITRVESENKV VILDSFDPLV AEEDEREISV PAEILRKSRR  2280
FAPALPIWAR PDYNPPLLET WKKPDYEPPV VHGCPLPPPQ SPPVPPPRKK RTVVLTESTV  2340
STALAELATK SFGSSSTSGI TGDNTTTSSE PAPSGCPPDS DAESYSSMPP LEGEPGDPDL  2400
SDGSWSTVSS EADTEDVVCC SMSYSWTGAL VTPCAAEEQK LPINALSNSL LRHHNLVYST  2460
TSRSACQRQK KVTFDRLQVL DSHYQDVLKE VKAAASKVKA NLLSVEEACS LTPPHSAKSK  2520
FGYGAKDVRC HARKAVNHIN SVWKDLLEDS VTPIDTTIMA KNEVFCVQPE KGGRKPARLI  2580
VFPDLGVRVC EKMALYDVVS KLPLAVMGSS YGFQYSPGQR VEFLVQAWKS KKTPMGFSYD  2640
TRCFDSTVTE SDIRTEEAIY QCCDLDPQAR VAIKSLTERL YVGGPLTNSR GENCGYRRCR  2700
ASGVLTTSCG NTLTCYIKAR AACRAAGLQD CTMLVCGDDL VVICESAGVQ EDAASLRAFT  2760
EAMTRYSAPP GDPPQPEYDL ELITSCSSNV SVAHDGAGKR VYYLTRDPTT PLARAAWETA  2820
RHTPVNSWLG NIIMFAPTLW ARMILMTHFF SVLIARDQLE QALDCEIYGA CYSIEPLDLP  2880
PIIQRLHGLS AFSLHSYSPG EINRVAACLR KLGVPPLRAW RHRARSVRAR LLSRGGRAAI  2940
CGKYLFNWAV RTKLKLTPIA AAGQLDLSGW FTAGYSGGDI YHSVSHARPR WFWFCLLLLA  3000
AGVGIYLLPN RX                                                      3012

SEQ ID NO: 96           moltype = AA  length = 3014
FEATURE                 Location/Qualifiers
VARIANT                 197
                        note = X can be any amino acid
VARIANT                 241
                        note = X can be any amino acid
VARIANT                 251
                        note = X can be any amino acid
VARIANT                 290
                        note = X can be any amino acid
VARIANT                 331
                        note = X can be any amino acid
VARIANT                 334
                        note = X can be any amino acid
VARIANT                 343..344
                        note = X can be any amino acid
VARIANT                 372
                        note = X can be any amino acid
VARIANT                 390
                        note = X can be any amino acid
VARIANT                 407
                        note = X can be any amino acid
VARIANT                 433
                        note = X can be any amino acid
VARIANT                 476
                        note = X can be any amino acid
VARIANT                 523
                        note = X can be any amino acid
VARIANT                 597
                        note = X can be any amino acid
VARIANT                 715
                        note = X can be any amino acid
VARIANT                 767
                        note = X can be any amino acid
VARIANT                 786
                        note = X can be any amino acid
VARIANT                 792
                        note = X can be any amino acid
VARIANT                 821
                        note = X can be any amino acid
VARIANT                 826
                        note = X can be any amino acid
VARIANT                 843
                        note = X can be any amino acid
VARIANT                 857
                        note = X can be any amino acid
VARIANT                 873..874
                        note = X can be any amino acid
VARIANT                 884
                        note = X can be any amino acid
VARIANT                 922
```

-continued

```
                      note = X can be any amino acid
VARIANT               928
                      note = X can be any amino acid
VARIANT               955
                      note = X can be any amino acid
VARIANT               1020
                      note = X can be any amino acid
VARIANT               1099
                      note = X can be any amino acid
VARIANT               1143
                      note = X can be any amino acid
VARIANT               1161
                      note = X can be any amino acid
VARIANT               1210
                      note = X can be any amino acid
VARIANT               1223
                      note = X can be any amino acid
VARIANT               1371
                      note = X can be any amino acid
VARIANT               1385
                      note = X can be any amino acid
VARIANT               1409
                      note = X can be any amino acid
VARIANT               1599
                      note = X can be any amino acid
VARIANT               1607
                      note = X can be any amino acid
VARIANT               1695
                      note = X can be any amino acid
VARIANT               1753
                      note = X can be any amino acid
VARIANT               1874
                      note = X can be any amino acid
VARIANT               2071..2072
                      note = X can be any amino acid
VARIANT               2074
                      note = X can be any amino acid
VARIANT               2087
                      note = X can be any amino acid
VARIANT               2106
                      note = X can be any amino acid
VARIANT               2134
                      note = X can be any amino acid
VARIANT               2279
                      note = X can be any amino acid
VARIANT               2321
                      note = X can be any amino acid
VARIANT               2335
                      note = X can be any amino acid
VARIANT               2358
                      note = X can be any amino acid
VARIANT               2361..2362
                      note = X can be any amino acid
VARIANT               2364
                      note = X can be any amino acid
VARIANT               2367
                      note = X can be any amino acid
VARIANT               2373..2374
                      note = X can be any amino acid
VARIANT               2376
                      note = X can be any amino acid
VARIANT               2383
                      note = X can be any amino acid
VARIANT               2487
                      note = X can be any amino acid
VARIANT               2496
                      note = X can be any amino acid
VARIANT               2542
                      note = X can be any amino acid
VARIANT               2546
                      note = X can be any amino acid
VARIANT               2572
                      note = X can be any amino acid
VARIANT               2601
                      note = X can be any amino acid
VARIANT               2653
                      note = X can be any amino acid
VARIANT               2660
                      note = X can be any amino acid
```

-continued

```
VARIANT                2676
                       note = X can be any amino acid
VARIANT                2689
                       note = X can be any amino acid
VARIANT                2695
                       note = X can be any amino acid
VARIANT                2722
                       note = X can be any amino acid
VARIANT                2757
                       note = X can be any amino acid
VARIANT                2798
                       note = X can be any amino acid
VARIANT                2857
                       note = X can be any amino acid
VARIANT                2863
                       note = X can be any amino acid
VARIANT                2966
                       note = X can be any amino acid
VARIANT                3002
                       note = X can be any amino acid
VARIANT                3014
                       note = X can be any amino acid
source                 1..3014
                       mol_type = protein
                       organism = synthetic construct
SEQUENCE: 96
MSTNPKPQRK TKRNTNRRPQ DVKFPGGGQI VGGVYLLPRR GPRLGVRATR KTSERSQPRG  60
RRQPIPKARR SEGRSWAQPG YPWPLYGNEG CGWAGWLLSP RGSRPSWGPT DPRRRSRNLG  120
KVIDTLTCGF ADLMGYIPLV GAPLGGVARA LAHGVRVLED GINYATGNLP GCSFSIFLLA  180
LLSCLTVPAS AYEVRNXSGL YHVTNDCPNS SIVYEADDAI LHTPGCVPCV REGNTSRCWV  240
XVTPTVAVRY XGAPTTSLRR HVDLLVGAAT LCSALYVGDL CGAVFLVGQX FTFSPRRHWT  300
VQDCNCSIYP GHITGHRMAW DMMMNWSPTT XLVXAQLLRI PQXXLDIIAG AHWGVLAGLA  360
YFSMQGNWAK VXVLLLFAGV DAETHTTGGX AARTTSGLTS LFSPGPXQNL QLINTNGSWH  420
INRTALNCND SLXTGFIAGL FYTHKFNSSG CPERLASCRP LTDFDQGWGP LTYANXISGP  480
SDDRPYCWHY PPRPCGIVPA RSVCGPVYCF TPSPVVVGTT DRXGVPTYTW GENETDVFLL  540
NSTRPPQGNW FGCTWMNSTG FTKTCGAPPC NIGGGGNNDL LCPTDCFRKH PEATYSXCGS  600
GPWLTPRCLV DYPYRLWHYP CTVNFTIFKV RMYVGGVEHR LEAACNWTRG ERCDLEDRDR  660
SELSPLLHST TEWAILPCSF TTLPALSTGL IHLHQNIVDV QYLYGVGSAV VSWAXKWEYV  720
VLLFLLLADA RVCACLWMML LISQAEAALE NLVVLNAASA AGTHGIXWFL VFFCAAWYLK  780
GRLVPXATYA LXGLWPLLLL LLALPQRAYA LDREVAASLG XAVLVXLTIF TLSPHYKHLL  840
SRXLWWLQYF ITRAEAXLQV WVPPLNVRGG RDXXILLTCL LHPXLVFDIT KLLLAVLGPL  900
YLLQASLLRV PYFVRAHALL RXCMLVRXLA GGKYVQMALL KLGRWTGTYI YDHLXPLSDW  960
AAAGLRDLAV AVEPVIFSPM EKKVITWGAD TAACGDILCG LPVSARLGRE ILLGPADDYX  1020
SKGWRLLAPI TAYAQQTRGL LGTIVTSLTG RDKNEVEGEV QVLSTATQTF LGTCINGVMW  1080
TVYHGAGSKT LAGPKGPVXQ MYTNVDQDLV GWPAPPGAKS LTPCTCGSSD LYLVTRHADV  1140
IPXRRRGDSR GSLLSPRPIS XLKGSSGGPV LCPSGHAVGI FRAAVCTRGV AKAVDFIPVE  1200
SLETTMRSPX FTDNSTPPAV PQXYQVGYLH APTGSGKSTK VPAAYAAQGY KVLVLNPSVA  1260
ATLGFGAYMS KAHGIDPNIR TGVRTVTTGA PITYSTYGKF LADGGCSGGA YDIIICDECH  1320
STDATTILGI GTVLDQAETA GVRLVVLATA TPPGSVTVPH PNIEEVALGT XGEIPFYGKA  1380
IPLEXIKGGR HLIFCHSKKK CDELAAKLXG LGLNAVAYYR GLDVSVIPTS GDVVVVATDA  1440
LMTGFTGDFD SVIDCNVAVT QTVDFSLDPT FTIETTTVPQ DAVSRSQRRG RTGRGRLGIY  1500
RYVSPGERPS GMFDSVVLCE CYDAGCAWYE LTPAETTVRL RAYLNTPGLP VCQDHLEFWE  1560
GVFTGLTHID AHFLSQTKQS GENFPYLVAY QATVCARAXA PPPSWDXMWK CLIRLKPTLH  1620
GPTPLLYRLG AVQNEVTLTH PITKYIMTCM SADLEVVTST WVLVGGVLAA LAAYCLSTGC  1680
VVIVGRIVLS GKPAXIPDRE VLYQQFDEME ECSQHLPYIE QGQQIAEQFK QKALGLLQTA  1740
TKQAEVIAPA VQXNWQKLEQ FWAKHMWNFI SGIQYLAGLS TLPGNPAVAS LMAFTAAVTS  1800
PLTTSQTLLF NILGGWVASQ LAPPTAATAF VVSGLAGAAV GSIGLGKVLV DILAGYGAGV  1860
AGALVAFKIM SGEXPSTEDL VNLLPAILSP GALVVGVVCA AILRRHVGPG EGAVQWMNRL  1920
IAFASRGNHV SPTHYVPESD AAARVTQILS SLTVTSLLRR LHQWINEDCS TPCSGSWLRD  1980
IWDWVCTVLS DFKTWLKAKL LPQLPGIPFL SCQRGYKGVW RGDGVMHTRC PCGAEITGHV  2040
KNGSMRIVGP KTCSNTWHGT FPINAYTTGP XXPXPAPNYK RALWRVXAEE YVEVRRVGDF  2100
HYVTGXTTDN LKCPCQVPAP EFFTEVDGVR LHRXAPPCKP LLRDEVTFSV GLNSYVVGSQ  2160
LPCEPEPDVA VLTSMLTDPS HITAETAARR LARGSPPSLA SSSASQLSAP SLKATCTTHH  2220
DHPDAELIEA NLLWRQEMGG NITRVESENK VVILDSFDPL VAEEDDREIS VPAECLRKXR  2280
KFPPALPIWA RPDYNPPLLE TWKRPDYEPP TVHGCALPPP XAPPVPPPRR KRTVXLTEST  2340
VSTALAELAE KSFGSSEXSG XXSXSGXDTT SSXXSXPPDC DAXSDAESYS SMPPLEGEPG  2400
DPDLSDGSWS TVSDEEDSVV CCSMSYSWTG ALITPCAAEE EKLPINPLSN SLLRHHNLVY  2460
STTSRSASQR QKKVTFDRLQ VLDDHYXDVL KEVKAXASKV KARLLSVEEA CALTPPHSAR  2520
SKFGYGAKDV RSLSRKAVNH IXSVWXDLLE DSTTPIPTTI MAKNEVFCVD PXKGGRKPAR  2580
LIVYPDLGVR VCEKRALYDV XQKLPKAVMG SSYGFQYSPA QRVEFLLKAW KSKKTPMGFS  2640
YDTRCFDSTV TEXDIRTEEX IYQCCDLDPE ARKAIXSLTE RLYVGGPMXN SKGQXCGYRR  2700
CRASGVLTTS MGNTLTCYIK AXAACRAAGL RDCTMLVCGD DLVVICESAG VZEDAAXLRA  2760
FTEAMTRYSA PPGDPPQPEY DLELITSCSS NVSVAHDXSG KRVYYLTRDP TTPLARAAWE  2820
TARHTPVNSW LGNIIMYAPT IWVRMVLMTH FFSILQXQEQ LEXALDFEMY GATYSVTPLD  2880
LPAIIQRLHG LSAFSLHSYS PGELNRVAAC LRKLGVPPLR AWRHARAVR AKLIAQGGRA  2940
AICGKYLFNW AVRTKLKLTP LPAAGXLDLS SWFTVGAGGG DIYHSVSRAR PRWLLLCLLL  3000
LXVGVGIFLL PARX                                                   3014

SEQ ID NO: 97          moltype = AA  length = 3012
```

-continued

FEATURE Location/Qualifiers
VARIANT 3012
note = X can be any amino acid
source 1..3012
mol_type = protein
organism = synthetic construct
SEQUENCE: 97
MSTNPKPQRK TKRNTNRRPQ DVKFPGGGQI VGGVYLLPRR GPRLGVRATR KTSERSQPRG 60
RRQPIPKARR PEGRTWAQPG YPWPLYGNEG CGWAGWLLSP RGSRPSWGPT DPRRRSRNLG 120
KVIDTLTCGF ADLMGYIPLV GAPLGGAARA LAHGVRVLED GVNYATGNLP GCSFSIFLLA 180
LLSCLTVPAS AYQVRNSTGL YHVTNDCPNS SIVYEAADAI LHTPGCVPCV REGNASRCWV 240
AVTPTVATRD GKLPTTQLRR HIDLLVGSAT LCSALYVGDL CGSVFLVGQL FTFSPRRHWT 300
TQDCNCSIYP GHITGHRMAW DMMMNWSPTT ALVVAQLLRI PQAILDMIAG AHWGVLAGIA 360
YFSMVGNWAK VLVVLLLFAG VDAETHVTGG SAARTTSGLA SLFTPGAKQN IQLINTNGSW 420
HINRTALNCN DSLNTGWLAG LFYYHKFNSS GCPERLASCR PLTDFDQGWG PISYANGSGP 480
DQRPYCWHYP PKPCGIVPAK SVCGPVYCFT PSPVVVGTTD RSGAPTYNWG ENDTDVFVLN 540
NTRPPLGNWF GCTWMNSTGF TKVCGAPPCV IGGVGNNTLH CPTDCFRKHP EATYSRCGSG 600
PWITPRCLVD YPYRLWHYPC TINYTIFKVR MYVGGVEHRL EAACNWTRGE RCDLEDRDRS 660
ELSPLLLSTT QWQVLPCSFT TLPALSTGLI HLHQNIVDVQ YLYGVGSSIA SWAIKWEYVV 720
LLFLLLADAR VCSCLWMMLL ISQAEAALEN LVVLNAASLA GTHGLVSFLV FFCFAWYLKG 780
RWVPGAAYAL YGMWPLLLLL LALPQRAYAL DTEVAASCGG VVLVGLMALT LSPYYKRYIS 840
WCLWWLQYFL TRVEAQLHVW VPPLNVRGGR DAVILLMCVV HPTLVFDITK LLLAVFGPLW 900
ILQASLLKVP YFVRVQGLLR ICALARKMAG GHYVQMAIIK LGALTGTYVY NHLTPLRDWA 960
HNGLRDLAVA VEPVVFSQME TKLITWGADT AACGDIINGL PVSARRGREI LLGPADGMVS 1020
KGWRLLAPIT AYAQQTRGLL GCIITSLTGR DKNQVEGEVQ IVSTAAQTFL ATCINGVCWT 1080
VYHGAGTRTI ASPKGPVIQM YTNVDQDLVG WPAPQGARSL TPCTCGSSDL YLVTRHADVI 1140
PVRRRGDSRG SLLSPRPISY LKGSSGGPLL CPAGHAVGIF RAAVCTRGVA KAVDFIPVEN 1200
LETTMRSPVF TDNSSPPAVP QSFQVAHLHA PTGSGKSTKV PAAYAAQGYK VLVLNPSVAA 1260
TLGFGAYMSK AHGIDPNIRT GVRTITTGSP ITYSTYGKFL ADGGCSGGAY DIIICDECHS 1320
TDATSILGIG TVLDQAETAG ARLVVLATAT PPGSVTVPHP NIEEVALSTT GEIPFYGKAI 1380
PLEVIKGGRH LIFCHSKKKC DELAAKLVAL GINAVAYYRG LDVSVIPTSG DVVVVATDAL 1440
MTGFTGDFDS VIDCNTCVTQ TVDFSLDPTF TIETTTLPQD AVSRTQRRGR TGRGKPGIYR 1500
FVAPGERPSG MFDSSVLCEC YDAGCAWYEL TPAETTVRLR AYMNTPGLPV CQDHLEFWEG 1560
VFTGLTHIDA HFLSQTKQSG ENLPYLVAYQ ATVCARAQAP PPSWDQMWKC LIRLKPTLHG 1620
PTPLLYRLGA VQNEVTLTHP ITKYIMTCMS ADLEVVTSTW VLVGGVLAAL AAYCLSTGCV 1680
VIVGRIVLSG KPAIIPDREV LYREFDEMEE CSQHLPYIEQ GMMLAEQFKQ KALGLLQTAS 1740
RQAEVIAPAV QTNWQKLEAF WAKHMWNFIS GIQYLAGLST LPGNPAIASL MAFTAAVTSP 1800
LTTSQTLLFN ILGGWVAAQL AAPGAATAFV GAGLAGAAIG SVGLGKVLVD ILAGYGAGVA 1860
GALVAFKIMS GEVPSTEDLV NLLPAILSPG ALVVGVVCAA ILRRHVGPGE GAVQWMNRLI 1920
AFASRGNHVS PTHYVPESDA AARVTAILSS LTVTQLLRRL HQWISSECTT PCSGSWLRDI 1980
WDWICEVLSD FKTWLKAKLM PQLPGIPFVS CQRGYRGVWR GDGIMHTRCH CGAEITGHVK 2040
NGTMRIVGPR TCRNMWSGTF PINAYTTGPC TPLPAPNYTF ALWRVSAEEY VEIRQVGDFH 2100
YVTGMTTDNL KCPCQVPSPE FFTELDGVRL HRFAPPCKPL LREEVSFRVG LHEYPVGSQL 2160
PCEPEPDVAV LTSMLTDPSH ITAEAAGRRL ARGSPPSVAS SSASQLSAPS LKATCTANHD 2220
SPDAELIEAN LLWRQEMGGN ITRVESENKV VILDSFDPLV AEEDEREISV PAEILRKSRR 2280
FAPALPIWAR PDYNPPLLET WKKPDYEPPV VHGCPLPPPQ SPPVPPPRKK RTVVLTESTV 2340
STALAELATK SFGSSSTSGI TGDNTTTSSE PAPSGCPPDS DAESYSSMPP LEGEPGDPDL 2400
SDGSWSTVSS EADTEDVVCC SMSYSWTGAL VTPCAAEEQK LPINALSNSL LRHHNLVYST 2460
TSRSACQRQK KVTFDRLQVL DSHYQDVLKE VKAAASKVKA NLLSVEEACS LTPPHSAKSK 2520
FGYGAKDVRC HARKAVNHIN SVWKDLLEDS VTPIDTTIMA KNEVFCVQPE KGGRKPARLI 2580
VFPDLGVRVC EKMALYDVVS KLPLAVMGSS YGFQYSPGQR VEFLVQAWKS KKTPMGFSYD 2640
TRCFDSTVTE SDIRTEEAIY QCCDLDPQAR VAIKSLTERL YVGGPLTNSR GENCGYRRCR 2700
ASGVLTTSCG NTLTCYIKAR AACRAAGLQD CTMLVCGDDL VVICESAGVQ EDAASLRAFT 2760
EAMTRYSAPP GDPPQPEYDL ELITSCSSNV SVAHDGAGKR VYYLTRDPTT PLARAAWETA 2820
RHTPVNSWLG NIIMFAPTLW ARMILMTHFF SVLIARDQLE QALDCEIYGA CYSIEPLDLP 2880
PIIQRLHGLS AFSLHSYSPG EINRVAACLR KLGVPPLRAW RHRARSVRAR LLSRGGRAAI 2940
CGKYLFNWAV RTKLKLTPIA AAGQLDLSGW FTAGYSGGDI YHSVSHARPR WFWFCLLLLA 3000
AGVGIYLLPN RX 3012

SEQ ID NO: 98 moltype = AA length = 3008
FEATURE Location/Qualifiers
VARIANT 3008
note = X can be any amino acid
source 1..3008
mol_type = protein
organism = synthetic construct
SEQUENCE: 98
MSTNPKPQRK TKRNTNRRPQ DVKFPGGGQI VGGVYLLPRR GPRLGVRATR KTSERSQPRG 60
RRQPIPKARR PEGRAWAQPG YPWPLYGNEG MGWAGWLLSP RGSRPSWGPT DPRRRSRNLG 120
KVIDTLTCGF ADLMGYIPLV GAPLGGAARA LAHGVRVLED GVNYATGNLP GCSFSIFLLA 180
LLSCLTIPAS AYEVRNVSGV YHVTNDCSNS SIVYEAADMI MHTPGCVPCV RENNSSRCWV 240
ALTPTLAARN ASVPTTTIRR HVDLLVGAAA FCSAMYVGDL CGSVFLVSQL FTFSPRRHET 300
VQDCNCSIYP GHVSGHRMAW DMMMNWSPTT ALVVSQLLRI PQAVVDMVAG AHWGVLAGLA 360
YYSMVGNWAK VLIVMLLFAG VDGTHVTGGA AARTTSGFTS LFSPGPSQKI QLINTNGSWH 420
INRTALNCND SLQTGFLAAL FYTHKFNSSG CPERMASCRP IDKFAQGWGP ITYAEPSSDQ 480
RPYCWHYAPR PCGIVPASQV CGPVYCFTPS PVVVGTTDRF GVPTYSWGEN ETDVLLLNNT 540
RPPQGNWFGC TWMNSTGFTK TCGGPPCNIG GVGNNTLTCP TDCFRKHPEA TYTKCGSGPW 600
LTPRCLVDYP YRLWHYPCTV NFTIFKVRMY VGGVEHRLNA ACNWTRGERC DLEDRDRSEL 660
SPLLLSTTEW QILPCSFTTL PALSTGLIHL HQNIVDVQYL YGIGSAVVSF AIKWEYVLLL 720

-continued

```
FLLLADARVC ACLWMMLLIA QAEAALENLV VLNAASVAGA HGILSFLVFF CAAWYIKGRL  780
VPGAAYAFYG VWPLLLLLLA LPPRAYAMDR EMAASCGGAV FVGLALLTLS PHYKVFLARL  840
IWWLQYFITR AEAHLQVWIP PLNVRGGRDA IILLTCAVHP ELIFDITKLL LAILGPLMVL  900
QAGITRVPYF VRAQGLIRAC MLVRKVAGGH YVQMAFMKLA ALTGTYVYDH LTPLRDWAHA  960
GLRDLAVAVE PVVFSDMETK IITWGADTAA CGDIILGLPV SARRGREILL GPADSLEGQG  1020
WRLLAPITAY SQQTRGLLGC IITSLTGRDK NQVEGEVQVV STATQSFLAT CVNGVCWTVY  1080
HGAGSKTLAG PKGPITQMYT NVDQDLVGWQ APPGARSLTP CTCGSSDLYL VTRHADVIPV  1140
RRRGDSRGSL LSPRPVSYLK GSSGGPLLCP SGHAVGIFRA AVCTRGVAKA VDFVPVESME  1200
TTMRSPVFTD NSSPPAVPQT FQVAHLHAPT GSGKSTKVPA AYAAQGYKVL VLNPSVAATL  1260
GFGAYMSKAH GVDPNIRTGV RTITTGAPIT YSTYGKFLAD GGCSGGAYDI IICDECHSTD  1320
STTILGIGTV LDQAETAGAR LVVLATATPP GSVTVPHPNI EEVALSNTGE IPFYGKAIPI  1380
ETIKGGRHLI FCHSKKKCDE LAAKLSGLGL NAVAYYRGLD VSVIPTSGDV VVVATDALMT  1440
GFTGDFDSVI DCNTCVTQTV DFSLDPTFTI ETTTVPQDAV SRSQRRGRTG RGRRGIYRFV  1500
TPGERPSGMF DSSVLCECYD AGCAWYELTP AETSVRLRAY LNTPGLPVCQ DHLEFWESVF  1560
TGLTHIDAHF LSQTKQAGDN FPYLVAYQAT VCARAQAPPP SWDQMWKCLI RLKPTLHGPT  1620
PLLYRLGAVQ NEVTLTHPIT KYIMACMSAD LEVVTSTWVL VGGVLAALAA YCLTTGSVVI  1680
VGRIILSGKP AIIPDREVLY QEFDEMEECA SHLPYIEQGM QLAEQFKQKA LGLLQTATKQ  1740
AEAAAPVVES KWRALEFWAK HMWNFISGIQ YLAGLSTLPG NPAIASLMAF TASITSPLTT  1800
QHTLLFNILG GWVAAQLAPP SAASAFVGAG IAGAAVGSIG LGKVLVDILA GYGAGVAGAL  1860
VAFKVMSGEM PSTEDLVNLL PAILSPGALV VGVVCAAILR RHVGPGEGAV QWMNRLIAFA  1920
SRGNHVSPTH YVPESDAAAR VTQILSSLTI TQLLKRLHQW INEDCSTPCS GSWLRDVWDW  1980
ICTVLTDFKT WLQSKLLPRL PGVPFLSCQR GYKGVWRGDG IMQTTCPCGA QITGHVKNGS  2040
MRIVGPKTCS NTWHGTFPIN AYTTGPCTPS PAPNYSRALW RVAAEEYVEV TRVGDFHYVT  2100
GMTTDNVKCP CQVPAPEFFT EVDGVRLHRY APACKPLLRE EVTFQVGLNQ YLVGSQLPCE  2160
PEPDVAVLTS MLTDPSHITA ETAKRRLARG SPPSLASSSA SQLSAPSLKA TCTTRHDSPD  2220
ADLIEANLLW RQEMGGNITR VESENKVVIL DSFDPLRAEE DEREVSVPAE ILRKSRKFPP  2280
AMPIWARPDY NPPLLESWKD PDYVPPVVHG CPLPPTKAPP IPPPRRKRTV VLTESTVSSA  2340
LAELATKTFG SSESSAVDSG TATAPPDQPS DDGDAGSDVE SYSSMPPLEG EPGDPDLSDG  2400
SWSTVSEEAS EDVVCCSMSY TWTGALITPC AAEESKLPIN ALSNSLLRHH NMVYATTSRS  2460
ASQRQKKVTF DRLQVLDDHY RDVLKEMKAK ASTVKAKLLS VEEACKLTPP HSARSKFGYG  2520
AKDVRNLSSK AVNHIRSVWK DLLEDTETPI DTTIMAKNEV FCVQPEKGGR KPARLIVFPD  2580
LGVRVCEKMA LYDVVSTLPQ AVMGSSYGFQ YSPGQRVEFL VNAWKSKKCP MGFAYDTRCF  2640
DSTVTESDIR VEESIYQCCD LAPEARQAIR SLTERLYIGG PLTNSKGQNC GYRRCRASGV  2700
LTTSCGNTLT CYLKASAACR AAKLQDCTML VCGDDLVVIC ESAGTQEDAA SLRVFTEAMT  2760
RYSAPPGDPP QPEYDLELIT SCSSNVSVAH DASGKRVYYL TRDPTTPLAR AAWETARHTP  2820
VNSWLGNIIM YAPTLWARMI LMTHFFSILL AQEQLEKALD CQIYGACYSI EPLDLPQIIQ  2880
RLHGLSAFSL HSYSPGEINR VASCLRKLGV PPLRVWRHRA RSVRAKLLSQ GGRAATCGKY  2940
LFNWAVRTKL KLTPIPAASQ LDLSGWFVAG YSGGDIYHSL SRARPRWFMW CLLLLSVGVG  3000
IYLLPNRX                                                           3008

SEQ ID NO: 99           moltype = AA  length = 3034
FEATURE                 Location/Qualifiers
VARIANT                 250
                        note = X can be any amino acid
VARIANT                 406
                        note = X can be any amino acid
VARIANT                 408..409
                        note = X can be any amino acid
VARIANT                 3023
                        note = X can be any amino acid
source                  1..3034
                        mol_type = protein
                        organism = synthetic construct
SEQUENCE: 99
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCITVPVS AAQVKNTSSS YMVTNDCSND SITWQLQAAV LHVPGCVPCE KVGNNTSRCW  240
IPVSPNVAVX QPGALTQGLR THIDMVVMSA TLCSALYVGD LCGGVMLAAQ MFIVSPQHHW  300
FVQECNCSIY PGTITGHRMA WDMMMNWSPT ATMILAYAMR VPEVIIDIIS GAHWGVMFGL  360
AYFSMQGAWA KVVVILLLAA GVDAGTHTVG GSAAHTTSGL AGLFSXGXXQ NIQLINTNGS  420
WHINRTALNC NDSLNTGFLA SLFYTHRFNS SGCPERLSAC RNIEAFRIGW GTLQYEDNVT  480
NPEDMRPYCW HYPPKQCGIV PARSVCGPVY CFTPSPVVVG TTDRLGVPTY TWGENETDVF  540
LLNSTRPPQG SWFGCTWMNS TGFTKTCGAP PCRIRADFNA STDLLCPTDC FRKHPEATYI  600
KCGSGPWLTP RCLVDYPYRL WHYPCTVNYT IFKIRMYVGG VEHRLTAACN FTRGDRCNLE  660
DRDRSQLSPL LHSTTEWAIL PCSYSDLPAL STGLLHLHQN IVDVQYMYGL SPALTKYVVR  720
WEWVVLLFLL LADARVCACL WMLILLGQAE AALEKLVVLH AASAASCNGF LYFVIFFVAA  780
WYIKGRAVPL AAYSLTGLWP FCLLLLALPQ QAYAYDASVH GQIGAALLIL ITLFTLTPGY  840
KTLLSRCLWW LCYLLTLGEA MVQEWAPPMQ ARGGRDGIIW AATIFCPGVV FDITKWLLAV  900
LGPAYLLRDA LTRVPYFVRA HALLRMCTMV RHLAGGRYVQ MALLALGRWT GTYIYDHLTP  960
MSDWAASGLR DLAVAVEPII FSPMEKKVIV WGAETAACGD ILHGLPVSAR LGREILLGPA  1020
DGYTSKGWRL LAPITAYAQQ TRGLLGAIVV SMTGRDKTEQ AGEIQVLSTV TQSFLGTSIS  1080
GVLWTVYHGA GNKTLAGSRG PVTQMYSSAE GDLVGWPSPP GTKSLEPCTC GAVDLYLVTR  1140
NADVIPARRR GDKRGALLSP RPLSTLKGSS GGPVLCPRGH AVGIFRAAVC SRGVAKSIDF  1200
IPVETLDIVT RSPTFSDNST PPAVPQTYQV GYLHAPTGSG KSTKVPVAYA AQGYKVLVLN  1260
PSVAATLGFG AYLSKAHGIN PNIRTGVRTV TTGEAITYST YGKFLADGGC AGGAYDIIIC  1320
DECHAVDATT ILGIGTVLDQ AETAGVRLTV LATATPPGSV TTPHPNIEEV ALGQEGEIPF  1380
YGRAIPLSYI KGGRHLIFCH SKKKCDELAA ALRGMGLNAV AYYRGLDVSI IPTQGDVVVV  1440
ATDALMTGYT GDFDSVIDCN VAVTQVVDFS LDPTFTITTQ TVPQDAVSRS QRRGRTGRGR  1500
```

-continued

```
LGIYRYVSTG ERASGMFDSV VLCECYDAGA AWYELTPAET TVRLRAYFNT PGLPVCQDHL  1560
EFWEAVFTGL THIDAHFLSQ TKQSGENFAY LVAYQATVCA RAKAPPPSWD VMWKCLTRLK  1620
PTLVGPTPLL YRLGSVTNEV TLTHPVTKYI ATCMQADLEV MTSTWVLAGG VLAAVAAYCL  1680
ATGCVSIIGR LHINQRAVVA PDKEVLYEAF DEMEECASRA ALIEEGQRIA EMLKSKIQGL  1740
LQQASKQAQD IQPAVQASWP KVEQFWAKHM WNFISGIQYL AGLSTLPGNP AVASMMAFSA  1800
ALTSPLSTST TILLNILGGW LASQIAPPAG ATGFVVSGLV GAAVGSIGLG KVLVDILAGY  1860
GAGISGALVA FKIMSGEKPS MEDVVNLLPG ILSPGALVVG VICAAILRRH VGPGEGAVQW  1920
MNRLIAFASR GNHVAPTHYV TESDASQRVT QLLGSLTITS LLRRLHNWIT EDCPIPCAGS  1980
WLRDVWDWVC TILTDFKNWL TSKLFPKMPG LPFISCQKGY KGVWAGTGIM TTRCPCGANI  2040
SGNVRLGSMR ITGPKTCMNT WQGTFPINCY TEGQCVPKPA PNFKTAIWRV AASEYAEVTQ  2100
HGSYSYITGL TTDNLKVPCQ LPSPEFFSWV DGVQIHRFAP TPKPFFRDEV SFCVGLNSFV  2160
VGSQLPCDPE PDTDVLMSML TDPSHITAEA AARRLARGSP PSEASSSASQ LSAPSLRATC  2220
TTHGKTYDVD MVDANLFMGG DVTRIESESK VVVLDSLDPM AEERSDLEPS IPSEYMLPRN  2280
RFPPALPAWA RPDYNPPLVE SWKRPDYQPP TVAGCALPPP KKTPTPPPRR RRTVGLSEST  2340
IGDALQQLAI KTFGQPPPSG DSGLSTGADA ADSGGRTPPD ELALSETGSI SSMPPLEGEP  2400
GDPDLEPEQV ELQPPPQGGE VAPGSDSGSW STCSEEDDSV VCCSMSYSWT GALITPCSPE  2460
EEKLPINPLS NSLLRYHNKV YCTTSKSASL RAKKVTFDRM QVLDAHYDSV LKDIKLAASK  2520
VSARLLTLEE ACQLTPPHSA RSKYGFGAKE VRSLSGRAVN HIKSVWKDLL EDSQTPIPTT  2580
IMAKNEVFCV DPTKGGKKAA RLIVYPDLGV RVCEKMALYD VTQKLPQAVM GASYGFQYSP  2640
AQRVEFLLKA WAEKKDPMGF SYDTRCFDST VTERDIRTEE SIYQACSLPE EARTAIHSLT  2700
ERLYVGGPMF NSKGQTCGYR RCRASGVLTT SMGNTITCYV KALAACKAAG IVAPTMLVCG  2760
DDLVVISESQ GTEEDERNLR AFTEAMTRYS APPGDPPRPE YDLELITSCS SNVSVALGPQ  2820
GRRRYYLTRD PTTPIARAAW ETVRHSPVNS WLGNIIQYAP TIWVRMVLMT HFFSILMAQD  2880
TLDQNLNFEM YGSVYSVSPL DLPAIIERLH GLDAFSLHTY TPHELTRVAS ALRKLGAPPL  2940
RAWKSRARAV RASLISRGGR AAVCGRYLFN WAVKTKLKLT PLPEARLLDL SSWFTVGAGG  3000
GDIYHSVSRA RPRLLLLSLL LLXVGVGLFL LPAR                             3034

SEQ ID NO: 100          moltype = AA  length = 3033
FEATURE                 Location/Qualifiers
REGION                  1..3033
                        note = Synthetic Sequence
source                  1..3033
                        mol_type = protein
                        organism = synthetic construct
SEQUENCE: 100
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG CGWAGWLLSP RGSRPTWGPT DPRHRSRNLG  120
KVIDTITCGF ADLMGYIPVV GAPVGGVARA LAHGVRVLED GINYATGNLP GCSFSIFLLA  180
LLSCVTVPVS AVEVRNISSS YYATNDCSNN SITWQLTNAV LHLPGCVPCE NDNGTLRCWI  240
QVTPNVAVKH RGALTHNLRT HVDMIVMAAT VCSALYVGDV CGAVMIVSQA LIVSPERHNF  300
TQECNCSIYQ GHITGHRMAW DMMLNWSPTL TMILAYAARV PELVLEVVFG GHWGVVFGLA  360
YFSMQGAWAK VIAILLLVAG VDATTYSSGA QAGRTTSGFA GLFSPGPKQN IQLINTNGSW  420
HINRTALNCN DSLQTGFIAS LFYTNNFNSS GCPERLSSCR GLDDFRIGWG TLEYETNVTN  480
DEDMRPYCWH YPPKPCGIVS ARTVCGPVYC FTPSPVVVGT TDRQGVPTYS WGENETDVFL  540
LNSTRPPQGA WFGCTWMNGT GFTKTCGAPP CRIRRDYNST LDLLCPTDCF RKHPDATYLK  600
CGAGPWLTPR CLVDYPYRLW HYPCTVNFTI FKVRMYVGGV EHRLSAACNF TRGDRCRLED  660
RDRGQQSPLL HSTTEWAVLP CSFSDLPALS TGLLHLHQNI VDVQYLYGLS PAITRYIVKW  720
EWVVLLFLLL ADARVCACLW MLIILGQAEA ALEKLIILHS ASAASANGPL WFFIFFTAAW  780
YLKGRVVPVA TYSVLGLWSF LLLVLALPQQ AYALDAAEQG ELGLVILVII SIFTLTPAYK  840
ILLSRSVWWL SYMLVLAEAQ IQQWVPPLEA RGGRDGIIWV AVILHPRLVF EVTKWLLAIL  900
GPAYLLKASL LRVPYFVRAH ALLRVCTLVR HLAGARYIQM LLITIGRWTG TYIYDHLSPL  960
STWAAQGLRD LAVAVEPVVF SPMEKKVIVW GAETVACGDI LHGLPVSARL GREVLLGPAD  1020
SYTSKGWKLL APITAYTQQT RGLLGAIVVS LTGRDKNEQA GQVQVLSSVT QSFLGTSISG  1080
VLWTVYHGAG NKTLAGPKGP VTQMYTSAEG DLVGWPSPPG TKSLDPCTCG AVDLYLVTRN  1140
ADVIPVRRKD DRRGALLSPR PLSTLKGSSG GPVLCPRGHA VGLFRAAVCA RGVAKSIDFI  1200
PVESLDIATR TPSFSDNSTP PAVPQSYQVG YLHAPTGSGK STKVPAAYAS QGYKVLVLNP  1260
SVAATLGFGA YMSKAHGINP NIRTGVRTVT TGDPITYSTY GKFLADGGCS AGAYDVIICD  1320
ECHSVDATTI LGIGTVLDQA ETAGARLVVL ATATPPGTVT TPHSNIEEVA LGHEGEIPFY  1380
GKAIPLAFIK GGRHLIFCHS KKKCDELAAA LRGMGVNAVA YYRGLDVSVI PTQGDVVVVA  1440
TDALMTGYTG DFDSVIDCNV AVTQIVDFSL DPTFTITTQT VPQDAVSRSQ RRGRTGRGRL  1500
GIYRYVSSGE RPSGMFDSVV LCECYDAGAA WYELTPAETT VRLRAYFNTP GLPVCQDHLE  1560
FWEAVFTGLT HIDAHFLSQT KQGGDNFAYL TAYQATVCAR AKAPPPSWDV MWKCLTRLKP  1620
TLTGPTPLLY RLGAVTNEVT LTHPVTKYIA TCMQADLEIM TSTWVLAGGV LAAVAAYCLA  1680
TGCISIIGRL HLNDQVVVAP DKEILYEAFD EMEECASKAA LIEEGQRMAE MLKSKIQGLL  1740
QQATRQAQDI QPAIQSSWPK LEQFWAKHMW NFISGIQYLA GLSTLPGNPA VASMMAFSAA  1800
LTSPLPTSTT ILLNIMGGWL ASQIAPPAGA TGFVVSGLVG AAVGSIGLGK ILVDVLAGYG  1860
AGISGALVAF KIMSGEKPSV EDVVNLLPAI LSPGALVVGV ICAAILRRHV GQGEGAVQWM  1920
NRLIAFASRG NHVAPTHYVA ESDASQRVTQ VLSSLTITSL LRRLHAWITE DCPVPCSGSW  1980
LRDIWDWVCS ILTDFKNWLS SKLLPKMPGL PFISCQKGYR GVWAGTGVMT TRCPCGANIS  2040
GHVRMGTMKI TGPKTCLNLW QGTFPINCYT EGPCVPKPPP NYKTAIWRVA ASEYVEVTQH  2100
GSFSYVTGLT SDNLKVPCQV PAPEFFSWVD GVQIHRFAPT PGPFFRDEVT FTVGLNSFVV  2160
GSQLPCDPEP DTEVLASMLT DPSHITAEAA ARRLARGSPP SQASSSASQL SAPSLKATCT  2220
THKMAYDCDM VDANLFMGGD VTRIESDSKV IVLDSLDSMT EVEDDREPSV PSEYLIRRRK  2280
FPPALPPWAR PDYNPPVIET WKRPGYEPPT VLGCALPPTP QAPVPPPRRR RAKVLTQDNV  2340
EGVLREMADK VLSPLQDHND SGHSTGADTG GDSVQQPSDE TAASEAGSLS SMPPLEGEPG  2400
DPDLEFEPAG SAPPSEGECE VIDSDSKSWS TVSDQEDSVI CCSMSYSWTG ALITPCGPEE  2460
EKLPINPLSN SLMRFHNKVY STTSRSASLR AKKVTFDRVQ VLDAHYDSVL QDVKRAASKV  2520
SARLLSVEEA CALTPPHSAK SRYGFGAKEV RSLSRRAVNH IRSVWEDLLE DQHTPIDTTI  2580
MAKNEVFCVD PTKGGKKPAR LIVYPDLGVR VCEKMALYDI AQKLPKAIMG PSYGFQYSPA  2640
```

-continued

```
ERVDFLLKAW GSKKDPMGFS YDTRCFDSTV TERDIRTEES IYQACSLPQE ARTVIHSLTE  2700
RLYVGGPMTN SKGQSCGYRR CRASGVFTTS MGNTMTCYIK ALAACKAAGI VDPIMLVCGD  2760
DLVVISESQG NEEDERNLRA FTEAMTRYSA PPGDLPRPEY DLELITSCSS NVSVALDSRG  2820
RRRYFLTRDP TTPITRAAWE TVRHSPVNSW LGNIIQYAPT IWVRMVIMTH FFSILLAQDT  2880
LNQNLNFEMY GAVYSVNPLD LPAIIERLHG LDAFSLHTYS PHELSRVAAT LRKLGAPPLR  2940
AWKSRARAVR ASLIAQGGRA AICGRYLFNW AVKTKLKLTP LPEASRLDLS GWFTVGAGGG  3000
DIFHSVSHAR PRLLLLCLLL LSVGVGIFLL PAR                              3033

SEQ ID NO: 101          moltype = AA  length = 3068
FEATURE                 Location/Qualifiers
VARIANT                 385
                        note = X can be any amino acid
VARIANT                 409
                        note = X can be any amino acid
VARIANT                 585
                        note = X can be any amino acid
VARIANT                 3048
                        note = X can be any amino acid
source                  1..3068
                        mol_type = protein
                        organism = synthetic construct
SEQUENCE: 101
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLEWRNTSGL YVLTNDCSNS SIVYEADDVI LHTPGCIPCV QTDGNTSTCW  240
TPVTPTVAVK YVGATTASIR SHVDLLVGAA TMCSALYVGD MCGAVFLVGQ AFTFRPRRHQ  300
TVQTCNCSLY PGHLSGHRMA WDMMMNWSPA VGMVVAHVLR LPQTLFDIIA GAHWGILAGL  360
AYYSMQGNWA KVAIIMVMFS GVDAXTHTTG GSAARGARGL TSLFSVGPXQ NLQLVNTNGS  420
WHINRTALNC NDSINTGFIA GLFYYHKFNS TGCPQRLSSC KPITFFRQGW GPLTDANNIT  480
GPSDDKPYCW HYAPRPCDVV PASSVCGPVY CFTPHHSPVV VGTTDAKGVP TYTWGENETD  540
VFLLESLRPP SGRWFGCTWM NSTRGFVKTC GAPPCNIYGG GGNPXNNESD LFCPTDCFRK  600
HPEATYSRCG AGPWLTPRCM VDYPYRLWHY PCTVNFTLFK VRMFVGGFEH RFTAACNWTR  660
GERCDIEDRD RSEQHPLLHS TTELAILPCS FTPMPALSTG LIHLHQNIVD VQYLYGVGSG  720
MVGWALKWEF VILVFLLLAD ARVCVALWLM LMISQAEAAL ENLVTLNAVA AAGTHGIGWY  780
LVAFCAAWHV RRAGKLVPLV TYSLTGLWSL ALLVLLLPQR AYAWSGEDSA TLGAGILVLF  840
GFFTLSPWYK HWIGRLMWWN QYTICRCEAA LQVWVPPLLA RGSRDGVILL TSLLYPSLIF  900
DITKLLIAVL GPLYLIQAAI TTTPYFVRAH VLVRLCMLVR SVMGGKYFQM IILSIGRWFN  960
TYLYDHLAPM QHWAAAGLKD LAVATEPVIF SPMEIKVITW GADTAACGDI LCGLPVSARL  1020
GREVLLGPAD DYREMGWRLL APITAYAQQT RGLLGTIVTS LTGRDKNVVT GEVQVLSTAT  1080
QTFLGTTVGG VMWTVYHGAG SRTLAGAKHP ALQMYTNVDQ DLVGWPAPPG AKSLEPCACG  1140
SADLYLVTRD ADVIPARRRG DSTASLLSPR PLACLKGSSG GPVMCPSGHV AGIFRAAVCT  1200
RGVAKALQFI PVETLSTQAR SPSFSDNSTP PAVPQSYQVG YLHAPTGSGK STKVPAAYVA  1260
QGYNVLVLNP SVAATLGFGS FMSRAYGIDP NIRTGNRTVT TGAKLTYSTY GKFLADGGCS  1320
GGAYDVIICD ECHAQDATSI LGIGTVLDQA ETAGVRLTVL ATATPPGSIT VPHSNIEEVA  1380
LGSEGEIPFY GKAIPIAQLK GGRHLIFCHS KKKCDEIASK LRGMGLNAVA YYRGLDVSVI  1440
PTTGDVVVCA TDALMTGFTG DFDSVIDCNV AVEQYVDFSL DPTFSIETRT APQDAVSRSQ  1500
RRGRTGRGRL GTYRYVTPGE RPSGMFDSVV LCECYDAGCS WYDLQPAETT VRLRAYLSTP  1560
GLPVCQDHLD FWESVFTGLT HIDAHFLSQT KQQGLNFSYL TAYQATVCAR AQAPPPSWDE  1620
TWKCLVRLKP TLHGPTPLLY RLGPVQNEIC LTHPITKYIM ACMSADLEVT TSTWSTWVLL  1680
GGVLAALAAY CLSVGCVVIV GHIELGGKPA LVPDKEVLYQ QYDEMEECSQ AAPYIEQAQV  1740
IAHQFKEKVL GLLQRATQQQ AVIEPIVATN WQKLEAFWHK HMWNFVSGIQ YLAGLSTLPG  1800
NPAVASLMAF TASVTSPLTT NQTMFFNILG GWVATHLAGP QSSSAFVVSG LAGAAIGGIG  1860
LGRVLLDILA GYGAGVSGAL VAFKIMGGEL PTAEDMVNLL PAILSPGALV VGVICAAILR  1920
RHVGPGEGAV QWMNRLIAFA SRGNHVSPTH YVPESDAAAR VTALLSSLTV TSLLRRLHQW  1980
INEDYPSPCS GDWLRTIWDW VCTVLSDFKT WLSAKIMPAL PGLPFISCQK GYKGVWRGDG  2040
VMSTRCPCGA SITGHVKNGS MRLAGPRTCA NMWHGTFPIN EYTTGPSTPC PSPNYTRALW  2100
RVAANSYVEV RRVGDFHYIT GATEDELKCP CQVPAAEFFT EVDGVRLHRY APPCKPLLRD  2160
EITFMVGLNS YAIGSQLPCE PEPDVSVLTS MLRDPSHITA ETAARRLARG SPPSEASSSA  2220
SQLSAPSLKA TCQTHRPHPD AELVDANLLW RQEMGSNITR VESETKVVIL DSFEPLRAET  2280
DDAELSVAAE CFKKPPKYPP ALPIWARPDY NPPLLDRWKA PDYVPPTVHG CALPPRGAPP  2340
VPPPRRKRTI QLDGSNVSAA LAALAEKSFP SSKPQEENSS SSGVDTQSST TSKVPPSPGG  2400
ESDSESCSSM PPLEGEPGDP DLSCDQVELQ PPPQGGGVAP GSGSGSWSTV SDSEEQSVVC  2460
CSMSYSWTGA LITPCSAEEE KLPISPLSNS LLRHHNLVYS TSSRSASQRQ KKVTFDRLQV  2520
LDDHYKTALK EVKERASRVK ARMLTIEEAC ALVPPHSARS KFGYSAKDVR SLSSKAINQI  2580
RSVWEDLLED TTTPIPTTIM AKNEVFCVDP AKGGRKPARL IVYPDLGVRV CEKRALYDVI  2640
QKLSIETMGS AYGFQYSPQQ RVERLLKMWT SKKTPLGVLF SYDTRCFDST VTGEQDIRVE  2700
EEIYQCCNLE PEARKVISSL TERLYCGGPM FNSKGAQCGY RRCRASGVLP TSFGNTITCY  2760
IKATAAARAA GLRNPDFLVC GDDLVVVAES DGVDEDRAAL RAFTEAMTRL WTRYYSAPPG  2820
DAPHRPTLQP TYDLELITSC SSNVSVARDN KGKRYYYLTR DATTPLARAA WETARHTPGW  2880
GVNSWLGNII MYAPTIWVRM VMMTHFFSIL QSQEILDRPL DFEMYGATYS VTPLDLPAII  2940
ERLHGLSAFT LHSYSPVELN RVAGTLRKLG CPPLRAWRHR ARAVRAKLIA QGGKAKICGL  3000
YLFNWAVRTK TKLTPLPAAG QLDLSSWFTV GVGGNDIYHS VSRARTRXLL LCLLLLTVGV  3060
GIFLLPAR                                                          3068

SEQ ID NO: 102          moltype = AA  length = 3035
FEATURE                 Location/Qualifiers
VARIANT                 232
                        note = X can be any amino acid
```

-continued

```
VARIANT              397
                     note = X can be any amino acid
VARIANT              407
                     note = X can be any amino acid
VARIANT              678
                     note = X can be any amino acid
VARIANT              1002
                     note = X can be any amino acid
source               1..3035
                     mol_type = protein
                     organism = synthetic construct
SEQUENCE: 102
MSTNPKPQRK TKRNTNRRPM DVKFPGGGQI VGGVYLLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRAVED GINYATGNLP GCSFSIFLLA  180
LLSCLTVPAS AINYRNTSGI YHVTNDCPNS SIVYEADHHI LHLPGCVPCV RXGNQSRCWV  240
ALTPTVAAPY IGAPLESLRS HVDLMVGAAT VCSALYIGDL CGGLFLVGQM FSFRPRRHWT  300
TQDCNCSIYT GHITGHRMAW DMMMNWSPTT TLVLAQVMRI PSTLVDLLAG GHWGVLVGVA  360
YFSMQANWAK VILVLFLFAG VDAETHVSGG AAGRTTXGLT SLFSPGXQQN LQLINSNGSW  420
HINRTALNCN DSLNTGFLAS LFYTHKFNSS GCPERLASCK SLDSFDQGWG PLGVANNISG  480
PSDDRPYCWH YPPRPCGIVP ASSVCGPVYC FTPSPVVVGT TDRLGVPTYT WGENESDVFL  540
LNSTRPPQGA WFGCVWMNST GFTKACGAPP CEVRTNNGTS TDWPCPTDCF RKHPETTYAK  600
CGSGPWITPR CLIHYPYRLW HYPCTVNFTV FKIRTFIGGI EHRMEAACNW TRGEVCGLEH  660
RDRAELSPLL LSTTTWQXLP CSFTTLPALS TGLIHLHQNI VDVQYLYGVG SAVVSWALKW  720
EYVVLAFLLL ADARVSACLW MMFMVSQVEA ALSNLININA ASAAGTHGFW YAIFFICIAW  780
HVKGRLPAAA TYAACGMWPL LLLLLMLPER AYAYDREVAG SLGGAVVVAL TILTLSPHYK  840
SWLARGLWWI QYFIARAEAL LHVYVPSFDV RGPRDSLIIL AVLACPHLVF DITKYLLAIL  900
GPLYILQASL LRVPYFVRAH ALVKICSLLR GVVYGKYCQM AVLKVGALTG TYIYDHLTPL  960
SDWAAEGLRD LAVALEPVVF TPMEKKVIVW GADTAACGDI IXGLPVSARL GNEILLGPAD  1020
SETSKGWRLL APITAYAQQT RGLFSTIITS LTGRDTNENC GEVQVLSTAT QSFLGTAVNG  1080
VMWTVYHGAG SKTISGPKGP VNQMYTNVDQ DLVGWPAPPG VKSLAPCTCG ASDLYLVTRH  1140
ADVVPVRRRG DTRGALLSPR PISTLKGSSG GPLLCPMGHA AGIFRAAVCT RGVAKAVDFV  1200
PVESLETTMR SPVFTDNSTP PAVPQTYQVA HLHAPTGSGK STKVPAAYAA QGYKVLVLNP  1260
SVAATLGFGA YMSKAYGIDP NIRSGVRTIT TGAPITYSTY GKFLADGGCS GGAYDIIICD  1320
ECHSTDSTTI LGIGTVLDQA ETAGVRLVVL ATATPPGSVT TPHSNIEEVA LPTTGEIPFY  1380
GKAIPLELIK GGRHLIFCHS KKKCDELAKQ LTSLGLNAVA YYRGLDVSVI PTSGDVVVCA  1440
TDALMTGFTG DFDSVIDCNT SVIQTVDFSL DPTFSIETTT VPQDAVSRSQ RRGRTGRGRL  1500
GIYRYVTPGE RPSGIFDTSV LCECYDAGCA WYELTPAETT TRLRAYFNTP GLPVCQDHLE  1560
FWESVFTGLT QIDGHFLSQT KQSGENFPYL VAYQATVCAR ALAPPPSWDT MWKCLIRLKP  1620
TLHGPTPLLY RLGSVQNEVT LTHPITKYIM ACMSADLEVV TSTWVLVGGV LAALAAYCLS  1680
VGSVVIVGRV VLSGQPAVIP DREVLYQQFD EMEECSKHLP LVEHGLQLAE QFKQKAVGLL  1740
NFAGKQAQEA TPVIQSNFAK LEQFWAKHMW NFISGIQYLA GLSTLPGNPA IASLMSFTAA  1800
VTSPLTTQQT LLFNILGGWV ASQIATPTAS TAFVVSGLAG AAVGSVGLGK ILVDILAGYG  1860
AGVAGAVVTF KIMSGEMPST EDLVNLLPAI LSPGALVVGV VCAAILRRHV GPGEGAVQWM  1920
NRLIAFASRG NHVSPTHYVP ESDAAARVTQ ILSSLTVTSL LRRLHKWINE DCSTPCAESW  1980
LWEVWDWVCT VLSDFKTWLK AKLLPLMPGI PFLSCQRGYK GEWRGDGVMH TTCPCGAELA  2040
GHIKNGSMRI TGPKTCSNTW HGTFPINAYT TGPGVPIPAP NYKFALWRVS AEEYVEVRRV  2100
GDFHYVTGVT QDNIKCPCQV PAPEFFTEVD GIRLHRHAPK CKPLLRDEVS FSVGLNSFVV  2160
GSQLPCEPEP DVAVLTSMLT DPSHITAETA SRRLARGSPP SLASSSASQL SAPSLKATCT  2220
ARHDSPGTDL LEANLLWGST ATRVETDEKV IILDSFEPCV AEPDDDREVS VAAEILRPTK  2280
KFPPALPIWA RPDYNPPLTE TWKQQDYKPP TVHGCALPPS KQPPVPPPRR KRTVQLTESV  2340
VSTALAELAA KTFGQSELGS DSGADLTTGP TETTDSGPIL VDDASDDGSY SSMPPLEGEP  2400
GDPDLTSDQV ELQPPPQGGG VAPGSGSGSW STVSGSEDTV VCCSMSYSWT GALVTPCAAE  2460
ESKLPISPLS NSLLRHHNMV YATTTRSAVT RQKKVTFDRL QVVDNHYNET LKEIKARASR  2520
VKARLLTTEE ACDLTPPHSA KSKFGYGAKD VRSHSRKAIN HINSVWEDLL EDNNTPIPTT  2580
IMAKNEVFAV NPAKGGRKPA RLIVYPDLGG VRVCEKRALH DVINQLPKAV MGAAYGFQYS  2640
PAQRVEFLLT SWKSKKTPMG FSYDTRCFDS TVTEKDIRTE EEVYQCCDLE PEARKVITAL  2700
TERLYVGGPM HNSKGDLCGY RRCRASGVYT TSFGNTLTCY LKATAAIKAA GLRDCTMLVC  2760
GDDLVVIAES DGVEEDNRAL RAFTEAMTRY SAPPGDAPQP AYDLELITSC SSNVSVAHDA  2820
TGKKVYYLTR DPETPLARAA WETVRHTPVN SWLGNIIVYA PTIWVRMVLM THFFSILQSQ  2880
EALEKALDFD MYGVTYSITP LDLPAIIQRL HGLSAFTLHG YSPHELNRVA GSLRKLGVPP  2940
LRAWRHRARA VRAKLIAQGG KAKICGIYLF NWAVKTKLKL TPLPAAANLD LSSWFTVGAG  3000
GGDIYHSVSR ARPRYLLLCL LLLSVGVGIF LLPAR                            3035

SEQ ID NO: 103       moltype = AA  length = 3013
FEATURE              Location/Qualifiers
VARIANT              178
                     note = X can be any amino acid
VARIANT              189
                     note = X can be any amino acid
VARIANT              232
                     note = X can be any amino acid
VARIANT              251
                     note = X can be any amino acid
VARIANT              257
                     note = X can be any amino acid
VARIANT              285
                     note = X can be any amino acid
VARIANT              297
```

-continued

```
                      note = X can be any amino acid
VARIANT               300
                      note = X can be any amino acid
VARIANT               333
                      note = X can be any amino acid
VARIANT               365
                      note = X can be any amino acid
VARIANT               384
                      note = X can be any amino acid
VARIANT               386
                      note = X can be any amino acid
VARIANT               391
                      note = X can be any amino acid
VARIANT               396..398
                      note = X can be any amino acid
VARIANT               404
                      note = X can be any amino acid
VARIANT               442
                      note = X can be any amino acid
VARIANT               444
                      note = X can be any amino acid
VARIANT               476
                      note = X can be any amino acid
VARIANT               502
                      note = X can be any amino acid
VARIANT               523
                      note = X can be any amino acid
VARIANT               525
                      note = X can be any amino acid
VARIANT               529
                      note = X can be any amino acid
VARIANT               532
                      note = X can be any amino acid
VARIANT               547
                      note = X can be any amino acid
VARIANT               723
                      note = X can be any amino acid
VARIANT               742
                      note = X can be any amino acid
VARIANT               763
                      note = X can be any amino acid
VARIANT               773
                      note = X can be any amino acid
VARIANT               775
                      note = X can be any amino acid
VARIANT               779
                      note = X can be any amino acid
VARIANT               794
                      note = X can be any amino acid
VARIANT               825
                      note = X can be any amino acid
VARIANT               839
                      note = X can be any amino acid
VARIANT               844
                      note = X can be any amino acid
VARIANT               857
                      note = X can be any amino acid
VARIANT               905
                      note = X can be any amino acid
VARIANT               908
                      note = X can be any amino acid
VARIANT               914
                      note = X can be any amino acid
VARIANT               931
                      note = X can be any amino acid
VARIANT               1020..1021
                      note = X can be any amino acid
VARIANT               1088
                      note = X can be any amino acid
VARIANT               1114
                      note = X can be any amino acid
VARIANT               1118
                      note = X can be any amino acid
VARIANT               1384
                      note = X can be any amino acid
VARIANT               1613
                      note = X can be any amino acid
VARIANT               1756
                      note = X can be any amino acid
```

-continued

```
VARIANT                 2262
                        note = X can be any amino acid
VARIANT                 2356
                        note = X can be any amino acid
VARIANT                 2374
                        note = X can be any amino acid
VARIANT                 2385
                        note = X can be any amino acid
VARIANT                 2540
                        note = X can be any amino acid
VARIANT                 2601
                        note = X can be any amino acid
VARIANT                 2636
                        note = X can be any amino acid
VARIANT                 2674
                        note = X can be any amino acid
VARIANT                 2994
                        note = X can be any amino acid
VARIANT                 3002
                        note = X can be any amino acid
source                  1..3013
                        mol_type = protein
                        organism = synthetic construct
SEQUENCE: 103
MSTNPKPQRK TKRNTNRRPQ DVKFPGGGQI VGGVYLLPRR GPRLGVRATR KTSERSQPRG  60
RRQPIPKARR PTGRSWGQPG YPWPLYANEG LGWAGWLLSP RGSRPNWGPN DPRRKSRNLG  120
KVIDTLTCGF ADLMGYIPLV GGPVGGVARA LAHGVRVLED GINYATGNLP GCSFSIFXLA  180
LLSCLTVPXS AVPYRNASGV YHVTNDCPNS SIVYEAENLI LHAPGCVPCV RXGNVSRCWV  240
QITPTLSAPS XGAVTAXLRR AVDYLAGGAA LCSALYVGDA CGAVXLVGQM FTYSPRXHTX  300
VQDCNCSIYS GHITGHRMAW DMMMNWSPTT ALXMAQLLRI PQVVIDIIAG AHWGVLFAAA  360
YFASXANWAK VILVLFLFAG VDAXTXTVGG XAGQGXXXLT SFFXPGPQQN LQLINTNGSW  420
HINRTALNCN DSLQTGFIAG LXYXHKFNSS GCPQRMASCR PLAAFDQGWG TISYAXVSGP  480
SDDKPYCWHY PPRPCGVVPA RXVCGPVYCF TPSPVVVGTT DRXGXPTYXW GXNETDIFLL  540
NNTRPPXGNW FGCTWMNSTG FVKTCGAPPC NLGPTGNNSL KCPTDCFRKH PDATYTKCGS  600
GPWLTPRCLV HYPYRLWHYP CTVNYTIFKV RMFIGGLEHR LEAACNWTRG ERCDLEDRDR  660
AELSPLLHTT TQWAILPCSF TPTPALSTGL IHLHQNIVDT QYLYGLSSSI VSWAVKWEYI  720
VLXFLLLADA RICTCLWILL LXCQAEAALE NVIVLNAAAA AGXHGFFWGL LVXCXAWHXK  780
GRLVPGATYL CLGXWPLLLL LLLLPQRALA LDSSDGGTVG CLVLXILTIF TLTPGYKKXV  840
VLVXWWLQYF IARVEAXIHV WVPPLQVRGG RDAIIMLTCL FHPALGFEVT KILLGILGPL  900
YLLQXSLXKV PYFXRARALL RACLLAKHLV XGKYVQAALL HLGRLTGTYI YDHLAPMKDW  960
AASGLRDLAV ATEPIIFSPM ETKVITWGAD TAACGDILAG LPVSARRGRE IFLGPADDIX  1020
XAGWRLLAPI TAYAQQTRGV LGAIVVSLTG RDKNEAEGEV QVLSTATQTF LGTCINGVMW  1080
TVFHGAGXKT LAGPKGPVVQ MYTNVDKDLV GWPXPPGXRS LTPCTCGSAD LYLVTRHADV  1140
IPARRRGDTR ASLLSPRPIS YLKGSSGGPI MCPSGHVVGV FRAAVCTRGV AKALDFIPVE  1200
NLETTMRSPV FTDNSTPPAV PHEFQVGHLH APTGSGKSTK VPAAYAAQGY KVLVLNPSVA  1260
ATLGFGAYMS RAYGVDPNIR TGVRTVTTGA AITYSTYGKF LADGGCSGGA YDVIICDECH  1320
SQDATTILGI GTVLDQAETA GARLVVLATA TPPGSVTTPH PNIEEVALPS EGEIPFYGRA  1380
IPLXLIKGGR HLIFCHSKKK CDELAKQLTS LGVNAVAYYR GLDVAVIPAT GDVVVCSTDA  1440
LMTGFTGDFD SVIDCNTAVT QTVDFSLDPT FTIETTTVPQ DAVSRSQRRG RTGRGRHGIY  1500
RYVSSGERPS GIFDSVVLCE CYDAGCAWYD LTPAETTVRL RAYLNTPGLP VCQDHLEFWE  1560
GVFTGLTNID AHMLSQTKQG GENFPYLVAY QATVCVRAKA PPPSWDTMWK CMXRLKPTLT  1620
GPTPLLYRLG AVQNEITLTH PITKYIMACM SADLEVITST WVLVGGVVAA LAAYCLTVGS  1680
VAIVGRIILS GRPAIIPDRE VLYQQFDEME ECSASLPYMD EARAIAEQFK EKVLGLIGTA  1740
GQKAETLKPA ATSMWXKAEQ FWAKHMWNFV SGIQYLAGLS TLPGNPAVAT LMSFTAAVTS  1800
PLTTQQTLLF NILGGWVASQ IAPPTAATAF VVSGMAGAAV GSIGLGRVLI DILAGYGAGV  1860
AGALVAFKIM CGERPTAEDL VNLLPSILCP GALVVGVICA AVLRRHIGPG EGAVQWMNRL  1920
IAFASRGNHV SPTHYVPETD ASAKVTQLLS SLTVTSLLKR LHTWIGEDYS TPCDGTWLRA  1980
IWDWVCTALT DFKAWLQAKL LPQLPGVPFL SCQRGYKGVW RGDGVNSTKC PCGATISGHV  2040
KNGTMRIVGP KLCSNTWHGT FPINATTTGP SVPAPAPNYK FALWRVGAAD YAEVRRVGDY  2100
HYITGVTQDN LKCPCQVPSP EFFTELDGVR IHRYAPPCNP LLREEVCFSV GLHSYVVGSQ  2160
LPCEPEPDVT VLTSMLSDPA HITAETAKRR LDRGSPPSLA SSSASQLSAP SLKATCTTQG  2220
HHPDADLIEA NLLWRQCMGG NITRVEAENK VVILDSFEPL KXEEDDREIS VSADCFRRGP  2280
AFPPALPIWA RPGYDPPLLE TWKRPDYDPP QVSGCPLPPA GLPPVPPPRR KRKPVELSDS  2340
TVSQVLADLA DARFKXDTPS IEGQDSAVGT SSQXDSGPEE KRDDXSDAAS YSSMPPLEGE  2400
PGDPDLSSGS WSTVSDEDSV VCCSMSYSWT GALITPCSAE EEKLPINPLS NTLLRHHNLV  2460
YSTSSRSAGL RQKKVTFDRL QVLDDHYREV VDEMKRLASK VKARLLPLEE ACGLTPPHSA  2520
RSKYGYGAKE VRSLDKKALX HIEGVWQDLL DDSDTPLPTT IMAKNEVFAV EPSKGGKKPA  2580
RLIVYPDLGV RVCEKRALYD XAQKLPTALM GPSYGFQYSP AQRVEFLLKT WKSKKXPMAF  2640
SYDTRCFDST VTEHDIMTEE SIYQSCDLQP EARXAIRSLT QRLYCGGPMY NSKGQQCGYR  2700
RCRASGVFTT SMGNTMTCYI KALASCRAAK LRDCTLLVCG DDLVAICESQ GTHEDEASLR  2760
AFTEAMTRYS APPGDPPVPA YDLELVTSCS SNVSVARDAS GNRVYYLTRD PQVPLARAAW  2820
ETAKHSPVNS WLGNIIMYAP TLWARIVLMT HFFSVLQSQE QLEKALAFEM YGSVYSVTPL  2880
DLPAIIQRLH GLSAFSLHSY SPSEINRVAS CLRKLGVPPL RAWRHRARAV RAKLIAQGGK  2940
AAICGIYLFN WAVKTKRKLT PLADADRLDL SSWFTVGAGG GDIYHSMSRA RPRXLLCLLL  3000
LXVGVGIFLL PAR                                                     3013

SEQ ID NO: 104          moltype = AA  length = 3014
FEATURE                 Location/Qualifiers
VARIANT                 195
```

```
                         note = X can be any amino acid
VARIANT                  237
                         note = X can be any amino acid
VARIANT                  389
                         note = X can be any amino acid
VARIANT                  400
                         note = X can be any amino acid
VARIANT                  403
                         note = X can be any amino acid
VARIANT                  572
                         note = X can be any amino acid
VARIANT                  1877
                         note = X can be any amino acid
VARIANT                  1944
                         note = X can be any amino acid
VARIANT                  1967
                         note = X can be any amino acid
source                   1..3014
                         mol_type = protein
                         organism = synthetic construct
SEQUENCE: 104
MSTLPKPQRK TKRNTNRRPM DVKFPGGGQI VGGVYLLPRR GPRLGVRATR KTSERSQPRG  60
RRQPIPKARQ PTGRHWAQPG YPWPLYGNEG CGWAGWLLSP RGSRPHWGPN DPRRRSRNLG  120
KVIDTLTCGF ADLMGYIPVV GAPLGGVAAA LAHGVRAIED GINYATGNLP GCSFSIFLLA  180
LLSCLTTPAS AVHYXNSSGI YHLTNDCPNS SIVYEADAMI LHLPGCVPCV RVGNQSXCWV  240
PVSPTLAVPN ASTPATGFRR HVDLLVGAAA FCSALYIGDL CGGVFLVGQL FTFRPRRHQT  300
VQDCNCSIYT GHVTGHRMAW DMMMNWSPTA TLVLSSILRV PQLLLDIFLG GHWGVLGAVL  360
YYSMVANWAK VLAVLLLFAG VDATTTTGXA AGRTTSGLTX LFXPGAKQNL QLINTNGSWH  420
INRTALNCND SLQTGFIAGL FYTHKFNSSG CPERMSSCKP LTDFDQGWGP ITYANISGPS  480
EDRPYCWHYA PRPCDVVPAR TVCGPVYCFT PSPVVVGTTD RRGLPTYTWG ENETDVFLLE  540
SLRPPTGGWF GCTWMNSTGF VKTCGAPPCN IXPNSSNNSL LCPTDCFRKH PEATYARCGS  600
GPWLTPRCLV DYPYRLWHYP CTVNFTIHKV RMFVGGVEHR FDAACNWTRG ERCELDDRDR  660
IEMSPLLFST TELAILPCSF TTMPALSTGL IHLHQNIVDV QYLYGVSSSV VSWAVKWEYV  720
VLAFLVLADA RICACLWLML LIGQAEAALE NLIVLNAASA ASTQGWWWGL LFLCCAWYVK  780
GRLVPACTYA LLQLWPLLLL VLALPRRAYA YDNEQAASLG ALVLLVITIF TLTPAYKQLL  840
VSFLWWNQYF IARAEAMLHV WVPSLRVRGG RDAVILLTCL LHPQLGFEVT KILLALLGPL  900
YLLQYSLLKV PYFVRAHILL RACLLVRRLA GGKYVQACLL RLGAWTGTYI YDHLAPLSDW  960
ASDGLRDLAV AVEPVIFSPM EKKVITWGAD TAACGDILAG LPVSARRGNL VLLGPADDMK  1020
RGGWRLLAPI TAYAQQTRGL LGTIVTSLTG RDKNEVEGEV QVVSTATQSF LATSINGVLW  1080
TVYHGAGSKT LAGPKGPVCQ MYTNVDQDLV GWPAPPGARS LTPCTCGSSD LYLVTRNADV  1140
IPARRRGDTR AALLSPRPIS TLKGSSGGPI LCPSGHVVGL FRAAVCTRGV AKSLDFVPVE  1200
NMETTMRSPS FTDNSTPPAV PQTYQVGYLH APTGSGKSTK VPAAYASQGY KVLVLNPSVA  1260
ATLGFGSYMS KAHGIDPNIR TGVRTITTGG AITYSTYGKF LADGGCSGGA YDIIICDECH  1320
STDPTTVLGI GTVLDQAETA GVRLTVLATA TPPGSVTVPH PNITETALPT TGEIPFYGKA  1380
IPLEYIKGGR HLIFCHSKKK CDELAKQLTS LGLNAVAFYR GVDVSVIPTS GDVVVCATDA  1440
LMTGYTGDFD SVIDCNVAVT QVVDFSLDPT FSIETTTVPQ DAVSRSQRRG RTGRGKPGVY  1500
RYVSQGERPS GMFDTVVLCE AYDTGCAWYE LTPSETTVRL RAYLNTPGLP VCQDHLEFWE  1560
GVFTGLTHID AHFLSQTKQG GENFAYLVAY QATVCARAKA PPPSWDTMWK CLIRLKPMLT  1620
GPTPLLYRLG AVQNEITTTH PITKYIMTCM SADLEVITST WVLVGGVLAA LAAYCLSVGC  1680
VVICGRITTT GKPAVIPDRE VLYQQFDEME ECSRHIPYLA EGQQIAEQFK QKVLGLLQTT  1740
AKQAEELKPA VHSAWPKLEQ FWQKHLWNFV SGIQYLAGLS TLPGNPAVAS LMSFSASLTS  1800
PLSTSTTLLL NILGGWVASQ LAPPTASTAF VVSGLAGAAV GSIGLGRVLV DILAGYGAGV  1860
SGALVAFKIM SGETPAXEDM VNLLPALLSP GALVVGVVCA AILRRHVGPA EGATQWMNRL  1920
IAFASRGNHV SPTHYVPETD ASRXVTTILS SLTITSLLRR LHEWINXDWS TPCATSWLRD  1980
IWDWVCTVLS DFKTWLKAKL VPSLPGIPFL SCQRGFRGVW RGDGVCHTTC TCGAVIAGHV  2040
KNGTMKISGP RTCSNTWHGT FPINATTGP SVPIPEPNYK RALWRVSAED YVEVVRVGDC  2100
HYVVGATADN LKCPCQVPAP EFFTEVDGVR LHRYAPPCKP LLRDEVTFSV GLSSYAIGSQ  2160
LPCEPEPDVT VVTSMLTDPS HITAETAARR LARGSPPSLA SSSASQLSAP SLKATCTTHG  2220
DHPDAELIEA NLLWRQEMGG NITRVESENK VIVLDSFDPL VAEYDDREIS VSAECHRPPR  2280
PKFPPALPIW ARPDYNPPLL ETWKAPDYEP PVVSGCALPP PGPPPIPPPR RKKVVHLDES  2340
TVSHALAQLA EKSFPESSSD STSSDSGLSI TSSGSPEPTT DDDACSEAGS YSSMPPLEGE  2400
PGDPDLSSGS WSTVSEEDSV VCCSMSYSWT GALITPCAAE EEKLPINPLS NSLIRHHNLV  2460
YSTTSRSASL RQKKVTFDRV QVLDQHYQDV LKEIKLRASQ VQARLLSTEE ACDLTPPHSA  2520
RSKFGYGAKD VRSHASKAIN HINSVWEDLL EDNQTPIPTT IMAKNEVFCV DPSKGGRKPA  2580
RLIVYPDLGV RVCEKRALYD ITRKLPVAVM GDAYGFQYSP KQRVDYLLKM WRSKKTPMGF  2640
SYDTRCFDST VTERDIRTEH DIYQSCQLDP EARKAITSLT ERLYVGGPMY NSKGQSCGYR  2700
RCRASGVLPT SLGNTLTCYL KAQAACRAAG LKDFDMLVCG DDLVVISESA GVQEDAAALR  2760
AFTEAMTRYS APPGDEPQPT YDLELITSCS SNVSVAHDGT GQRYYYLTRD PTTPLARAAW  2820
ETARHTPVNS WLGNIIMYAP TIWVRMVLMT HFFQILQSQE QLHKALDFDI YGVTYSITPL  2880
DLPAIIQRLH GMAAFSLHGY SPGELNRVAA CLRKLGAPPL RAWRHRARAV RAKLIAQGGK  2940
AACICGKYLFN WAVKTKLKLT PLRGASKLDL SGWFVAGYSG GDIYHSVSRA RPRMLLLCLL  3000
LLTVGVGIFL LPAR                                                   3014

SEQ ID NO: 105           moltype = AA  length = 3013
FEATURE                  Location/Qualifiers
source                   1..3013
                         mol_type = protein
                         organism = hepatitis C virus
SEQUENCE: 105
```

-continued

MSTNPKPQRL TKRNTVRRPQ NVKFPGGGQI VGGVYLLPRR GPRLGVRGTR KSSERSQPRG 60
RRQRIPKAAS SQGKAWGKPG YPWPLYGNEG CGWAGWLLSP RGSRPTWGPT DPRHRSRNLG 120
KVIDTMTCGF ADLMGYIPVL GAPLGGVARA LAHGVRVLED GVNYATGNLP GCSFSIFLLA 180
LLSCLTVPAS AYEVRNSSGV YHLTNDCPNA SIVYETDNAI LHEPGCVPCV REGNTSRCWE 240
PVAPTLAVRY RGALTDDLRT HIDLVVASAT LCSALYVGDI CGAIFIASQA VLWKPGGGRI 300
VQDCNCSIYP GHVTGHRMAW DMMQNWAPAL SMVAAYAVRV PGVIITTVAG GHWGVLFGLA 360
YFGMAGNWAK VILIMLLMSG VDAETMAVGA RAAHTTGALV SLLNPGPSQR LQLINTNGSW 420
HINRTALNCN DSLQTGFIAA LFYTHRFNSS GCPERMASCK PLSDFDQGWG PLWYNSTERP 480
SDQRPYCWHY APSPCGIVPA KDVCGPVYCF TPSPVVVGTT DRRGVPTYTW GENESDVFLL 540
NSTRPPQGSW FGCSWMNTTG FTKTCGGPPC KIRPQGAQSN TSLTCPTDCF RKHPRATYSA 600
CGSGPWLTPR CMVHYPYRLW HYPCTVNFTI HKVRLYIGGV EHRLDAACNW TRGERCDLED 660
RDRVDMSPLL HSTTELAILP CSFVPLPALS TGLIHLHQNI VDAQYLYGLS PAIISWAIRW 720
EWVVLVFLLL ADARICACLW MMMLMAQAEA ALENLIHLNA ASLAGTHGIW WLLLVFCASW 780
HLRGRVVPLV TYGICGMWPF FLMLLSLPPR AYALDREVSA ALGTGMLAII LLVTLGPHYK 840
RLLALILWWV TYFLTRCEAA LQTWVPPLNP RGGRDGFILC VLLCYPGLVF DITKWLLVMM 900
CPLYLLQLCL VRTPYFVRAQ ALIRVCSLFK TLAGGRYVQA ALLTIGRWTG TYIYNHLAPL 960
ETWAAGGLRD LAVAVEPVIF SPMEKKIIVW GAETTACGDI LCGLPVSARL GREVLLGPAD 1020
DYRSMGWQLL APISAYAQQT RGLISTLVVS LTGRDKNETA GEVQVLSTST QTFLGTNVGG 1080
VMWGPYHGAG TRTVAGRGGP VLQMYTSVSD DLVGWPAPPG SKSLEPCSCG SADLYLVTRN 1140
ADVLPLRRKG DGTASLLSPR PVSSLKGSSG GPVLCPQSHC VGIFRAAVCT RGVAKAVQFV 1200
PIEKMQVAQR SPSFSDNSTP PAVPSTYQVG YLHAPTGSGK STKVPAAYAS QGYKVLVLNP 1260
SVAATLGFGA YMSKAYGIDP SVRTGARTVT TGAPITYSTY GKFLADGGCS GGAYDIIICD 1320
ECHAIDATTV VGIGTVLDQA ETSGVRLVVL ATATPPGSVT VPHPNIEEVA LGNDGEIPFY 1380
GKAIPLQHIK GGRHLIFCHS KKKCDELAGK LTSLGLTAVA YYRGLDVSVI PTSGDVVVVA 1440
TDALMTGFTG DFDSVIDCNV AVTQTVDFSL DPTFTIETTT VPQDSVSRSQ RRGRTGRGRL 1500
GIYRYVSSGE RPSGMFDTSV LCECYDLGCS WYELTPSETT TRLRAYLNCP GLPVCQDHLE 1560
FWEGVFTGLT HIDAHFLSQT KQEGQNYAYL TAYQATVCAR AKAPPPSWDV QWKCLQRLKP 1620
LLVGPTPLLY RLGSVTNEVT FTHPITKYIA TCMAADLEVT TSTWVIVGGV LAAVAAYCMS 1680
TGSVVVVGRV VLGSNVVTAP DREVLYQHFD EMEECSKAPE LLKHAQTIGG MFKDKALAVL 1740
DTLKPAAQAA VPIVETNFQK VEKLWNQHMW NFISGIQYLA GLSTLPGNPT VASLMAFTAS 1800
VTSPLATSTT LLVNILGGWF ASQLAPPSAA TTFVVSGLAG AAVGSVGLGK VLVDVLAGYG 1860
AGIAGALVAF KIMSGEVPST EDLANLLPAI LSPGALVVGV VCAAIIKRHT GTSEGVTQWM 1920
NRLIAFASRG NHVSPTHYIQ DDDASKRVMG ILSSLTITSL IKRVLAWAQT DYSAPCAGSW 1980
LREVWDWVCM VLSDFASWLK AKVLPSLPGI PFLSCQKGYK GEWRNDGIMN TKCPCGALIA 2040
GHVKNGSMRI VGPKTCRNTW WGTFPINSHT TGPSSPVPSH CYQRALWRVS ATEYVEILRH 2100
NDQHYVVGVT AEDLKCPCQV PSPEFFSFVD GVRIHRFAPE PKPMIREEAA FVVGLHSYVV 2160
GSQLPCEPEP DVQTVSQLLT DPSHITAETA ARRLRRGSPP SNASSSASQL SAPSLKATHT 2220
TLPQHPDAEL IEANLMWEHK VGAIRRMETD TKVIILDSFD SASSVEDDME PSTAAECLRT 2280
RKVFPPAMPI WARPDYNPPV VENWKDPEYA PPQVSGCALP PAQTPPVPPP RRKRAVIQLT 2340
ESAVSTALAE LAERSFPKEE APPSDSAISL DSPAANDPPS DCDQGSEISF SSMPPLEGEP 2400
GDPDLSDGSW STVSTRSDVI CCSMSYSWTG ALVTPSGPEE ERLPINALSN TMLRHYNMVY 2460
STTSRSASQR AKKVTFDRLQ VLDDHYKRAL ADVKADASTV KAQLLSVEEA AALTPAHSAR 2520
SKFGYGAKEV RSLAPKAMSH IKEVWKDLLQ DMTTPIPTTI MAKNEVFCVN PAKGGKKPAR 2580
LIVYPDLGVR VCEKRALYDI AQKLPKAIMG QAYGFQYSPS QRVEYLVKTW KSKRTPMGFS 2640
YDTRCFDSTV TEQDIRTESE IYQCCNLDPE ARTIINALTE RLYVGGPMFN SKGQRVGYRR 2700
CRASGVFPTS MGNTMTCYIK AKAAAAAAGL ESTDFLVCGD DLVVICESKG VERDRADLQA 2760
FAAAMTRYSA PPGDMPQPAY DLEHIDSCSS NVSVARDNSG KRVYYLTRDP TNPLSRAAWE 2820
TARHSPVNSW VGNIIMFAPT IWVRMVLMTH FFALLLNEER LNDPVSFEMY GATYTVCPTD 2880
LPDIIQRLHG LRAFELHTYS PAELTRVAAT LRKLGVPPLR TWRQRARKVR AGLIGQGGRA 2940
RICGLYLFNW AVRTKIKLTP LAGAGRLDLS SWFSVCAGEA DVDHSTPRAH PRPLLLCLLL 3000
LAVGVGIFLL PAR 3013

SEQ ID NO: 106 moltype = AA length = 3008
FEATURE Location/Qualifiers
VARIANT 1871
note = X can be any amino acid
source 1..3008
mol_type = protein
organism = hepatitis C virus
SEQUENCE: 106
MSTNPKPQRK TKRNTNRRPQ DVKFPGGGQI VGGVYLLPRR GPRLGVRATR KTSERSQPRG 60
RRQPIPKARR PEGRTWAQPG YPWPLYGNEG CGWAGWLLSP RGSRPSWGPT DPRRRSRNLG 120
KVIDTLTCGF ADLMGYIPLV GAPLGGAARA LAHGVRVLED GVNYATGNLP GCSFSIFLLA 180
LLSCLTVPAS AYQVRNSTGL YHVTNDCPNS SIVYEAADAI LHTPGCVPCV REGNTSRCWV 240
AMTPTVATRD GKLPTTQLRR HIDLLVGSAT LCSALYVGDL CGSVFLVGQM FTFSPRRHWT 300
TQDCNCSLYP GHITGHRMAW DMMMNWSPTA ALITAQLLRI PQAILDMIAG AHWGVLAGIA 360
YFSMVGNWAK VLVVLLLFAG VDAQTHVTGG RAAHITAGLT SLFSPGPSQK LQLVNTNGSW 420
HINSTALNCN DSLKTGWIAG LLYSYKFNSS GCPERLASCR RLTDFAQGWG PISHANGSGP 480
DERPYCWHYP PRPCGIVPAK SVCGPVYCFT PSPVVVGTTD KSGAPTYNWG ENDWDVFVLN 540
NTRPPLGNWF GCTWMNSTGF TKVCGAPPCV IGGAGNNTLR CPTDCFRKHP DATYSRCGSG 600
PWITPRCLVD YPYRLWHYPC TVNYSIFKIR MYLGGVEHRL EAACNWTRGE RCDLEDRDRS 660
ELSPLLLSTT QWQVLPCSFT TLPALSTGLI HLHQNIVDVQ YLYGVGSSVA SWAIKWDYVV 720
LLFLLLADAR ICSCLWMMLL ISQAEAALEN LVVLNAASLA GTHGLAPFLV FFCLAWYLKG 780
KWAPGAVYAV YGMWPLLLLL LALPQRAYAL DTEVAASCGG AVLVGLMVLT LSPHYKHYIS 840
WCLWWLQYFL TRAEAQLHVW VPPLNVRGGR DAVILLMCVV HPTLVFDITK LLLAVGPLWI 900
LQTSLLKVPY FVRVQGLLRI CALARKIAGG HYVQMAIIKL GALTGTYIYD HLTPLRDWAH 960
NGLRDLAVAV EPVVFSRMET KLITWGADTA ACGDIINGLP VSARRGQEIL LGPADGMVSK 1020
GWRLLAPITA YAQQTRGLLG CIITSLTGRD KNQVEGEVQI VSTAAQTFLA TCINGVCWTV 1080
YHGAGTRTIA SPKGPVIQMY TNVDKDLVGW PAPPGSRSLT PCTCGSSDLY LVTRHADVIP 1140

-continued

```
VRRRGDSRGS LLSPRPISYL KGSSGGPLLC PAGHAVGIFR AAVCTRGVAK AVDFIPVESL  1200
ETTMRSPVFT DNSSPPVVPQ SFQVAHLHAP TGSGKSTKVP AAYAAQGYKV LVLNPSVAAT  1260
LFGAYMSKAH GVDPNIRTGV RTITTGSPIT YSTYGKFLAD GGCSGGAYDI IICDECHSTD  1320
ATSILGIGTV LDQAETAGAR LVVLATATPP GSVTVPHPNI EEVALSTTGE IPFYGKAIPL  1380
EVIKGGRHLI FCHSKKKCDE LAAKLVALGI NAVAYYRGLD VSVIPTSGDV VVVATDALMT  1440
GYTGDFDSVI DCNTCVTQTV DFSLDPTFTI ETTTLPQDAV SRTQRRGRTG RGKPGIYRFV  1500
APGERPSGMF DSSVLCECYD AGCAWYELTP AETTVRLRAY MNTPGLPVCQ DHLEFWEGVF  1560
TGLTHIDAHF LSQTKQSGEN FPYLVAYQAT VCARAQAPPP SWDQMWKCLI RLKPTLHGPT  1620
PLLYRLGAVQ NEVVLTHPIT KYIMTCMSAD LEVVTSTWVL VGGVLAALAA YCLSTGCVVI  1680
VGRVVLSGKP AIIPDREVLY QEFDEMEECS QHLPYIEQGM MLAEQFKQKA LGLLQTASRQ  1740
AEVIAPAVQT NWQKLEAFWA KHMWNFISGI QYLAGLSTLP GTPAIASLMA FTAAVTSPLT  1800
TSQTLLFNIL GGWVAAQLAA PGAATAFVGA GLAGAAIGSV GLGKVLVDIL AGYGAGVAGA  1860
LVAFKIMSGE XPSTEDLVNL LPAILSPGAL VVGVVCAAIL RRHVGPGEGA VQWMNRLIAF  1920
ASRGNHVSPT HYVPESDAAA RVTAILSSLT VTQLLRRLHQ WISSECTTPC SGSWLRDIWD  1980
WICEVLSDFK TWLKAKLMPQ LPGIPFVSCQ RGYRGVWRGD GIMHTRCHCG AEITGHVKNG  2040
TMRIVGPRTC RNMWSGTFPI NAYTTGPCTP LPAPNYKFAL WRVSAEEYVE IRQVGDFHYV  2100
TGMTTDDLKC PCQVPSPEFF TELDGVRLHR FAPPCKPLLR EEVSFRVGLH AYPVGSQLPC  2160
EPEPDVAVLT SMLTDPSHIT AETARRLARG SPPSVASSSA SQLSAPSLKA TCTANHDSPD  2220
AELIEANLLW RQEMGGNITR VESENKVVIL DSFDPLVAEE DEREISVPAE ILRKSRRFTQ  2280
ALPVWARPDY NPPLVEAWKK PDYEPPVVHG CPLPPPKSPP VPPPRKKRTV VLTESTLSTA  2340
LAELATKSFG SSSTSGITGD NTTTSSEPAP PGCSPDSDAE SCSSMPPLEG EPGDPDLSDG  2400
SWSTVSSEAD TEDVVCCSMS YTWTGALITP CAAEEQKLPI NALSNSLLRH HNLVYSTTSR  2460
SACQRQKKVT FDRLQVLDNH YQDVLKEVKA AASKVKANLL SVEEACSLTP PHSAKSKFGY  2520
GAKDVRCHAR KAVNHINSVW KDLLEDSVTP IDTTIMAKNE VFCVQPEKGG RKPARLIVFP  2580
DLGVRVCEKM ALYDVVSKLP LAVMGDSYGF QYSPGQRVEF LVQAWKSKKT PMGFSYDTRC  2640
FDSTVTESDI RTEEAIYQCC DLDPQARVAI KSLTERLYVG GPLTNSRGEN CGYRRCRASG  2700
VLTTSCGNTL TCYIKAKAAC RAAGLQNCTM LVCGDDLVVI CESAGVQEDA ASLRAFTEAM  2760
TRYSAPPGDP PQPEYDLELI TSCSSNVSVA HDGAGKRVYY LTRDPTTPLA RAAWETARHT  2820
PVNSWLGNII MFAPTLWARM VLMTHFFSVL IARDQLEQAL DCEIYGACYS IEPLDLPPII  2880
QRLHGLSAFS LHSYSPGEIN RVAACLRKLG VPPLRTWRHR ARSVRAKLLS RGGRAAICGK  2940
YLFNWAVRTK LKLTPIAAAG RLDLSGWFTA GYSGGDIYHS VSHARPRWFW FCLLLLAAGV  3000
GIYLLPNR                                                           3008

SEQ ID NO: 107          moltype = AA  length = 3021
FEATURE                 Location/Qualifiers
source                  1..3021
                        mol_type = protein
                        organism = hepatitis C virus
SEQUENCE: 107
MSTLPKPQRK TKRNTIRRPQ DVKFPGGGQI VGGVYVLPRR GPRLGVRATR KTSERSQPRE  60
RRQPIPKARR SDGRSWAQPG YPWPLYGNEG CGWAGWLLSP RGSRPSWGPN DPRRRSRNLG  120
KVIDTLTCGF ADLMGYIPIV GAPVGGVARA LAHGVRALED GINFATGNLP GCSFSIFLLA  180
LLSCLIHPAA SLEWRNTSGL YILTNDCPNS SIVYEADDVI LHTPGCIPCV QDGNTSTCWT  240
SVSPTVAVRY VGATTASIRS HVDLLVGAAT LCSALYVGDM CGAVFLVGQA FTFRPRRHQT  300
VQTCNCSLYP GHLTGHRMAW DMMMNWSPAV GMVVAHVLRM PQTVFDIIAG AHWGILAGLA  360
YYSMQGNWAK VAIIMVMFSG VDAETHTTGG TAARNAFTLT GLFTQGARQK LQLINTNGSW  420
HINRTALNCN ESLNTGFIAG LFYLHKFNST GCPERLSSCK PITFFRQGWG SLTDANITGP  480
SDDKPYCWHY APRPCEVVPA LNVCGPVYCF TPSPVVVGTT DRQGVPTYTW GENETDVFLL  540
RSLRPPSGQW FGCTWMNSTG FVKTCGAPPC DIYGGGGNRC NESDLFCPTD CFRKHPEATY  600
SRCGAGPWLT PRCLVDYPYR LWHYPCTVNF TLFKVRMFVG GFEHRFTAAC NWTRGERCNI  660
EDRDRSEQHP LLHSTTELAI LPCSFTPMPA LSTGLIHLHQ NIVDVQYLYG VGSGVVGWAL  720
RWEFVVLVFL LLADARVCVA LWLMLMISQA EAALENLVTL NAVAAAGTHG IGWYLVAFCA  780
AWHLRGKLVP LVTYSLTGLW SLAVLVLLLP QRAYAWSGED SATLGAGILV LFGFFTLSPW  840
YKHWIGRLMW WNQYTICRCE AALQVWVPPL LARGSRDGAI LLTSLLYPSL IFDITKLLIA  900
VLGPLYLIQA AITTTPYFVR AHVLVRLCML VRSVMGGKYF QMIILSIGRW FNTYLYDHLA  960
PMQHWAAAGL KDLAVATEPV IFSPMEIKVI TWGADTAACG DILCGLPVSA RLGHEVLLGP  1020
ADDYREMGWR LLAPITAYAQ QTRGLLGTIV TSLTGRDKNV VTGEVQVLST ATQTFLGTTI  1080
GGVMWTVYHG AGSRTLAGVK HPALQMYTNV DQDLVGWPAP PGAKSLEPCS CGSTDLYLVT  1140
READVIPARR RGDSTASLLS PRPLACLKGS SGGPVMCPSG HVAGIFRAAV CTRGVAKALQ  1200
FIPVETLSAQ ARSPSFSDNS TPPIVPQSYQ VGYLHAPTGS GKSTKVPAAY VAQGYNVLVL  1260
NPSVAATLGF GSFMSRAYGI DPNIRTGNRT VTTGAKLTYS TYGKFLADGG CSGGAYDVII  1320
CDECHAQDAT SILGIGTVLD QAETAGVRLT VLATATPPGS ITVPHSNIEE VALGSEGEIP  1380
FYGKAIPLAQ LKGGRHLIFC HSKKKCDEMA SKLRGMGLNA VAYYRGLDVS VIPTAGDVVV  1440
CATDALMTGF TGDFDSVIDC NVTVEQYVDF SLDPTFSIET RTAPQDAVSR SQRRGRTGRG  1500
RLGTYRYVAP GERPSGMFDS VVLCECYDAG CSWYDLQPAE TTVRLRAYLS TPGLPVCQDH  1560
LDFWESVFTG LTHIDAHFLS QTKQQGLNFS YLTAYQATVC ARAQAPPPSW DEMWKCLLRL  1620
KPTLHGPTPL LYRLGPVQNE TCLTHPVTKY IMACMSADLE VTTSTWVLLG GVLAALAAYC  1680
LSVGCVVIVG HIELGGKPAL IPDKEVLYQQ YDEMEECSQA APYVEQAQAI AHQFKEKLLG  1740
LLQRATQQQA VIEPIVATNW QKLEAFWHKH MWNFVSGIQY LAGLSTLPGN PAVASLMAFT  1800
ASVTSPLTTN QTMFFNILGG WVATHLAGPQ SSSAFVVSGL AGAAIGGIGL GRVLLDILAG  1860
YGAGVSGALV AFKIMGGEIP TAEDMVNLLP AILSPGALVV GVICAAILRR HVGPGEGAVQ  1920
WMNRLIAFAS RGNHVSPTHY VPESDAAARV TALLSSLTVT SLLRRLHHWI NEDYPSPCSG  1980
DWLRTIWDWV CMVLSDFRTW LSAKIMPALP GLPFLSCQKG YKGVWRGDGV VSTRCPCGAS  2040
ITGHVKNGSM RLAGPRTCAN MWHGTFPINE YTTGPSTPCP SPNYTRALWR VAANSYVEVR  2100
QVGDFHYITG ATEDGLKCPC QVPAAEFFTE VDGVRLHRYA PPCKPLLRDE ITFMVGLNSY  2160
AIGSQLPCEP EPDVSVLTSM LRDPSHITAE TAARRLARGS PPSEASSSAS QLSAPSLKAT  2220
CQTHRPHPDA ELVDANLLWR QEMGSNITRV ESETKVVILD SFEPLRAEAD DAELSVAAEC  2280
FKKPPKYPPA LPIWARPDYN PPLLDRWKTP DYVPPTVHGC ALPPRGAPPV PPPRRKRTVQ  2340
LDGSNVSAAL AALAEKSFPS LEPQGENSSS SGIDIQSSTA SEVPPSPEGE SDSESCTSMP  2400
```

-continued

```
PLEGEPGDPD LSCDSWSTVS DSEEQSVVCC SMSYSWTGAL ITPCSAEEEK LPISPLSNSL  2460
LRHHNLVYST SSRSASQRQK KVTFDRLQVL DDHYKAVLKE VKERASRVKA RMLTIEEACA  2520
LVPPHSARSK FGYSAKDVRS LSGRAVNQIR SVWEDLLEDT TTPIPTTIMA KNEVFCVDPS  2580
KGGRKPARLI VYPDLGVRVC EKRALYDVIQ KLSIATMGSA YGFQYSPQQR VERLLEMWTS  2640
KKTPMGFSYD TRCFDSTVTE QDIRVEEEIY QCCNLEPEAR KVISSLTERL YCGGPMFNSK  2700
GAQCGYRRCR ASGVLPTSFG NTITCYIKAT AAARAAGLRN PDFLVCGDDL VLVAESDGVD  2760
EDRAALRAFT EAMTRYSAPP GDAPQPTYDL ELITSCSSNV SVARDNKGKR YYYLTRDATT  2820
PLARAAWETA RHTPVNSWLG NIIMYAPTIW VRMVMMTHFF SILQSQEILD RPLDFEMYGA  2880
TYSVTPLDLP AIIERLHGLS AFTLHSYSPV ELNRVAGTLR KLGCPPLRAW RHRARAVRAK  2940
LIAQGGKAKI CGLYLFNWAV RTKTNLTPLP AAGQLDLSSW FTVGVGGNDI YHSVSRARTR  3000
HLLLCLLLLT VGVGIFLLPA R                                           3021

SEQ ID NO: 108          moltype = AA  length = 5
FEATURE                 Location/Qualifiers
REGION                  1..5
                        note = Synthetic Sequence
REGION                  1..5
                        note = Misc_feature - This stretch of residues may be
                         repeated
source                  1..5
                        mol_type = protein
                        organism = synthetic construct
SEQUENCE: 108
GSGGS                                                             5

SEQ ID NO: 109          moltype = AA  length = 6
FEATURE                 Location/Qualifiers
REGION                  1..6
                        note = Synthetic Sequence
REGION                  1..6
                        note = Misc_feature - This stretch of residues may be
                         repeated
source                  1..6
                        mol_type = protein
                        organism = synthetic construct
SEQUENCE: 109
GGSGGS                                                            6

SEQ ID NO: 110          moltype = AA  length = 4
FEATURE                 Location/Qualifiers
REGION                  1..4
                        note = Synthetic Sequence
REGION                  1..4
                        note = Misc_feature - This stretch of residues may be
                         repeated
source                  1..4
                        mol_type = protein
                        organism = synthetic construct
SEQUENCE: 110
GGGS                                                              4

SEQ ID NO: 111          moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 111
GGSG                                                              4

SEQ ID NO: 112          moltype = AA  length = 5
FEATURE                 Location/Qualifiers
REGION                  1..5
                        note = Synthetic Sequence
source                  1..5
                        mol_type = protein
                        organism = synthetic construct
SEQUENCE: 112
GGSGG                                                             5

SEQ ID NO: 113          moltype = AA  length = 5
FEATURE                 Location/Qualifiers
REGION                  1..5
                        note = Synthetic Sequence
source                  1..5
                        mol_type = protein
                        organism = synthetic construct
SEQUENCE: 113
```

```
GSGSG                                                          5

SEQ ID NO: 114         moltype = AA  length = 5
FEATURE                Location/Qualifiers
REGION                 1..5
                       note = Synthetic Sequence
source                 1..5
                       mol_type = protein
                       organism = synthetic construct
SEQUENCE: 114
GSGGG                                                          5

SEQ ID NO: 115         moltype = AA  length = 5
FEATURE                Location/Qualifiers
REGION                 1..5
                       note = Synthetic Sequence
source                 1..5
                       mol_type = protein
                       organism = synthetic construct
SEQUENCE: 115
GGGSG                                                          5

SEQ ID NO: 116         moltype = AA  length = 5
FEATURE                Location/Qualifiers
REGION                 1..5
                       note = Synthetic Sequence
source                 1..5
                       mol_type = protein
                       organism = synthetic construct
SEQUENCE: 116
GSSSG                                                          5

SEQ ID NO: 117         moltype = AA  length = 8
FEATURE                Location/Qualifiers
REGION                 1..8
                       note = Synthetic Sequence
source                 1..8
                       mol_type = protein
                       organism = synthetic construct
SEQUENCE: 117
LEVLFQGP                                                       8

SEQ ID NO: 118         moltype = AA  length = 7
FEATURE                Location/Qualifiers
REGION                 1..7
                       note = Synthetic Sequence
source                 1..7
                       mol_type = protein
                       organism = synthetic construct
SEQUENCE: 118
ENLYFQS                                                        7

SEQ ID NO: 119         moltype = AA  length = 7
FEATURE                Location/Qualifiers
REGION                 1..7
                       note = Synthetic Sequence
source                 1..7
                       mol_type = protein
                       organism = synthetic construct
SEQUENCE: 119
ENLYFQG                                                        7

SEQ ID NO: 120         moltype = AA  length = 6
FEATURE                Location/Qualifiers
REGION                 1..6
                       note = Synthetic Sequence
source                 1..6
                       mol_type = protein
                       organism = synthetic construct
SEQUENCE: 120
LVPRGS                                                         6

SEQ ID NO: 121         moltype =   length =
SEQUENCE: 121
000

SEQ ID NO: 122         moltype = AA  length = 6
FEATURE                Location/Qualifiers
REGION                 1..6
```

```
                        note = Synthetic Sequence
source                  1..6
                        mol_type = protein
                        organism = synthetic construct
SEQUENCE: 122
LEVLFQ                                                          6

SEQ ID NO: 123          moltype = AA  length = 5
FEATURE                 Location/Qualifiers
REGION                  1..5
                        note = Synthetic Sequence
source                  1..5
                        mol_type = protein
                        organism = synthetic construct
SEQUENCE: 123
DDDDK                                                           5

SEQ ID NO: 124          moltype = AA  length = 4
FEATURE                 Location/Qualifiers
REGION                  1..4
                        note = Synthetic Sequence
source                  1..4
                        mol_type = protein
                        organism = synthetic construct
SEQUENCE: 124
LVPR                                                            4

SEQ ID NO: 125          moltype =   length =
SEQUENCE: 125
000

SEQ ID NO: 126          moltype = AA  length = 8
FEATURE                 Location/Qualifiers
REGION                  1..8
                        note = Synthetic Sequence
source                  1..8
                        mol_type = protein
                        organism = synthetic construct
SEQUENCE: 126
DYKDDDDK                                                        8

SEQ ID NO: 127          moltype = AA  length = 9
FEATURE                 Location/Qualifiers
REGION                  1..9
                        note = Synthetic Sequence
source                  1..9
                        mol_type = protein
                        organism = synthetic construct
SEQUENCE: 127
YPYDVPDYA                                                       9

SEQ ID NO: 128          moltype = AA  length = 10
FEATURE                 Location/Qualifiers
REGION                  1..10
                        note = Synthetic Sequence
source                  1..10
                        mol_type = protein
                        organism = synthetic construct
SEQUENCE: 128
EQKLISEEDL                                                      10

SEQ ID NO: 129          moltype = AA  length = 191
FEATURE                 Location/Qualifiers
REGION                  1..191
                        note = Synthetic Sequence
source                  1..191
                        mol_type = protein
                        organism = synthetic construct
SEQUENCE: 129
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS A                                                    191

SEQ ID NO: 130          moltype = AA  length = 14
FEATURE                 Location/Qualifiers
REGION                  1..14
                        note = Synthetic Sequence
source                  1..14
```

```
                        mol_type = protein
                        organism = synthetic construct
SEQUENCE: 130
QYIKANSKFI GIFE                                                     14

SEQ ID NO: 131          moltype = AA  length = 14
FEATURE                 Location/Qualifiers
REGION                  1..14
                        note = Synthetic Sequence
source                  1..14
                        mol_type = protein
                        organism = synthetic construct
SEQUENCE: 131
QYIKANSKFI GITE                                                     14

SEQ ID NO: 132          moltype = AA  length = 124
FEATURE                 Location/Qualifiers
REGION                  1..124
                        note = Synthetic Sequence
source                  1..124
                        mol_type = protein
                        organism = synthetic construct
SEQUENCE: 132
MIKLKFGVFF TVLLSSAYAH GTPQNITDLC AEYHNTQIHT LNDKIFSYTE SLAGKREMAI  60
ITFKNGATFQ VEVPGSQHID SQKKAIERMK DTLRIAYLTE AKVEKLCVWN NKTPHAIAAI  120
SMAN                                                                124

SEQ ID NO: 133          moltype = AA  length = 15
FEATURE                 Location/Qualifiers
REGION                  1..15
                        note = Synthetic Sequence
source                  1..15
                        mol_type = protein
                        organism = synthetic construct
SEQUENCE: 133
ILMQYIKANS KFIGI                                                    15

SEQ ID NO: 134          moltype = AA  length = 7
FEATURE                 Location/Qualifiers
REGION                  1..7
                        note = Synthetic Sequence
source                  1..7
                        mol_type = protein
                        organism = synthetic construct
SEQUENCE: 134
VNNESSE                                                             7

SEQ ID NO: 135          moltype = AA  length = 17
FEATURE                 Location/Qualifiers
REGION                  1..17
                        note = Synthetic Sequence
source                  1..17
                        mol_type = protein
                        organism = synthetic construct
SEQUENCE: 135
PGINGKAIHL VNNESSE                                                  17

SEQ ID NO: 136          moltype = AA  length = 6
FEATURE                 Location/Qualifiers
REGION                  1..6
                        note = Synthetic Sequence
source                  1..6
                        mol_type = protein
                        organism = synthetic construct
SEQUENCE: 136
PNRDIL                                                              6

SEQ ID NO: 137          moltype = AA  length = 7
FEATURE                 Location/Qualifiers
REGION                  1..7
                        note = Synthetic Sequence
source                  1..7
                        mol_type = protein
                        organism = synthetic construct
SEQUENCE: 137
FIGITEL                                                             7

SEQ ID NO: 138          moltype = AA  length = 6
FEATURE                 Location/Qualifiers
```

```
REGION                 1..6
                       note = Synthetic Sequence
source                 1..6
                       mol_type = protein
                       organism = synthetic construct
SEQUENCE: 138
SYFPSV                                                          6

SEQ ID NO: 139         moltype = AA  length = 20
FEATURE                Location/Qualifiers
REGION                 1..20
                       note = Synthetic Sequence
source                 1..20
                       mol_type = protein
                       organism = synthetic construct
SEQUENCE: 139
NSVDDALINS TKIYSYFPSV                                           20

SEQ ID NO: 140         moltype = AA  length = 20
FEATURE                Location/Qualifiers
REGION                 1..20
                       note = Synthetic Sequence
source                 1..20
                       mol_type = protein
                       organism = synthetic construct
SEQUENCE: 140
IDKISDVSTI VPYIGPALNI                                           20

SEQ ID NO: 141         moltype = AA  length = 15
FEATURE                Location/Qualifiers
REGION                 1..15
                       note = Synthetic Sequence
source                 1..15
                       mol_type = protein
                       organism = synthetic construct
SEQUENCE: 141
QSIALSSLMV AQAIP                                                15

SEQ ID NO: 142         moltype = AA  length = 19
FEATURE                Location/Qualifiers
REGION                 1..19
                       note = Synthetic Sequence
source                 1..19
                       mol_type = protein
                       organism = synthetic construct
SEQUENCE: 142
PVFAGANYAA WAVNVAQVI                                            19

SEQ ID NO: 143         moltype = AA  length = 20
FEATURE                Location/Qualifiers
REGION                 1..20
                       note = Synthetic Sequence
source                 1..20
                       mol_type = protein
                       organism = synthetic construct
SEQUENCE: 143
VHHNTEEIVA QSIALSSLMV                                           20

SEQ ID NO: 144         moltype = AA  length = 20
FEATURE                Location/Qualifiers
REGION                 1..20
                       note = Synthetic Sequence
source                 1..20
                       mol_type = protein
                       organism = synthetic construct
SEQUENCE: 144
QSIALSSLMV AQAIPLVGEL                                           20

SEQ ID NO: 145         moltype = AA  length = 20
FEATURE                Location/Qualifiers
REGION                 1..20
                       note = Synthetic Sequence
source                 1..20
                       mol_type = protein
                       organism = synthetic construct
SEQUENCE: 145
VDIGFAAYNF VESIINLFQV                                           20

SEQ ID NO: 146         moltype = AA  length = 20
```

-continued

```
FEATURE                Location/Qualifiers
REGION                 1..20
                       note = Synthetic Sequence
source                 1..20
                       mol_type = protein
                       organism = synthetic construct
SEQUENCE: 146
QGESGHDIKI TAENTPLPIA                                          20

SEQ ID NO: 147         moltype = AA  length = 20
FEATURE                Location/Qualifiers
REGION                 1..20
                       note = Synthetic Sequence
source                 1..20
                       mol_type = protein
                       organism = synthetic construct
SEQUENCE: 147
GVLLPTIPGK LDVNKSKTHI                                          20

SEQ ID NO: 148         moltype = AA  length = 534
FEATURE                Location/Qualifiers
REGION                 1..534
                       note = Synthetic Sequence
source                 1..534
                       mol_type = protein
                       organism = synthetic construct
SEQUENCE: 148
ADDVVDSSKS FVMENFSSYH GTKPGYVDSI QKGIQKPKSG TQGNYDDDWK EFYSTDNKYD  60
AAGYSVDNEN PLSGKAGGVV KVTYPGLTKV LALKVDNAET IKKELGLSLT EPLMEQVGTE  120
EFIKRFGDGA SRVVLSLPFA EGSSSVEYIN NWEQAKALSV ELEINFETRG KRGQDAMYEY  180
MAQACAGNRV RRSVGSSLSC INLDWDVIRD KTKTKIESLK EHGPIKNKMS ESPNKTVSEE  240
KAKQYLEEFH QTALEHPELS ELKTVTGTNP VFAGANYAAW AVNVAQVIDS ETADNLEKTT  300
AALSILPGIG SVMGIADGAV HHNTEEIVAQ SIALSSLMVA QAIPLVGELV DIGFAAYNFV  360
ESIINLFQVV HNSYNRPAYS PGHKTQPFLH DGYAVSWNTV EDSIIRTGFQ GESGHDIKIT  420
AENTPLPIAG VLLPTIPGKL DVNKSKTHIS VNGRKIRMRC RAIDGDVTFC RPKSPVYVGN  480
GVHANLHVAF HRSSSEKIHS NEISSDSIGV LGYQKTVDHT KVNSKLSLFF EIKS        534

SEQ ID NO: 149         moltype = AA  length = 26
FEATURE                Location/Qualifiers
REGION                 1..26
                       note = Synthetic Sequence
source                 1..26
                       mol_type = protein
                       organism = synthetic construct
SEQUENCE: 149
IMQYIKANSK FIGIQSIALS SLMVAQ                                   26

SEQ ID NO: 150         moltype = AA  length = 7
FEATURE                Location/Qualifiers
REGION                 1..7
                       note = Synethetic Sequence
source                 1..7
                       mol_type = protein
                       organism = synthetic construct
SEQUENCE: 150
ENLYYFQ                                                        7

SEQ ID NO: 151         moltype = AA  length = 7
FEATURE                Location/Qualifiers
REGION                 1..7
                       note = Synthetic Sequence
source                 1..7
                       mol_type = protein
                       organism = synthetic construct
SEQUENCE: 151
ENLYYFQ                                                        7
```

What is claimed is:

1. An immunogenic composition comprising:

a) a cyclic dinucleotide (CDN); and b) a hepatitis C virus (HCV) E1/E2 heterodimer; and c) a heterologous polypeptide comprising a T-cell epitope present in an HCV protein other than E1 and E2, wherein the heterologous polypeptide comprises:

i) an amino acid sequence having at least 20% amino acid sequence identity to the TP29 amino acid sequence set forth in SEQ ID NO:1, wherein the heterologous polypeptide has a length of from 29 amino acids to 32 amino acids;

ii) an amino acid sequence having at least 20% amino acid sequence identity to the TP50 amino acid sequence set forth in SEQ ID NO:11, wherein the heterologous polypeptide has a length of from 50 amino acids to 55 amino acids;

iii) an amino acid sequence having at least 20% amino acid sequence identity to the TP52 amino acid sequence set forth in SEQ ID NO:2, wherein the heterologous polypeptide has a length of from 52 amino acids to 55 amino acids;

iv) an amino acid sequence having at least 20% amino acid sequence identity to the TP70 amino acid sequence set forth in SEQ ID NO:3, wherein the heterologous polypeptide has a length of from 70 amino acids to 75 amino acids;

v) an amino acid sequence having at least 20% amino acid sequence identity to the TP100 amino acid sequence set forth in SEQ ID NO:4, wherein the heterologous polypeptide has a length of from 100 amino acids to 105 amino acids;

vi) an amino acid sequence having at least 20% amino acid sequence identity to the TP171 amino acid sequence set forth in SEQ ID NO:63, wherein the heterologous polypeptide has a length of from 171 amino acids to 175 amino acids;

vii) an amino acid sequence having at least 20% amino acid sequence identity to the TP228 amino acid sequence set forth in SEQ ID NO:10, wherein the heterologous polypeptide has a length of from 228 amino acids to 232 amino acids;

viii) an amino acid sequence having at least 20% amino acid sequence identity to the TP553 amino acid sequence set forth in SEQ ID NO:12, wherein the heterologous polypeptide has a length of from 553 amino acids to 560 amino acids;

ix) an amino acid sequence having at least 20% amino acid sequence identity to the TP778 amino acid sequence set forth in SEQ ID NO:64, wherein the heterologous polypeptide has a length of about 778 amino acids; or x) an amino acid sequence having at least 20% amino acid sequence identity to the TP1985 amino acid sequence set forth in SEQ ID NO:13, wherein the heterologous polypeptide has a length of about 1985 amino acids.

2. The immunogenic composition of claim 1, wherein the CDN is fluorinated.

3. The immunogenic composition of claim 2, wherein the CDN is 2'-F-c-di-GMP.

4. The immunogenic composition of claim 1, wherein the CDN is of Formula (I):

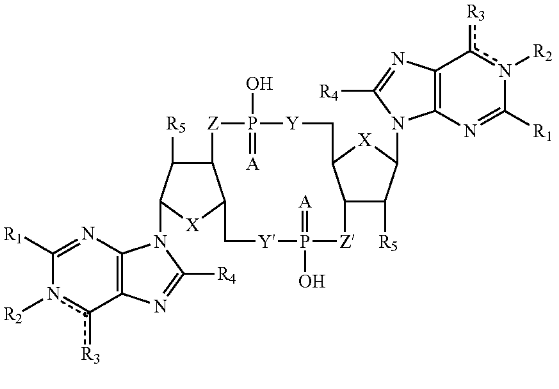

wherein:

A is S or O;

X is S, N, O, $CH_2$;

Y, Y' is NH, $CH_2$, O;

Z, Z' is NH, $CH_2$, O;

R1 represents hydrogen or $NH_2$ which may be substituted;

R2 is hydrogen or absent;

R3 represents $NH_2$, O, OH, H, or a halogen;

R4 represents hydrogen, halogen, or a straight or branched $C_1$-$C_6$ alkyl group which may optionally be substituted;

R5 represents hydrogen, OH or a straight or branched $C_1$-$C_6$ alkyl chain or $C_1$-$C_6$ straight or branched alkoxy chain which may optionally be substituted;

 is a single or double bond;

or conjugates thereof, and salts or solvates thereof.

5. The immunogenic composition of claim 4, wherein the CDN is c-diGMP, c-diAMP, c-dilMP, c-dXMP, c-GpAp, c-Gplp, c-GpXp, c-Aplp, c-ApXp, or c-lpXp.

6. The immunogenic composition of claim 1, wherein the CDN is cyclic-GMP-AMP (cGAMP).

7. The immunogenic composition of claim 6, wherein the cGAMP is 2'3'-cGAMP, 2'2-cGAMP, 3'2'-cGAMP, or 3'3'-GAMP.

8. The immunogenic composition of claim 1, wherein the heterologous polypeptide comprises:

i) an amino acid sequence having at least 50% amino acid sequence identity to the TP29 amino acid sequence set forth in SEQ ID NO:1, wherein the heterologous polypeptide has a length of from 29 amino acids to 32 amino acids;

ii) an amino acid sequence having at least 50% amino acid sequence identity to the TP50 amino acid sequence set forth in SEQ ID NO:11, wherein the heterologous polypeptide has a length of from 50 amino acids to 55 amino acids;

iii) an amino acid sequence having at least 50% amino acid sequence identity to the TP52 amino acid sequence set forth in SEQ ID NO:2, wherein the heterologous polypeptide has a length of from 52 amino acids to 55 amino acids;

iv) an amino acid sequence having at least 50% amino acid sequence identity to the TP70 amino acid sequence set forth in SEQ ID NO:3, wherein the heterologous polypeptide has a length of from 70 amino acids to 75 amino acids;

v) an amino acid sequence having at least 50% amino acid sequence identity to the TP100 amino acid sequence set forth in SEQ ID NO:4, wherein the heterologous polypeptide has a length of from 100 amino acids to 105 amino acids;

vi) an amino acid sequence having at least 50% amino acid sequence identity to the TP171 amino acid sequence set forth in SEQ ID NO:63, wherein the heterologous polypeptide has a length of from 171 amino acids to 175 amino acids;

vii) an amino acid sequence having at least 50% amino acid sequence identity to the TP228 amino acid sequence set forth in SEQ ID NO:10, wherein the heterologous polypeptide has a length of from 228 amino acids to 232 amino acids;

viii) an amino acid sequence having at least 50% amino acid sequence identity to the TP553 amino acid sequence set forth in SEQ ID NO:12, wherein the heterologous polypeptide has a length of from 553 amino acids to 560 amino acids;

ix) an amino acid sequence having at least 50% amino acid sequence identity to the TP778 amino acid sequence set forth in SEQ ID NO:64, wherein the heterologous polypeptide has a length of about 778 amino acids; or x) an amino acid sequence having at least 50% amino acid sequence identity to the TP1985 amino acid sequence set forth in SEQ ID NO:13, wherein the heterologous polypeptide has a length of about 1985 amino acids.

9. The immunogenic composition of claim 1, wherein the heterologous polypeptide comprises:

i) an amino acid sequence having at least 80% amino acid sequence identity to the TP29 amino acid sequence set forth in SEQ ID NO:1, wherein the heterologous polypeptide has a length of from 29 amino acids to 32 amino acids;

ii) an amino acid sequence having at least 80% amino acid sequence identity to the TP50 amino acid sequence set forth in SEQ ID NO:11, wherein the heterologous polypeptide has a length of from 50 amino acids to 55 amino acids;

iii) an amino acid sequence having at least 80% amino acid sequence identity to the TP52 amino acid sequence set forth in SEQ ID NO:2, wherein the heterologous polypeptide has a length of from 52 amino acids to 55 amino acids;

iv) an amino acid sequence having at least 80% amino acid sequence identity to the TP70 amino acid sequence set forth in SEQ ID NO:3, wherein the heterologous polypeptide has a length of from 70 amino acids to 75 amino acids;

v) an amino acid sequence having at least 80% amino acid sequence identity to the TP100 amino acid sequence set forth in SEQ ID NO:4, wherein the heterologous polypeptide has a length of from 100 amino acids to 105 amino acids;

vi) an amino acid sequence having at least 80% amino acid sequence identity to the TP171 amino acid sequence set forth in SEQ ID NO:63, wherein the heterologous polypeptide has a length of from 171 amino acids to 175 amino acids;

vii) an amino acid sequence having at least 80% amino acid sequence identity to the TP228 amino acid sequence set forth in SEQ ID NO:10, wherein the heterologous polypeptide has a length of from 228 amino acids to 232 amino acids;

viii) an amino acid sequence having at least 80% amino acid sequence identity to the TP553 amino acid sequence set forth in SEQ ID NO:12, wherein the heterologous polypeptide has a length of from 553 amino acids to 560 amino acids;

ix) an amino acid sequence having at least 80% amino acid sequence identity to the TP778 amino acid sequence set forth in SEQ ID NO:64, wherein the heterologous polypeptide has a length of about 778 amino acids; or x) an amino acid sequence having at least 80% amino acid sequence identity to the TP1985 amino acid sequence set forth in SEQ ID NO:13, wherein the heterologous polypeptide has a length of about 1985 amino acids.

10. The immunogenic composition of claim 1, wherein:

a) the HCV E2 polypeptide of the HCV E1/E2 heterodimer is derived from an HCV of genotype 1, 2, 3, 4, 5, 6, or 7; and b) the HCV E1 polypeptide of the HCV E1/E2 heterodimer is derived from an HCV of genotype 1, 2, 3, 4, 5, 6, or 7.

11. A method of inducing an immune response to HCV in an individual, the method comprising administering to the individual an effective amount of the immunogenic composition of claim 1.

12. The method of claim 11, wherein said administering is via intramuscular administration, intranasal administration, subcutaneous administration, or a combination thereof.

13. The method of claim 11, wherein said administering comprises a prime and a boost.

14. The method of claim 11, wherein the individual is an intravenous drug user.

15. The method of claim 11, wherein the individual is a recipient of blood or a blood product from a donor.

16. The method of claim 11, wherein the individual is a recipient of cells, a tissue, or an organ from a donor.

* * * * *